United States Patent
Congreve et al.

(10) Patent No.: US 9,555,044 B2
(45) Date of Patent: Jan. 31, 2017

(54) OREXIN RECEPTOR ANTAGONISTS

(71) Applicant: Heptares Therapeutics Limited, Welwyn Garden City, Hertfordshire (GB)

(72) Inventors: Miles Stuart Congreve, Welwyn Garden City (GB); John Andrew Christopher, Welwyn Garden City (GB); Benjamin Gerald Tehan, Welwyn Garden City (GB); Sukhbinder Singh Klair, Welwyn Garden City (GB); Sarah Joanne Aves, Welwyn Garden City (GB)

(73) Assignee: Heptares Therapeutics Limited, Walwyn Garden City, Hertfordshire (GB)

( * ) Notice: Subject to any disclaimer, the term of this patent is extended or adjusted under 35 U.S.C. 154(b) by 0 days.

(21) Appl. No.: 14/994,607

(22) Filed: Jan. 13, 2016

(65) Prior Publication Data
US 2016/0213678 A1 Jul. 28, 2016

Related U.S. Application Data

(63) Continuation of application No. 14/411,269, filed as application No. PCT/GB2013/051761 on Jul. 3, 2013, now Pat. No. 9,249,160.

(60) Provisional application No. 61/667,540, filed on Jul. 3, 2012.

(51) Int. Cl.
| | |
|---|---|
| *C07D 513/04* | (2006.01) |
| *C07D 285/24* | (2006.01) |
| *C07D 417/04* | (2006.01) |
| *C07D 417/14* | (2006.01) |
| *A61K 31/549* | (2006.01) |
| *C07D 417/06* | (2006.01) |

(52) U.S. Cl.
CPC .......... *A61K 31/549* (2013.01); *C07D 285/24* (2013.01); *C07D 417/04* (2013.01); *C07D 417/06* (2013.01); *C07D 417/14* (2013.01); *C07D 513/04* (2013.01)

(58) Field of Classification Search
CPC ... C07D 514/04; C07D 285/24; C07D 417/04; C07D 417/06; C07D 417/14; C07D 513/04

USPC .................................... 514/223.2, 222.8
See application file for complete search history.

(56) References Cited

U.S. PATENT DOCUMENTS

| | | |
|---|---|---|
| 2002/0099208 A1 | 7/2002 | Yu et al. |
| 2003/0207868 A1 | 11/2003 | Yu et al. |
| 2006/0258694 A1 | 11/2006 | Bressi et al. |
| 2010/0035866 A1 | 2/2010 | Seong et al. |

FOREIGN PATENT DOCUMENTS

| | | |
|---|---|---|
| WO | 02/051232 A2 | 7/2002 |
| WO | 2008/008517 A2 | 1/2008 |

OTHER PUBLICATIONS

Roecker, et al., "Orexin Receptor Antagonists: New Therapeutic Agents for the Treatment of Insomnia", J. Med. Chem., 2016, 59: 504-530.
Christopher, "Small-Molecule Antagonists of the Orexin Receptors" Pharm. Pat. Anal. 2014, 3(6): 625-638.
Andrews, et al, "Orexin Receptor Antagonists: Historical Perspectives and Future Opportunities", Current Topics in Medicinal Chemistry, 2016, 16: 1-32.
Cai et al., "Antagonists of the orexin receptors", Expert Opinion Ther. Patents, vol. 16, No. 5, p. 631-646, 2006.
Coleman et al., "Orexin receptor antagonists: a review of promising compounds", Expert Opinion Ther. Patents, vol. 20, No. 3, pp. 307-324, 2010.
Magnien et al., "The preparation of 4-Substituted Benzothiadiazines", J. Med Chem, vol. 7, No. 6, pp. 821-823, 1964.

*Primary Examiner* — Kahsay Habte
(74) *Attorney, Agent, or Firm* — McCarter & English, LLP; Steven G. Davis; Mei Bai

(57) ABSTRACT

The disclosures herein relate to novel compounds of formula wherein W, X and $Y_1$, $Y_2$, $Y_3$ and $Y_4$ are defined herein, and their use in treating, preventing, ameliorating, controlling or reducing the risk of neurological or psychiatric disorders associated with orexin receptors.

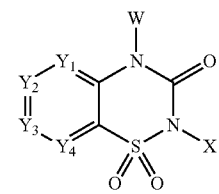

10 Claims, 1 Drawing Sheet

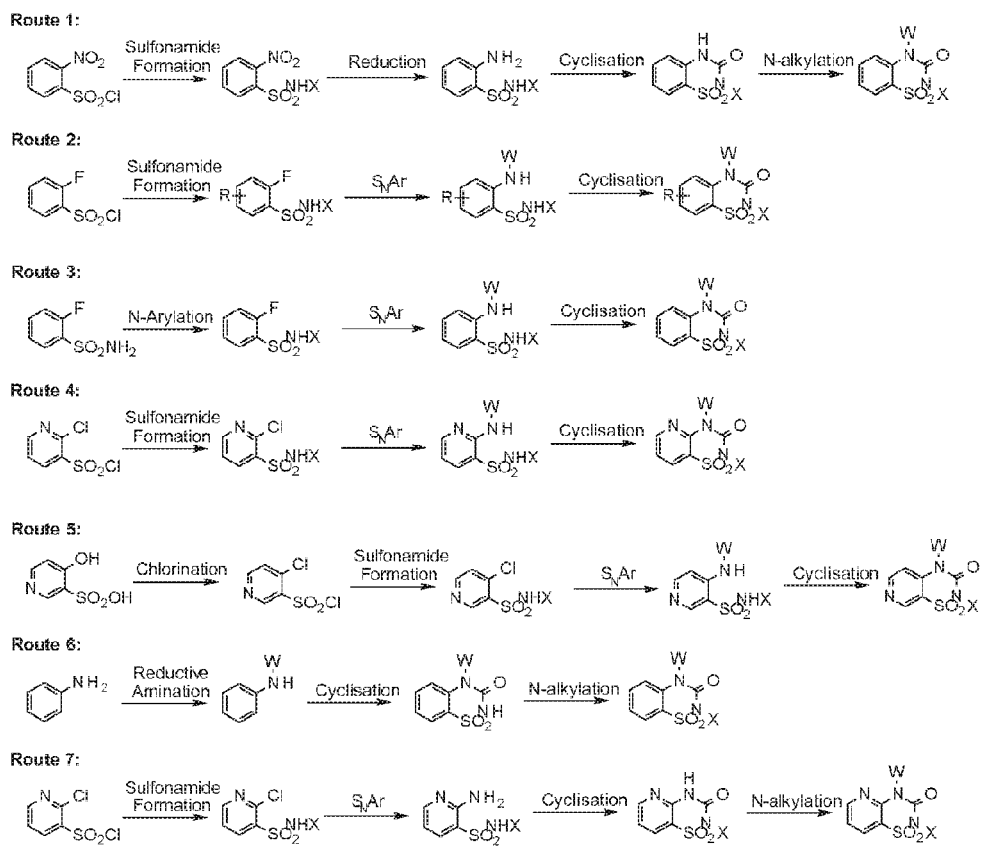

OREXIN RECEPTOR ANTAGONISTS

RELATED APPLICATION INFORMATION

This application is a continuation of U.S. application Ser. No. 14/411,269, filed Dec. 24, 2014, which is a 371 of International Application No. PCT/GB2013/051761, filed Jul. 3, 2013, which claims benefit of U.S. Provisional Application No. 61/667,540, filed Jul. 3, 2012, all of which are incorporated herein by reference.

This application relates to novel compounds and their use as orexin receptor antagonists. Compounds described herein may be useful in the treatment or prevention of diseases in which orexin receptors are involved. The application is also directed to pharmaceutical compositions comprising these compounds and the manufacture and use of these compounds and compositions in the prevention or treatment of such diseases in which orexin receptors are involved.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide). Two orexin receptors have been studied in mammals, both belonging to the super family of G-protein coupled receptors. The orexin-1 receptor ($OX_1$ or OX1R) is selective for OX-A and the orexin-2 receptor ($OX_2$ or OX2R) is capable to bind OX-A as well as OX-B. The physiological actions in which orexins are presumed to participate are thought to be expressed via one or both of $OX_1$ receptor and $OX_2$ receptor as the two subtypes of orexin receptors.

Orexins also regulate states of sleep and wakefulness, opening potentially novel medicament based therapeutic approaches for narcoleptic or insomniac patients. Orexin receptors are found in the mammalian brain and may have numerous implications in pathologies related to general orexin system dysfunction. Prior art compounds for the treatment of orexin system dysfunction are shown in, for example WO2008008517 and WO2010122151. The structures of the compounds contained in these prior art disclosures are entirely different to the structures disclosed below.

The most advanced orexin receptor antagonists are almorexant, suvorexant (MK-4305) and MK-6096; these compounds are dual orexin receptor antagonists (DORA), displaying similar affinities for both $OX_1$ and $OX_2$ receptor subtypes. These compounds have been shown to be effective in promoting sleep in preclinical species, reducing active wake and increasing both non-REM and REM sleep in rodent and dog studies. In a Phase II clinical trial, almorexant dose-dependently increased sleep efficiency in patients with primary insomnia and tended to improve wake after sleep onset and reduce the latency to persistent sleep. Similarly, suvorexant increased sleep efficiency in a Phase IIb study; significant dose-related effects were also observed for sleep induction and maintenance parameters, and has shown efficacy in several Phase III trials in primary insomnia patients. In both cases, DORAs were well tolerated. MK-6096 shows efficacy in preclinical sleep models and has completed a Phase II clinical trial evaluating efficacy in the treatment of patients with primary insomnia.

Orexins have been found to stimulate food consumption in rats, suggesting a physiological role for these peptides as mediators in the central feedback mechanism that regulates feeding behaviour. Orexin-A is believed to be an endogenous regulator of appetite and an $OX_1$ receptor antagonist reduces food intake in rats. Antagonists of the orexin-A receptor(s) may therefore be useful in the treatment of obesity and diabetes via regulation of appetite. Orexin receptor antagonists may also be useful in the treatment of binge eating disorder and other compulsive disorders including impulse control disorders. The search for new therapies to treat obesity and other eating disorders is an important and increasing challenge, particularly in westernised societies. Current treatments for obesity and diabetes are often either ineffective or show unacceptably high toxicity.

Orexinergic neurons project from the lateral hypothalamus to the ventral tegmental area, amygdala, nucleus accumbens and pre-frontal cortex, indicating a role in reward pathways. Orexin receptor antagonists have been shown to ameliorate sensitisation, withdrawal and self-administration of a number of drugs of abuse in animal models, suggesting that such compounds could have utility in the treatment of dependence and addiction. Many of the regions innervated and modulated by orexin neurons are dopaminergic, suggesting an interplay between these neurotransmitter systems. Antagonists of orexin receptors could modulate central dopaminergic transmission and be effective in the treatment of movement disorders in which dopamine levels are abnormal.

Orexin peptides also play a role in arousal, vigilance and in centrally-controlled autonomic function and have been shown to be involved in the development of a panic-prone state in rodents, an effect that could be reversed by orexin receptor antagonists, suggesting that these would have utility in the treatment of anxiety and panic. Furthermore, levels of beta-amyloid, the pathological hallmark of Alzheimer's disease, were increased by sleep deprivation and orexin peptide infusion in mice. In contrast, levels of beta-amyloid and amyloid placque formation were reduced in amyloid precursor protein transgenic mice upon treatment with an orexin receptor antagonist, suggesting that such compounds may have utility in the treatment of Azheimer's disease and other dementia-related cognitive dysfunction.

MK-6096 has also completed a Phase II trial evaluating safety and efficacy versus placebo for preventing migraines in participants with episodic migraine. This observation suggests that orexin receptor antagonists may have utility in the treatment or prevention of migraine or other headache disorders, such as tension-type headache, cluster headache, other trigeminal autonomic cephalalgias, other primary headaches such as hemicrania continua or those listed in the International Headache Society 2nd Edition of The International Headache Classification (ICHD-2), secondary headaches such as those listed in ICHD-2, cranial neuralgias such as trigeminal neuralgia or those listed in ICHD-2, or other causes of headache, cranial neuralgia, central or primary facial pain such as those listed in ICHD-2.

A Phase II trial of MK-6096 is currently recruiting to evaluate the safety and efficacy as an adjunctive therapy in participants with major depressive disorder and partial response to antidepressant monotherapy. This observation suggests that orexin receptor antagonists may have utility in the treatment of depression and related disorders.

MK-6096 has also completed a Phase II trial evaluating safety and efficacy in the treatment of painful diabetic neuropathy (PDN) in adults. This observation suggests that orexin receptor antagonists may have utility in the treatment of neuropathic pain or other pain disorders.

Whilst there has been disclosure of related compounds in the prior chemical art, there has been no disclosure of chemically related compounds as antagonists of orexin receptors or for the treatment of orexin system dysfunction.

SUMMARY OF THE INVENTION

The invention relates to novel compounds. The invention further relates to the first medical use of known compounds. The invention also relates to the use of both novel and known compounds as antagonists of orexin receptors or for the treatment of orexin system dysfunction. The invention further relates to the use of both novel and known compounds in the manufacture of medicaments for use as orexin receptor antagonists or for the treatment of orexin system dysfunction. The invention further relates to compounds, compositions and medicaments for the treatment of diabetes, obesity, insomnia, neurological or psychiatric disorders. Embodiments of the invention may be compounds according to the formula

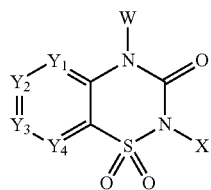

wherein $Y_1$, $Y_2$, $Y_3$ and $Y_4$ are independently an optionally substituted carbon or a nitrogen atom and W is an methylene group substituted by a substituted aryl, or optionally substituted heteroaryl or heterocycloalkyl moiety; and X comprises an optionally substituted aryl, optionally substituted heteroaryl, optionally substituted cycloalkyl, or optionally substituted heterocycloalkyl moiety; and wherein either at least one of $Y_1$-$Y_4$ is a nitrogen atom; or X comprises an optionally substituted heteroaryl, or optionally substituted heterocycloalkyl moiety; or W is a moiety of formula

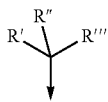

wherein R' and R" are independently H or alkyl and R''' is 2,4,6-trisubstituted aryl, or optionally substituted heteroaryl group.

Alternative embodiments of the invention may be a compound of formula

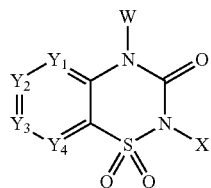

wherein $Y_1$, $Y_2$, $Y_3$ are independently an optionally substituted carbon or a nitrogen atom; and $Y_4$ is is C-alkyl, C-halogen, C—H or N and W is a methylene group substituted by an optionally substituted aryl, optionally substituted cycloalkyl, optionally substituted heterocycloalkyl or optionally substituted heteroaryl moiety; and X comprises an optionally substituted aryl, optionally substituted heteroaryl, optionally substituted cycloalkyl, or optionally substituted heterocycloalkyl moiety, wherein X is not cyclopropyl, for use in medicine.

FIGURES

FIG. 1: A schematic of different routes available to prepare compounds described herein.

DETAILED DESCRIPTION OF THE INVENTION

The invention relates to novel compounds. In the cases where compounds are novel, the compounds themselves may be claimed. In cases where the compounds have been synthesised previously, but no medical use has been reported, the first medical use of known compounds may be claimed. The invention also relates to the use of both novel and known compounds as antagonists of orexin receptors or for the treatment of orexin system dysfunction. The invention further relates to the use of compounds in the manufacture of medicaments for use as orexin receptor antagonists or for the treatment of orexin system dysfunction. The invention further relates to compounds, compositions and medicaments for the treatment of insomnia, migraine, cluster headache and other headache disorders, diabetes, obesity, substance dependence, addiction, movement disorders, anxiety disorders, panic disorders, cognitive impairment or Alzheimer's disease.

Thus, in specific embodiments the present invention provides methods for treating, preventing, ameliorating, controlling or reducing the risk of a variety of neurological and psychiatric disorders associated with orexin receptors, including disturbed biological and circadian rhythms, sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; altering the timing, frequency or duration of REM sleep bouts; altering the timing, frequency or duration of slow wave sleep bouts; reducing daytime drowsiness; treating or reducing excessive daytime sleepiness, REM sleep interruptions, sleep apnea, narcolepsy, insomnia, parasomnia, jet-lag, shift workers' sleep disturbances, dyssomnias, night terror, sleep disturbances associated with diseases such as neurological disorders, insomnias associated with depression, emotional/mood disorders, Alzheimer's disease or cognitive impairment, as well as sleep walking and enuresis, and sleep disorders which accompany aging.

In addition, the present invention provides methods for treatment of pain disorders including neuropathic pain and restless leg syndrome, migraine, cluster headache, tension-type headache, trigeminal autonomic cephalalgias, hemicrania continua, trigeminal neuralgia, other headache disorders, hyperalgesia, pain, enhanced or exaggerated sensitivity to pain such as hyperalgesia, causalgia, and allodynia, acute pain, burn pain, atypical facial pain, neuropathic pain, back pain, complex regional pain syndrome I and II, arthritic pain, sports injury pain, pain related to infection e.g. HIV, post-chemotherapy pain, post-stroke pain, post-operative pain, neuralgia, conditions associated with visceral pain such as irritable bowel syndrome, and angina; obesity-related disorders including overeating and bulimia nervosa, hypertension, congestive heart failure, pathological conditions showing reduced metabolic activity or a decrease in resting energy expenditure as a percentage of total fat-free mass, diabetes, impaired glucose tolerance; cardiovascular disease including acute and congestive heart failure, hypotension, hypertension, angina pectoris, myocardinal infarction; eating disorders including anorexia, cachexia, addictive feeding behaviors; binge/purge feeding behaviours such as binge eating disorder, appetite/taste disorders; addictive behaviours including dependence or withdrawal from substances including, but not limited to, alcohol, amphetamines, cannabis, cocaine, hallucinogens, inhalants, nicotine, opioids, phencyclidine, sedatives, hypnotics or anxiolytics; tolerance to narcotics or withdrawal from narcotics; movement disorders including Parkinson's disease, akinesias, drug-induced parkinsonism, dystonia, restless leg syndrome; anxiety or panic disorders including generalized anxiety disorder, panic disorder, obsessive compulsive disorder and impulse control disorder; cancer including bowel, colon, stomach, breast, endometrial, pancreatic or prostate cancer; hypothalamic/pituitary diseases including Cushing's syndrome/disease, basophile adenoma, prolactinoma, hyperprolactinemia, hypophysis tumour/adenoma, hypothalamic diseases, Froehlich's syndrome, adrenohypophysis disease, hypophysis disease, adrenohypophysis hypofunction, adrenohypophysis hyperfunction, hypothalamic hypogonadism, Kallman's syndrome (anosmia, hyposmia), functional or psychogenic amenorrhea, hypopituitarism, hypothalamic hypothyroidism, hypothalamic-adrenal dysfunction, idiopathic hyperprolactinemia, hypothalamic disorders of growth hormone deficiency, idiopathic growth deficiency, dwarfism, gigantism, acromegaly; psychiatric disorders including depression, anxiety, addictions, affective neurosis, depressive neurosis, anxiety neurosis, dysthymic disorder, behaviour disorder, mood disorder, sexual dysfunction, psychosexual dysfunction, sex disorder, schizophrenia, manic depression, delirium, severe mental retardation; other CNS disorders including dementia, dyskinesias such as Huntington's disease and Tourette syndrome, ischemic or haemorrhagic stroke, subarachnoid haemorrhage, nosological entities such as disinhibition-dementia-parkinsonism-amyotrophy complex, pallido-ponto-nigral degeneration, epilepsy, seizure disorders; inflammatory disorders including inflammatory bowel disease; renal/urinary disorders including urinary retention, benign prostatic hypertrophy, chronic renal failure, renal disease; cognitive impairment or Alzheimer's disease in a mammalian patient in need thereof which comprises administering to the patient a therapeutically effective amount of a compound of the present invention.

Compounds exemplified herein are based around the structure:

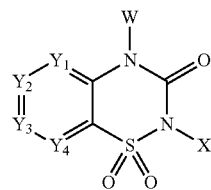

In which any of $Y_1$, $Y_2$, $Y_3$ or $Y_4$ are independently carbon atoms or nitrogen atoms. The carbon atoms $Y_1$, $Y_2$, $Y_3$ or $Y_4$ may bear hydrogen atoms (i.e. form CH groups) or may be substituted, for example with halo groups (fluoro, chloro, bromo or iodo), hydroxyl groups, alkyl groups or substituted alkyl groups, alkenyl or alkynyl groups or alkoxy groups. For example any of $Y_1$, $Y_2$, $Y_3$ or $Y_4$ may be independently N, C—H, C—F, C—Cl, C—Br, C—I, C-alkyl or C—OH. The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be a cyclic group such as cyclopropyl or cyclobutyl. Preferably, no more than one of $Y_1$, $Y_2$, $Y_3$ and $Y_4$ is N. In particular examples $Y_1$ may be nitrogen. Alternatively, in particular examples, $Y_3$ may be nitrogen. In particular examples $Y_1$ or $Y_3$ may be CF. Each of $Y_1$-$Y_4$ may be C—H. $Y_4$ may be CH or N.

In certain prior art compounds, for example as disclosed in PCT application WO2007108569, $Y_4$ has been described for a variety of carbon linked mono, bi or tri cyclic amino groups. All medical uses of the compounds described in WO2007108569 require that $Y_4$ is a carbon atom linked to a nitrogen atom. The preparation of said compounds was carried out using intermediates where $Y_4$ consists of a carbon-halogen bond, or similar reactive leaving group. This prior art does not disclose compounds as disclosed herein wherein X and W are both ring structures as described herein where $Y_4$ is CH, or where $Y_4$ is a nitrogen atom in the ring itself. Furthermore, said document does not disclose a medical use for the synthetic intermediates where $Y_4$ is CF, CCl, CBr or Cl, and thus the medical use of any compound as described herein is not disclosed with the exception of where $Y_4$ contains a nitrogen atom linked to the aromatic carbon of $Y_4$.

In particular aspects, compounds of the invention may be exemplified herein based around the structure:

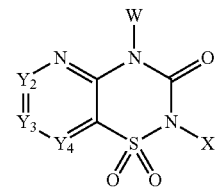

in which any of $Y_2$, $Y_3$ or $Y_4$ are independently carbon atoms or nitrogen atoms. The carbon atoms $Y_2$, $Y_3$ or $Y_4$ may be further substituted, for example with halo groups (fluoro, chloro, bromo or iodo), hydroxyl groups, alkyl groups or substituted alkyl groups, alkenyl or alkynyl groups or alkoxy groups. For example any of $Y_2$, $Y_3$ or $Y_4$ may be independently N, C—H, C—F, C—Cl, C—Br, C—I, C-alkyl or C—OH. The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be a cyclic group such as cyclopropyl or cyclobutyl. W is a methylene group or CH(alkyl) group substituted by an optionally substituted aryl, optionally substituted cycloalkyl, optionally substituted heterocycloalkyl or optionally substituted heteroaryl moiety. X comprises an optionally substituted aryl, optionally substituted heteroaryl, optionally substituted cycloalkyl, or optionally substituted heterocycloalkyl moiety.

In particular aspects, compounds of the invention may be exemplified herein based around the structure:

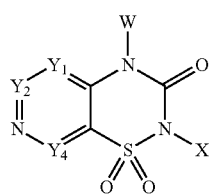

in which any of $Y_1$, $Y_2$ or $Y_4$ are independently carbon atoms or nitrogen atoms. The carbon atoms $Y_1$, $Y_2$ or $Y_4$ may be further substituted, for example with halo groups (fluoro, chloro, bromo or iodo), hydroxyl groups, alkyl groups or substituted alkyl groups, alkenyl or alkynyl groups or alkoxy groups. For example any of $Y_1$, $Y_2$ or $Y_4$ may be independently N, C—H, C—F, C—Cl, C—Br, C—I, C-alkyl or C—OH. The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be cyclic groups such as cyclopropyl or cyclobutyl. W is a methylene group or CH(alkyl) group substituted by an optionally substituted aryl, optionally substituted cycloalkyl, optionally substituted heterocycloalkyl or optionally substituted heteroaryl moiety. X comprises an optionally substituted aryl, optionally substituted heteroaryl, optionally substituted cycloalkyl, or optionally substituted heterocycloalkyl moiety.

The moiety W may be a methylene group substituted by a substituted aryl, or optionally substituted heteroaryl or heterocycloalkyl moiety.

The substituted aryl and heteroaryl groups may be any of the aryl and heteroaryl groups listed below in the "Definitions" section of this application.

Typically, however, the aryl group is a phenyl group which is substituted as defined herein.

The heteroaryl group, which may be optionally substituted as defined herein, can be monocyclic or polycyclic (e.g bicyclic or tricyclic) and may, for example, contain up to 14 ring members, more typically 5 to 10. When the heteroaryl group is monocyclic, preferably it is 5- or 6-membered. The heteroaryl (e.g. 5- or 6-membered heteroaryl) group contains one or more (e.g. 1, 2 or 3) heteroatoms which are typically selected from nitrogen, oxygen and sulphur. Examples of heteroaryl groups are 5- and 6-membered heteroaryl groups containing a nitrogen atom ring member and optionally a second heteroatom ring member selected from nitrogen, oxygen and sulphur. Particular heteroaryl groups are pyridyl and pyrazolyl groups In one embodiment, W is a methylene group substituted with a substituted phenyl, or optionally substituted monocyclic 5- or 6-membered heteroaryl moiety containing up to two heteroatom ring members selected from nitrogen, oxygen and sulphur.

In a further embodiment, W is a methylene group substituted with a substituted phenyl or optionally substituted pyridyl or pyrazolyl group.

As defined herein, the aryl group forming part of W is substituted and the heteroaryl group is optionally substituted. The substituents may be as defined below in the "Definitions" section below.

In one general embodiment, the substituents for the aryl and heteroaryl groups forming part of W may be selected from halo (fluoro, chloro, bromo or iodo), $C_{1-4}$ alkyl, $C_{1-4}$ alkylsulfanyl, $C_{1-4}$ alkylsulfinyl, $C_{1-4}$ alkylsulphonyl, $C_{3-6}$ cycloalkyl, hydroxy, $C_{1-4}$ alkoxy, cyano, nitro, amino, $C_{1-4}$ alkylamino, $C_{2-4}$ alkenylamino, di-$C_{1-4}$ alkylamino, $C_{1-4}$ acylamino, phenyl, phenylamino, benzoylamino, benzylamino, phenylamido, carboxy, $C_{1-4}$ alkoxycarbonyl or phenyl-$C_{1-10}$ alkoxycarbonyl, carbamoyl, mono-$C_{1-4}$ carbamoyl, di-$C_{1-4}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

More particularly, the substituents for the aryl and heteroaryl groups forming part of W may be selected from halo (fluoro, chloro, bromo or iodo), $C_{1-4}$ alkyl, $C_{3-6}$ cycloalkyl, hydroxy, $C_{1-4}$ alkoxy, cyano, amino, $C_{1-4}$ alkylamino, di-$C_{1-4}$ alkylamino, $C_{1-4}$ acylamino, carboxy, $C_{1-4}$ alkoxycarbonyl, carbamoyl, mono-$C_{1-4}$ carbamoyl, di-$C_{1-4}$ carbamoyl or any of the above substituents in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

In a particular embodiment, the substituents for the aryl and heteroaryl groups forming part of W may be selected from fluoro, chloro, bromo, $C_{1-3}$ alkyl, $C_{3-6}$ cycloalkyl, hydroxy, $C_{1-4}$ alkoxy, cyano, amino, $C_{1-2}$ alkylamino, di-$C_{1-2}$ alkylamino, $C_{1-2}$ acylamino, carboxy, $C_{1-2}$ alkoxycarbonyl, carbamoyl, mono-$C_{1-2}$ carbamoyl, di-$C_{1-2}$ carbamoyl or any of the above substituents in which a hydrocarbyl moiety is itself substituted by one or more fluorine atoms or by cyano, hydroxy, $C_{1-2}$ alkoxy, amino, carbamoyl, carboxy or $C_{1-2}$ alkoxycarbonyl.

In a more particular embodiment, the substituents for the aryl and heteroaryl groups forming part of W may be selected from fluoro, chloro, bromo, cyano, $C_{1-3}$ alkyl and $C_{1-3}$ alkoxy, wherein the $C_{1-3}$ alkyl and $C_{1-3}$ alkoxy moieties are each optionally substituted with one or more fluorine atoms.

The moiety W comprises one or more carbon atoms in the form of a ring structure. In particular examples, W is a formula of

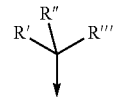

wherein R' and R" are independently H or alkyl (e.g. $C_{1-2}$ alkyl, more preferably methyl) and R''' is an optionally substituted aryl, optionally substituted cycloalkyl, optionally substituted heteroaryl or optionally substituted heterocycloalkyl group. R' may be methyl. R" may be methyl.

The optional substituents may consist of one or more halo, alkyl or alkoxy groups, or may be selected from the list of optional substituents shown below. The R''' group may comprise a substituted aryl or heteroaryl group. In a 6-membered aromatic ring the substituents may be located at the 2, 3, 4, 5 or 6 positions. The aryl or heteroaryl group may comprise one, two, three, four or more substituents. The aryl group may be disubstituted, with the substitutions at any two of positions 2 to 6. The aryl group may be a 2,3-disubstituted, 2,4-disubstituted, 2,5-disubstituted, 2,6-disubstituted, 3,4-disubstituted or 3,5-disubstituted aryl group. Examples of disubstituted aryl groups include 2-fluoro-6-chloro or 2-chloro-4-fluoro. In the case of alkoxy groups, the groups may be linked together to form a further ring, for example a 2,3 or 3,4 cyclic acetal group of type O—$CH_2$—O. The aryl group may comprise a 2, 3 or 4 methoxy group. The aryl group may comprise a fluoro, chloro, bromo, methyl or cyano group, which may be at the 2, 3 or 4 position. The substituents may be acyl groups of type CO-alkyl or acyl esters of type —CO—O— alkyl, for example —CO$_2$CH$_3$. The substituents may be primary, secondary or tertiary amide groups of type CO—NH$_2$, CO—NH-alkyl or CO—N(alkyl)$_2$. In particular the aryl group may be a 2,4-disubstituted, 2,6-disubstituted or 2,4,6-trisubstituted aryl group.

The R''' group may comprise an optionally substituted cyclopropyl, cyclobutyl, cyclopentyl or cyclohexyl group.

The R''' group may be a heteroaryl group, for example 2, 3 or 4 pyridyl. The heteroaryl group may optionally be further substituted, for example 2-fluoro,4-pyridyl or disubstituted, for example 2,6-difluoro,4-pyridyl. The heteroaryl group may be 3, 4, 5, 6 or 7 membered, and contain one or more heteroatoms. The heteroaryl group may be a 5 membered ring containing two or more heteroatoms. The heteroatoms may be independently nitrogen, oxygen or sulphur. The heteroaryl group may be further substituted with one or more rings, which may be linked onto one or more positions of the heteroaryl group, for example to form a bicyclic heteroaryl group selected from the definitions of heteroaryl found herein.

In certain examples, W may be selected from one of the following groups

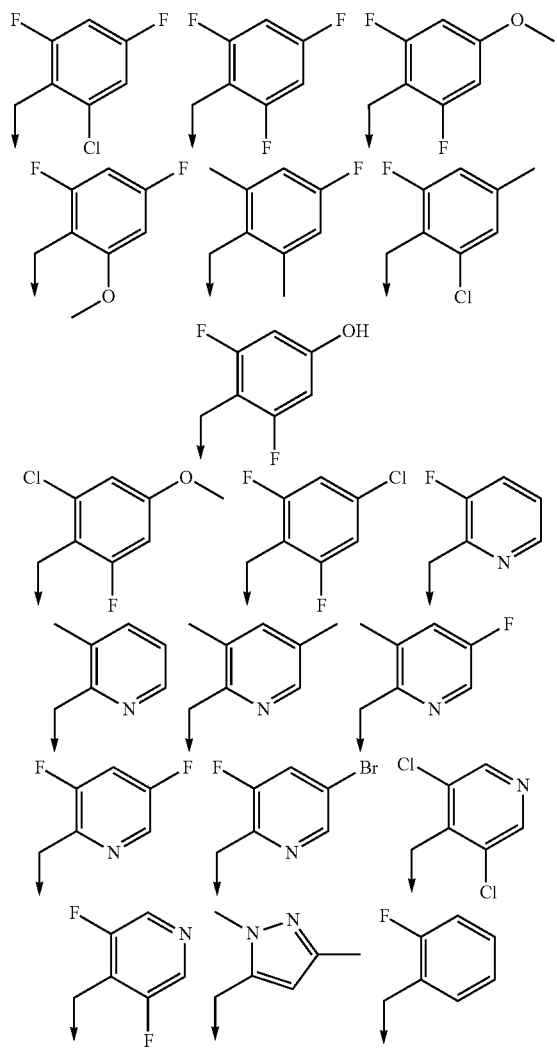

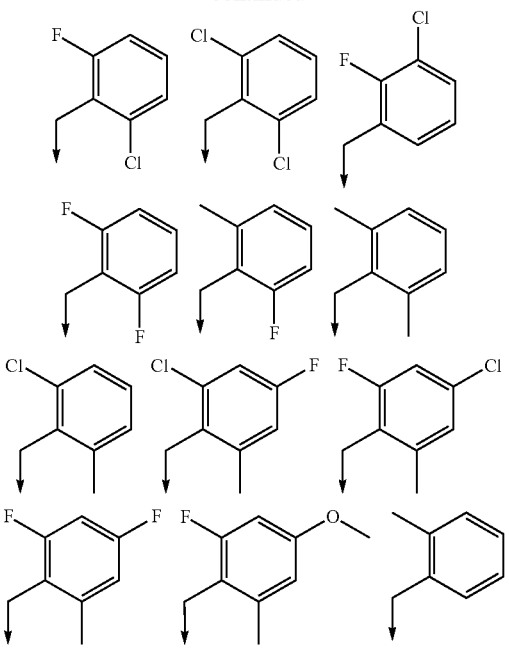

In embodiments in which Y$_1$ is a nitrogen atom, or where X comprises an optionally substituted heteroaryl or optionally substituted heterocycloalkyl moiety, W can be selected from the list above.

In embodiments in which Y$_1$ is a carbon atom, or where X comprises an optionally substituted aryl or optionally substituted cycloalkyl group, W may be selected from one of the following groups:

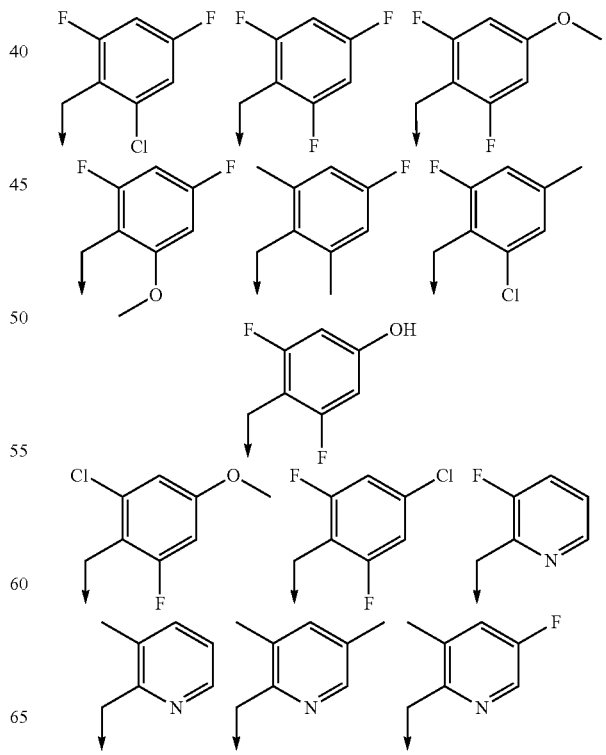

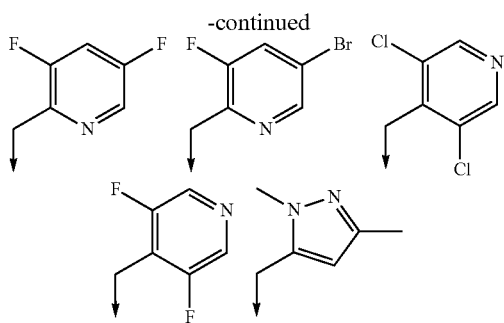

In particular aspects, compounds of the invention may be exemplified herein based around the structure:

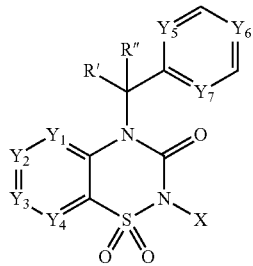

in which any of $Y_1$, $Y_2$, $Y_3$, $Y_4$, are independently carbon atoms or nitrogen atoms. The carbon atoms $Y_1$, $Y_2$, $Y_3$, $Y_4$, may be further substituted, for example with halo groups (fluoro, chloro, bromo or iodo), hydroxyl groups, alkyl groups or substituted alkyl groups, alkenyl or alkynyl groups or alkoxy groups. For example any of $Y_1$, $Y_2$, $Y_3$, $Y_4$ may be independently N, C—H, C—F, C—Cl, C—Br, C—I, C-alkyl or C—OH. Preferably, no more than one of $Y_1$, $Y_2$, $Y_3$ and $Y_4$ is N. The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be cyclic groups such as cyclopropyl or cyclobutyl. R' and R" are independently H or alkyl. $Y_5$, $Y_6$, and $Y_7$ are each independently substituted carbon atoms or heteroatoms. For example each of $Y_5$, $Y_6$, and $Y_7$ may be independently N, C—F, C—Cl, C—Br, C—I, C-alkyl, C—O-alkyl or C—OH. X comprises an optionally substituted aryl, optionally substituted heteroaryl, optionally substituted cycloalkyl, or optionally substituted heterocycloalkyl moiety.

X comprises an optionally substituted aryl, optionally substituted heteroaryl, optionally substituted cycloalkyl, or optionally substituted heterocycloalkyl moiety which may either be attached directly to the thiadiazinone ring or attached through an alkylene linker group. The alkylene linker group, when present, may have a chain length (extending between the thiadiazinone ring and the cyclic moiety) of up to 3 carbon atoms, one or more of which may optionally bear an alkyl side chain. The alkylene linker group, when present, typically contains a maximum of 6 carbon atoms.

The moiety X comprises one or more carbon atoms in the form of a ring structure. In particular examples, X may comprise an optionally substituted aryl, optionally substituted cycloalkyl, optionally substituted heteroaryl or optionally substituted heterocycloalkyl group. As indicated above, the optionally substituted aryl, optionally substituted cycloalkyl, optionally substituted heteroaryl or optionally substituted heterocycloalkyl group may be connected directly to the nitrogen atom, or may have one or more intervening aliphatic carbon atoms. The intervening carbon atoms may be in the form of a $CH_2$, $CH_2CH_2$ or CH(alkyl)- group. For example therefore, an aryl group at position X may therefore be in the form of N-aryl, or N—$CH_2$-aryl (benzyl) or N—$CH_2CH_2$-aryl etc, and the term 'comprising' an optionally substituted aryl, optionally substituted cycloalkyl, optionally substituted heteroaryl or optionally substituted heterocycloalkyl group includes the optional aliphatic groups as well as the directly attached rings.

The optional substituents may be selected from the list of optional substituents shown below.

In one general embodiment, the substituents for the optionally substituted aryl, optionally substituted heteroaryl, optionally substituted cycloalkyl, or optionally substituted heterocycloalkyl moiety forming part of X may be selected from halo (fluoro, chloro, bromo or iodo), oxo, $C_{1-4}$ alkyl, $C_{1-4}$ alkylsulfanyl, $C_{1-4}$ alkylsulfinyl, $C_{1-4}$ alkylsulphonyl, $C_{3-6}$ cycloalkyl, hydroxy, $C_{1-4}$ alkoxy, cyano, nitro, amino, $C_{1-4}$ alkylamino, $C_{2-4}$ alkenylamino, di-$C_{1-4}$ alkylamino, $C_{1-4}$ acylamino, phenyl, phenylamino, benzoylamino, benzylamino, phenylamido, carboxy, $C_{1-4}$ alkoxycarbonyl or phenyl-$C_{1-10}$ alkoxy)carbonyl, carbamoyl, mono-$C_{1-4}$ carbamoyl, di-$C_{1-4}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

More particularly, the substituents for the optionally substituted aryl, optionally substituted heteroaryl, optionally substituted cycloalkyl, or optionally substituted heterocycloalkyl moiety forming part of X may be selected from halo (fluoro, chloro, bromo or iodo), oxo, $C_{1-4}$ alkyl, $C_{3-6}$ cycloalkyl, $C_{1-4}$ alkylsulfanyl, $C_{1-4}$ alkylsulfinyl, $C_{1-4}$ alkylsulphonyl, hydroxy, $C_{1-4}$ alkoxy, cyano, amino, $C_{1-4}$ alkylamino, di-$C_{1-4}$ alkylamino, $C_{1-4}$ acylamino, carboxy, $C_{1-4}$ alkoxycarbonyl, carbamoyl, mono-$C_{1-4}$ carbamoyl, di-$C_{1-4}$ carbamoyl or any of the above substituents in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

In a particular embodiment, the substituents for the optionally substituted aryl, optionally substituted heteroaryl, optionally substituted cycloalkyl, or optionally substituted heterocycloalkyl moiety forming part of X may be selected from fluoro, chloro, bromo, oxo, $C_{1-3}$ alkyl, $C_{3-6}$ cycloalkyl, $C_{1-3}$ alkylsulfanyl, $C_{1-3}$ alkylsulfinyl, $C_{1-3}$ alkylsulphonyl, hydroxy, $C_{1-3}$ alkoxy, cyano, amino, $C_{1-2}$ alkylamino, di-$C_{1-2}$ alkylamino, $C_{1-2}$ acylamino, carboxy, $C_{1-2}$ alkoxycarbonyl, carbamoyl, mono-$C_{1-2}$ carbamoyl, di-$C_{1-2}$ carbamoyl or any of the above substituents in which a hydrocarbyl moiety is itself substituted by one or more fluorine atoms or by cyano, hydroxy, $C_{1-2}$ alkoxy, amino, carbamoyl, carboxy or $C_{1-2}$ alkoxycarbonyl.

In a more particular embodiment, the substituents for the optionally substituted aryl, optionally substituted heteroaryl, optionally substituted cycloalkyl, or optionally substituted heterocycloalkyl moiety forming part of X, may be selected from fluoro, chloro, bromo, oxo, $C_{1-3}$ alkyl, $C_{1-3}$ alkylsulfanyl, $C_{1-3}$ alkylsulfinyl, $C_{1-3}$ alkylsulphonyl, hydroxy, $C_{1-3}$ alkoxy, cyano, amino, $C_{1-2}$ alkylamino and di-$C_{1-2}$ alkylamino.

In another more particular embodiment, the substituents for the optionally substituted aryl, optionally substituted heteroaryl, optionally substituted cycloalkyl, or optionally substituted heterocycloalkyl moiety forming part of X, may be selected from oxo, $C_{1-3}$ alkyl, $C_{1-3}$ alkylsulfanyl, $C_{1-3}$ alkylsulfinyl, $C_{1-3}$ alkylsulphonyl, hydroxy, $C_{1-3}$ alkoxy and di-$C_{1-2}$ alkylamino.

In a further embodiment, the substituents may consist of one or more halo, alkyl or alkoxy groups.

The moiety X may comprise a substituted aryl or heteroaryl group. When the aryl or heteroaryl group is 6-membered, the substituents may be located at the 2, 3, 4, 5 or 6 positions. The aryl or heteroaryl group may comprise one, two, three, four or more substituents as defined herein, and more particularly may comprise one, two or three substituents. The aryl group may be disubstituted, with the substitutions at any two of positions 2-6. The aryl group may be a 2,3-disubstituted, 2,4-disubstituted, 2,5-disubstituted, 2,6-disubstituted, 3,4-disubstituted or 3,5-disubstituted aryl group. Examples of disubstituted aryl groups include 3,4-dimethoxy, 3,5-dimethoxy, 3,4-dimethyl and 3,5-dimethyl, 3-fluoro,4-cyano and 3-fluoro,4-methyl. In the case of alkoxy groups, the groups may be linked together to form a further ring, for example a 2,3 or 3,4 cyclic acetal group of type O—CH$_2$—O. The aryl group may comprise a 2, 3 or 4 methoxy group, ethoxy group or thio-alkyl group. The alkoxy or thio-alkoxy groups may be further substituted, for example to make O—CF$_3$ or S—CF$_3$ groups. The aryl group may comprise a fluoro, chloro, bromo, methyl, ethyl or cyano group, which may be at the 2, 3 or 4 position. The substituents may be acyl groups of type CO-alkyl or acyl esters of type —CO—O-alkyl, for example —CO$_2$CH$_3$. The substituents may be primary, secondary or tertiary amide groups of type CO—NH$_2$, CO—NH-alkyl or CO—N(alkyl)$_2$. The aryl group may be a trisubstituted aryl group, for example a 3,4,5-trisubstituted aryl group.

The X group may comprise an optionally substituted cyclopropyl, cyclobutyl, cyclopentyl or cyclohexyl group. The cyclopropyl, cyclobutyl, cyclopentyl or cyclohexyl group may be attached directly to the nitrogen atom, or may comprise one or more CH$_2$ or CH(alkyl) groups.

In certain examples X may be of the following structure

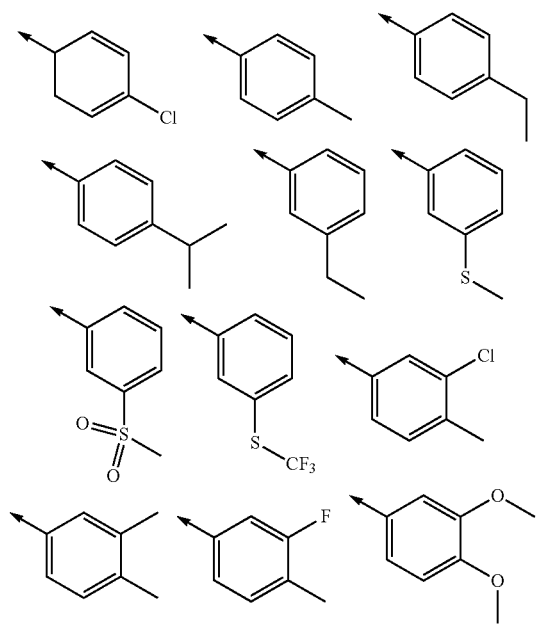

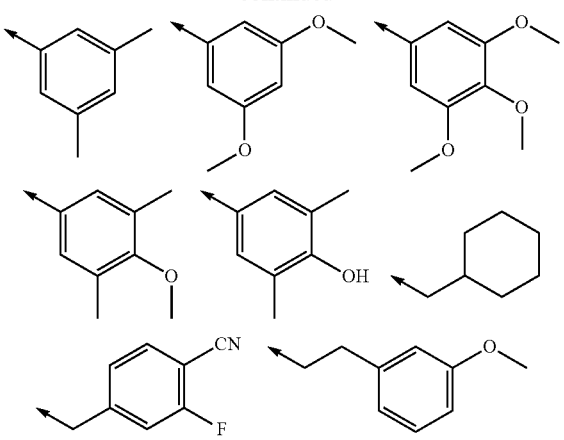

The X group may comprise an optionally substituted heterocycloalkyl group. The heterocycloalkyl group may comprise a cyclopropyl, cyclobutyl, cyclopentyl or cyclohexyl group comprising one or more heteroatoms. The heterocyclopropyl, heterocyclobutyl, heterocyclopentyl or heterocyclohexyl group may be attached directly to the nitrogen atom, or may comprise one or more CH$_2$ or CH(alkyl) groups. The heteroatoms may be oxygen, nitrogen or sulphur.

The X group may be a heteroaryl group, for example 2, 3 or 4 pyridyl, or 2 or 3 pyrryl. The heterocycle group may optionally be further substituted, for example 2-fluoro,4-pyridyl or disubstituted, for example 2,6-difluoro, 4-pyridyl. The heteroaryl group may be 3, 4, 5, 6 or 7 membered, and contain one or more heteroatoms. The heteroaryl group may be a 5 or 6 membered ring containing two or more heteroatoms. The heteroatoms may be independently nitrogen, oxygen or sulphur, and the heteroatoms may be further optionally substituted. The heteroaryl group may comprise, for example, a N-substituted triazole moiety or an N-substituted imidazoyl moiety. The heteroaryl group may comprise one or more further rings, which may have aromatic conjugation. For example X may be a benzothiazolyl, indazolyl or quinolinyl group.

In certain Examples X may be of the following structure

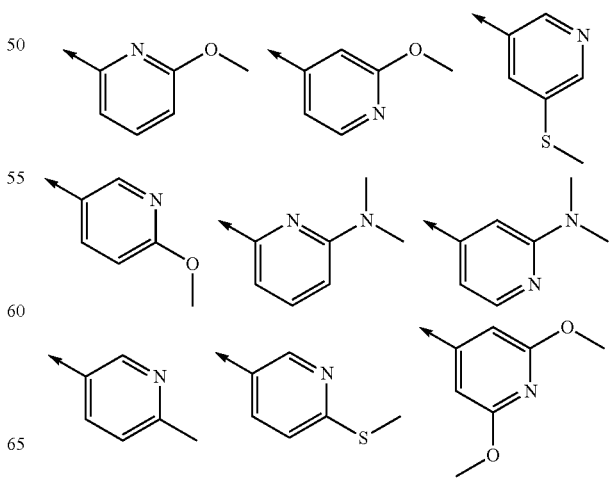

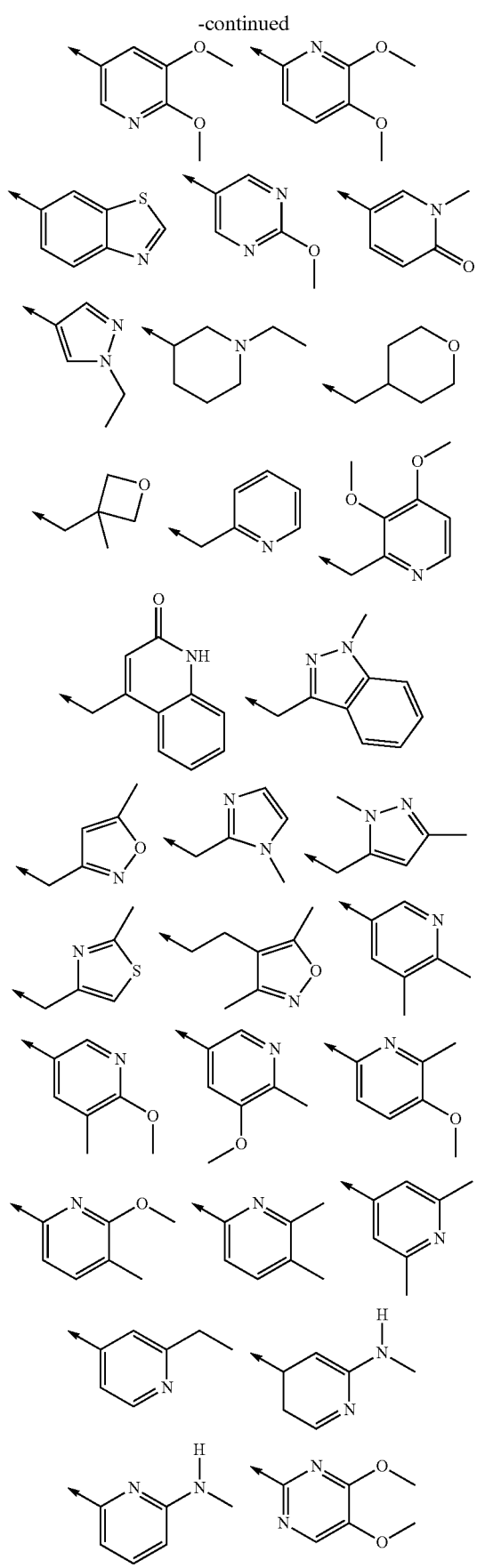
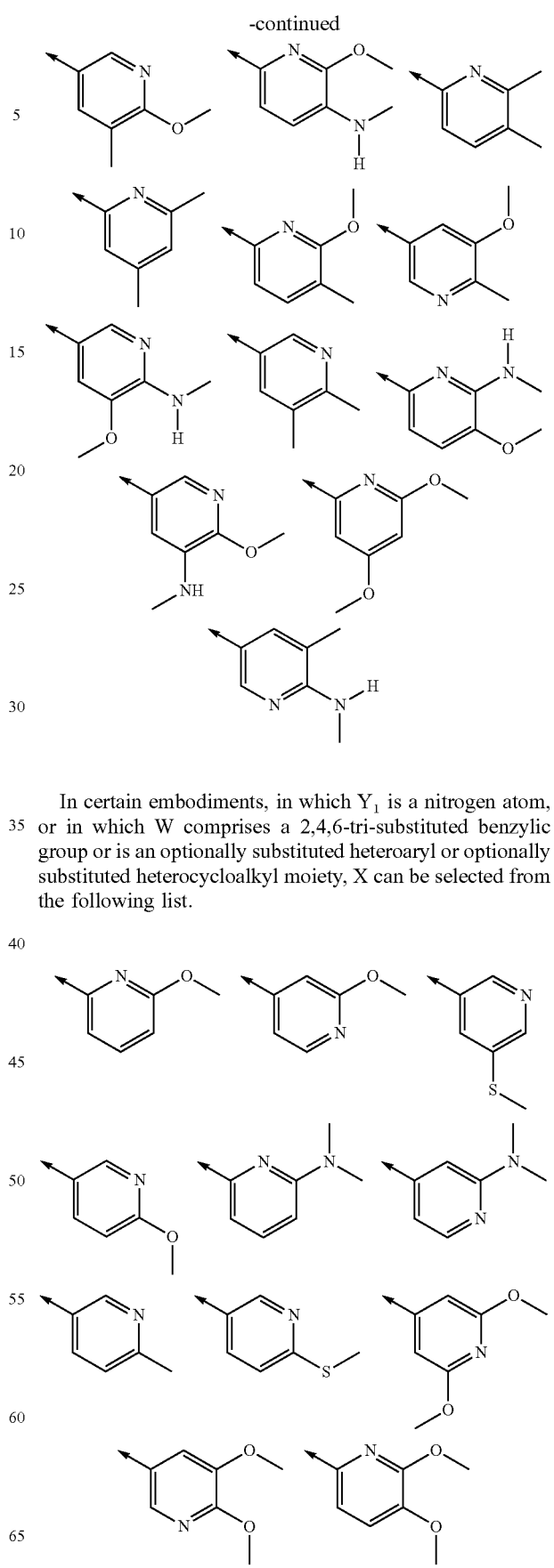
In certain embodiments, in which $Y_1$ is a nitrogen atom, or in which W comprises a 2,4,6-tri-substituted benzylic group or is an optionally substituted heteroaryl or optionally substituted heterocycloalkyl moiety, X can be selected from the following list.

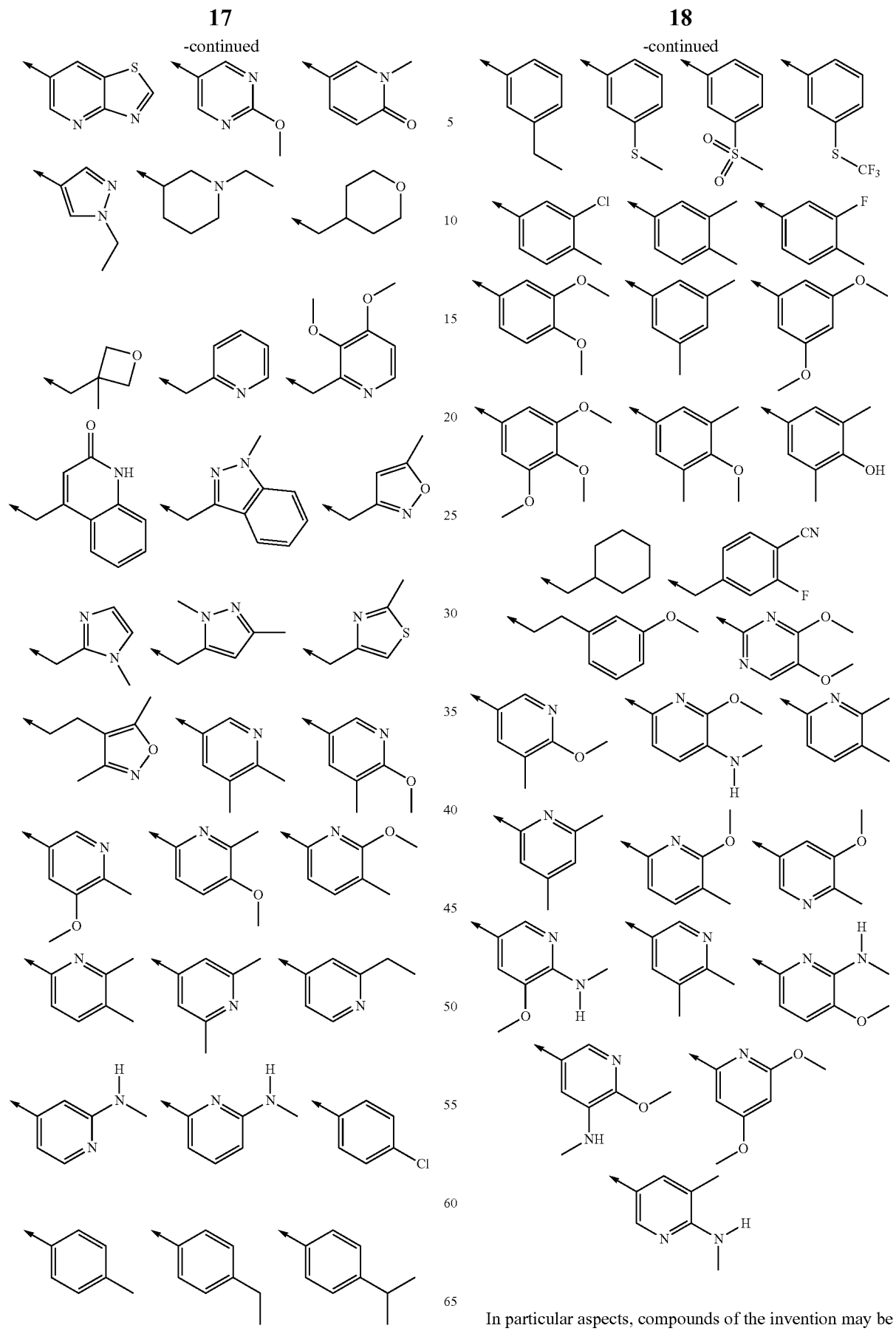
In particular aspects, compounds of the invention may be exemplified herein based around the structure:

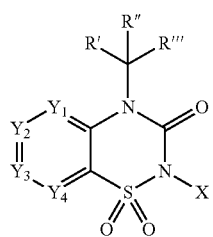

In which any of $Y_1$, $Y_2$, $Y_3$, $Y_4$, are independently carbon atoms or heteroatoms. The carbon atoms $Y_1$, $Y_2$, $Y_3$, $Y_4$, may be further substituted, for example with halo groups (fluoro, chloro, bromo or iodo), hydroxyl groups, alkyl groups or substituted alkyl groups, alkenyl or alkynyl groups or alkoxy groups. For example any of $Y_1$, $Y_2$, $Y_3$, $Y_4$ may be independently N, C—H, C—F, C—Cl, C—Br, C—I, C-alkyl or C—OH. Preferably, no more than one of $Y_1$, $Y_2$, $Y_3$ and $Y_4$ is N The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be cyclic groups such as cyclopropyl or cyclobutyl. R' and R" are independently H or alkyl. R''' is a substituted aryl, optionally substituted cycloalkyl, optionally substituted heteroaryl or optionally substituted heterocycloalkyl group. X comprises an optionally substituted heteroaryl, or optionally substituted heterocycloalkyl moiety.

In particular aspects, compounds of the invention may be exemplified herein based around the structure:

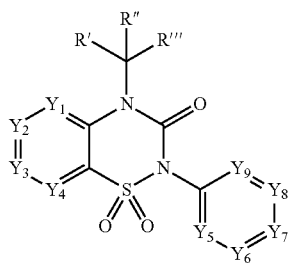

In which any of $Y_1$, $Y_2$, $Y_3$, $Y_4$, are independently carbon atoms or heteroatoms. The carbon atoms $Y_1$, $Y_2$, $Y_3$, $Y_4$, may be further substituted, for example with halo groups (fluoro, chloro, bromo or iodo), hydroxyl groups, alkyl groups or substituted alkyl groups, alkenyl or alkynyl groups or alkoxy groups. For example any of $Y_1$, $Y_2$, $Y_3$, $Y_4$ may be independently N, C—H, C—F, C—Cl, C—Br, C—I, C-alkyl or C—OH. The alkyl groups may be for example methyl, ethyl, propyl or any other alkyl group as defined under the definitions of alkyl groups found herein. The alkyl, alkenyl or alkynyl group may contain 1-4 carbon atoms. The alkyl group may be cyclic groups such as cyclopropyl or cyclobutyl. R' and R" are independently H or alkyl. R''' is a substituted aryl, optionally substituted cycloalkyl, optionally substituted heteroaryl or optionally substituted heterocycloalkyl group. $Y_5$, $Y_6$, $Y_7$, $Y_8$, and $Y_9$ are independently carbon atoms or heteroatoms. The carbon atoms $Y_5$, $Y_6$, $Y_7$, $Y_8$, and $Y_9$ may be further substituted, for example with halo groups (fluoro, chloro, bromo or iodo), hydroxyl groups, alkyl groups or substituted alkyl groups, alkenyl or alkynyl groups, amino or alkoxy groups. For example any of $Y_5$, $Y_6$, $Y_7$, $Y_8$, and $Y_9$ may be independently N, C—H, C—F, C—Cl, C—Br, C—I, C-Me, C—OMe, C—$NH_2$, CNH-Me, C—$N(Me)_2$ or C—OH. Compounds where $Y_8$ is N, C-Me, C—OMe or C—$N(Me)_2$ show high affinity as orexin receptor binders and may be preferred.

In one embodiment, there is provided a compound as hereinbefore defined, or a salt thereof;
wherein
$Y^1$ is CH, C-halo or N, where halo is a halogen atom;
$Y^2$ is CH;
$Y^3$ is CH or N, provided that no more than one of $Y^1$ and $Y^3$ may be N;
$Y^4$ is CH;
W is a methylene group substituted with a phenyl, pyridyl or pyrazole group, wherein the pyrazole or pyridyl groups are each optionally substituted with one or more $C_{1-4}$ alkyl groups, and the phenyl group is substituted with one or more substituents selected from halogen, $C_{1-4}$ alkyl and $C_{1-4}$ alkoxy;
and
X is selected from:
  phenyl, pyridyl and pyridylmethyl, the aromatic rings of which in each case are optionally substituted with one or more substituents selected from $C_{1-4}$ alkyl, hydroxy, $C_{1-4}$ alkoxy, $C_{1-4}$ alkylsulphanyl, $C_{1-4}$ alkylsulphanonyl and di-$C_{1-4}$ alkylamino;
  a group —$(CH_2)_q$—Cyc wherein q is 0, 1 or 2 and Cyc is a group selected from imidazolyl, pyrazolyl, isothiazolyl, isoxazolyl, thiazolyl, oxazolyl, piperidinyl, pyrrolidinyl, azetidinyl, tetrahydropyranyl, tetrahydrofuranyl, oxetanyl, indazolyl, benzothiazolyl, wherein each of the Cyc groups is optionally substituted with one or more methyl groups;
  1-methyl-6-oxo-1,6-dihydropyridine;
  methoxyprimidinyl; and
  2-oxo-1,2-dihydroquinolinylmethyl;
provided that:
(i) at least one of $Y_1$ and $Y_3$ is nitrogen; and/or (ii) X is a group —$(CH_2)_q$—Cyc; and/or
(iii) when W is a methylene group substituted with a phenyl group, the phenyl group is a 2,4,6-trisubstituted phenyl group.

In another embodiment, there is provided a compound as hereinbefore defined, or a salt thereof;
wherein
$Y^1$ is CH, CF or N;
$Y^2$ is CH;
$Y^3$ is CH or N, provided that no more than one of $Y^1$ and $Y^3$ may be N;
$Y^4$ is CH;
W is a methylene group substituted with a moiety selected from:
  a phenyl group substituted with one or more substituents selected from fluorine, chlorine, methyl and methoxy;
  a pyridyl group substituted with one or more substituents selected from fluorine, chlorine, bromine and methyl; and
  a dimethylpyrazole group;
and
X is selected from:
  phenyl substituted with one or more substituents selected from methyl, hydroxy, methoxy, methylsulphanyl and methylsulphonyl;
  pyridyl substituted with one or more substituents selected from methyl, methoxy, methylsulphanyl, hydroxy and dimethylamino;
  pyridylmethyl wherein the pyridyl moiety is optionally substituted with one or more methoxy groups;

benzothiazolyl;
ethylpyrazolyl;
methoxyprimidinyl;
ethylpiperidinyl;
1-methyl-1H-indazol-3-yl;
dimethylisoxazolylethyl;
dimethylpyrazolylmethyl;
tetrahydropyranylmethyl;
methyloxetanylmethyl;
methylthiazolylmethyl;
methylisoxazolylmethyl;
methylimidazolylmethyl;
2-oxo-1,2-dihydroquinolinylmethyl;

provided that:
(i) at least one of $Y_1$ and $Y_3$ is nitrogen; and/or (ii) X is other than a substituted phenyl group; and/or (iii) when W is a methylene group substituted with a phenyl group, the phenyl group is a 2,4,6-trisubstituted phenyl group.

Certain compounds have been produced in the prior art for medical uses. In particular examples, compounds where X is a cyclopropyl group have been reported. Examples of known compounds include:

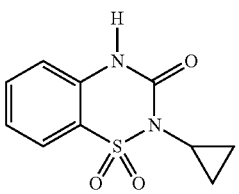

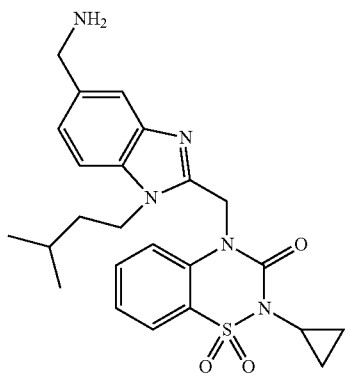

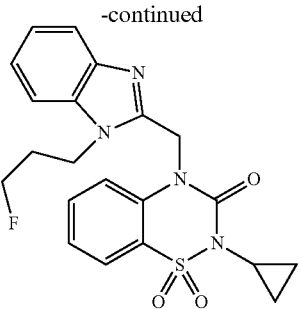

Any medical uses of the compounds described herein may disclaim specific examples where X is a cyclopropyl group.

The following compounds are known, but have not been associated with a particular medical use. In all cases the compounds do not contain a substituted aryl group at position W. In all cases, the compounds do not disclose where $Y_4$ is CH, or where $Y_4$ is N.

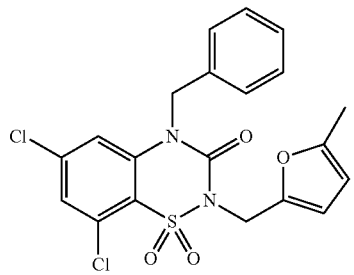 [SMILES: Cc1ccc(CN2C(=O)N(Cc3ccccc3)c3cc(Cl)cc(Cl)c3S2(=O)=O)o1]

2H-1,2,4-Benzothiadiazin-3(4H)-one,6,8-dichloro-2-[(5-methyl-2-furanyl)methyl]-4-(phenylmethyl)-,1,1-dioxide

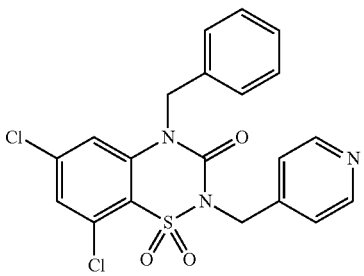 [SMILES: O=C1N(Cc2ccccc2)c2cc(Cl)cc(Cl)c2S(=O)(=O)N1Cc1ccncc1]

2H-1,2,4-Benzothiadiazin-3(4H)-one,6,8-dichloro-4-(phenylmethyl)-2-(4-pyridinylmethyl)-,1,1-dioxide Any of the features of W, X and $Y_1$-$Y_9$ defined herein may be combined with any of the other features of W, X and Y. Thus, for example, $Y_1$ may or may not comprise a heteroatom and X may or may not be a heterocyclic group, and thus all combinations of $Y_1$ is and is not a heteroatom, and X is and is not a heterocycle are envisaged. In certain combinations, compounds will be novel.

Certain specific examples of compounds are shown below. Each of the compounds shown below is either novel by way of structure, or novel by way of medical use, particularly its medical use as an orexin receptor antagonist.

Further embodiments of the invention include methods of treatment comprising administering a compound of formula

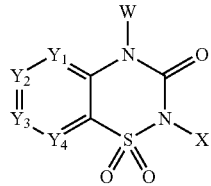

wherein $Y_1$, $Y_2$, $Y_3$ are independently an optionally substituted carbon or a nitrogen atom; and $Y_4$ is is C-alkyl, C-halogen, C—H or N, W is a methylene group or CH(alkyl) group substituted by an optionally substituted aryl, optionally substituted cycloalkyl, optionally substituted heterocycloalkyl or optionally substituted heteroaryl moiety and X comprises an optionally substituted aryl, optionally substituted heteroaryl, optionally substituted cycloalkyl, or optionally substituted heterocycloalkyl moiety, wherein X is not cyclopropyl.

The methods of treatment may be used in treating, preventing, ameliorating, controlling or reducing the risk of neurological or psychiatric disorders associated with orexin receptors, for example insomnia, diabetes, obesity, the treatment or prevention of substance dependence, addiction, movement disorders, anxiety disorders, panic disorders, cognitive impairment or Alzheimer's disease.

The methods of treatment will typically involve the administration of a therapeutically effective amount (preferably a non-toxic amount) of the compound to a subject (e.g. a mammalian subject such as a human) in need thereof.

The following compounds in list 1 are novel in their own right, and useful in treating certain medical conditions, for example conditions involving orexin receptors.

List 1

Compounds 83-186 from Table 1

The following compounds in list 2 are useful in treating certain medical conditions, for example conditions involving orexin receptors.

List 2

Compounds 1-82 from Table 1

Certain novel compounds of the invention show particularly high activities as orexin antagonists; for example
2-(3,4-Dimethoxyphenyl)-4-(2,4,6-trifluorobenzyl)-2H-pyrido[2,3-e][1,2,4]thiadiazin-3(4H)-one 1,1-dioxide 93
4-(4-Chloro-2,6-difluorobenzyl)-2-(3,4-dimethoxyphenyl)-2H-pyrido[2,3-e][1,2,4]thiadiazin-3(4H)-one 1,1-dioxide 97
2-(2,6-Dimethoxypyridin-4-yl)-4-(2,4,6-trifluorobenzyl)-2H-pyrido[2,3-e][1,2,4]thiadiazin-3(4H)-one 1,1-dioxide 98
2-(5,6-Dimethoxypyridin-2-yl)-4-(2,4,6-trifluorobenzyl)-2H-pyrido[2,3-e][1,2,4]thiadiazin-3(4H)-one 1,1-dioxide 99
2-(5,6-Dimethoxypyridin-3-yl)-4-(2,4,6-trifluorobenzyl)-2H-pyrido[2,3-e][1,2,4]thiadiazin-3(4H)-one 1,1-dioxide 100
2-(3,4-Dimethoxyphenyl)-4-(2,6-difluoro-4-methoxybenzyl)-2H-1,2,4-benzothiadiazin-3(4H)-one 1,1-dioxide 108
4-(2-Chloro-6-fluoro-4-methoxybenzyl)-2-(3,4-dimethoxyphenyl)-2H-1,2,4-benzothiadiazin-3(4H)-one 1,1-dioxide 113
2-(4-methoxy-3,5-dimethylphenyl)-4-(2,4,6-trifluorobenzyl)-2H-1,2,4-benzothiadiazin-3(4H)-one 1,1-dioxide 115
4-(2,6-Difluoro-4-hydroxybenzyl)-2-(3,4-dimethoxyphenyl)-2H-1,2,4-benzothiadiazin-3(4H)-one 1,1-dioxide 116
4-(2,6-Difluoro-4-methoxybenzyl)-2-(2-methoxypyridin-4-yl)-2H-1,2,4-benzothiadiazin-3(4H)-one 1,1-dioxide 140
2-(5,6-Dimethoxypyridin-3-yl)-4-(2,4,6-trifluorobenzyl)-2H-1,2,4-benzothiadiazin-3(4H)-one 1,1-dioxide 145
4-(2,6-difluoro-4-methoxybenzyl)-2-(5,6-Dimethoxypyridin-3-yl)-2H-1,2,4-benzothiadiazin-3(4H)-one 1,1-dioxide 146
2-(2,6-Dimethoxypyridin-4-yl)-4-(2,4,6-trifluorobenzyl)-2H-1,2,4-benzothiadiazin-3(4H)-one 1,1-dioxide 148
4-(2,6-Difluoro-4-methoxybenzyl)-2-(2,6-dimethoxypyridin-4-yl)-2H-1,2,4-benzothiadiazin-3(4H)-one 1,1-dioxide 149
4-(2-Chloro-4,6-difluorobenzyl)-2-(5,6-dimethoxypyridin-3-yl)-2H-1,2,4-benzothiadiazin-3(4H)-one 1,1-dioxide 155
4-(2-Chloro-4,6-difluorobenzyl)-2-(2,6-dimethoxypyridin-4-yl)-2H-1,2,4-benzothiadiazin-3(4H)-one 1,1-dioxide 157
2-[6-(Dimethylamino)pyridin-2-yl]-4-(2,4,6-trifluorobenzyl)-2H-1,2,4-benzothiadiazin-3(4H)-one 1,1-dioxide 158
2-[2-(Dimethylamino)pyridin-4-yl]-4-(2,4,6-trifluorobenzyl)-2H-1,2,4-benzothiadiazin-3(4H)-one 1,1-dioxide 159
4-(2,6-Difluoro-4-methoxybenzyl)-2-(2,6-dimethoxypyridin-4-yl)-2H-pyrido[2,3-e][1,2,4]thiadiazin-3(4H)-one 1,1-dioxide 163
4-(2,6-Difluoro-4-methoxybenzyl)-2-(5,6-dimethoxypyridin-2-yl)-2H-pyrido[2,3-e][1,2,4]thiadiazin-3(4H)-one 1,1-dioxide 164
4-(2,6-Difluoro-4-methoxybenzyl)-2-(5,6-dimethoxypyridin-3-yl)-2H-pyrido[2,3-e][1,2,4]thiadiazin-3(4H)-one 1,1-dioxide 165
4-(2-Chloro-6-fluorobenzyl)-2-(2,6-dimethoxypyridin-4-yl)-2H-1,2,4-benzothiadiazin-3(4H)-one 1,1-dioxide 166
4-(2,6-Difluorobenzyl)-2-(2,6-dimethoxypyridin-4-yl)-2H-1,2,4-benzothiadiazin-3(4H)-one 1,1-dioxide 167
4-(2-Chloro-6-fluorobenzyl)-2-(5,6-dimethoxypyridin-2-yl)-2H-pyrido[2,3-e][1,2,4]thiadiazin-3(4H)-one 1,1-dioxide 168
4-(2,-Difluorobenzyl)-2-(5,6-dimethoxypyridin-2-yl)-2H-pyrido[2,3-e][1,2,4]thiadiazin-3(4H)-one 1,1-dioxide 169
2-(4,5-dimethoxypyrimidin-2-yl)-4-(2,4,6-trifluorobenzyl)-2H-1,2,4-benzothiadiazin-3(4H)-one 1,1-dioxide 170
4-(2,6-difluoro-4-methoxybenzyl)-2-(6-methoxy-5-methylpyridin-3-yl)-2H-1,2,4-benzothiadiazin-3(4H)-one 1,1-dioxide 171
2-[6-methoxy-5-(methylamino)pyridin-2-yl]-4-(2,4,6-trifluorobenzyl)-2H-pyrido[2,3-e][1,2,4]thiadiazin-3(4H)-one 1,1-dioxide 172
4-(2,6-difluoro-4-methoxybenzyl)-2-(5, 6-dimethylpyridin-2-yl)-2H-pyrido[2,3-e][1,2,4]thiadiazin-3(4H)-one 1,1-dioxide 173
4-(2,6-difluoro-4-methoxybenzyl)-2-(4,6-dimethylpyridin-2-yl)-2H-pyrido[2,3-e][1,2,4]thiadiazin-3(4H)-one 1,1-dioxide 174
4-(2,6-difluoro-4-methoxybenzyl)-2-(6-methoxy-5-methylpyridin-2-yl)-2H-pyrido[2,3-e][1,2,4]thiadiazin-3(4H)-one 1,1-dioxide 175

2-(5-methoxy-6-methylpyridin-3-yl)-4-(2,4,6-trifluorobenzyl)-2H-pyrido[2,3-e][1,2,4]thiadiazin-3(4H)-one 1,1-dioxide 176

4-(2,6-difluoro-4-methoxybenzyl)-2-[5-methoxy-6-(methylamino)pyridin-3-yl]-2H-pyrido[2,3-e][1,2,4]thiadiazin-3(4H)-one 1,1-dioxide 177

4-(2,6-difluoro-4-methoxybenzyl)-2-(5,6-dimethylpyridin-3-yl)-2H-1,2,4-benzothiadiazin-3(4H)-one 1,1-dioxide 178

4-(2,6-difluoro-4-methoxybenzyl)-2-[5-methoxy-6-(methylamino)pyridin-2-yl]-2H-1,2,4-benzothiadiazin-3(4H)-one 1,1-dioxide 179

4-(2-chloro-4,6-difluorobenzyl)-2-(2,6-dimethoxypyridin-4-yl)-2H-pyrido[2,3-e][1,2,4]thiadiazin-3(4H)-one 1,1-dioxide 180

4-(2,6-difluoro-4-methoxybenzyl)-2-[6-methoxy-5-(methylamino)pyridin-3-yl]-2H-1,2,4-benzothiadiazin-3(4H)-one 1,1-dioxide 181

4-(2,6-difluoro-4-methoxybenzyl)-2-(4,6-dimethoxypyridin-2-yl)-2H-1,2,4-benzothiadiazin-3(4H)-one 1,1-dioxide 183

4-(2,6-difluoro-4-methoxybenzyl)-2-[5-methyl-6-(methylamino)pyridin-3-yl]-2H-pyrido[2,3-e][1,2,4]thiadiazin-3(4H)-one 1,1-dioxide 184

4-(2-chloro-4,6-difluorobenzyl)-2-(5,6-dimethoxypyridin-3-yl)-2H-pyrido[2,3-e][1,2,4]thiadiazin-3(4H)-one 1,1-dioxide 185

4-(2,6-difluoro-4-methoxybenzyl)-2-[6-methoxy-5-(methylamino)pyridin-3-yl]-2H-pyrido[2,3-e][1,2,4]thiadiazin-3(4H)-one 1,1-dioxide 186

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

"Pharmaceutically functional derivatives" of compounds as defined herein includes ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

DEFINITIONS

Alkyl

Alkyl means an aliphatic hydrocarbon group. The alkyl group may be straight or branched. "Branched" means that at least one carbon branch point is present in the group. Thus, for example, tert-butyl and isopropyl are both branched groups. The alkyl group may be a lower alkyl group. "Lower alkyl" means an alkyl group, straight or branched, having 1 to about 6 carbon atoms, e.g. 2, 3, 4, 5 or 6 carbon atoms.

Exemplary alkyl groups include methyl, ethyl, n-propyl, i-propyl, n-butyl, t-butyl, s-butyl, n-pentyl, 2-pentyl, 3-pentyl, n-hexyl, 2-hexyl, 3-hexyl, n-heptyl, 2-heptyl, 3-heptyl, 4-heptyl, 2-methyl-but-1-yl, 2-methyl-but-3-yl, 2-methyl-pent-1-yl, 2-methyl-pent-3-yl.

The alkyl group may be optionally substituted, e.g. as exemplified below.

The term alkyl also includes aliphatic hydrocarbon groups such as alkenyl, and alkylidene.

Alkenyl

Alkenyl means an unsaturated aliphatic hydrocarbon group. The unsaturation may include one or more double bond, one or more triple bond or any combination thereof. The alkenyl group may be straight or branched. "Branched" means that at least one carbon branch point is present in the group. Any double bond may, independently of any other double bond in the group, be in either the (E) or the (Z) configuration.

The alkenyl group may be a lower alkenyl group. "Lower alkenyl" means an alkenyl group, straight or branched, having 2 to 6 carbon atoms, e.g. 2, 3, 4, 5 or 6 carbon atoms.

Exemplary alkenyl groups include ethenyl, n-propenyl, i-propenyl, but-1-en-1-yl, but-2-en-1-yl, but-3-en-1-yl, pent-1-en-1-yl, pent-2-en-1-yl, pent-3-en-1-yl, pent-4-en-1-yl, pent-1-en-2-yl, pent-2-en-2-yl, pent-3-en-2-yl, pent-4-en-2-yl, pent-1-en-3-yl, pent-2-en-3-yl, pentadien-1-yl, pentadien-2-yl, pentadien-3-yl. Where alternative (E) and (Z) forms are possible, each is to be considered as individually identified.

The alkenyl group may be optionally substituted, e.g. as exemplified below.

Alkylidene

Alkylidene means any alkyl or alkenyl group linked to the remainder of the molecule via a double bond. The definitions and illustrations provided herein for alkyl and alkenyl groups apply with appropriate modification also to alkylidene groups.

Cycloalkyl

Cycloalkyl means a cyclic non-aromatic hydrocarbon group. The cycloalkyl group may include non-aromatic unsaturation. The cycloalkyl group may have 3 to 6 carbon atoms, e.g. 3, 4, 5 or 6 carbon atoms. Exemplary cycloalkyl groups include cyclopropyl, cyclobutyl, cyclopentyl, cyclohexyl, cyclopentenyl, cyclohexenyl.

The cycloalkyl group may be optionally substituted, as defined below, e.g. as exemplified below. Exemplary substituted cycloalkyl groups include mono- or poly-alkyl-substituted cycloalkyl groups such as 1-methylcyclopropyl, 1-methylcyclobutyl, 1-methylcyclopentyl, 1-methylcyclohexyl, 2-methylcyclopropyl, 2-methylcyclobutyl, 2-methylcyclopentyl, 2-methylcyclohexyl, 1,2-dimethylcyclohexyl or 1,3-dimethylcyclohexyl.

Cycloalkylidene Group

Cycloalkylidene means any cycloalkyl group linked to the remainder of the molecule via a double bond. The definitions and illustrations provided herein for cycloalkyl groups apply with appropriate modification also to cycloalkylidene groups.

Aryl

Aryl means any aromatic group in which all of the ring members are carbon atoms, for example having up to 12 carbon atom ring members, e.g. 6, 7, 8, 9, 10, 11 or 12 carbon atom ring members. The aryl group may comprise one, two or more rings. Where two or more rings are present they may if desired be fused. The aryl groups may be optionally substituted further, as described below. The aryl group may comprise one or more phenyl ring. The point of attachment of aryl groups may be via any atom of the ring system.

Exemplary aryl groups include phenyl, naphthyl, tetrahydronaphthyl, biphenyl, indanyl and dihydroindanyl groups. The point of attachment may be via any atom of the ring system.

Heteroaryl

Heteroaryl means an aromatic group in which at least one ring member is other than carbon. For example, at least one ring member (for example one, two or three ring members) may be selected from nitrogen, oxygen and sulphur.

The heteroaryl group may comprise one, two or more rings. Where two or more rings are present they may if desired be fused. The heteroaryl groups may be optionally substituted further, as described below. When the heteroaryl group contains more than one ring, a second and/or third ring may be heteroaromaic or may be a phenyl ring. The point of attachment of heteroaryl groups may be via any atom of the ring system.

Exemplary heteroaryl groups include pyridyl, pyrazinyl, pyrimidinyl, furyl, thiophenyl, pyrrolyl, oxazolyl, thiazolyl, pyrazolyl, 1,2,3-triazolyl, 1,2,4-triazolyl, tetrazolyl, indolyl, indolizinyl, isoindolyl, indolinyl, purinyl, furazanyl, imidazolyl, indazolyl, isothiazolyl, isoxazolyl, 1,2,3-oxadiazolyl, 1,2,4-oxadiazolyl, 1,2,5-oxadiazolyl, 1,3,4-oxadiazolyl, 1,2-oxazinanyl, 1,3-oxazinanyl, pyrazolyl, tetrazolyl, 1,2,3-thiadiazolyl, 1,2,4-thiadiazolyl, 1,2,5-thiadiazolyl, 1,3,4-thiadiazolyl, benzofuranyl, isobenzofuranyl, benzothiophenyl, isobenzothiophenyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, quinoxalinyl and the like. The point of attachment may be via any atom of the ring system.

Heterocycloalkyl

Heterocycloalkyl group means a non-aromatic cyclic group which contains one or more heteroatoms in the ring. The heterocycloalkyl group may contain O, N or S atoms. The heterocycloalkyl group may be fully saturated or partially unsaturated. The heterocycloalkyl group is typically monocyclic or bicyclic, and more usually is monocyclic.

Exemplary heterocycloalkyl groups include azetidinyl, pyrrolidinyl, piperidinyl, azepinyl, diazepinyl, dihydrofuranyl (e.g. 2,3-dihydrofuranyl, 2,5-dihydrofuranyl), 4,5-dihydro-1H-maleimido, dioxolanyl, 2-imidazolinyl, imidazolidinyl, isoxazolidinyl, morpholinyl, oxazolidinyl, piperazinyl, pyrrolidinonyl, 2-pyrrolinyl, 3-pyrrolinyl, sulfolanyl, 3-sulfolenyl, tetrahydrofuranyl, thiomorpholinyl, dihydropyranyl (e.g. 3,4-dihydropyranyl, 3,6-dihydropyranyl), dioxanyl, hexahydropyrimidinyl, 2-pyrazolinyl, pyrazolidinyl, pyridazinyl, 4H-quinolizinyl, quinuclinyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, tetramethylenesulfoxide, thiazolidinyl, 1,3,5-triazinanyl, 1,2,4-triazinanyl, hydantoinyl, and the like. The point of attachment may be via any atom of the ring system.

Heterocycloalkylidene Group

Heterocycloalkylidene means any heterocycloalkyl group linked to the remainder of the molecule via a double bond. The definitions and illustrations provided herein for heterocycloalkyl groups apply with appropriate modification also to heterocycloalkylidene groups.

Optionally Substituted

"Optionally substituted" as applied to any group means that the said group may if desired be substituted with one or more substituents, which may be the same or different.

Examples of suitable substituents for "substituted" and "optionally substituted" moieties include halo (fluoro, chloro, bromo or iodo), $C_{1-6}$ alkyl, $C_{3-6}$ cycloalkyl, hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-5}$ alkoxycarbonyl or $(C_{1-6}$ aryl$)(C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore includes groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substituted groups thus include for example CN, CFH$_2$, CF$_2$H, CF$_3$, CH$_2$NH$_2$, CH$_2$OH, CH$_2$CN, CH$_2$SCH$_3$, CH$_2$OCH$_3$, OMe, OEt, Me, Et, —OCH$_2$O—, CO$_2$Me, C(O)Me, i-Pr, SCF$_3$, SO$_2$Me, NMe$_2$ etc. In the case of aryl groups, the substitutions may be in the form of rings from adjacent carbon atoms in the aryl ring, for example cyclic acetals such as O—CH$_2$—O.

"Acyl" means an H—CO— or $C_{1-10}$ alkyl-CO— group wherein the alkyl group is as defined herein. Exemplary acyl groups include formyl, acetyl, propanoyl, 2-methylpropanoyl and butanoyl.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The dosages may be varied depending upon the requirements of the patient, the severity of the condition being treated, and the compound being employed.

Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Preparation of the Compounds of the Invention

Compounds may be prepared via a variety of synthetic routes. A schematic of some of the different routes available is shown in FIG. 1.

Compounds of the invention may be prepared by routes including those in FIG. 1, where in each case the starting aromatic or heteroaromatic ring may be optionally substituted by groups in addition to those shown. Details of many of the standard transformations such as those in the routes below and others which could be used to perform the same transformations can be found in standard reference textbooks such as "Organic Synthesis", M. B. Smith, McGraw-Hill (1994) or "Advanced Organic Chemistry", 4$^{th}$ edition, J. March, John Wiley & Sons (1992).

Sulphonamide formations (for example Step 1 of Routes 1, 2 and 4, and Step 2 of Route 5) can be achieved by reaction of an amine with an aromatic or heteroaromatic sulfonyl chloride in a suitable solvent such as 1,4-dioxane, diethyl ether, DCM or 1,2-dichloroethane, in the absence of a base, or in the presence of base such as triethylamine, pyridine or N,N-diisopropylethylamine. Typically this coupling procedure is conducted at a temperature of between −10° C. and 100° C. Alternatively, (e.g. as described in Trani et al *Bioorg. Med. Chem. Lett.* 2008, 18, 5698) the coupling can be conducted in the presence of bis(trimethylsilyl)trifluoroacetamide and pyridine in DCM.

Reduction of an aromatic nitro group (for example Route 1, Step 2) can be performed under reaction conditions known to those skilled in the art; for example catalytic hydrogenation using a catalyst such as palladium on charcoal, palladium oxide or platinum oxide in a suitable solvent such as ethanol, water, ethyl acetate or combinations thereof under an atmosphere of hydrogen. Alternative conditions will be known to those skilled in the art, for example reduction with tin(II) chloride in ethanol, typically at an elevated temperature such as 100° C. or with iron powder and acetic acid, typically at an elevated temperature such as 60° C.

Intramolecular cyclisation reactions between adjacent aromatic and sulphonamide groups on an aromatic or heteroaromatic ring (such as Route 1-4 inclusive, Step 3; Route 5, Step 4 and Route 7, Step 3) can be performed for example with 1,1'-carbonyldiimidazole and a base such as triethylamine in a suitable solvent such as DMF at elevated temperature, for example 100° C., as described by Hanson et al in *Tetrahedron Lett.* 2009, 50, 6935. Alternative conditions will be known to those skilled in the art, for example the use of triphosgene in a suitable solvent (e.g. 1,4-dioxane) at elevated temperature, for example 100° C.

N-alkylation reactions (for example Route 1, Step 4 and Route 6, Step 3) can be performed under reaction conditions known to those skilled in the art and detailed in standard reference textbooks such as those above. For example $S_N2$ reactions with an alkyl (or benzyl) halide or other electrophilic species such as an alkyl (or benzyl) tosylate or mesylate, in the presence of a base (e.g. potassium carbonate or cesium carbonate) in a suitable solvent such as 1,4-dioxane or DMF at a suitable temperature such as room temperature to 130° C. Alternatively, Mitsunobu coupling conditions (see Mitsunobu, O. *Synthesis* 1981, 1) using a dialkyl azodicarboxylate (such as diethyl azodicarboxylate or diisopropyl azodicarboxylate) or 1,1'-azobis(N,N-dimethylformamide), triphenylphosphine and an alcohol in a suitable solvent such as THF can be used for N-alkylation. In some instances, sonication is used to aid solubility of the reaction mixtures.

Nucleophilic aromatic substitution reactions ($S_NAr$ reactions) (for example Routes 2-4 inclusive, Step 2 and Route 5, Step 3) are typically conducted at elevated temperature (e.g. 100-200° C.), in some instances in a microwave reactor, in a suitable solvent (e.g. acetonitrile), in some instances with additional base such as triethylamine or N,N-diisopropylethylamine. In some instances (e.g. Route 7, Step 2) autoclave conditions are used.

Sulfonamide N-arylation reactions (for example Route 3, Step 1) are widely described in the literature, and typically use an aryl halide, a palladium or copper(I) calatyst and a suitable ligand, for example as described in Han, *Tetrahedron Lett.* 2010, 51, 360.

Chlorination reactions to convert a hydroxy to a chloro substituent in heteroaromatic systems (Route 5, Step 1) and reductive amination reactions (Route 6, Step 1) can be formed under reaction conditions which will be known to those skilled in the art, for example using phosphorous(V) oxychloride in a suitable solvent such as 1,2-dichloroethane.

Cyclisation of a substituted aromatic amine to form a 4-substituted-2H-1,2,4-benzothiadiazin-3(4H)-one 1,1-dioxide ring system (Route 6, Step 1) can be performed using chlorosulfonylisocyanate in a suitable solvent (e.g. nitroethane or nitromethane) at low temperature (e.g. −40° C. to −45° C.); followed by treatment with aluminium chloride and heating (see for example Tedesco et al, *J. Med. Chem.* 2006, 49, 971).

In the processes described above and hereinafter, the functional groups of intermediate compounds may need to be protected by protecting groups. The protection and deprotection of functional groups may take place before or after a reaction in the below-mentioned schemes. Protecting groups may be removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "Protective Groups in Organic Chemistry", edited by J. W. F. McOmie, Plenum Press (1973), and "Protective Groups in Organic Synthesis", 4th edition, T.W. Greene & P.G.M. Wuts, Wiley (2006).

Examples of the invention may be transformed into further examples of the invention by modification of substituents, for example an aromatic or heteroaromatic methyl ether may be transformed into an aromatic or heteroaromatic hydroxyl group by removal of the methyl ether under standard conditions (e.g. $BBr_3$ in DCM at low temperature). In another example an aromatic or heteroaromatic sulphide can be oxidised to an aromatic or heteroaromatic sulfone in the presence of a suitable oxidising agent (for example meta chloroperoxybenzoic acid, $KMnO_4$, t-butylammoniumperiodate and/or potassium peroxymonosulfate (e.g. Oxone).

Exemplary compounds of the invention, and their corresponding biological data are shown below:

TABLE 1

| STRUCTURE | ref number | Name | OX2 pKi ave |
|---|---|---|---|
| 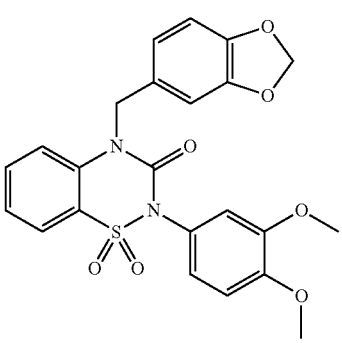 [SMILES: COc1ccc(N2C(=O)N(Cc3ccc4c(c3)OCO4)c3ccccc3S2(=O)=O)cc1OC] | 1 | 4-(1,3-benzodioxol-5-ylmethyl)-2-(3,4-dimethoxyphenyl)-2H-1,2,4-benzothiadiazin-3(4H)-one 1,1-dioxide | 6.5 |

TABLE 1-continued

| STRUCTURE | ref number | Name | OX2 pKi ave |
|---|---|---|---|
| 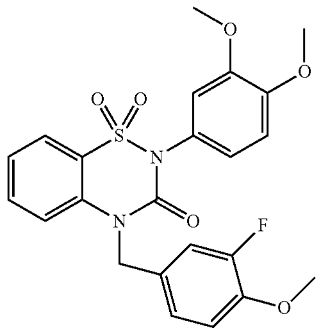 [SMILES: COc1ccc(CN2C(=O)N(c3ccc(OC)c(OC)c3)S(=O)(=O)c3ccccc32)cc1F] | 2 | 2-(3,4-dimethoxyphenyl)-4-(3-fluoro-4-methoxybenzyl)-2H-1,2,4-benzothiadiazin-3(4H)-one 1,1-dioxide | 6.85 |
| 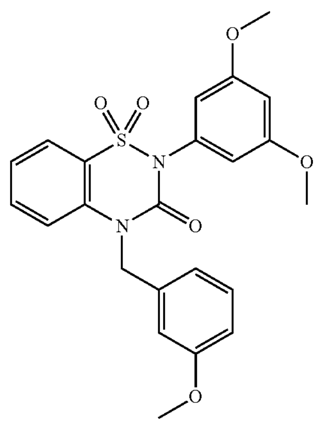 [SMILES: COc1cccc(CN2C(=O)N(c3cc(OC)cc(OC)c3)S(=O)(=O)c3ccccc32)c1] | 3 | 2-(3,5-dimethoxyphenyl)-4-(3-methoxybenzyl)-2H-1,2,4-benzothiadiazin-3(4H)-one 1,1-dioxide | 6.35 |
| 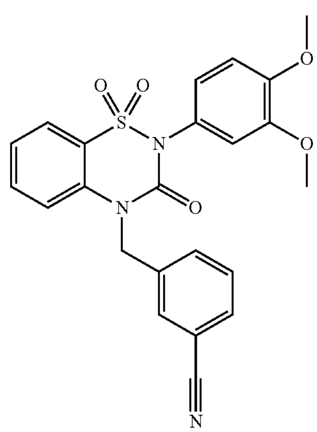 [SMILES: COc1ccc(N2C(=O)N(Cc3cccc(C#N)c3)c3ccccc3S2(=O)=O)cc1OC] | 4 | 3-{[2-(3,4-dimethoxyphenyl)-1,1-dioxido-3-oxo-2,3-dihydro-4H-1,2,4-benzothiadiazin-4-yl]methyl}benzonitrile | 6.45 |
| 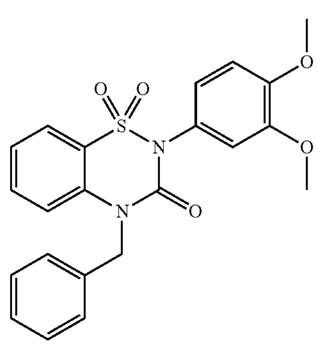 [SMILES: COc1ccc(N2C(=O)N(Cc3ccccc3)c3ccccc3S2(=O)=O)cc1OC] | 5 | 4-benzyl-2-(3,4-dimethoxyphenyl)-2H-1,2,4-benzothiadiazin-3(4H)-one 1,1-dioxide | 7.05 |

TABLE 1-continued

| STRUCTURE | ref number | Name | OX2 pKi ave |
|---|---|---|---|
| 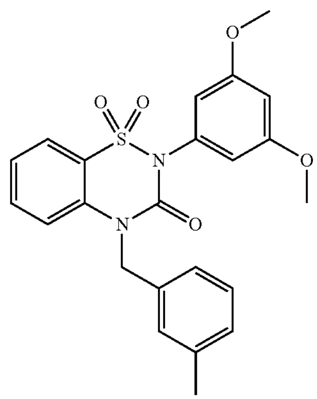 [SMILES: COc1cc(OC)cc(N2C(=O)N(Cc3cccc(C)c3)c3ccccc3S2(=O)=O)c1] | 6 | 2-(3,5-dimethoxyphenyl)-4-(3-methylbenzyl)-2H-1,2,4-benzothiadiazin-3(4H)-one 1,1-dioxide | 6.33 |
| 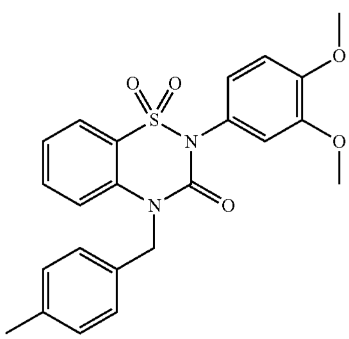 | 7 | 2-(3,4-dimethoxyphenyl)-4-(4-methylbenzyl)-2H-1,2,4-benzothiadiazin-3(4H)-one 1,1-dioxide | 7.43 |
| 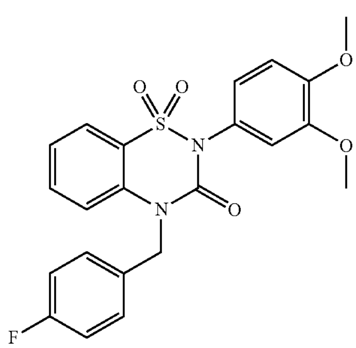 [SMILES: COc1ccc(N2C(=O)N(Cc3ccc(F)cc3)c3ccccc3S2(=O)=O)cc1OC] | 8 | 2-(3,4-dimethoxyphenyl)-4-(4-fluorobenzyl)-2H-1,2,4-benzothiadiazin-3(4H)-one 1,1-dioxide | 7.25 |
| 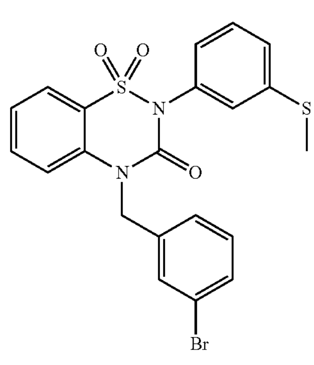 [SMILES: CSc1cccc(N2C(=O)N(Cc3cccc(Br)c3)c3ccccc3S2(=O)=O)c1] | 9 | 4-(3-bromobenzyl)-2-[3-(methylsulfanyl)phenyl]-2H-1,2,4-benzothiadiazin-3(4H)-one 1,1-dioxide | 7.45 |

TABLE 1-continued

| STRUCTURE | ref number | Name | OX2 pKi ave |
|---|---|---|---|
| 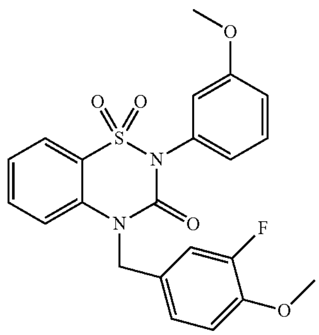 [SMILES: COc1cccc(N2C(=O)N(Cc3ccc(OC)c(F)c3)c3ccccc3S2(=O)=O)c1] | 10 | 4-(3-fluoro-4-methoxybenzyl)-2-(3-methoxyphenyl)-2H-1,2,4-benzothiadiazin-3(4H)-one 1,1-dioxide | 6.93 |
| 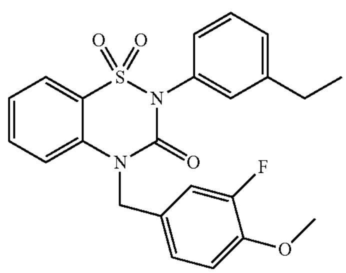 [SMILES: CCc1cccc(N2C(=O)N(Cc3ccc(OC)c(F)c3)c3ccccc3S2(=O)=O)c1] | 11 | 2-(3-ethylphenyl)-4-(3-fluoro-4-methoxybenzyl)-2H-1,2,4-benzothiadiazin-3(4H)-one 1,1-dioxide | 7.32 |
| 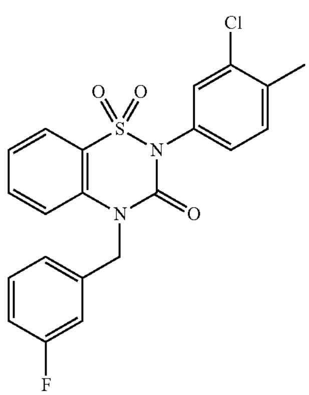 [SMILES: Cc1ccc(N2C(=O)N(Cc3cccc(F)c3)c3ccccc3S2(=O)=O)cc1Cl] | 12 | 4-(3-fluorobenzyl)-2-(3-chloro-4-methylphenyl)-2H-1,2,4-benzothiadiazin-3(4H)-one 1,1-dioxide | 7.46 |
| 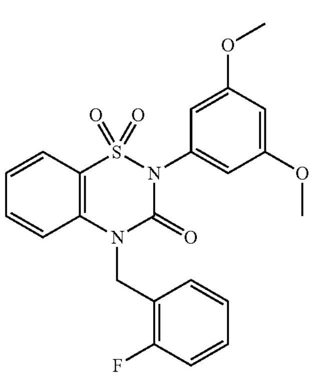 [SMILES: COc1cc(OC)cc(N2C(=O)N(Cc3ccccc3F)c3ccccc3S2(=O)=O)c1] | 13 | 2-(3,5-dimethoxyphenyl)-4-(2-fluorobenzyl)-2H-1,2,4-benzothiadiazin-3(4H)-one 1,1-dioxide | 7.57 |

TABLE 1-continued

| STRUCTURE | ref number | Name | OX2 pKi ave |
|---|---|---|---|
| 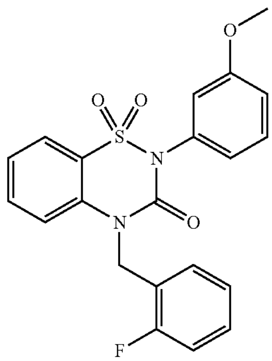 [SMILES: COc1cccc(N2C(=O)N(Cc3ccccc3F)c3ccccc3S2(=O)=O)c1] | 14 | 4-(2-fluorobenzyl)-2-(3-methoxyphenyl)-2H-1,2,4-benzothiadiazin-3(4H)-one 1,1-dioxide | 6.7 |
| 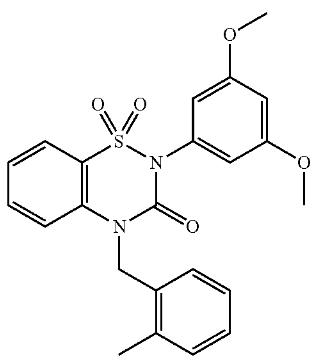 [SMILES: COc1cc(OC)cc(N2C(=O)N(Cc3ccccc3C)c3ccccc3S2(=O)=O)c1] | 15 | 2-(3,5-dimethoxyphenyl)-4-(2-methylbenzyl)-2H-1,2,4-benzothiadiazin-3(4H)-one 1,1-dioxide | 7.53 |
| 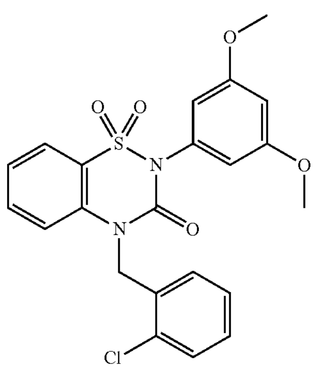 [SMILES: COc1cc(OC)cc(N2C(=O)N(Cc3ccccc3Cl)c3ccccc3S2(=O)=O)c1] | 16 | 4-(2-chlorobenzyl)-2-(3,5-dimethoxyphenyl)-2H-1,2,4-benzothiadiazin-3(4H)-one 1,1-dioxide | 7.5 |
| 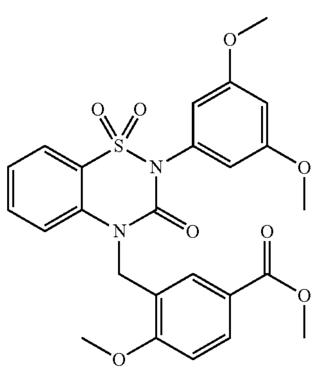 [SMILES: COC(=O)c1ccc(OC)c(CN2C(=O)N(c3cc(OC)cc(OC)c3)S(=O)(=O)c3ccccc32)c1] | 17 | methyl 3-{[2-(3,5-dimethoxyphenyl)-1,1-dioxido-3-oxo-2,3-dihydro-4H-1,2,4-benzothiadiazin-4-yl]methyl}-4-methoxybenzoate | 7.87 |

TABLE 1-continued

| STRUCTURE | ref number | Name | OX2 pKi ave |
|---|---|---|---|
| 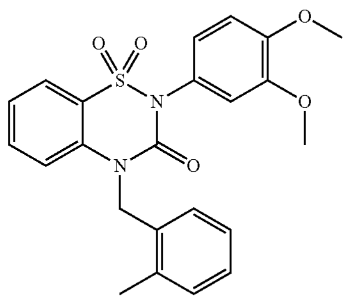 [SMILES: COc1ccc(N2C(=O)N(Cc3ccccc3C)c3ccccc3S2(=O)=O)cc1OC] | 18 | 2-(3,4-dimethoxyphenyl)-4-(2-methylbenzyl)-2H-1,2,4-benzothiadiazin-3(4H)-one 1,1-dioxide | 7.83 |
| 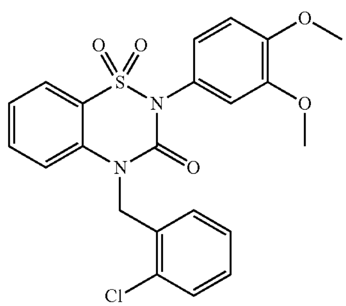 [SMILES: COc1ccc(N2C(=O)N(Cc3ccccc3Cl)c3ccccc3S2(=O)=O)cc1OC] | 19 | 4-(2-chlorobenzyl)-2-(3,4-dimethoxyphenyl)-2H-1,2,4-benzothiadiazin-3(4H)-one 1,1-dioxide | 7.73 |
| 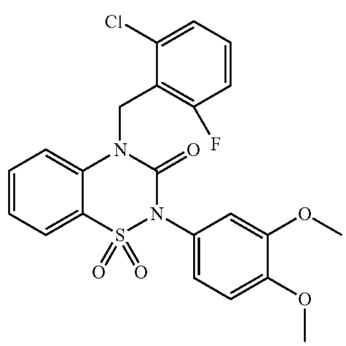 [SMILES: COc1ccc(N2C(=O)N(Cc3c(F)cccc3Cl)c3ccccc3S2(=O)=O)cc1OC] | 20 | 4-(2-chloro-6-fluorobenzyl)-2-(3,4-dimethoxyphenyl)-2H-1,2,4-benzothiadiazin-3(4H)-one 1,1-dioxide | 9.13 |
| 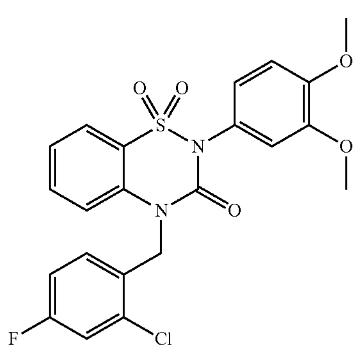 [SMILES: COc1ccc(N2C(=O)N(Cc3ccc(F)cc3Cl)c3ccccc3S2(=O)=O)cc1OC] | 21 | 4-(2-chloro-4-fluorobenzyl)-2-(3,4-dimethoxyphenyl)-2H-1,2,4-benzothiadiazin-3(4H)-one 1,1-dioxide | 7.63 |

TABLE 1-continued

| STRUCTURE | ref number | Name | OX2 pKi ave |
|---|---|---|---|
| 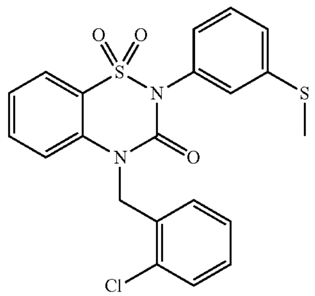 [SMILES: CSc1cccc(N2C(=O)N(Cc3ccccc3Cl)c3ccccc3S2(=O)=O)c1] | 22 | 4-(2-chlorobenzyl)-2-[3-(methylsulfanyl)phenyl]-2H-1,2,4-benzothiadiazin-3(4H)-one 1,1-dioxide | 7.63 |
| 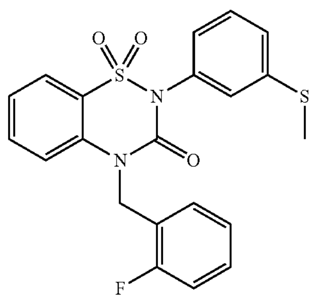 [SMILES: CSc1cccc(N2C(=O)N(Cc3ccccc3F)c3ccccc3S2(=O)=O)c1] | 23 | 4-(2-fluorobenzyl)-2-[3-(methylsulfanyl)phenyl]-2H-1,2,4-benzothiadiazin-3(4H)-one 1,1-dioxide | 7.68 |
| 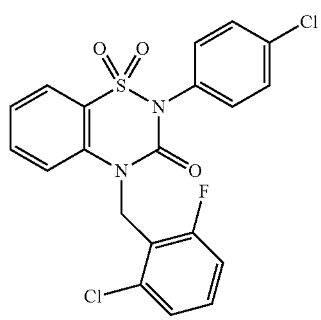 [SMILES: O=C1N(Cc2c(F)cccc2Cl)c2ccccc2S(=O)(=O)N1c1ccc(Cl)cc1] | 24 | 4-(2-chloro-6-fluorobenzyl)-2-(4-chlorophenyl)-2H-1,2,4-benzothiadiazin-3(4H)-one 1,1-dioxide | 8.15 |
| 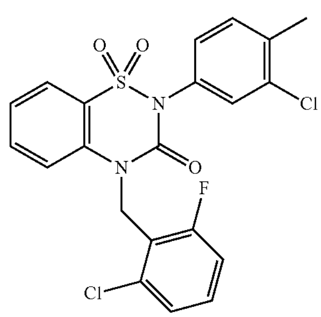 [SMILES: Cc1ccc(N2C(=O)N(Cc3c(F)cccc3Cl)c3ccccc3S2(=O)=O)cc1Cl] | 25 | 4-(2-chloro-6-fluorobenzyl)-2-(3-chloro-4-methylphenyl)-2H-1,2,4-benzothiadiazin-3(4H)-one 1,1-dioxide | 8.6 |
| 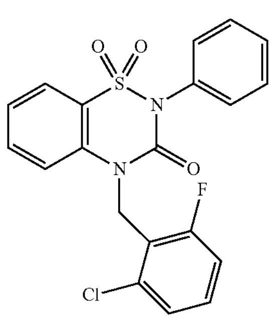 [SMILES: O=C1N(Cc2c(F)cccc2Cl)c2ccccc2S(=O)(=O)N1c1ccccc1] | 26 | 4-(2-chloro-6-fluorobenzyl)-2-phenyl-2H-1,2,4-benzothiadiazin-3(4H)-one 1,1-dioxide | 7.1 |

TABLE 1-continued

| STRUCTURE | ref number | Name | OX2 pKi ave |
|---|---|---|---|
| 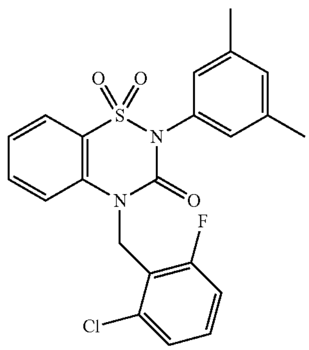 [SMILES: Cc1cc(C)cc(N2C(=O)N(Cc3c(F)cccc3Cl)c3ccccc3S2(=O)=O)c1] | 27 | 4-(2-chloro-6-fluorobenzyl)-2-(3,5-dimethylphenyl)-2H-1,2,4-benzothiadiazin-3(4H)-one 1,1-dioxide | 9.2 |
| 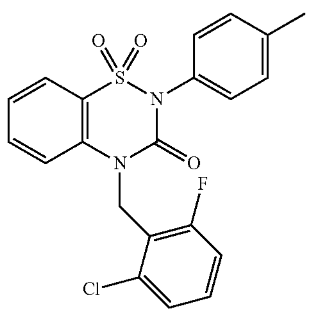 [SMILES: Cc1ccc(N2C(=O)N(Cc3c(F)cccc3Cl)c3ccccc3S2(=O)=O)cc1] | 28 | 4-(2-chloro-6-fluorobenzyl)-2-(4-methylphenyl)-2H-1,2,4-benzothiadiazin-3(4H)-one 1,1-dioxide | 8.25 |
| 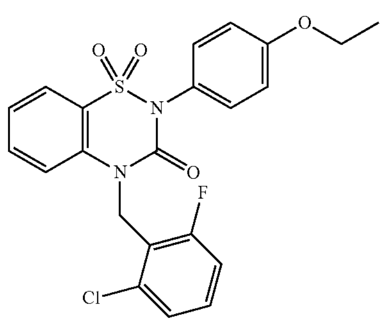 [SMILES: CCOc1ccc(N2C(=O)N(Cc3c(F)cccc3Cl)c3ccccc3S2(=O)=O)cc1] | 29 | 4-(2-chloro-6-fluorobenzyl)-2-(4-ethoxyphenyl)-2H-1,2,4-benzothiadiazin-3(4H)-one 1,1-dioxide | 7.5 |
| 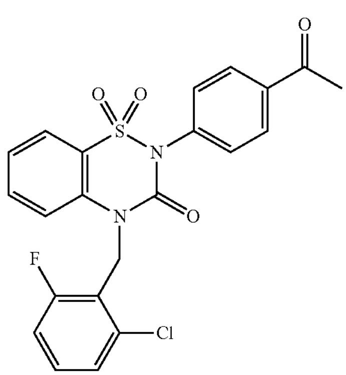 [SMILES: CC(=O)c1ccc(N2C(=O)N(Cc3c(F)cccc3Cl)c3ccccc3S2(=O)=O)cc1] | 30 | 2-(4-acetylphenyl)-4-(2-chloro-6-fluorobenzyl)-2H-1,2,4-benzothiadiazin-3(4H)-one 1,1-dioxide | 7.7 |

TABLE 1-continued

| STRUCTURE | ref number | Name | OX2 pKi ave |
|---|---|---|---|
| 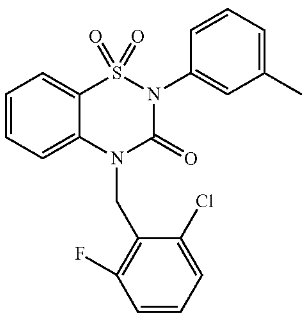 [SMILES: Cc1cccc(N2C(=O)N(Cc3c(F)cccc3Cl)c3ccccc3S2(=O)=O)c1] | 31 | 4-(2-chloro-6-fluorobenzyl)-2-(3-methylphenyl)-2H-1,2,4-benzothiadiazin-3(4H)-one 1,1-dioxide | 7.98 |
| 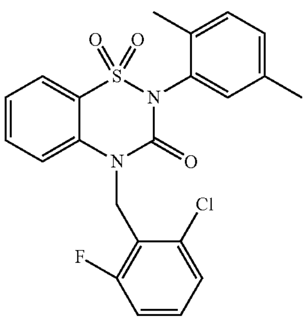 [SMILES: Cc1ccc(C)c(N2C(=O)N(Cc3c(F)cccc3Cl)c3ccccc3S2(=O)=O)c1] | 32 | 4-(2-chloro-6-fluorobenzyl)-2-(2,5-dimethylphenyl)-2H-1,2,4-benzothiadiazin-3(4H)-one 1,1-dioxide | 7.55 |
| 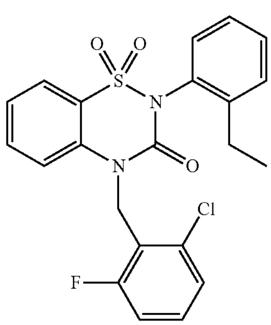 [SMILES: CCc1ccccc1N1C(=O)N(Cc2c(F)cccc2Cl)c2ccccc2S1(=O)=O] | 33 | 4-(2-chloro-6-fluorobenzyl)-2-(2-ethylphenyl)-2H-1,2,4-benzothiadiazin-3(4H)-one 1,1-dioxide | 7.55 |
| 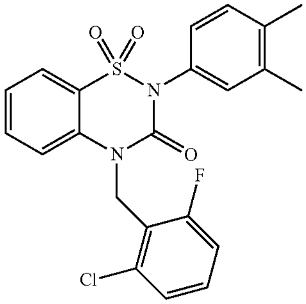 [SMILES: Cc1ccc(N2C(=O)N(Cc3c(F)cccc3Cl)c3ccccc3S2(=O)=O)cc1C] | 34 | 4-(2-chloro-6-fluorobenzyl)-2-(3,4-dimethylphenyl)-2H-1,2,4-benzothiadiazin-3(4H)-one 1,1-dioxide | 8.95 |

TABLE 1-continued

| STRUCTURE | ref number | Name | OX2 pKi ave |
|---|---|---|---|
| 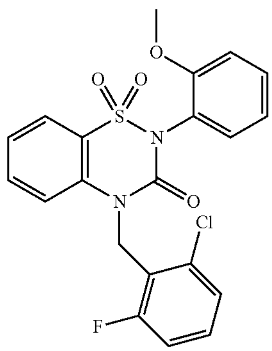 [SMILES: COc1ccccc1N1C(=O)N(Cc2c(F)cccc2Cl)c2ccccc2S1(=O)=O] | 35 | 4-(2-chloro-6-fluorobenzyl)-2-(2-methoxyphenyl)-2H-1,2,4-benzothiadiazin-3(4H)-one 1,1-dioxide | 7.5 |
| 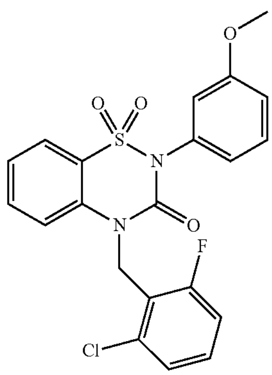 [SMILES: COc1cccc(N2C(=O)N(Cc3c(F)cccc3Cl)c3ccccc3S2(=O)=O)c1] | 36 | 4-(2-chloro-6-fluorobenzyl)-2-(3-methoxyphenyl)-2H-1,2,4-benzothiadiazin-3(4H)-one 1,1-dioxide | 7.8 |
| 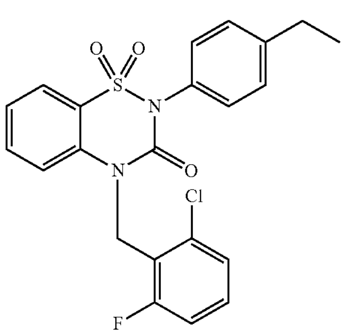 [SMILES: CCc1ccc(N2C(=O)N(Cc3c(F)cccc3Cl)c3ccccc3S2(=O)=O)cc1] | 37 | 4-(2-chloro-6-fluorobenzyl)-2-(4-ethylphenyl)-2H-1,2,4-benzothiadiazin-3(4H)-one 1,1-dioxide | 8.3 |
| 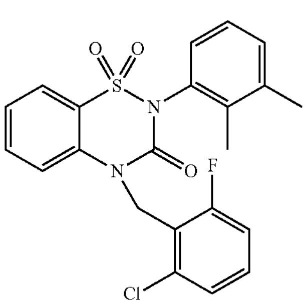 [SMILES: Cc1cccc(N2C(=O)N(Cc3c(F)cccc3Cl)c3ccccc3S2(=O)=O)c1C] | 38 | 4-(2-chloro-6-fluorobenzyl)-2-(2,3-dimethylphenyl)-2H-1,2,4-benzothiadiazin-3(4H)-one 1,1-dioxide | 7.8 |

TABLE 1-continued
| STRUCTURE | ref number | Name | OX2 pKi ave |
|---|---|---|---|
| 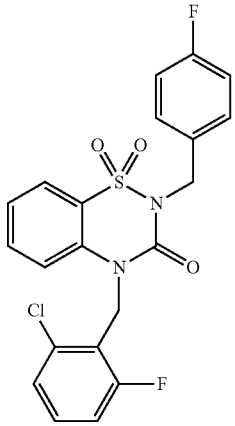 [SMILES: O=C1N(Cc2c(F)cccc2Cl)c2ccccc2S(=O)(=O)N1Cc1ccc(F)cc1] | 39 | 4-(2-chloro-6-fluorobenzyl)-2-(4-fluorobenzyl)-2H-1,2,4-benzothiadiazin-3(4H)-one 1,1-dioxide | 7.7 |
| 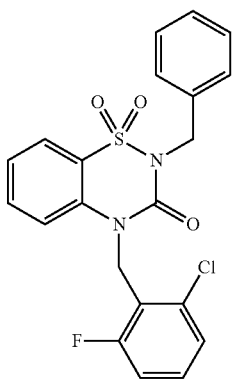 [SMILES: O=C1N(Cc2c(F)cccc2Cl)c2ccccc2S(=O)(=O)N1Cc1ccccc1] | 40 | 2-benzyl-4-(2-chloro-6-fluorobenzyl)-2H-1,2,4-benzothiadiazin-3(4H)-one 1,1-dioxide | 7.58 |
| 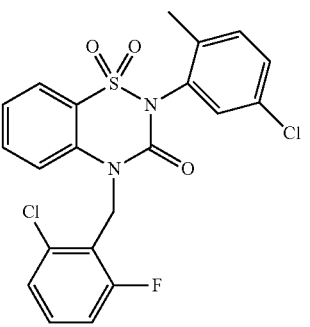 [SMILES: Cc1ccc(Cl)cc1N1C(=O)N(Cc2c(F)cccc2Cl)c2ccccc2S1(=O)=O] | 41 | 4-(2-chloro-6-fluorobenzyl)-2-(5-chloro-2-methylphenyl)-2H-1,2,4-benzothiadiazin-3(4H)-one 1,1-dioxide | 7.6 |
| 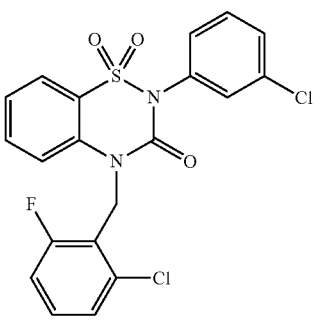 [SMILES: O=C1N(Cc2c(F)cccc2Cl)c2ccccc2S(=O)(=O)N1c1cccc(Cl)c1] | 42 | 4-(2-chloro-6-fluorobenzyl)-2-(3-chlorophenyl)-2H-1,2,4-benzothiadiazin-3(4H)-one 1,1-dioxide | 7.85 |

TABLE 1-continued

| STRUCTURE | ref number | Name | OX2 pKi ave |
|---|---|---|---|
| 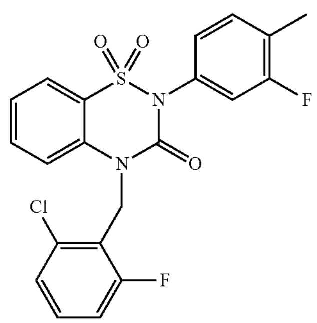 [SMILES: Cc1ccc(N2C(=O)N(Cc3c(F)cccc3Cl)c3ccccc3S2(=O)=O)cc1F] | 43 | 4-(2-chloro-6-fluorobenzyl)-2-(3-fluoro-4-methylphenyl)-2H-1,2,4-benzothiadiazin-3(4H)-one 1,1-dioxide | 8.33 |
| 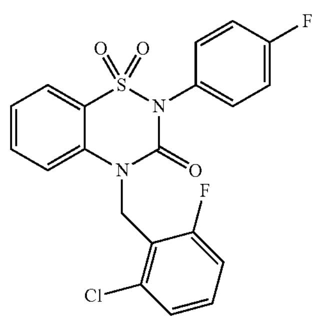 [SMILES: O=C1N(Cc2c(F)cccc2Cl)c2ccccc2S(=O)(=O)N1c1ccc(F)cc1] | 44 | 4-(2-chloro-6-fluorobenzyl)-2-(4-fluorophenyl)-2H-1,2,4-benzothiadiazin-3(4H)-one 1,1-dioxide | 7.5 |
| 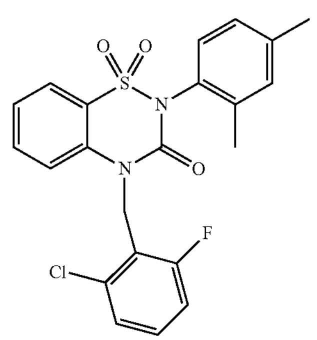 [SMILES: Cc1ccc(N2C(=O)N(Cc3c(F)cccc3Cl)c3ccccc3S2(=O)=O)c(C)c1] | 45 | 4-(2-chloro-6-fluorobenzyl)-2-(2,4-dimethylphenyl)-2H-1,2,4-benzothiadiazin-3(4H)-one 1,1-dioxide | 7.78 |
| 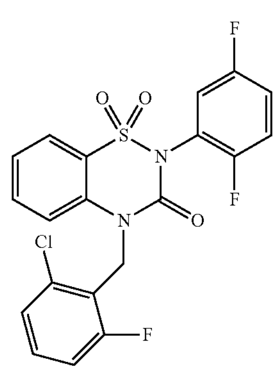 [SMILES: O=C1N(Cc2c(F)cccc2Cl)c2ccccc2S(=O)(=O)N1c1cc(F)ccc1F] | 46 | 4-(2-chloro-6-fluorobenzyl)-2-(2,5-difluorophenyl)-2H-1,2,4-benzothiadiazin-3(4H)-one 1,1-dioxide | 7.2 |

TABLE 1-continued

| STRUCTURE | ref number | Name | OX2 pKi ave |
|---|---|---|---|
| 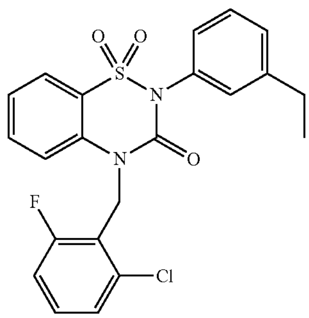 [SMILES: CCc1cccc(N2C(=O)N(Cc3c(F)cccc3Cl)c3ccccc3S2(=O)=O)c1] | 47 | 4-(2-chloro-6-fluorobenzyl)-2-(3-ethylphenyl)-2H-1,2,4-benzothiadiazin-3(4H)-one 1,1-dioxide | 8.6 |
| 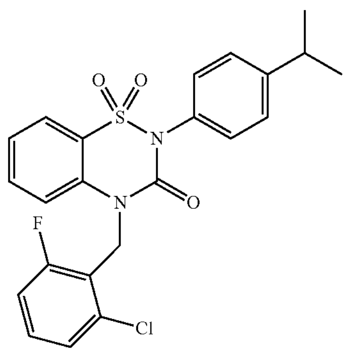 [SMILES: CC(C)c1ccc(N2C(=O)N(Cc3c(F)cccc3Cl)c3ccccc3S2(=O)=O)cc1] | 48 | 4-(2-chloro-6-fluorobenzyl)-2-[4-(propan-2-yl)phenyl]-2H-1,2,4-benzothiadiazin-3(4H)-one 1,1-dioxide | 8.43 |
| 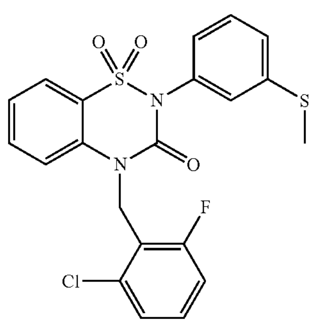 [SMILES: CSc1cccc(N2C(=O)N(Cc3c(F)cccc3Cl)c3ccccc3S2(=O)=O)c1] | 49 | 4-(2-chloro-6-fluorobenzyl)-2-[3-(methylsulfanyl)phenyl]-2H-1,2,4-benzothiadiazin-3(4H)-one 1,1-dioxide | 8.98 |
| 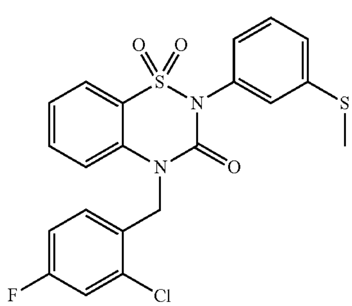 [SMILES: CSc1cccc(N2C(=O)N(Cc3ccc(F)cc3Cl)c3ccccc3S2(=O)=O)c1] | 50 | 4-(2-chloro-4-fluorobenzyl)-2-[3-(methylsulfanyl)phenyl]-2H-1,2,4-benzothiadiazin-3(4H)-one 1,1-dioxide | 7.45 |

TABLE 1-continued

| STRUCTURE | ref number | Name | OX2 pKi ave |
|---|---|---|---|
| 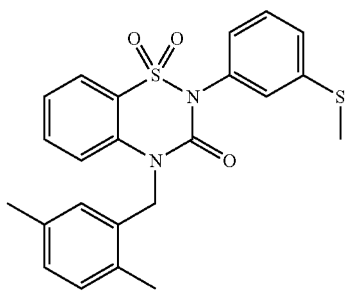 | 51 | 4-(2,5-dimethylbenzyl)-2-[3-(methylsulfanyl)phenyl]-2H-1,2,4-benzothiadiazin-3(4H)-one 1,1-dioxide | 7.75 |
| 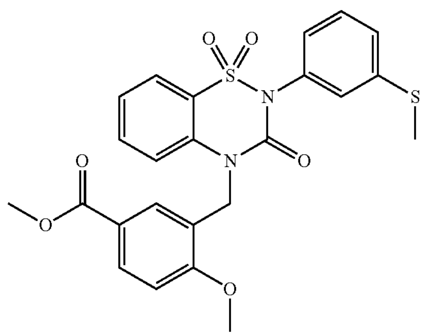 | 52 | methyl 3-({2-[3-(methylsulfanyl)phenyl]-1,1-dioxido-3-oxo-2,3-dihydro-4H-1,2,4-benzothiadiazin-4-yl}methyl)-4-methoxybenzoate | 8.58 |
| 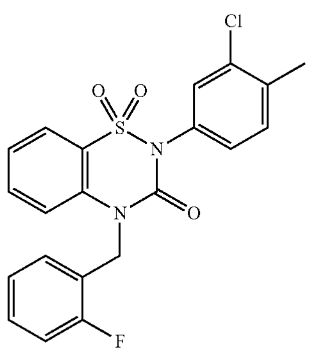 [SMILES: Cc1ccc(N2C(=O)N(Cc3ccccc3F)c3ccccc3S2(=O)=O)cc1Cl] | 53 | 4-(2-fluorobenzyl)-2-(3-chloro-4-methylphenyl)-2H-1,2,4-benzothiadiazin-3(4H)-one 1,1-dioxide | 7.5 |
| 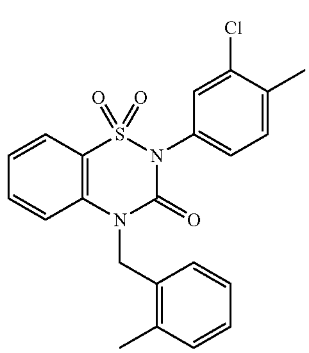 [SMILES: Cc1ccc(N2C(=O)N(Cc3ccccc3C)c3ccccc3S2(=O)=O)cc1Cl] | 54 | 4-(2-methylbenzyl)-2-(3-chloro-4-methylphenyl)-2H-1,2,4-benzothiadiazin-3(4H)-one 1,1-dioxide | 7.36 |

TABLE 1-continued

| STRUCTURE | ref number | Name | OX2 pKi ave |
|---|---|---|---|
| 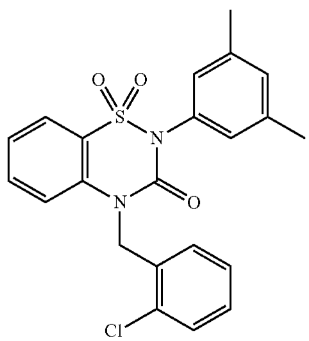 [SMILES: Cc1cc(C)cc(N2C(=O)N(Cc3ccccc3Cl)c3ccccc3S2(=O)=O)c1] | 55 | 4-(2-chlorobenzyl)-2-(3,5-dimethylphenyl)-2H-1,2,4-benzothiadiazin-3(4H)-one 1,1-dioxide | 7.51 |
| 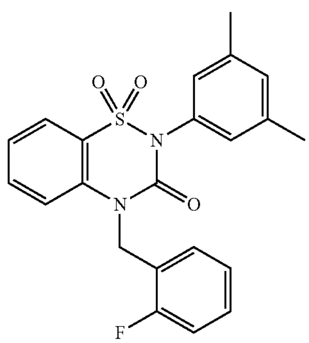 [SMILES: Cc1cc(C)cc(N2C(=O)N(Cc3ccccc3F)c3ccccc3S2(=O)=O)c1] | 56 | 4-(2-fluorobenzyl)-2-(3,5-dimethylphenyl)-2H-1,2,4-benzothiadiazin-3(4H)-one 1,1-dioxide | 7.68 |
| 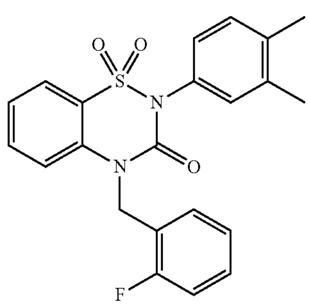 [SMILES: Cc1ccc(N2C(=O)N(Cc3ccccc3F)c3ccccc3S2(=O)=O)cc1C] | 57 | 4-(2-fluorobenzyl)-2-(3,4-dimethylphenyl)-2H-1,2,4-benzothiadiazin-3(4H)-one 1,1-dioxide | 7.63 |
| 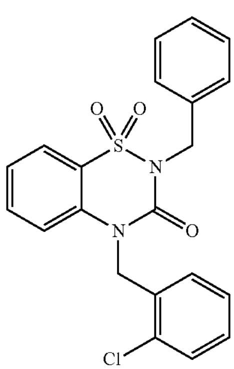 [SMILES: O=C1N(Cc2ccccc2Cl)c2ccccc2S(=O)(=O)N1Cc1ccccc1] | 58 | 2-benzyl-4-(2-chlorobenzyl)-2H-1,2,4-benzothiadiazin-3(4H)-one 1,1-dioxide | 6.03 |

TABLE 1-continued

| STRUCTURE | ref number | Name | OX2 pKi ave |
|---|---|---|---|
| 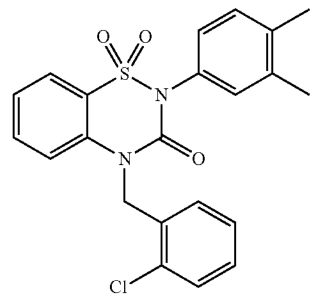 [SMILES: Cc1ccc(N2C(=O)N(Cc3ccccc3Cl)c3ccccc3S2(=O)=O)cc1C] | 59 | 4-(2-chlorobenzyl)-2-(3,4-dimethylphenyl)-2H-1,2,4-benzothiadiazin-3(4H)-one 1,1-dioxide | 7.36 |
| 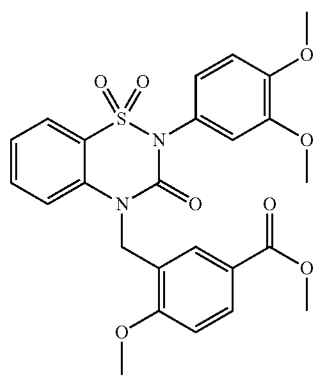 [SMILES: COC(=O)c1ccc(OC)c(CN2C(=O)N(c3ccc(OC)c(OC)c3)S(=O)(=O)c3ccccc32)c1] | 60 | methyl 3-{[2-(3,4-dimethoxyphenyl)-1,1-dioxido-3-oxo-2,3-dihydro-4H-1,2,4-benzothiadiazin-4-yl]methyl}-4-methoxybenzoate | 7.39 |
| 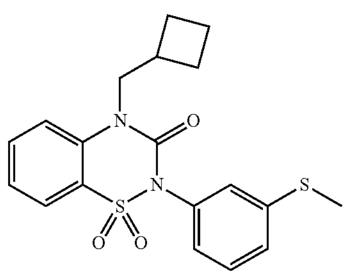 [SMILES: CSc1cccc(N2C(=O)N(CC3CCC3)c3ccccc3S2(=O)=O)c1] | 61 | 4-(Cyclobutylmethyl)-2-[3-(methylsulfanyl)phenyl]-2H-1,2,4-benzothiadiazin-3(4H)-one 1,1-dioxide | 6.57 |
| 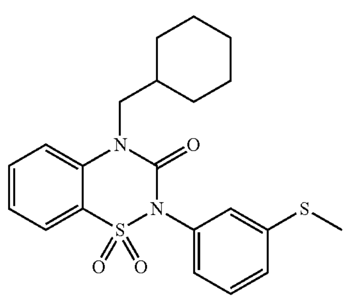 [SMILES: CSc1cccc(N2C(=O)N(CC3CCCCC3)c3ccccc3S2(=O)=O)c1] | 62 | 4-(Cyclohexylmethyl)-2-[3-(methylsulfanyl)phenyl]-2H-1,2,4-benzothiadiazin-3(4H)-one 1,1-dioxide | 6.06 |
| 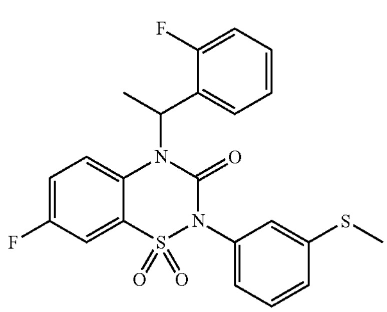 [SMILES: CSc1cccc(N2C(=O)N(C(C)c3ccccc3F)c3ccc(F)cc3S2(=O)=O)c1] | 63 | 7-Fluoro-4-[1-(2-fluorophenyl)ethyl]-2-[3-(methylsulfanyl)phenyl]-2H-1,2,4-benzothiadiazin-3(4H)-one 1,1-dioxide | 6.08 |

TABLE 1-continued

| STRUCTURE | ref number | Name | OX2 pKi ave |
|---|---|---|---|
| 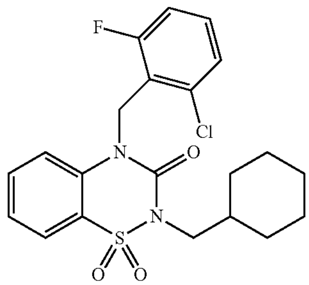 [SMILES: O=C1N(Cc2c(F)cccc2Cl)c2ccccc2S(=O)(=O)N1CC1CCCCC1] | 64 | 4-(2-Chloro-6-fluorobenzyl)-2-(cyclohexylmethyl)-2H-1,2,4-benzothiadiazin-3(4H)-one 1,1-dioxide | 6.18 |
| 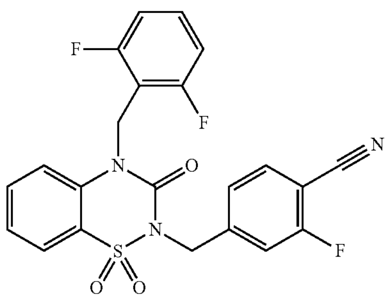 [SMILES: N#Cc1ccc(CN2C(=O)N(Cc3c(F)cccc3F)c3ccccc3S2(=O)=O)cc1F] | 65 | 4-{[4-(2,6-Difluorobenzyl)-1,1-dioxido-3-oxo-3,4-dihydro-2H-1,2,4-benzothiadiazin-2-yl]methyl}-2-fluorobenzonitrile | 6.7 |
| 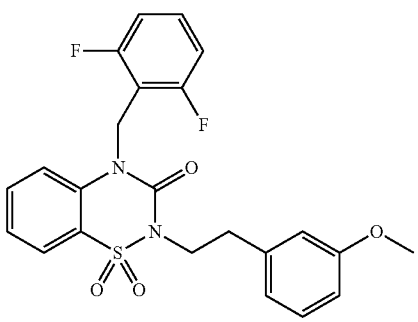 [SMILES: COc1cccc(CCN2C(=O)N(Cc3c(F)cccc3F)c3ccccc3S2(=O)=O)c1] | 66 | 4-(2,6-Difluorobenzyl)-2-[2-(3-methoxyphenyl)ethyl]-2H-1,2,4-benzothiadiazin-3(4H)-one 1,1-dioxide | 6.26 |
| 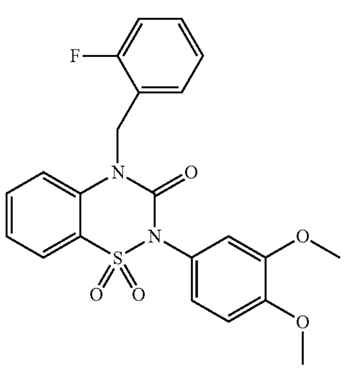 [SMILES: COc1ccc(N2C(=O)N(Cc3ccccc3F)c3ccccc3S2(=O)=O)cc1OC] | 67 | 2-(3,4-Dimethoxyphenyl)-4-(2-fluorobenzyl)-2H-1,2,4-benzothiadiazin-3(4H)-one 1,1-dioxide | 8.15 |

TABLE 1-continued

| STRUCTURE | ref number | Name | OX2 pKi ave |
|---|---|---|---|
| 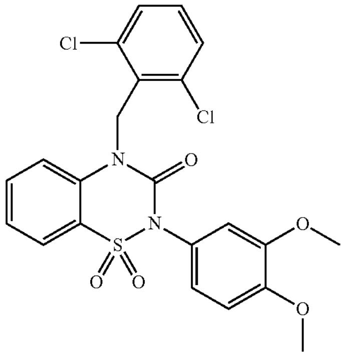 [SMILES: COc1ccc(N2C(=O)N(Cc3c(Cl)cccc3Cl)c3ccccc3S2(=O)=O)cc1OC] | 68 | 4-(2,6-Dichlorobenzyl)-2-(3,4-dimethoxyphenyl)-2H-1,2,4-benzothiadiazin-3(4H)-one 1,1-dioxide | 9.15 |
| 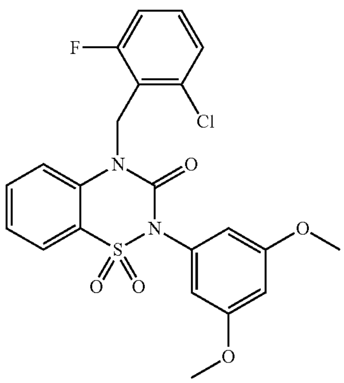 [SMILES: COc1cc(OC)cc(N2C(=O)N(Cc3c(F)cccc3Cl)c3ccccc3S2(=O)=O)c1] | 69 | 4-(2-Chloro-6-fluorobenzyl)-2-(3,5-dimethoxyphenyl)-2H-1,2,4-benzothiadiazin-3(4H)-one 1,1-dioxide | 8.97 |
| 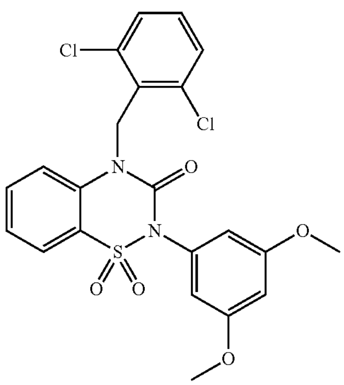 [SMILES: COc1cc(OC)cc(N2C(=O)N(Cc3c(Cl)cccc3Cl)c3ccccc3S2(=O)=O)c1] | 70 | 4-(2,6-Dichlorobenzyl)-2-(3,5-dimethoxyphenyl)-2H-1,2,4-benzothiadiazin-3(4H)-one 1,1-dioxide | 8.7 |
| 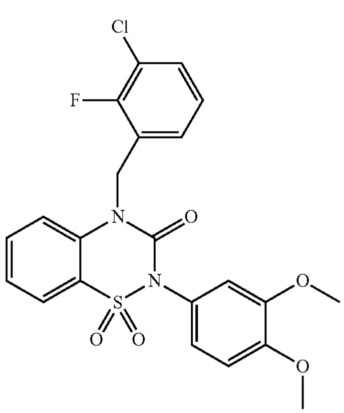 [SMILES: COc1ccc(N2C(=O)N(Cc3cccc(Cl)c3F)c3ccccc3S2(=O)=O)cc1OC] | 71 | 4-(3-Chloro-2-fluorobenzyl)-2-(3,4-dimethoxyphenyl)-2H-1,2,4-benzothiadiazin-3(4H)-one 1,1-dioxide | 8.15 |

TABLE 1-continued

| STRUCTURE | ref number | Name | OX2 pKi ave |
|---|---|---|---|
| 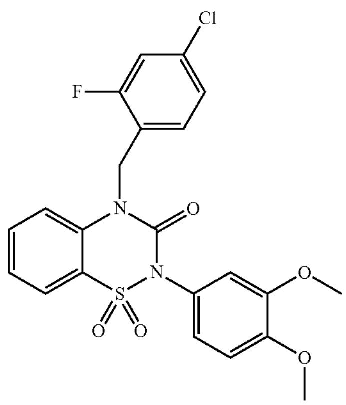 [SMILES: COc1ccc(N2C(=O)N(Cc3ccc(Cl)cc3F)c3ccccc3S2(=O)=O)cc1OC] | 72 | 4-(4-Chloro-2-fluorobenzyl)-2-(3,4-dimethoxyphenyl)-2H-1,2,4-benzothiadiazin-3(4H)-one 1,1-dioxide | 7.98 |
| 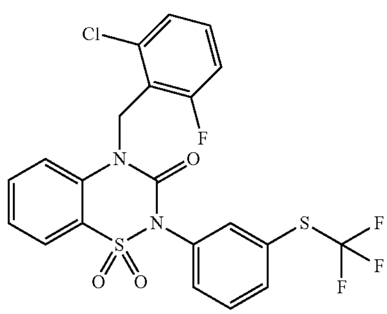 [SMILES: O=C1N(Cc2c(F)cccc2Cl)c2ccccc2S(=O)(=O)N1c1cccc(SC(F)(F)F)c1] | 73 | 4-(2-Chloro-6-fluorobenzyl)-2-{3-[(trifluoromethyl)sulfanyl]phenyl}-2H-1,2,4-benzothiadiazin-3(4H)-one 1,1-dioxide | 8.68 |
| 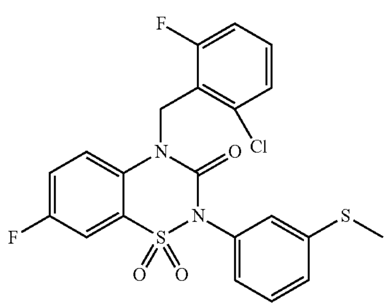 [SMILES: CSc1cccc(N2C(=O)N(Cc3c(F)cccc3Cl)c3ccc(F)cc3S2(=O)=O)c1] | 74 | 4-(2-Chloro-6-fluorobenzyl)-7-fluoro-2-[3-(methylsulfanyl)phenyl]-2H-1,2,4-benzothiadiazin-3(4H)-one 1,1-dioxide | 7.93 |
| 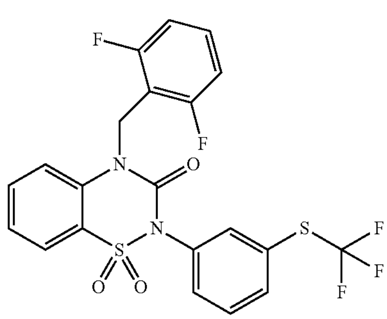 [SMILES: O=C1N(Cc2c(F)cccc2F)c2ccccc2S(=O)(=O)N1c1cccc(SC(F)(F)F)c1] | 75 | 4-(2,6-Difluorobenzyl)-2-{3-[(trifluoromethyl)sulfanyl]phenyl}-2H-1,2,4-benzothiadiazin-3(4H)-one 1,1-dioxide | 8.08 |

TABLE 1-continued

| STRUCTURE | ref number | Name | OX2 pKi ave |
|---|---|---|---|
| 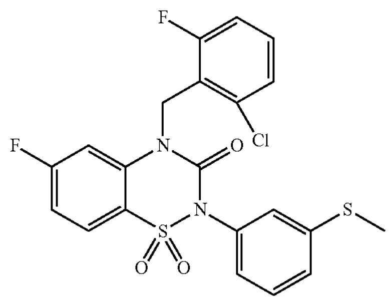 [SMILES: CSc1cccc(N2C(=O)N(Cc3c(F)cccc3Cl)c3cc(F)ccc3S2(=O)=O)c1] | 76 | 4-(2-Chloro-6-fluorobenzyl)-6-fluoro-2-[3-(methylsulfanyl)phenyl]-2H-1,2,4-benzothiadiazin-3(4H)-one 1,1-dioxide | 7.83 |
| 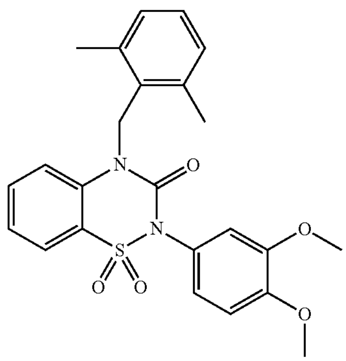 [SMILES: COc1ccc(N2C(=O)N(Cc3c(C)cccc3C)c3ccccc3S2(=O)=O)cc1OC] | 77 | 4-(2,6-Dimethylbenzyl)-2-(3,4-methoxyphenyl)-2H-1,2,4-benzothiadiazin-3(4H)-one 1,1-dioxide | 8.05 |
| 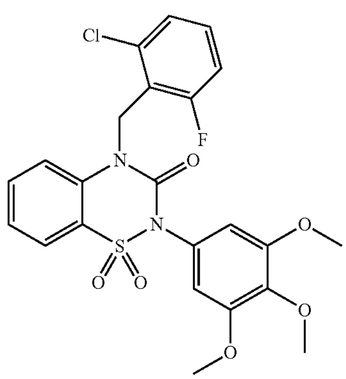 [SMILES: COc1cc(N2C(=O)N(Cc3c(F)cccc3Cl)c3ccccc3S2(=O)=O)cc(OC)c1OC] | 78 | 4-(2-Chloro-6-fluorobenzyl)-2-(3,4,5-trimethoxyphenyl)-2H-1,2,4-benzothiadiazin-3(4H)-one 1,1-dioxide | 8.39 |
| 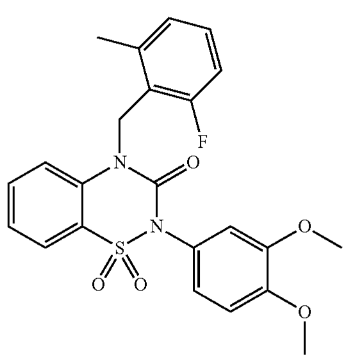 [SMILES: COc1ccc(N2C(=O)N(Cc3c(C)cccc3F)c3ccccc3S2(=O)=O)cc1OC] | 79 | 4-(2-Fluoro,6-methylbenzyl)-2-(3,4-methoxyphenyl)-2H-1,2,4-benzothiadiazin-3(4H)-one 1,1-dioxide | 9.41 |

TABLE 1-continued

| STRUCTURE | ref number | Name | OX2 pKi ave |
|---|---|---|---|
| 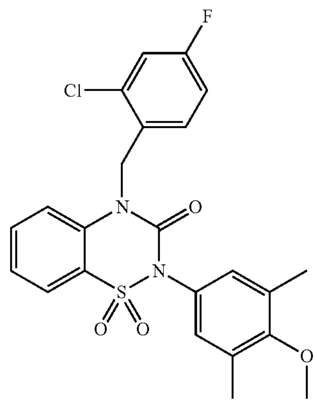 [SMILES: COc1c(C)cc(N2C(=O)N(Cc3ccc(F)cc3Cl)c3ccccc3S2(=O)=O)cc1C] | 80 | 4-(2-Chloro-4-fluorobenzyl)-2-(4-methoxy-3,5-dimethylphenyl)-2H-1,2,4-benzothiadiazin-3(4H)-one 1,1-dioxide | 8.12 |
| 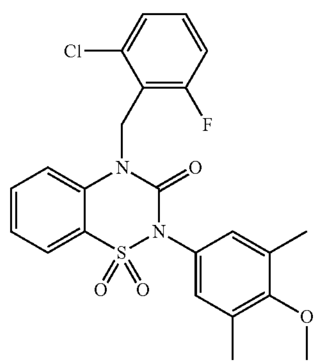 [SMILES: COc1c(C)cc(N2C(=O)N(Cc3c(F)cccc3Cl)c3ccccc3S2(=O)=O)cc1C] | 81 | 4-(2-chloro-6-fluorobenzyl)-2-(4-methoxy-3,5-dimethylphenyl)-2H-1,2,4-benzothiadiazin-3(4H)-one 1,1-dioxide | 10.08 |
| 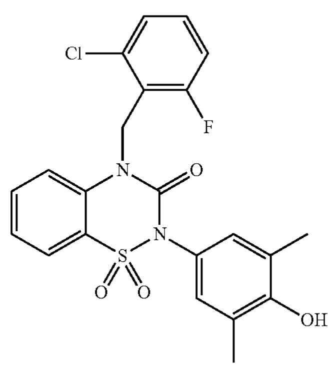 [SMILES: Cc1cc(N2C(=O)N(Cc3c(F)cccc3Cl)c3ccccc3S2(=O)=O)cc(C)c1O] | 82 | 4-(2-Chloro-6-fluorobenzyl)-2-(4-hydroxy-3,5-dimethylphenyl)-2H-1,2,4-benzothiadiazin-3(4H)-one 1,1-dioxide | 8.48 |
| 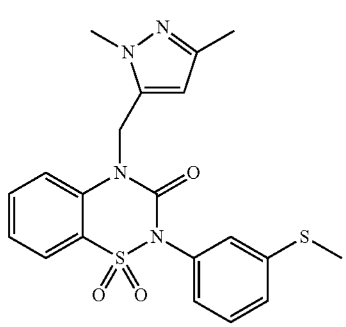 [SMILES: CSc1cccc(N2C(=O)N(Cc3cc(C)nn3C)c3ccccc3S2(=O)=O)c1] | 83 | 4-[(1,3-Dimethyl-1H-pyrazol-5-yl)methyl]-2-[3-(methylsulfanyl)phenyl]-2H-1,2,4-benzothiadiazin-3(4H)-one 1,1-dioxide | 6.53 |

TABLE 1-continued

| STRUCTURE | ref number | Name | OX2 pKi ave |
|---|---|---|---|
| 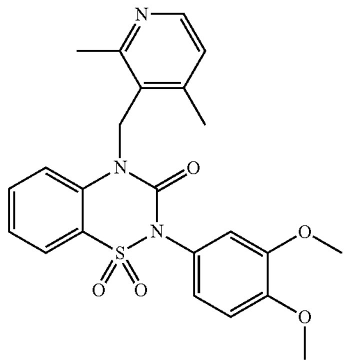 [SMILES: COc1ccc(N2C(=O)N(Cc3c(C)ccnc3C)c3ccccc3S2(=O)=O)cc1OC] | 84 | 2-(3,4-Dimethoxyphenyl)-4-[(2,4-dimethylpyridin-3-yl)methyl]-2H-1,2,4-benzothiadiazin-3(4H)-one 1,1-dioxide | 6.31 |
| 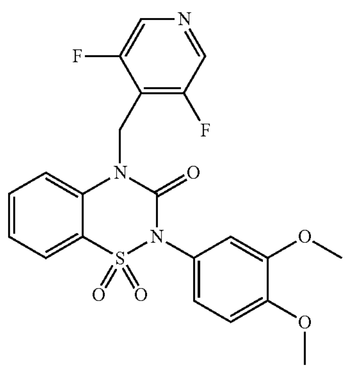 [SMILES: COc1ccc(N2C(=O)N(Cc3c(F)cncc3F)c3ccccc3S2(=O)=O)cc1OC] | 85 | 4-[(3,5-Difluoropyridin-4-yl)methyl]-2-(3,4-dimethoxyphenyl)-2H-1,2,4-benzothiadiazin-3(4H)-one 1,1-dioxide | 7.22 |
| 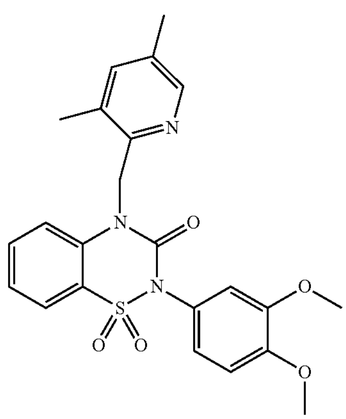 [SMILES: COc1ccc(N2C(=O)N(Cc3ncc(C)cc3C)c3ccccc3S2(=O)=O)cc1OC] | 86 | 4-[(3,5-Dimethylpyridin-2-yl)methyl]-2-(3,4-dimethoxyphenyl)-2H-1,2,4-benzothiadiazin-3(4H)-one 1,1-dioxide | 7.13 |
| 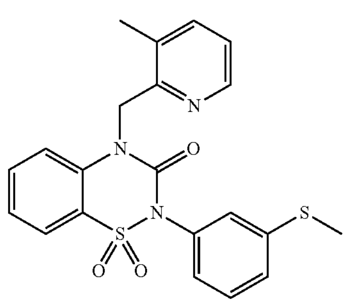 [SMILES: CSc1cccc(N2C(=O)N(Cc3ncccc3C)c3ccccc3S2(=O)=O)c1] | 87 | 4-[(3-Methylpyridin-2-yl)methyl]-2-[3-(methylsulfanyl)phenyl]-2H-1,2,4-benzothiadiazin-3(4H)-one 1,1-dioxide | 7.45 |

TABLE 1-continued

| STRUCTURE | ref number | Name | OX2 pKi ave |
|---|---|---|---|
| 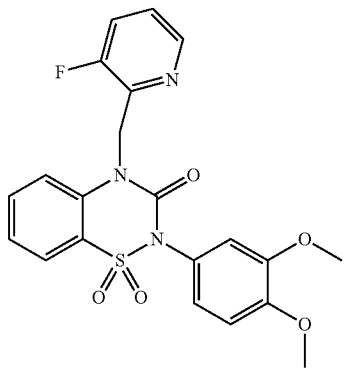 [SMILES: COc1ccc(N2C(=O)N(Cc3ncccc3F)c3ccccc3S2(=O)=O)cc1OC] | 88 | 2-(3,4-Dimethoxyphenyl)-4-[(3-fluoropyridin-2-yl)methyl]-2H-1,2,4-benzothiadiazin-3(4H)-one 1,1-dioxide | 7.55 |
| 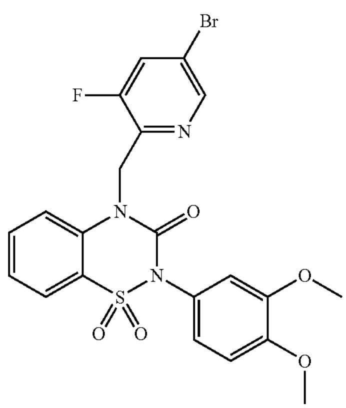 [SMILES: COc1ccc(N2C(=O)N(Cc3ncc(Br)cc3F)c3ccccc3S2(=O)=O)cc1OC] | 89 | 4-[(5-Bromo-3-fluoropyridin-2-yl)methyl]-2-(3,4-dimethoxyphenyl)-2H-1,2,4-benzothiadiazin-3(4H)-one 1,1-dioxide | 7.41 |
| 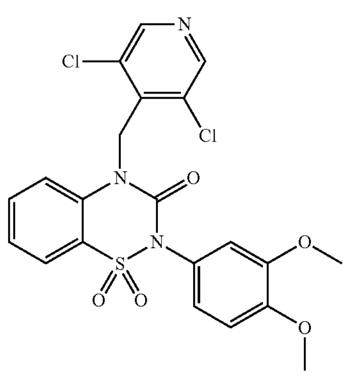 [SMILES: COc1ccc(N2C(=O)N(Cc3c(Cl)cncc3Cl)c3ccccc3S2(=O)=O)cc1OC] | 90 | 4-[(3,5-Dichloropyridin-4-yl)methyl]-2-(3,4-dimethoxyphenyl)-2H-1,2,4-benzothiadiazin-3(4H)-one 1,1-dioxide | 8.52 |
| 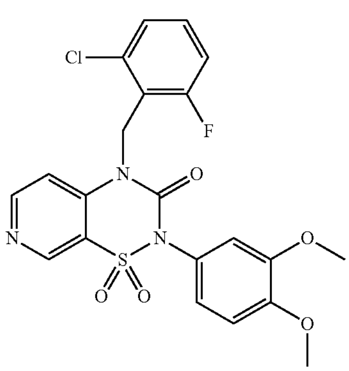 [SMILES: COc1ccc(N2C(=O)N(Cc3c(F)cccc3Cl)c3ccncc3S2(=O)=O)cc1OC] | 91 | 4-(2-Chloro-6-fluorobenzyl)-2-(3,4-dimethoxyphenyl)-2H-pyrido[4,3-e][1,2,4]thiadiazin-3(4H)-one 1,1-dioxide | 7.42 |

TABLE 1-continued

| STRUCTURE | ref number | Name | OX2 pKi ave |
|---|---|---|---|
| 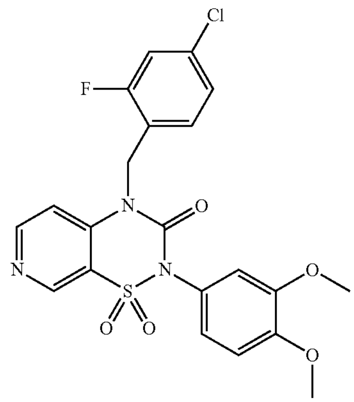 [SMILES: COc1ccc(N2C(=O)N(Cc3ccc(Cl)cc3F)c3ccncc3S2(=O)=O)cc1OC] | 92 | 4-(4-Chloro-2-fluorobenzyl)-2-(3,4-dimethoxyphenyl)-2H-pyrido[4,3-e][1,2,4]thiadiazin-3(4H)-one 1,1-dioxide | 6.13 |
| 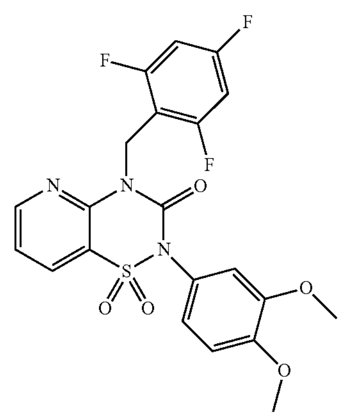 | 93 | 2-(3,4-Dimethoxyphenyl)-4-(2,4,6-trifluorobenzyl)-2H-pyrido[2,3-e][1,2,4]thiadiazin-3(4H)-one 1,1-dioxide | 8.92 |
| 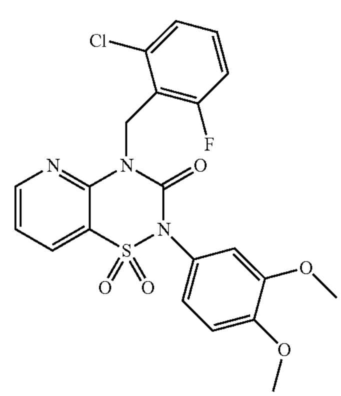 [SMILES: COc1ccc(N2C(=O)N(Cc3c(F)cccc3Cl)c3ncccc3S2(=O)=O)cc1OC] | 94 | 4-(2-Chloro-6-fluorobenzyl)-2-(3,4-dimethoxyphenyl)-2H-pyrido[2,3-e][1,2,4]thiadiazin-3(4H)-one 1,1-dioxide | 9.11 |

TABLE 1-continued

| STRUCTURE | ref number | Name | OX2 pKi ave |
|---|---|---|---|
| 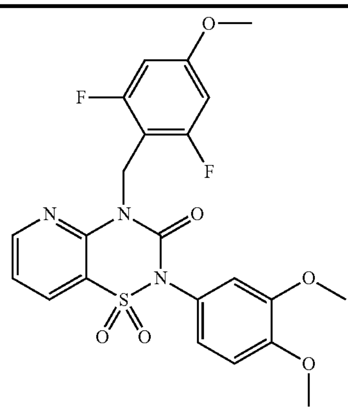 | 95 | 4-(2,6-Difluoro-4-methoxybenzyl)-2-(3,4-dimethoxyphenyl)-2H-pyrido[2,3-e][1,2,4]thiadiazin-3(4H)-one 1,1-dioxide | 9.89 |
| 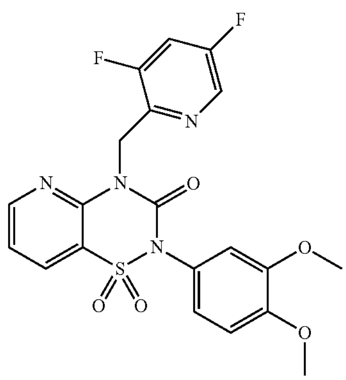 [SMILES: COc1ccc(N2C(=O)N(Cc3ncc(F)cc3F)c3ncccc3S2(=O)=O)cc1OC] | 96 | 4-[(3,5-Difluoropyridin-2-yl)methyl]-2-(3,4-dimethoxyphenyl)-2H-pyrido[2,3-e][1,2,4]thiadiazin-3(4H)-one 1,1-dioxide | 7.88 |
| 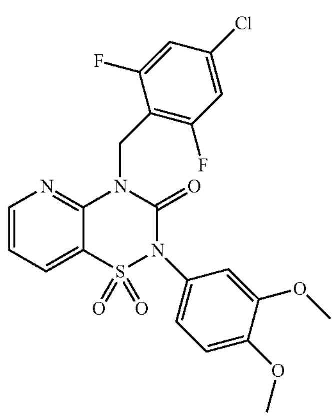 [SMILES: COc1ccc(N2C(=O)N(Cc3c(F)cc(Cl)cc3F)c3ncccc3S2(=O)=O)cc1OC] | 97 | 4-(4-Chloro-2,6-difluorobenzyl)-2-(3,4-dimethoxyphenyl)-2H-pyrido[2,3-e][1,2,4]thiadiazin-3(4H)-one 1,1-dioxide | 9.18 |
| 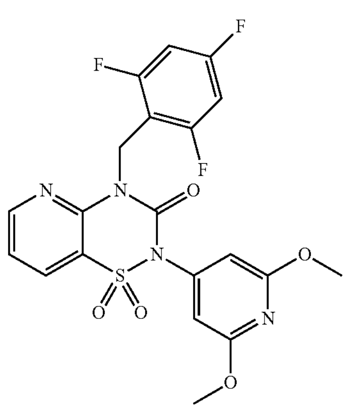 [SMILES: COc1cc(N2C(=O)N(Cc3c(F)cc(F)cc3F)c3ncccc3S2(=O)=O)cc(OC)n1] | 98 | 2-(2,6-Dimethoxypyridin-4-yl)-4-(2,4,6-trifluorobenzyl)-2H-pyrido[2,3-e][1,2,4]thiadiazin-3(4H)-one 1,1-dioxide | 8.83 |

TABLE 1-continued

| STRUCTURE | ref number | Name | OX2 pKi ave |
|---|---|---|---|
| 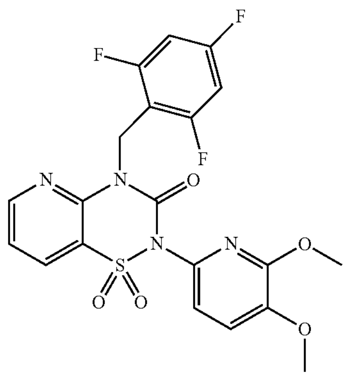 [SMILES: COc1ccc(N2C(=O)N(Cc3c(F)cc(F)cc3F)c3ncccc3S2(=O)=O)nc1OC] | 99 | 2-(5,6-Dimethoxypyridin-2-yl)-4-(2,4,6-trifluorobenzyl)-2H-pyrido[2,3-e][1,2,4]thiadiazin-3(4H)-one 1,1-dioxide | 8.81 |
| 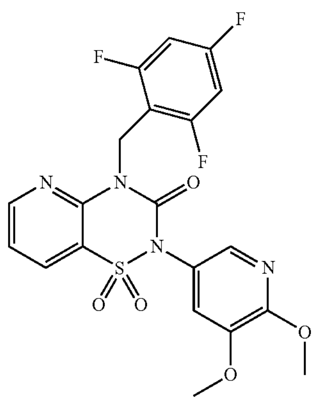 [SMILES: COc1cc(N2C(=O)N(Cc3c(F)cc(F)cc3F)c3ncccc3S2(=O)=O)cnc1OC] | 100 | 2-(5,6-Dimethoxypyridin-3-yl)-4-(2,4,6-trifluorobenzyl)-2H-pyrido[2,3-e][1,2,4]thiadiazin-3(4H)-one 1,1-dioxide | 8.61 |
| 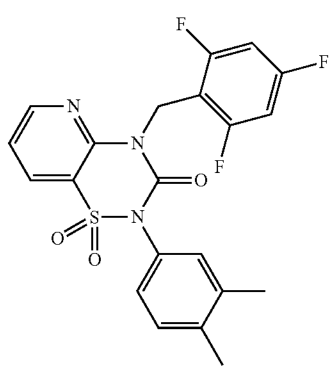 [SMILES: Cc1ccc(N2C(=O)N(Cc3c(F)cc(F)cc3F)c3ncccc3S2(=O)=O)cc1C] | 101 | 2-(3,4-Dimethylphenyl)-4-(2,4,6-trifluorobenzyl)-2H-pyrido[2,3-e][1,2,4]thiadiazin-3(4H)-one 1,1-dioxide | 8.46 |
| 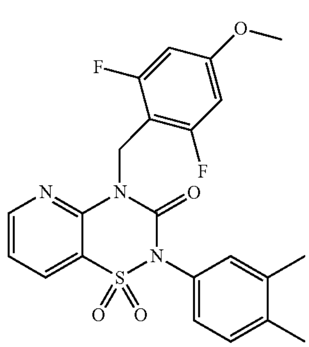 [SMILES: COc1cc(F)c(CN2C(=O)N(c3ccc(C)c(C)c3)S(=O)(=O)c3cccnc32)c(F)c1] | 102 | 4-(2,6-Difluoro-4-methoxybenzyl)-2-(3,4-dimethylphenyl)-2H-pyrido[2,3-e][1,2,4]thiadiazin-3(4H)-one 1,1-dioxide | 9.11 |

TABLE 1-continued

| STRUCTURE | ref number | Name | OX2 pKi ave |
|---|---|---|---|
| 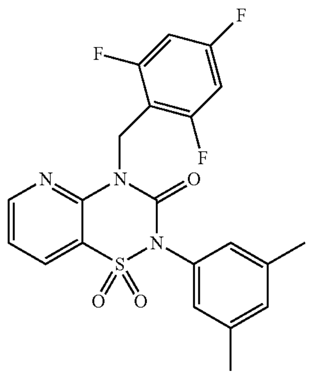 [SMILES: Cc1cc(C)cc(N2C(=O)N(Cc3c(F)cc(F)cc3F)c3ncccc3S2(=O)=O)c1] | 103 | 2-(3,5-Dimethylphenyl)-4-(2,4,6-trifluorobenzyl)-2H-pyrido[2,3-e][1,2,4]thiadiazin-3(4H)-one 1,1-dioxide | 8.37 |
| 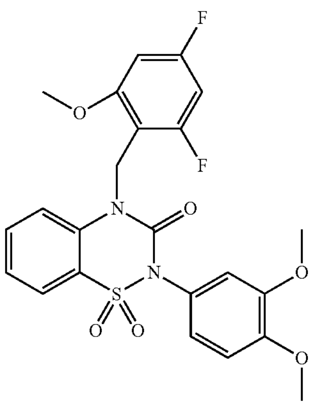 [SMILES: COc1ccc(N2C(=O)N(Cc3c(F)cc(F)cc3OC)c3ccccc3S2(=O)=O)cc1OC] | 104 | 4-(2,4-Difluoro-6-methoxybenzyl)-2-(3,4-dimethoxyphenyl)-2H-1,2,4-benzothiadiazin-3(4H)-one 1,1-dioxide | 8.15 |
| 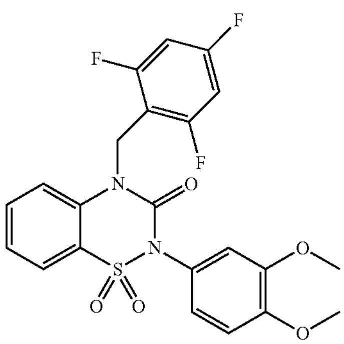 [SMILES: COc1ccc(N2C(=O)N(Cc3c(F)cc(F)cc3F)c3ccccc3S2(=O)=O)cc1OC] | 105 | 2-(3,4-Dimethoxyphenyl)-4-(2,4,6-trifluorobenzyl)-2H-1,2,4-benzothiadiazin-3(4H)-one 1,1-dioxide | 8.71 |
| 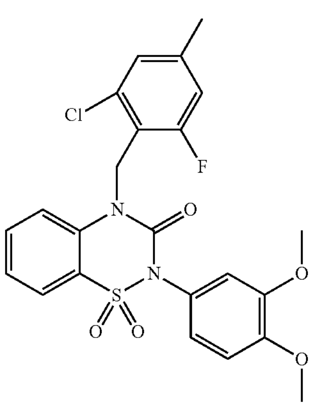 [SMILES: COc1ccc(N2C(=O)N(Cc3c(F)cc(C)cc3Cl)c3ccccc3S2(=O)=O)cc1OC] | 106 | 4-(2-Chloro-6-fluoro-4-methylbenzyl)-2-(3,4-dimethoxyphenyl)-2H-1,2,4-benzothiadiazin-3(4H)-one 1,1-dioxide | 9.13 |

TABLE 1-continued

| STRUCTURE | ref number | Name | OX2 pKi ave |
|---|---|---|---|
| 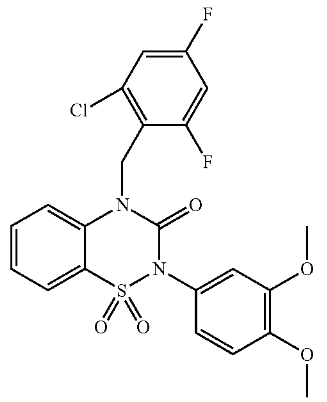 [SMILES: COc1ccc(N2C(=O)N(Cc3c(F)cc(F)cc3Cl)c3ccccc3S2(=O)=O)cc1OC] | 107 | 4-(2-Chloro-4,6-difluorobenzyl)-2-(3,4-dimethoxyphenyl)-2H-1,2,4-benzothiadiazin-3(4H)-one 1,1-dioxide | 8.98 |
| 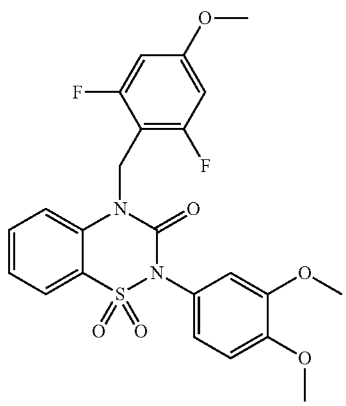 [SMILES: COc1cc(F)c(CN2C(=O)N(c3ccc(OC)c(OC)c3)S(=O)(=O)c3ccccc32)c(F)c1] | 108 | 2-(3,4-Dimethoxyphenyl)-4-(2,6-difluoro-4-methoxybenzyl)-2H-1,2,4-benzothiadiazin-3(4H)-one 1,1-dioxide | 9.33 |
| 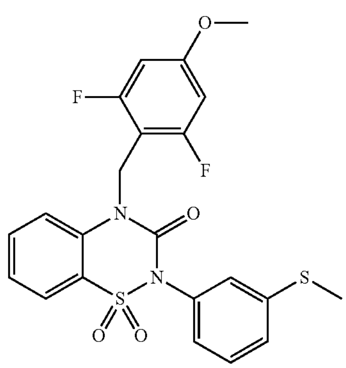 [SMILES: COc1cc(F)c(CN2C(=O)N(c3cccc(SC)c3)S(=O)(=O)c3ccccc32)c(F)c1] | 109 | 4-(2,6-Difluoro-4-methoxybenzyl)-2-[3-(methylsulfanyl)phenyl]-2H-1,2,4-benzothiadiazin-3(4H)-one 1,1-dioxide | 8.49 |
| 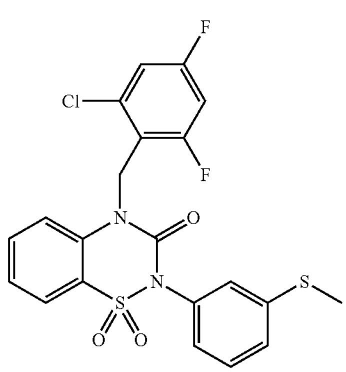 [SMILES: CSc1cccc(N2C(=O)N(Cc3c(F)cc(F)cc3Cl)c3ccccc3S2(=O)=O)c1] | 110 | 4-(2-Chloro-4,6-difluorobenzyl)-2-[3-(methylsulfanyl)phenyl]-2H-1,2,4-benzothiadiazin-3(4H)-one 1,1-dioxide | 8.57 |

TABLE 1-continued

| STRUCTURE | ref number | Name | OX2 pKi ave |
|---|---|---|---|
| 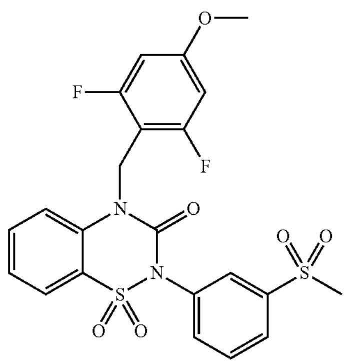 [SMILES: COc1cc(F)c(CN2C(=O)N(c3cccc(S(C)(=O)=O)c3)S(=O)(=O)c3ccccc32)c(F)c1] | 111 | 4-(2,6-Difluoro-4-methoxybenzyl)-2-[3-(methylsulfonyl)phenyl]-2H-1,2,4-benzothiadiazin-3(4H)-one 1,1-dioxide | 8.65 |
| 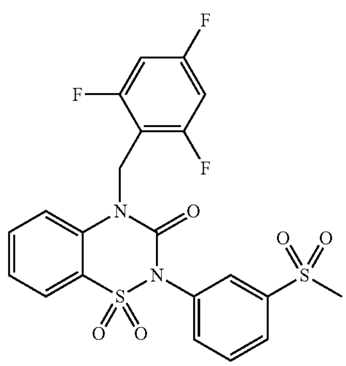 [SMILES: CS(=O)(=O)c1cccc(N2C(=O)N(Cc3c(F)cc(F)cc3F)c3ccccc3S2(=O)=O)c1] | 112 | 2-[3-(Methylsulfonyl)phenyl]-4-(2,4,6-trifluorobenzyl)-2H-1,2,4-benzothiadiazin-3(4H)-one 1,1-dioxide | 7.57 |
| 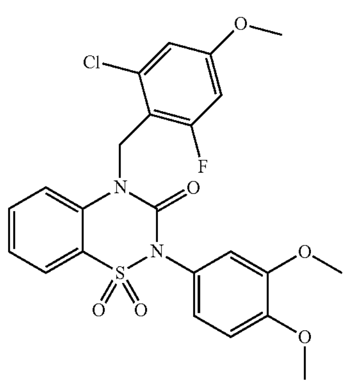 [SMILES: COc1cc(F)c(CN2C(=O)N(c3ccc(OC)c(OC)c3)S(=O)(=O)c3ccccc32)c(Cl)c1] | 113 | 4-(2-Chloro-6-fluoro-4-methoxybenzyl)-2-(3,4-dimethoxyphenyl)-2H-1,2,4-benzothiadiazin-3(4H)-one 1,1-dioxide | 10.04 |
| 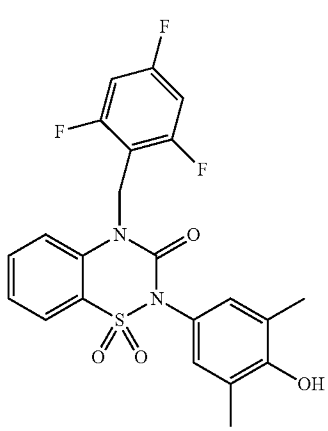 [SMILES: Cc1cc(N2C(=O)N(Cc3c(F)cc(F)cc3F)c3ccccc3S2(=O)=O)cc(C)c1O] | 114 | 2-(4-Hydroxy-3,5-dimethylphenyl)-4-(2,4,6-trifluorobenzyl)-2H-1,2,4-benzothiadiazin-3(4H)-one 1,1-dioxide | 7.89 |

TABLE 1-continued

| STRUCTURE | ref number | Name | OX2 pKi ave |
|---|---|---|---|
| 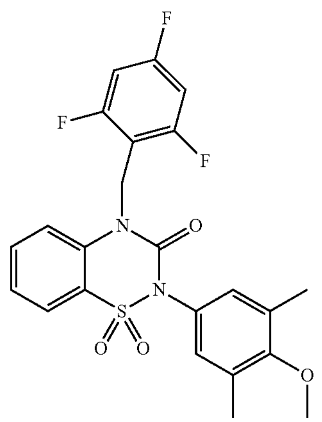 [SMILES: COc1c(C)cc(N2C(=O)N(Cc3c(F)cc(F)cc3F)c3ccccc3S2(=O)=O)cc1C] | 115 | 2-(4-methoxy-3,5-dimethylphenyl)-4-(2,4,6-trifluorobenzyl)-2H-1,2,4-benzothiadiazin-3(4H)-one 1,1-dioxide | 9.45 |
| 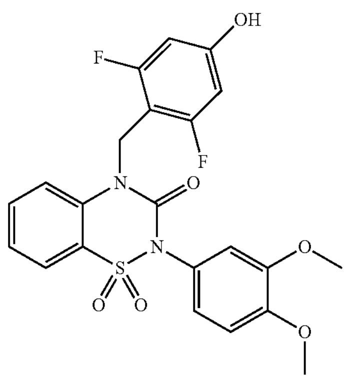 [SMILES: COc1ccc(N2C(=O)N(Cc3c(F)cc(O)cc3F)c3ccccc3S2(=O)=O)cc1OC] | 116 | 4-(2,6-Difluoro-4-hydroxybenzyl)-2-(3,4-dimethoxyphenyl)-2H-1,2,4-benzothiadiazin-3(4H)-one 1,1-dioxide | 8.94 |
| 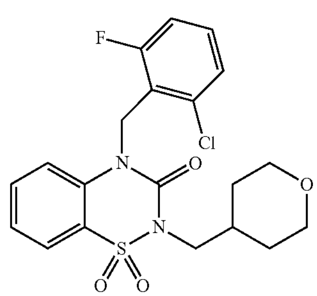 [SMILES: O=C1N(Cc2c(F)cccc2Cl)c2ccccc2S(=O)(=O)N1CC1CCOCC1] | 117 | 4-(2-Chloro-6-fluorobenzyl)-2-(tetrahydro-2H-pyran-4-ylmethyl)-2H-1,2,4-benzothiadiazin-3(4H)-one 1,1-dioxide | 6.43 |
| 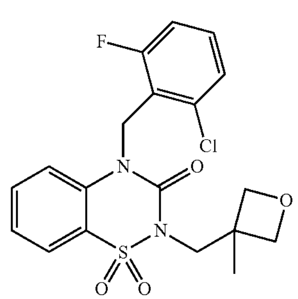 [SMILES: CC1(CN2C(=O)N(Cc3c(F)cccc3Cl)c3ccccc3S2(=O)=O)COC1] | 118 | 4-(2-Chloro-6-fluorobenzyl)-2-[(3-methyloxetan-3-yl)methyl]-2H-1,2,4-benzothiadiazin-3(4H)-one 1,1-dioxide | 6.43 |

TABLE 1-continued

| STRUCTURE | ref number | Name | OX2 pKi ave |
|---|---|---|---|
| 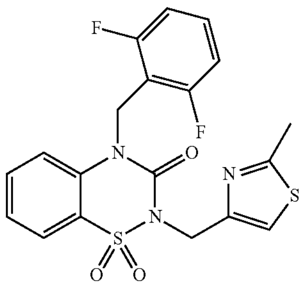 [SMILES: Cc1nc(CN2C(=O)N(Cc3c(F)cccc3F)c3ccccc3S2(=O)=O)cs1] | 119 | 4-(2,6-Difluorobenzyl)-2-[(2-methyl-1,3-thiazol-4-yl)methyl]-2H-1,2,4-benzothiadiazin-3(4H)-one 1,1-dioxide | 7.18 |
| 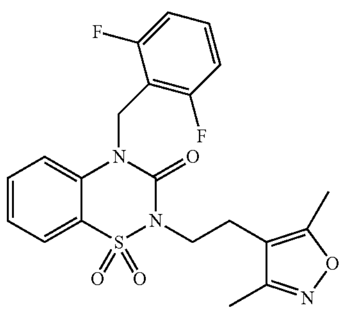 [SMILES: Cc1noc(C)c1CCN1C(=O)N(Cc2c(F)cccc2F)c2ccccc2S1(=O)=O] | 120 | 4-(2,6-Difluorobenzyl)-2-[2-(3,5-dimethyl-1,2-oxazol-4-yl)ethyl]-2H-1,2,4-benzothiadiazin-3(4H)-one 1,1-dioxide | 6.75 |
| 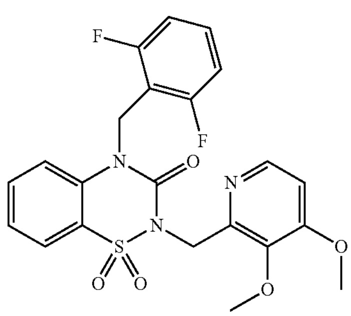 [SMILES: COc1ccnc(CN2C(=O)N(Cc3c(F)cccc3F)c3ccccc3S2(=O)=O)c1OC] | 121 | 4-(2,6-Difluorobenzyl)-2-[(3,4-dimethoxypyridin-2-yl)methyl]-2H-1,2,4-benzothiadiazin-3(4H)-one 1,1-dioxide | 7.06 |
| 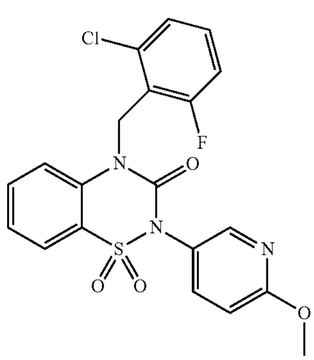 [SMILES: COc1ccc(N2C(=O)N(Cc3c(F)cccc3Cl)c3ccccc3S2(=O)=O)cn1] | 122 | 4-(2-Chloro-6-fluorobenzyl)-2-(6-methoxypyridin-3-yl)-2H-1,2,4-benzothiadiazin-3(4H)-one 1,1-dioxide | 7.78 |

TABLE 1-continued

| STRUCTURE | ref number | Name | OX2 pKi ave |
|---|---|---|---|
| 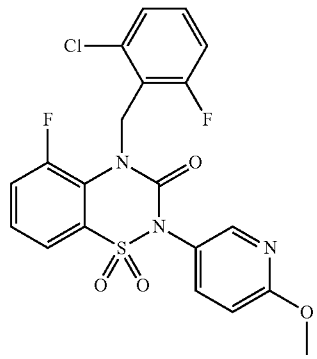 [SMILES: COc1ccc(N2C(=O)N(Cc3c(F)cccc3Cl)c3c(F)cccc3S2(=O)=O)cn1] | 123 | 4-(2-Chloro-6-fluorobenzyl)-5-fluoro-2-(6-methoxypyridin-3-yl)-2H-1,2,4-benzothiadiazin-3(4H)-one 1,1-dioxide | 7.36 |
| 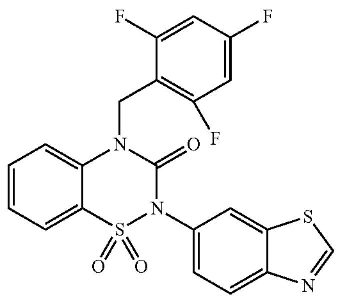 [SMILES: O=C1N(Cc2c(F)cc(F)cc2F)c2ccccc2S(=O)(=O)N1c1ccc2ncsc2c1] | 124 | 2-(1,3-Benzothiazol-6-yl)-4-(2,4,6-trifluorobenzyl)-2H-1,2,4-benzothiadiazin-3(4H)-one 1,1-dioxide | 8.3 |
| 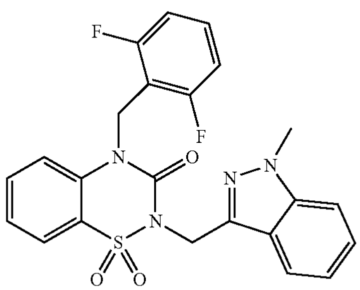 [SMILES: Cn1nc(CN2C(=O)N(Cc3c(F)cccc3F)c3ccccc3S2(=O)=O)c2ccccc21] | 125 | 4-(2,6-Difluorobenzyl)-2-[(1-methyl-1H-indazol-3-yl)methyl]-2H-1,2,4-benzothiadiazin-3(4H)-one 1,1-dioxide | 7.42 |
| 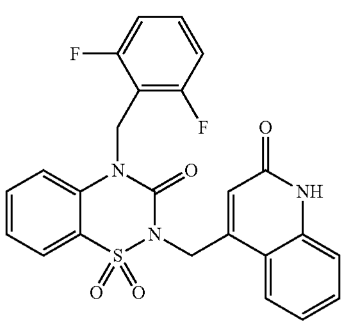 [SMILES: O=C1N(Cc2c(F)cccc2F)c2ccccc2S(=O)(=O)N1Cc1cc(=O)[nH]c2ccccc12] | 126 | 4-(2,6-Difluorobenzyl)-2-[(2-oxo-1,2-dihydroquinolin-4-yl)methyl]-2H-1,2,4-benzothiadiazin-3(4H)-one 1,1-dioxide | 7.45 |
| 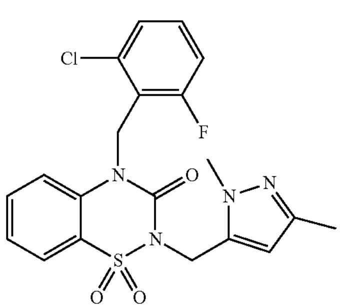 [SMILES: Cc1cc(CN2C(=O)N(Cc3c(F)cccc3Cl)c3ccccc3S2(=O)=O)n(C)n1] | 127 | 4-(2-Chloro-6-fluorobenzyl)-2-[(1,3-dimethyl-1H-pyrazol-5-yl)methyl]-2H-1,2,4-benzothiadiazin-3(4H)-one 1,1-dioxide | 7.23 |

TABLE 1-continued

| STRUCTURE | ref number | Name | OX2 pKi ave |
|---|---|---|---|
| 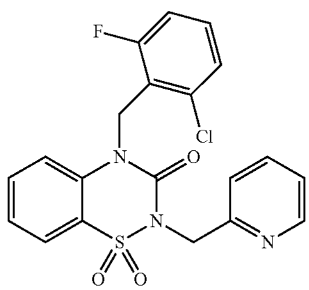 [SMILES: O=C1N(Cc2c(F)cccc2Cl)c2ccccc2S(=O)(=O)N1Cc1ccccn1] | 128 | 4-(2-Chloro-6-fluorobenzyl)-2-(pyridin-2-ylmethyl)-2H-1,2,4-benzothiadiazin-3(4H)-one 1,1-dioxide | 7.1 |
| 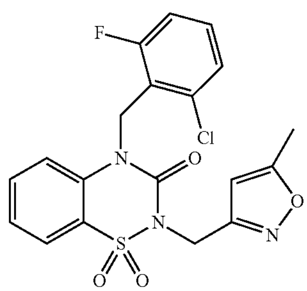 [SMILES: Cc1cc(CN2C(=O)N(Cc3c(F)cccc3Cl)c3ccccc3S2(=O)=O)no1] | 129 | 4-(2-Chloro-6-fluorobenzyl)-2-[(5-methyl-1,2-oxazol-3-yl)methyl]-2H-1,2,4-benzothiadiazin-3(4H)-one 1,1-dioxide | 6.94 |
| 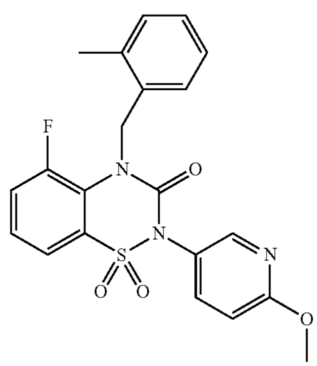 [SMILES: COc1ccc(N2C(=O)N(Cc3ccccc3C)c3c(F)cccc3S2(=O)=O)cn1] | 130 | 5-Fluoro-2-(6-methoxypyridin-3-yl)-4-(2-methylbenzyl)-2H-1,2,4-benzothiadiazin-3(4H)-one 1,1-dioxide | 7.06 |
| 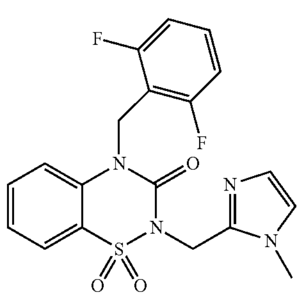 [SMILES: Cn1ccnc1CN1C(=O)N(Cc2c(F)cccc2F)c2ccccc2S1(=O)=O] | 131 | 4-(2,6-Difluorobenzyl)-2-[(1-methyl-1H-imidazol-2-yl)methyl]-2H-1,2,4-benzothiadiazin-3(4H)-one 1,1-dioxide | 6.53 |
| 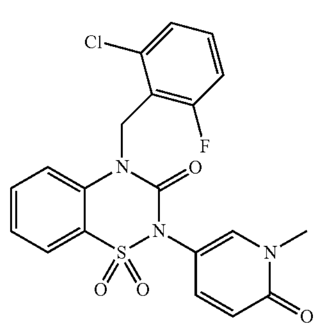 [SMILES: Cn1cc(N2C(=O)N(Cc3c(F)cccc3Cl)c3ccccc3S2(=O)=O)ccc1=O] | 132 | 4-(2-Chloro-6-fluorobenzyl)-2-(1-methyl-6-oxo-1,6-dihydropyridin-3-yl)-2H-1,2,4-benzothiadiazin-3(4H)-one 1,1-dioxide | 6.52 |

TABLE 1-continued

| STRUCTURE | ref number | Name | OX2 pKi ave |
|---|---|---|---|
| 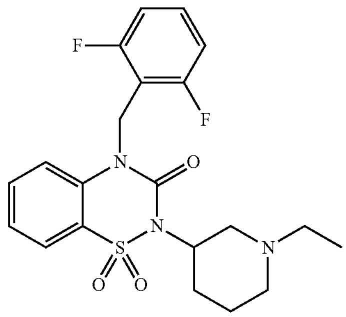 [SMILES: CCN1CCCC(N2C(=O)N(Cc3c(F)cccc3F)c3ccccc3S2(=O)=O)C1] | 133 | 4-(2,6-Difluorobenzyl)-2-(1-ethylpiperidin-3-yl)-2H-1,2,4-benzothiadiazin-3(4H)-one 1,1-dioxide | 6.18 |
| 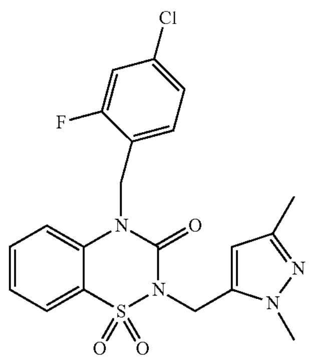 [SMILES: Cc1cc(CN2C(=O)N(Cc3ccc(Cl)cc3F)c3ccccc3S2(=O)=O)n(C)n1] | 134 | 4-(4-Chloro-2-fluorobenzyl)-2-[(1,3-dimethyl-1H-pyrazol-5-yl)methyl]-2H-1,2,4-benzothiadiazin-3(4H)-one 1,1-dioxide | 7.4 |
| 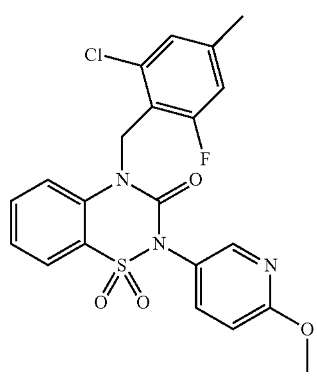 [SMILES: COc1ccc(N2C(=O)N(Cc3c(F)cc(C)cc3Cl)c3ccccc3S2(=O)=O)cn1] | 135 | 4-(2-Chloro-6-fluoro-4-methylbenzyl)-2-(6-methoxypyridin-3-yl)-2H-1,2,4-benzothiadiazin-3(4H)-one 1,1-dioxide | 7.86 |
| 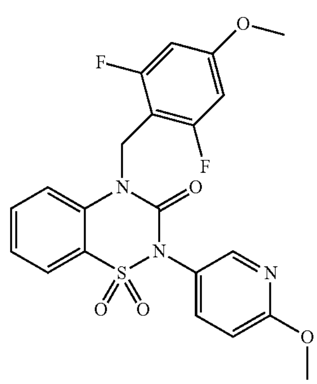 [SMILES: COc1cc(F)c(CN2C(=O)N(c3ccc(OC)nc3)S(=O)(=O)c3ccccc32)c(F)c1] | 136 | 4-(2,6-Difluoro-4-methoxybenzyl)-2-(6-methoxypyridin-3-yl)-2H-1,2,4-benzothiadiazin-3(4H)-one 1,1-dioxide | 7.97 |

TABLE 1-continued

| STRUCTURE | ref number | Name | OX2 pKi ave |
|---|---|---|---|
| 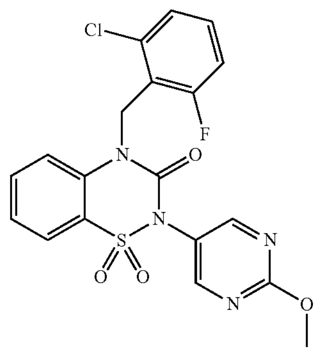 [SMILES: COc1ncc(N2C(=O)N(Cc3c(F)cccc3Cl)c3ccccc3S2(=O)=O)cn1] | 137 | 4-(2-Chloro-6-fluorobenzyl)-2-(2-methoxypyrimidin-5-yl)-2H-1,2,4-benzothiadiazin-3(4H)-one 1,1-dioxide | 7.42 |
| 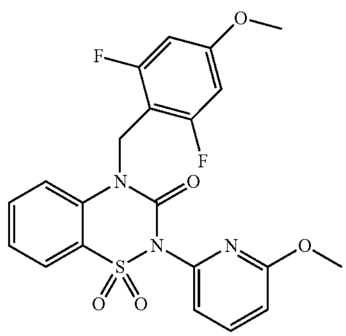 [SMILES: COc1cc(F)c(CN2C(=O)N(c3cccc(OC)n3)S(=O)(=O)c3ccccc32)c(F)c1] | 138 | 4-(2,6-Difluoro-4-methoxybenzyl)-2-(6-methoxypyridin-2-yl)-2H-1,2,4-benzothiadiazin-3(4H)-one 1,1-dioxide | 8.84 |
| 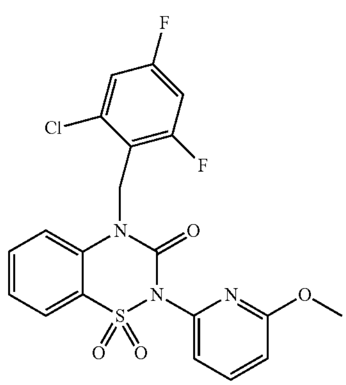 [SMILES: COc1cccc(N2C(=O)N(Cc3c(F)cc(F)cc3Cl)c3ccccc3S2(=O)=O)n1] | 139 | 4-(2-Chloro-4,6-difluorobenzyl)-2-(6-methoxypyridin-2-yl)-2H-1,2,4-benzothiadiazin-3(4H)-one 1,1-dioxide | 7.86 |
| 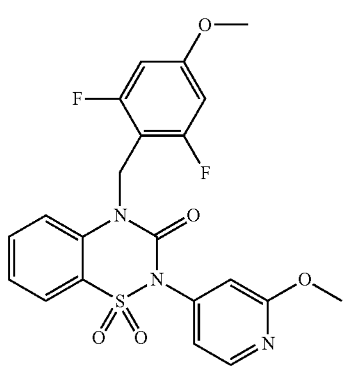 [SMILES: COc1cc(F)c(CN2C(=O)N(c3ccnc(OC)c3)S(=O)(=O)c3ccccc32)c(F)c1] | 140 | 4-(2,6-Difluoro-4-methoxybenzyl)-2-(2-methoxypyridin-4-yl)-2H-1,2,4-benzothiadiazin-3(4H)-one 1,1-dioxide | 8.48 |

TABLE 1-continued

| STRUCTURE | ref number | Name | OX2 pKi ave |
|---|---|---|---|
| 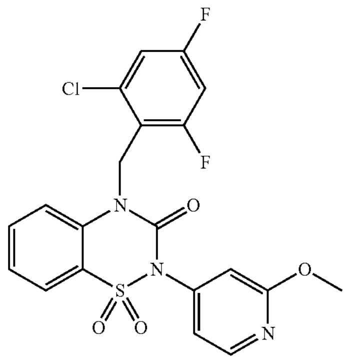 [SMILES: COc1cc(N2C(=O)N(Cc3c(F)cc(F)cc3Cl)c3ccccc3S2(=O)=O)ccn1] | 141 | 4-(2-Chloro-4,6-difluorobenzyl)-2-(2-methoxypyridin-4-yl)-2H-1,2,4-benzothiadiazin-3(4H)-one 1,1-dioxide | 8.16 |
| 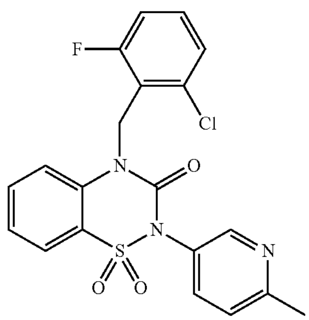 [SMILES: Cc1ccc(N2C(=O)N(Cc3c(F)cccc3Cl)c3ccccc3S2(=O)=O)cn1] | 142 | 4-(2-Chloro-6-fluorobenzyl)-2-(6-methylpyridin-3-yl)-2H-1,2,4-benzothiadiazin-3(4H)-one 1,1-dioxide | 7.53 |
| 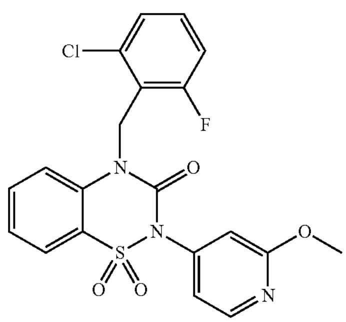 [SMILES: COc1cc(N2C(=O)N(Cc3c(F)cccc3Cl)c3ccccc3S2(=O)=O)ccn1] | 143 | 4-(2-Chloro-6-fluorobenzyl)-2-(2-methoxypyridin-4-yl)-2H-1,2,4-benzothiadiazin-3(4H)-one 1,1-dioxide | 7.8 |
| 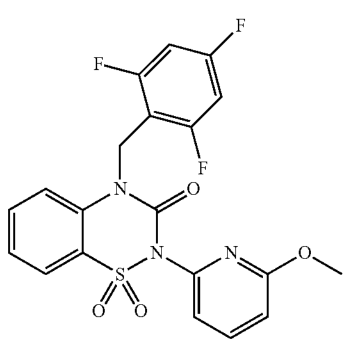 [SMILES: COc1cccc(N2C(=O)N(Cc3c(F)cc(F)cc3F)c3ccccc3S2(=O)=O)n1] | 144 | 2-(6-Methoxypyridin-2-yl)-4-(2,4,6-trifluorobenzyl)-2H-1,2,4-benzothiadiazin-3(4H)-one 1,1-dioxide | 7.3 |

TABLE 1-continued

| STRUCTURE | ref number | Name | OX2 pKi ave |
|---|---|---|---|
| 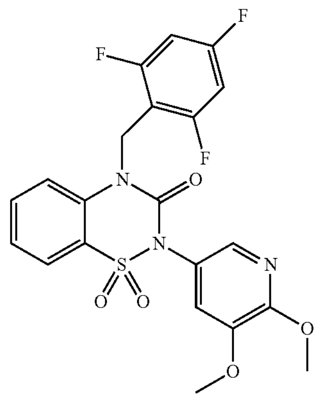 [SMILES: COc1cc(N2C(=O)N(Cc3c(F)cc(F)cc3F)c3ccccc3S2(=O)=O)cnc1OC] | 145 | 2-(5,6-Dimethoxypyridin-3-yl)-4-(2,4,6-trifluorobenzyl)-2H-1,2,4-benzothiadiazin-3(4H)-one 1,1-dioxide | 8.33 |
| 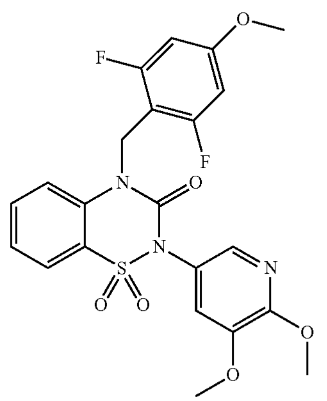 [SMILES: COc1cc(F)c(CN2C(=O)N(c3cnc(OC)c(OC)c3)S(=O)(=O)c3ccccc32)c(F)c1] | 146 | 4-(2,6-difluoro-4-methoxybenzyl)-2-(5,6-Dimethoxypyridin-3-yl)-2H-1,2,4-benzothiadiazin-3(4H)-one 1,1-dioxide | 9.44 |
| 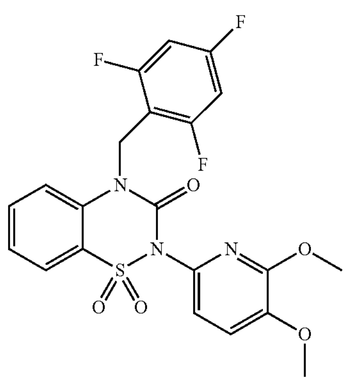 [SMILES: COc1ccc(N2C(=O)N(Cc3c(F)cc(F)cc3F)c3ccccc3S2(=O)=O)nc1OC] | 147 | 2-(5,6-Dimethoxypyridin-2-yl)-4-(2,4,6-trifluorobenzyl)-2H-1,2,4-benzothiadiazin-3(4H)-one 1,1-dioxide | 8.8 |
| 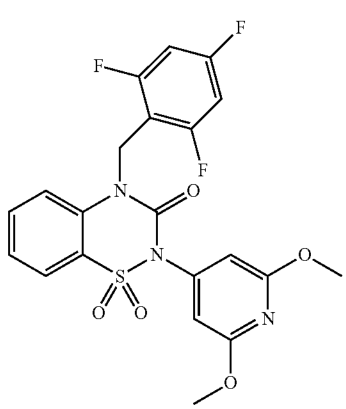 [SMILES: COc1cc(N2C(=O)N(Cc3c(F)cc(F)cc3F)c3ccccc3S2(=O)=O)cc(OC)n1] | 148 | 2-(2,6-Dimethoxypyridin-4-yl)-4-(2,4,6-trifluorobenzyl)-2H-1,2,4-benzothiadiazin-3(4H)-one 1,1-dioxide | 8.86 |

TABLE 1-continued

| STRUCTURE | ref number | Name | OX2 pKi ave |
|---|---|---|---|
| 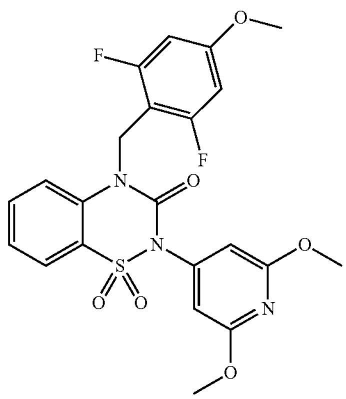 [SMILES: COc1cc(F)c(CN2C(=O)N(c3cc(OC)nc(OC)c3)S(=O)(=O)c3ccccc32)c(F)c1] | 149 | 4-(2,6-Difluoro-4-methoxybenzyl)-2-(2,6-dimethoxypyridin-4-yl)-2H-1,2,4-benzothiadiazin-3(4H)-one 1,1-dioxide | 9.86 |
| 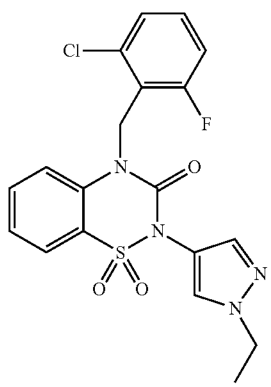 [SMILES: CCn1cc(N2C(=O)N(Cc3c(F)cccc3Cl)c3ccccc3S2(=O)=O)cn1] | 150 | 4-(2-Chloro-6-fluorobenzyl)-2-(1-ethyl-1H-pyrazol-4-yl)-2H-1,2,4-benzothiadiazin-3(4H)-one 1,1-dioxide | 7.76 |
| 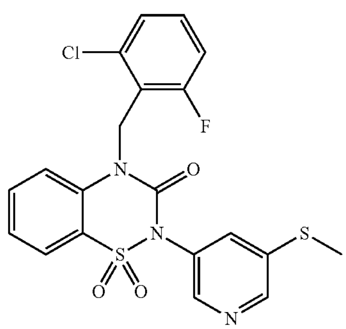 [SMILES: CSc1cncc(N2C(=O)N(Cc3c(F)cccc3Cl)c3ccccc3S2(=O)=O)c1] | 151 | 4-(2-Chloro-6-fluorobenzyl)-2-[5-(methylsulfanyl)pyridin-3-yl]-2H-1,2,4-benzothiadiazin-3(4H)-one 1,1-dioxide | 8.7 |
| 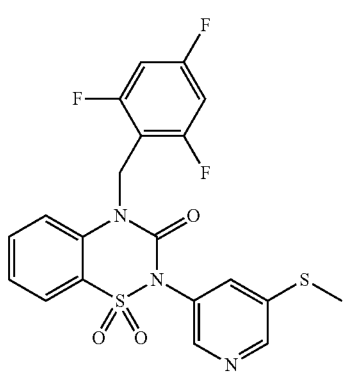 [SMILES: CSc1cncc(N2C(=O)N(Cc3c(F)cc(F)cc3F)c3ccccc3S2(=O)=O)c1] | 152 | 2-[5-(Methylsulfanyl)pyridin-3-yl]-4-(2,4,6-trifluorobenzyl)-2H-1,2,4-benzothiadiazin-3(4H)-one 1,1-dioxide | 8.23 |

TABLE 1-continued

| STRUCTURE | ref number | Name | OX2 pKi ave |
|---|---|---|---|
| 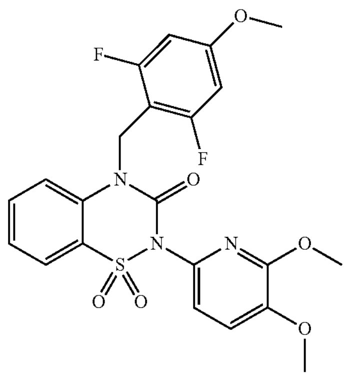 [SMILES: COc1cc(F)c(CN2C(=O)N(c3ccc(OC)c(OC)n3)S(=O)(=O)c3ccccc32)c(F)c1] | 153 | 4-(2,6-Difluoro-4-methoxybenzyl)-2-(5,6-dimethoxypyridin-2-yl)-2H-1,2,4-benzothiadiazin-3(4H)-one 1,1-dioxide | 9.65 |
| 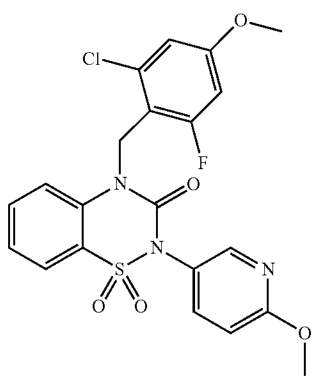 [SMILES: COc1cc(F)c(CN2C(=O)N(c3ccc(OC)nc3)S(=O)(=O)c3ccccc32)c(Cl)c1] | 154 | 4-(2-Chloro-6-fluoro-4-methoxybenzyl)-2-(6-methoxypyridin-3-yl)-2H-1,2,4-benzothiadiazin-3(4H)-one 1,1-dioxide | 8.52 |
| 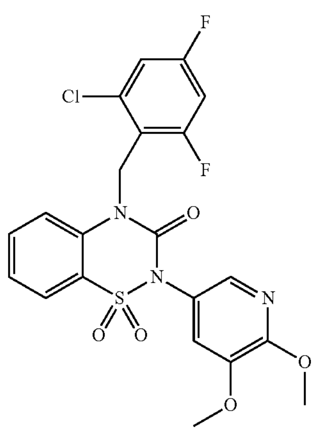 [SMILES: COc1cc(N2C(=O)N(Cc3c(F)cc(F)cc3Cl)c3ccccc3S2(=O)=O)cnc1OC] | 155 | 4-(2-Chloro-4,6-difluorobenzyl)-2-(5,6-dimethoxypyridin-3-yl)-2H-1,2,4-benzothiadiazin-3(4H)-one 1,1-dioxide | 8.76 |
| 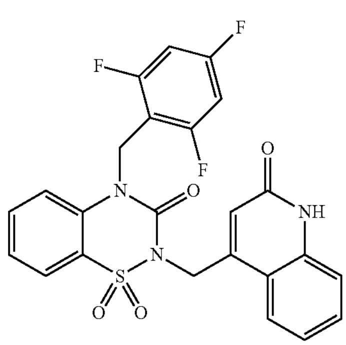 [SMILES: O=C1N(Cc2c(F)cc(F)cc2F)c2ccccc2S(=O)(=O)N1Cc1cc(=O)[nH]c2ccccc12] | 156 | 4-(2,4,6-Trifluorobenzyl)-2-[(2-oxo-1,2-dihydroquinolin-4-yl)methyl]-2H-1,2,4-benzothiadiazin-3(4H)-one 1,1-dioxide | 7.95 |

TABLE 1-continued

| STRUCTURE | ref number | Name | OX2 pKi ave |
|---|---|---|---|
| 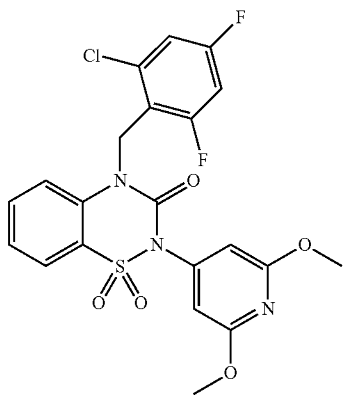 | 157 | 4-(2-Chloro-4,6-difluorobenzyl)-2-(2,6-dimethoxypyridin-4-yl)-2H-1,2,4-benzothiadiazin-3(4H)-one 1,1-dioxide | 9.24 |
| 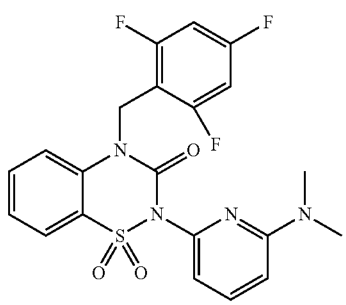 [SMILES: CN(C)c1cccc(N2C(=O)N(Cc3c(F)cc(F)cc3F)c3ccccc3S2(=O)=O)n1] | 158 | 2-[6-(Dimethylamino)pyridin-2-yl]-4-(2,4,6-trifluorobenzyl)-2H-1,2,4-benzothiadiazin-3(4H)-one 1,1-dioxide | 8.47 |
| 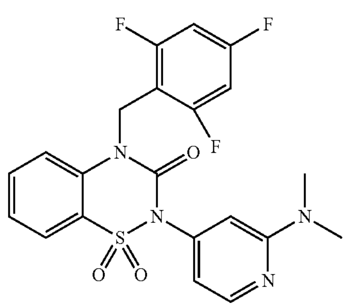 [SMILES: CN(C)c1cc(N2C(=O)N(Cc3c(F)cc(F)cc3F)c3ccccc3S2(=O)=O)ccn1] | 159 | 2-[2-(Dimethylamino)pyridin-4-yl]-4-(2,4,6-trifluorobenzyl)-2H-1,2,4-benzothiadiazin-3(4H)-one 1,1-dioxide | 8.51 |
| 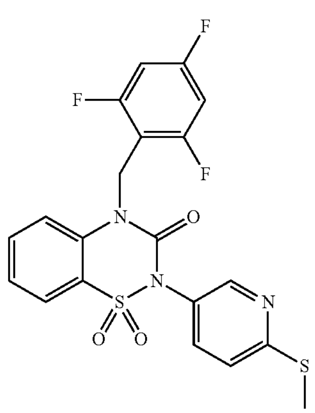 [SMILES: CSc1ccc(N2C(=O)N(Cc3c(F)cc(F)cc3F)c3ccccc3S2(=O)=O)cn1] | 160 | 2-[6-(Methylsulfanyl)pyridin-3-yl]-4-(2,4,6-trifluorobenzyl)-2H-1,2,4-benzothiadiazin-3(4H)-one 1,1-dioxide | 7.76 |

TABLE 1-continued

| STRUCTURE | ref number | Name | OX2 pKi ave |
|---|---|---|---|
| 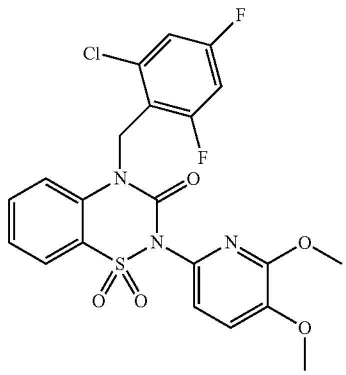 [SMILES: COc1ccc(N2C(=O)N(Cc3c(F)cc(F)cc3Cl)c3ccccc3S2(=O)=O)nc1OC] | 161 | 4-(2-Chloro-4,6-difluorobenzyl)-2-(5,6-dimethoxypyridin-2-yl)-2H-1,2,4-benzothiadiazin-3(4H)-one 1,1-dioxide | 8.9 |
| 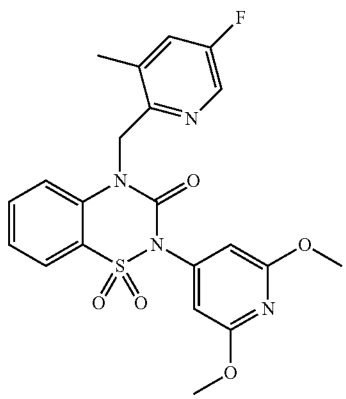 [SMILES: COc1cc(N2C(=O)N(Cc3ncc(F)cc3C)c3ccccc3S2(=O)=O)cc(OC)n1] | 162 | 2-(2,6-Dimethoxypyridin-4-yl)-4-[(5-fluoro-3-methylpyridin-2-yl)methyl]-2H-1,2,4-benzothiadiazin-3(4H)-one 1,1-dioxide | 7.73 |
| 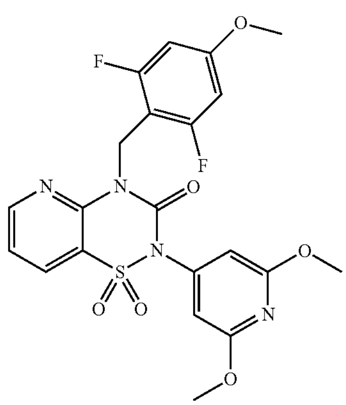 [SMILES: COc1cc(F)c(CN2C(=O)N(c3cc(OC)nc(OC)c3)S(=O)(=O)c3cccnc32)c(F)c1] | 163 | 4-(2,6-Difluoro-4-methoxybenzyl)-2-(2,6-dimethoxypyridin-4-yl)-2H-pyrido[2,3-e][1,2,4]thiadiazin-3(4H)-one 1,1-dioxide | 8.86 |
| 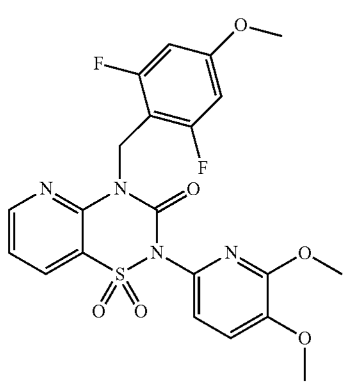 [SMILES: COc1cc(F)c(CN2C(=O)N(c3ccc(OC)c(OC)n3)S(=O)(=O)c3cccnc32)c(F)c1] | 164 | 4-(2,6-Difluoro-4-methoxybenzyl)-2-(5,6-dimethoxypyridin-2-yl)-2H-pyrido[2,3-e][1,2,4]thiadiazin-3(4H)-one 1,1-dioxide | 9.18 |

TABLE 1-continued

| STRUCTURE | ref number | Name | OX2 pKi ave |
|---|---|---|---|
| 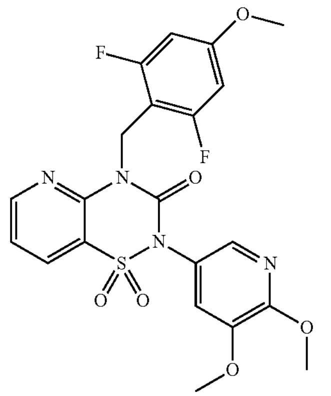 [SMILES: COc1cc(F)c(CN2C(=O)N(c3cnc(OC)c(OC)c3)S(=O)(=O)c3cccnc32)c(F)c1] | 165 | 4-(2,6-Difluoro-4-methoxybenzyl)-2-(5,6-dimethoxypyridin-3-yl)-2H-pyrido[2,3-e][1,2,4]thiadiazin-3(4H)-one 1,1-dioxide | 9.17 |
| 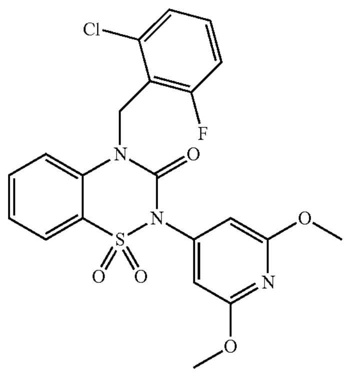 | 166 | 4-(2-Chloro-6-fluorobenzyl)-2-(2,6-dimethoxypyridin-4-yl)-2H-1,2,4-benzothiadiazin-3(4H)-one 1,1-dioxide | 8.57 |
| 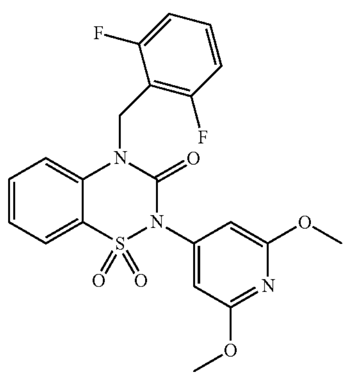 [SMILES: COc1cc(N2C(=O)N(Cc3c(F)cccc3F)c3ccccc3S2(=O)=O)cc(OC)n1] | 167 | 4-(2,6-Difluorobenzyl)-2-(2,6-dimethoxypyridin-4-yl)-2H-1,2,4-benzothiadiazin-3(4H)-one 1,1-dioxide | 8.66 |
| 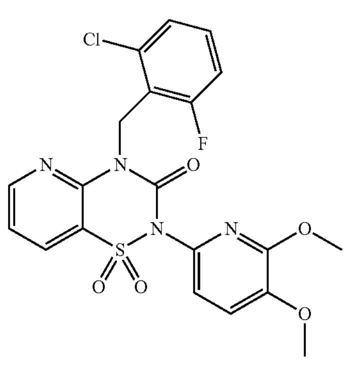 [SMILES: COc1ccc(N2C(=O)N(Cc3c(F)cccc3Cl)c3ncccc3S2(=O)=O)nc1OC] | 168 | 4-(2-Chloro-6-fluorobenzyl)-2-(5,6-dimethoxypyridin-2-yl)-2H-pyrido[2,3-e][1,2,4]thiadiazin-3(4H)-one 1,1-dioxide | 8.91 |

TABLE 1-continued

| STRUCTURE | ref number | Name | OX2 pKi ave |
|---|---|---|---|
| 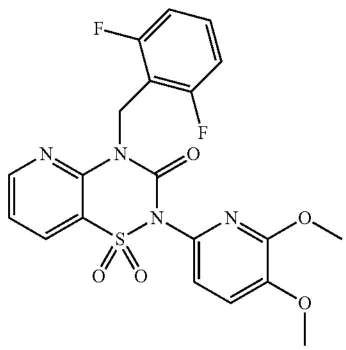 [SMILES: COc1ccc(N2C(=O)N(Cc3c(F)cccc3F)c3ncccc3S2(=O)=O)nc1OC] | 169 | 4-(2,-Difluorobenzyl)-2-(5,6-dimethoxypyridin-2-yl)-2H-pyrido[2,3-e][1,2,4]thiadiazin-3(4H)-one 1,1-dioxide | 9.07 |
| 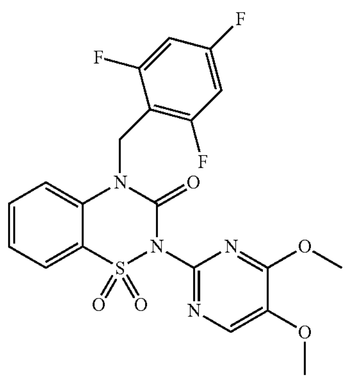 [SMILES: COc1cnc(N2C(=O)N(Cc3c(F)cc(F)cc3F)c3ccccc3S2(=O)=O)nc1OC] | 170 | 2-(4,5-dimethoxypyrimidin-2-yl)-4-(2,4,6-trifluorobenzyl)-2H-1,2,4-benzothiadiazin-3(4H)-one 1,1-dioxide | 8.14 |
| 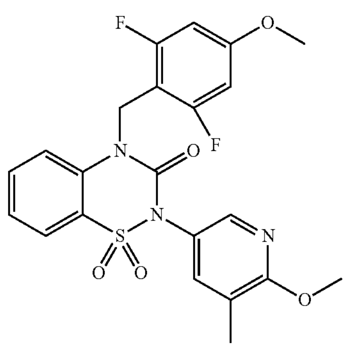 [SMILES: COc1cc(F)c(CN2C(=O)N(c3cnc(OC)c(C)c3)S(=O)(=O)c3ccccc32)c(F)c1] | 171 | 4-(2,6-difluoro-4-methoxybenzyl)-2-(6-methoxy-5-methylpyridin-3-yl)-2H-1,2,4-benzothiadiazin-3(4H)-one 1,1-dioxide | 8.75 |
| 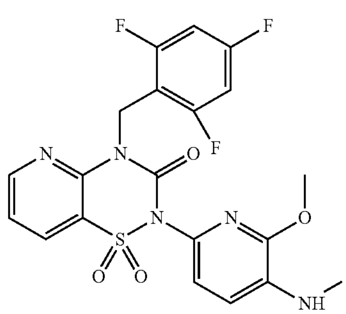 [SMILES: CNc1ccc(N2C(=O)N(Cc3c(F)cc(F)cc3F)c3ncccc3S2(=O)=O)nc1OC] | 172 | 2-[6-methoxy-5-(methylamino)pyridin-2-yl]-4-(2,4,6-trifluorobenzyl)-2H-pyrido[2,3-e][1,2,4]thiadiazin-3(4H)-one 1,1-dioxide | 8.11 |

TABLE 1-continued

| STRUCTURE | ref number | Name | OX2 pKi ave |
|---|---|---|---|
| 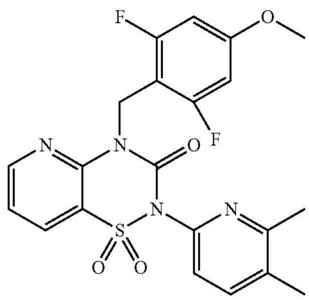 [SMILES: COc1cc(F)c(CN2C(=O)N(c3ccc(C)c(C)n3)S(=O)(=O)c3cccnc32)c(F)c1] | 173 | 4-(2,6-difluoro-4-methoxybenzyl)-2-(5,6-dimethylpyridin-2-yl)-2H-pyrido[2,3-e][1,2,4]thiadiazin-3(4H)-one 1,1-dioxide | 8.62 |
| 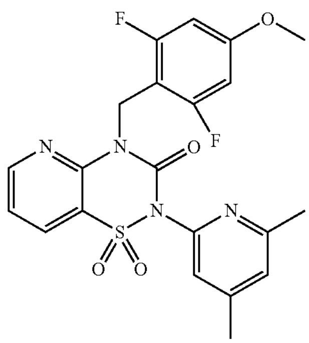 [SMILES: COc1cc(F)c(CN2C(=O)N(c3cc(C)cc(C)n3)S(=O)(=O)c3cccnc32)c(F)c1] | 174 | 4-(2,6-difluoro-4-methoxybenzyl)-2-(4,6-dimethylpyridin-2-yl)-2H-pyrido[2,3-e][1,2,4]thiadiazin-3(4H)-one 1,1-dioxide | 8.14 |
| 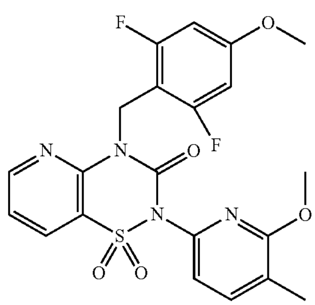 [SMILES: COc1cc(F)c(CN2C(=O)N(c3ccc(C)c(OC)n3)S(=O)(=O)c3cccnc32)c(F)c1] | 175 | 4-(2,6-difluoro-4-methoxybenzyl)-2-(6-methoxy-5-methylpyridin-2-yl)-2H-pyrido[2,3-e][1,2,4]thiadiazin-3(4H)-one 1,1-dioxide | 8.87 |
| 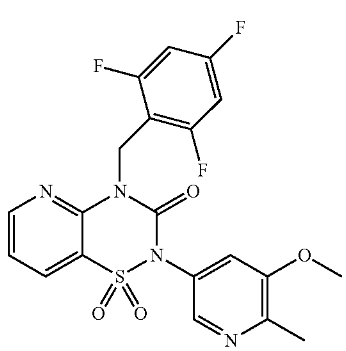 [SMILES: COc1cc(N2C(=O)N(Cc3c(F)cc(F)cc3F)c3ncccc3S2(=O)=O)cnc1C] | 176 | 2-(5-methoxy-6-methylpyridin-3-yl)-4-(2,4,6-trifluorobenzyl)-2H-pyrido[2,3-e][1,2,4]thiadiazin-3(4H)-one 1,1-dioxide | 8.19 |

TABLE 1-continued

| STRUCTURE | ref number | Name | OX2 pKi ave |
|---|---|---|---|
| 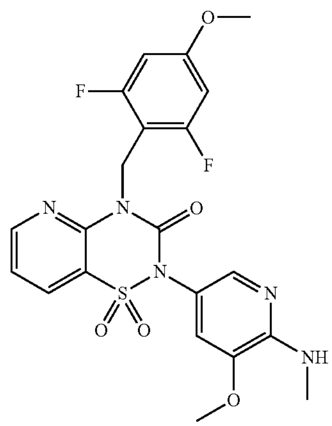 [SMILES: CNc1ncc(N2C(=O)N(Cc3c(F)cc(OC)cc3F)c3ncccc3S2(=O)=O)cc1OC] | 177 | 4-(2,6-difluoro-4-methoxybenzyl)-2-[5-methoxy-6-(methylamino)pyridin-3-yl]-2H-pyrido[2,3-e][1,2,4]thiadiazin-3(4H)-one 1,1-dioxide | 8.66 |
| 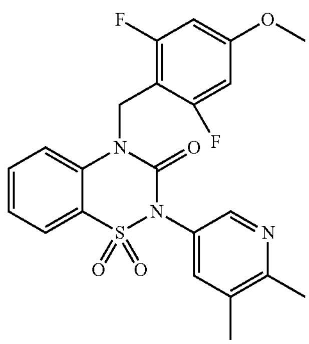 [SMILES: COc1cc(F)c(CN2C(=O)N(c3cnc(C)c(C)c3)S(=O)(=O)c3ccccc32)c(F)c1] | 178 | 4-(2,6-difluoro-4-methoxybenzyl)-2-(5,6-dimethylpyridin-3-yl)-2H-1,2,4-benzothiadiazin-3(4H)-one 1,1-dioxide | 8.36 |
| 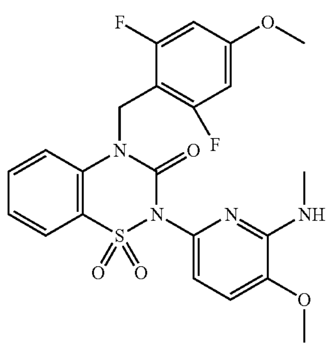 [SMILES: CNc1nc(N2C(=O)N(Cc3c(F)cc(OC)cc3F)c3ccccc3S2(=O)=O)ccc1OC] | 179 | 4-(2,6-difluoro-4-methoxybenzyl)-2-[5-methoxy-6-(methylamino)pyridin-2-yl]-2H-1,2,4-benzothiadiazin-3(4H)-one 1,1-dioxide | 8.43 |
| 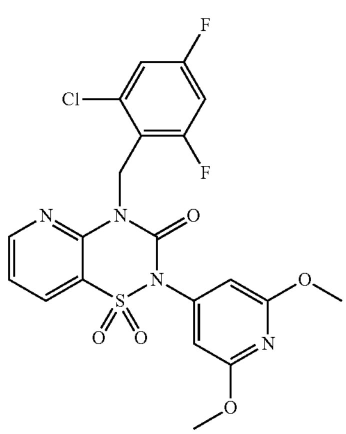 [SMILES: COc1cc(N2C(=O)N(Cc3c(F)cc(F)cc3Cl)c3ncccc3S2(=O)=O)cc(OC)n1] | 180 | 4-(2-chloro-4,6-difluorobenzyl)-2-(2,6-dimethoxypyridin-4-yl)-2H-pyrido[2,3-e][1,2,4]thiadiazin-3(4H)-one 1,1-dioxide | 8.69 |

TABLE 1-continued

| STRUCTURE | ref number | Name | OX2 pKi ave |
|---|---|---|---|
| 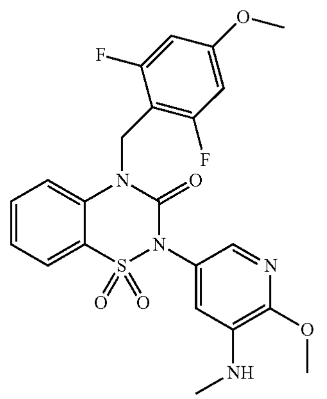 [SMILES: CNc1cc(N2C(=O)N(Cc3c(F)cc(OC)cc3F)c3ccccc3S2(=O)=O)cnc1OC] | 181 | 4-(2,6-difluoro-4-methoxybenzyl)-2-[6-methoxy-5-(methylamino)pyridin-3-yl]-2H-1,2,4-benzothiadiazin-3(4H)-one 1,1-dioxide | 8.79 |
| 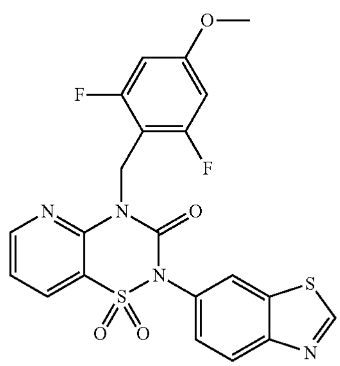 [SMILES: COc1cc(F)c(CN2C(=O)N(c3ccc4ncsc4c3)S(=O)(=O)c3cccnc32)c(F)c1] | 182 | 2-(1,3-benzothiazol-6-yl)-4-(2,6-difluoro-4-methoxybenzyl)-2H-pyrido[2,3-e][1,2,4]thiadiazin-3(4H)-one 1,1-dioxide | 8.35 |
| 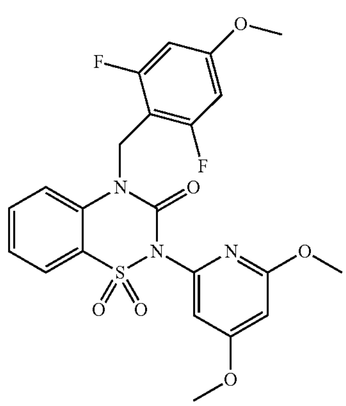 [SMILES: COc1cc(OC)nc(N2C(=O)N(Cc3c(F)cc(OC)cc3F)c3ccccc3S2(=O)=O)c1] | 183 | 4-(2,6-difluoro-4-methoxybenzyl)-2-(4,6-dimethoxypyridin-2-yl)-2H-1,2,4-benzothiadiazin-3(4H)-one 1,1-dioxide | 8.56 |
| 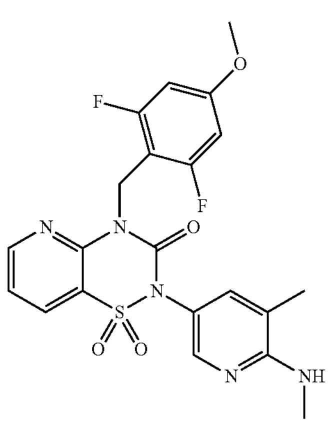 [SMILES: CNc1ncc(N2C(=O)N(Cc3c(F)cc(OC)cc3F)c3ncccc3S2(=O)=O)cc1C] | 184 | 4-(2,6-difluoro-4-methoxybenzyl)-2-[5-methyl-6-(methylamino)pyridin-3-yl]-2H-pyrido[2,3-e][1,2,4]thiadiazin-3(4H)-one 1,1-dioxide | 8.07 |

TABLE 1-continued

| STRUCTURE | ref number | Name | OX2 pKi ave |
|---|---|---|---|
| 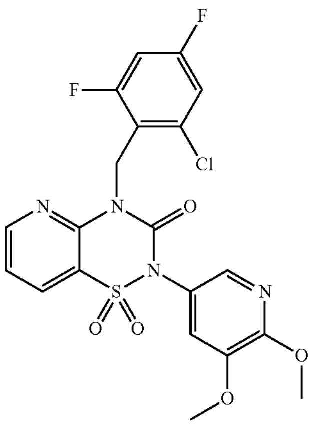 [SMILES: COc1cc(N2C(=O)N(Cc3c(F)cc(F)cc3Cl)c3ncccc3S2(=O)=O)cnc1OC] | 185 | 4-(2-chloro-4,6-difluorobenzyl)-2-(5,6-dimethoxypyridin-3-yl)-2H-pyrido[2,3-e][1,2,4]thiadiazin-3(4H)-one 1,1-dioxide | 8.38 |
| 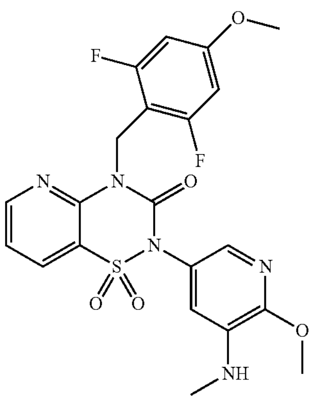 | 186 | 4-(2,6-difluoro-4-methoxybenzyl)-2-[6-methoxy-5-(methylamino)pyridin-3-yl]-2H-pyrido[2,3-e][1,2,4]thiadiazin-3(4H)-one 1,1-dioxide | 8.90 |

Synthesis of Examples

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on Bruker or JEOL instruments. Chemical shift values are expressed in parts per million (ppm), i.e. (□)-values. The following abbreviations are used for the multiplicity of the NMR signals: s=singlet, br=broad, d=doublet, t=triplet, q=quartet, quin=quintet, h=heptet, dd=doublet of doublets, dt=double of triplets, m=multiplet. Coupling constants are listed as J values, measured in Hz. $^1$H NMR and mass spectroscopy results were corrected to account for background peaks.

Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

Mass spectroscopy was carried out on Shimadzu LC-2010 EV, Waters ZQ-2000, UPLC-Mass SQD-3100 or Applied Biosystem API-2000 spectrometers using electrospray conditions as specified for each compound in the detailed experimental section.

Preparative HPLC was typically carried out under the following conditions. Method A (Gilson HPLC): Column: PrepHT Extend C-18, 21.2×100 mm, 5 micron; Mobile phase: Gradients of water and MeCN (each containing 0.1% Formic Acid); Gradient: 5% MeCN to 95% MeCN in water over 16.30 minutes at 28 mL/min. Method B (Waters HPLC): Column: XSelect CSH Prep C-18, 19×50 mm, 5 micron; Mobile phase: Gradients of water and MeCN (each containing 0.1% Formic Acid); Gradient: 5% MeCN to 95% MeCN in water over 16.30 minutes at 28 mL/min. Method C (Gilson HPLC): Column: Waters XBridge Prep C-18, 19×150 mm, 5 micron; Mobile phase: Gradients of water and MeOH (each containing 0.1% NH$_3$); Gradient: 10% MeOH to 95% MeOH in water over 14.50 minutes at 18 mL/min.

LCMS experiments were typically carried out using electrospray conditions as specified for each compound under the following conditions. Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L H$_2$O+2.5 mL ammonia solution; solvent D=2.5 L MeCN+ 135 mL H$_2$O+2.5 mL ammonia solution); Injection volume 3 uL; UV detection 230 to 400 nM; column temperature 45° C.; Flow rate 1.5 mL/min. LCMS data in the experimental section are given in the format: Mass ion, retention time, approximate purity.

ABBREVIATIONS

Ar=argon
BINAP=2,2'-bis(diphenylphosphino)-1,1'-binaphthalene
Boc$_2$O=Di-tert-butyl dicarbonate
d=day(s)
DCM=dichloromethane
DMAC=N,N-dimethylacetamide
DMF=dimethylformamide
DMSO=dimethylsulfoxide
ESI=electrospray ionisation
EtOAc=ethyl acetate
h=hour(s)
HPβCD=(2-hydroxypropyl)-β-cyclodextrin
HPLC=high performance liquid chromatography
L=Liter
LC=liquid chromatography
MeCN=acetonitrile
min=minute(s)
MS=mass spectrometry
NMR=nuclear magnetic resonance
rt=room temperature
TFA=trifluoroacetic acid
THF=tetrahydrofuran
TLC=thin layer chromatography Prefixes n-, s-, i-, t- and tert-have their usual meanings: normal, secondary, iso, and tertiary.

SYNTHESIS OF INTERMEDIATES

Route 1

Typical procedure for the preparation of cyclised intermediates, as exemplified by the preparation of 2-(3,4-dimethoxyphenyl)-2H-1,2,4-benzothiadiazin-3(4H)-one 1,1-dioxide (IntA1)

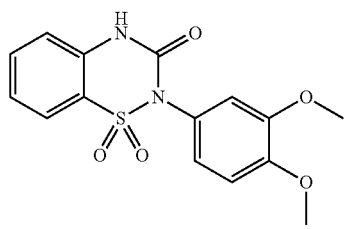 [SMILES: COc1ccc(N2C(=O)Nc3ccccc3S2(=O)=O)cc1OC]

Step 1: Preparation of N-(3,4-dimethoxyphenyl)-2-nitrobenzenesulfonamide

A mixture of 2-nitrobenzenesulfonyl chloride (3.0 g, 13.5 mmol) and 3,4-dimethoxyaniline (2.1 g, 14.9 mmol) in 1,4-dioxane (30 mL) in a sealed reaction tube was heated at 80° C. for 24 h with TLC monitoring (hexane:EtOAc, 1:1). The reaction mixture was diluted with H$_2$O (30 mL), extracted with EtOAc (3×100 mL) and the combined organic phases dried over Na$_2$SO$_4$, filtered and concentrated in vacuo. Purification by gradient flash chromatography, eluting with 20-25% EtOAc in hexane yielded the title compound (2.5 g, 7.39 mmol).

Mass spectroscopy: (ESI+ve) 339 [M+H]$^+$

Step 2: Preparation of 2-amino-N-(3,4-dimethoxyphenyl)benzenesulfonamide

A mixture of N-(3,4-dimethoxyphenyl)-2-nitrobenzenesulfonamide (2.5 g, 7.39 mmol) and SnCl$_2$ (8.34 g, 36.9 mmol) in ethanol was heated at 100° C. for 5 h in a sealed tube with TLC monitoring (hexane:EtOAc, 1:1). After concentration in vacuo H$_2$O (30 mL) was added and the mixture was extracted with EtOAc (3×100 mL). The combined organic layer was dried over Na$_2$SO$_4$, filtered and concentrated in vacuo. Purification by gradient flash chromatography, eluting with 20-25% EtOAc in hexane yielded the title compound (2.0 g, 6.49 mmol).

Mass spectroscopy: (ESI+ve) 309.1 [M+H]$^+$

Step 3: Preparation of 2-(3,4-dimethoxyphenyl)-2H-1,2,4-benzothiadiazin-3(4H)-one 1,1-dioxide A mixture of 2-amino-N-(3,4-dimethoxyphenyl)benzenesulfonamide (0.8 g, 2.6 mmol) and triphosgene (0.99 g, 3.4 mmol) in anhydrous 1,4-dioxane was heated in a sealed tube at 100° C. overnight with TLC monitoring (hexane:EtOAc, 1:1). After concentration in vacuo H$_2$O (30 mL) was added and the mixture was extracted with EtOAc (3×100 mL). The combined organic layer was dried over Na$_2$SO$_4$, filtered and concentrated in vacuo. Purification by gradient flash chromatography, eluting with 20-25% EtOAc in hexane yielded the title compound (0.4 g, 1.20 mmol).

Mass spectroscopy: (ESI+ve) 335.1 [M+H]$^+$ $^1$H NMR: (400 MHz, DMSO) δ: 3.73 (s, 3H), 3.82 (s, 3H), 6.89-7.02 (m, 2H), 7.08 (d, J=8.5, 1H), 7.30-7.41 (m, 2H), 7.71-7.81 (m, 1H), 7.89 (d, J=7.3, 1H), 11.53 (s, 1H)

2-(3,4,5-Trimethoxyphenyl)-2H-1,2,4-benzothiadiazin-3(4H)-one 1,1-dioxide (IntA2, Y48A)

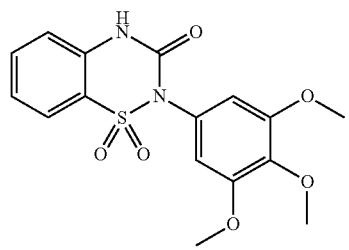 [SMILES: COc1cc(N2C(=O)Nc3ccccc3S2(=O)=O)cc(OC)c1OC]

The title compound (2.0 g, 5.49 mmol) was prepared in three steps from 2-nitrobenzenesulfonyl chloride (7.0 g, 31.6 mmol) and 3,4,5-trimethoxyaniline (6.3 g, 31.6 mmol) using the methods of (IntA1).

Mass spectroscopy: (ESI+ve) 365.0 [M+H]$^+$ $^1$H NMR: (400 MHz, DMSO) δ: 3.73 (s, 3H), 3.77 (s, 6H), 6.73 (s, 2H), 7.27-7.43 (m, 2H), 7.77 (t, J=7.8, 1H), 7.90 (d, J=7.9, 1H), 11.58 (s, 1H)

2-(6-Methylpyridin-3-yl)-2H-1,2,4-benzothiadiazin-3(4H)-one 1,1-dioxide (IntA3)

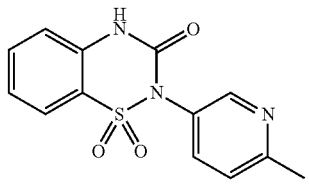 [SMILES: Cc1ccc(N2C(=O)Nc3ccccc3S2(=O)=O)cn1]

The title compound (2.18 g, 7.53 mmol) was prepared in three steps from 2-nitrobenzenesulfonyl chloride (6.15 g, 27.7 mmol) and 6-methylpyridin-3-amine (3.0 g, 27.7 mmol) using the methods of (IntA1).

Mass spectroscopy: (ESI+ve) 290.0 [M+H]$^+$ $^1$H NMR: (400 MHz, DMSO) δ: 2.56 (s, 3H), 7.26-7.43 (m, 2H), 7.46 (d, J=7.9, 1H), 7.72-7.86 (m, 2H), 7.93 (d, J=7.9, 1H), 8.47 (d, J=1.2, 1H), 11.72 (s, 1H)

2-(2-Methoxypyridin-4-yl)-2H-1,2,4-benzothiadiazin-3(4H)-one 1,1-dioxide (IntA4)

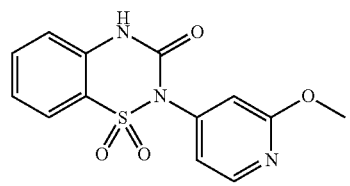 [SMILES: COc1cc(N2C(=O)Nc3ccccc3S2(=O)=O)ccn1]

The title compound (2.2 g, 7.21 mmol) was prepared in three steps from 2-nitrobenzenesulfonyl chloride (16.0 g, 72.5 mmol), 2-methoxy-4-aminopyridine (10.0 g, 80.6 mmol) and triethylamine (8.95 g, 88.6 mmol) using the methods of (IntA1).

Mass spectroscopy: (ESI+ve) 305.9 [M+H]$^+$ $^1$H NMR: (400 MHz, DMSO) δ: 3.92 (s, 3H), 6.94 (d, J=1.5, 1H), 7.11 (dd, J=5.3, 1.7, 1H), 7.30-7.45 (m, 2H), 7.72-7.85 (m, 1H), 7.93 (d, J=7.6, 1H), 8.34 (d, J=5.5, 1H), 11.75 (s, 1H)

2-(6-Methoxypyridin-2-yl)-2H-1,2,4-benzothiadiazin-3(4H)-one 1,1-dioxide (IntA5)

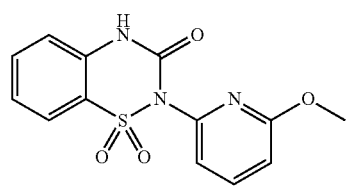 [SMILES: COc1cccc(N2C(=O)Nc3ccccc3S2(=O)=O)n1]

The title compound (0.6 g, 1.97 mmol) was prepared in three steps from 2-nitrobenzenesulfonyl chloride (5.5 g, 24.8 mmol), 2-amino-6-methoxypyridine (3.08 g, 24.8 mmol) and triethylamine (2.75 g, 27.2 mmol) using the methods of (IntA1).

Mass spectroscopy: (ESI+ve) 305.9 [M+H]$^+$ $^1$H NMR: (400 MHz, DMSO) δ: 3.83 (s, 3H), 7.01 (d, J=8.2, 1H), 7.14 (d, J=7.3, 1H), 7.33-7.43 (m, 2H), 7.78 (t, J=7.9, 1H), 7.86-7.96 (m, 2H), 11.67 (s, 1H)

2-(4-Methoxy-3,5-dimethylphenyl)-2H-1,2,4-benzothiadiazin-3(4H)-one 1,1-dioxide (IntA6)

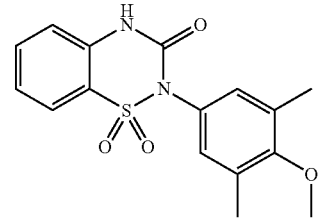 [SMILES: COc1c(C)cc(N2C(=O)Nc3ccccc3S2(=O)=O)cc1C]

The title compound (1.3 g, 5.42 mmol) was prepared in three steps from 2-nitrobenzenesulfonyl chloride (2.93 g, 13.2 mmol) and 4-methoxy-3,5-dimethylaniline (2.0 g, 13.20 mmol) using the methods of (IntA1).

Mass spectroscopy: (ESI+ve) 332.6 [M+H]$^+$ $^1$H NMR: (400 MHz, DMSO) δ: 2.26 (s, 6H), 3.72 (s, 3H), 7.09 (s, 2H), 7.31-7.40 (m, 2H), 7.77 (t, J=7.8, 1H), 7.89 (d, J=7.9, 1H), 11.59 (s, 1H) 2-(1,3-Benzothiazol-6-yl)-2H-1,2,4-benzothiadiazin-3(4H)-one 1,1-dioxide (IntA7)

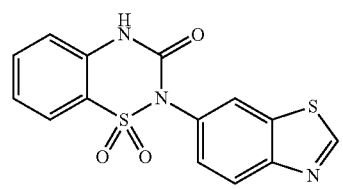 [SMILES: O=C1Nc2ccccc2S(=O)(=O)N1c1ccc2ncsc2c1]

The title compound (0.80 g, 2.41 mmol) was prepared in three steps from 2-nitrobenzenesulfonyl chloride (5.0 g, 22.6 mmol) and 6-aminobenzothiazole (3.39 g, 22.6 mmol) using the methods of (IntA1).

Mass spectroscopy: (ESI+ve) 331.6 [M+H]$^+$ $^1$H NMR: (400 MHz, DMSO) δ: 7.30-7.45 (m, 2H), 7.58 (d, J=8.5, 1H), 7.80 (t, J=7.6, 1H), 7.94 (d, J=7.9, 1H), 8.22 (d, J=8.5, 1H), 8.36 (s, 1H), 9.56 (s, 1H), 11.70 (br s, 1H)

2-(1-Ethyl-1H-pyrazol-4-yl)-2H-1,2,4-benzothiadiazin-3(4H)-one 1,1-dioxide (IntA8)

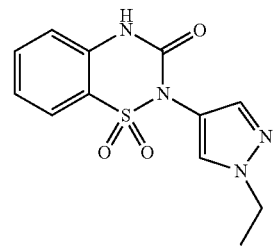 [SMILES: CCn1cc(N2C(=O)Nc3ccccc3S2(=O)=O)cn1]

The title compound (0.80 g, 2.74 mmol) was prepared in three steps from 2-nitrobenzenesulfonyl chloride (2.65 g, 11.9 mmol), 1-ethyl-1H-pyrazol-4-amine hydrochloride (1.8 g, 12.0 mmol) and triethylamine (3.0 g, 2.99 mmol) using the methods of (IntA1).

Mass spectroscopy: (ESI+ve) 292.5 [M+H]$^+$
$^1$H NMR: (400 MHz, DMSO) δ: 1.41 (t, J=7.2, 3H), 4.19 (q, J=7.1, 2H), 7.25-7.42 (m, 2H), 7.50-7.60 (m, 1H), 7.71-7.81 (m, 1H), 7.87-7.96 (m, 1H), 8.09 (s, 1H), 11.60 (s, 1H)

2-[5-(Methylsulfanyl)pyridin-3-yl]-2H-1,2,4-benzothiadiazin-3(4H)-one 1,1-dioxide (IntA9)

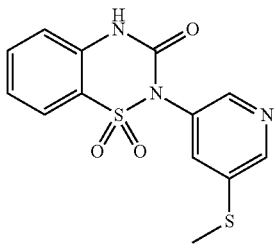 [SMILES: CSc1cncc(N2C(=O)Nc3ccccc3S2(=O)=O)c1]

The title compound (0.40 g, 1.24 mmol) was prepared in three steps from 2-nitrobenzenesulfonyl chloride (0.78 g, 3.57 mmol) and 5-(methylsulfanyl)pyridin-3-amine (0.5 g, 3.57 mmol) using the methods of (IntA1).
Mass spectroscopy: (ESI+ve) 322.7 [M+H]$^+$
$^1$H NMR: (400 MHz, DMSO) δ: 2.57 (s, 3H), 7.25-7.48 (m, 2H), 7.72-7.89 (m, 2H), 7.94 (d, J=7.3, 1H), 8.39 (d, J=1.8, 1H), 8.62 (d, J=2.1, 1H), 11.75 (s, 1H)

2-[6-(Methylsulfanyl)pyridin-3-yl]-2H-1,2,4-benzothiadiazin-3(4H)-one 1,1-dioxide (IntA10)

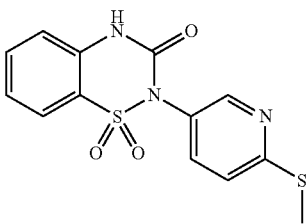 [SMILES: CSc1ccc(N2C(=O)Nc3ccccc3S2(=O)=O)cn1]

The title compound (2.0 g, 6.22 mmol) was prepared in three steps from 2-nitrobenzenesulfonyl chloride (4.02 g, 19.6 mmol) and 6-(methylsulfanyl)pyridin-3-amine (2.5 g, 17.9 mmol) using the methods of (IntA1).
Mass spectroscopy: (ESI+ve) 322.7 [M+H]$^+$
$^1$H NMR: (400 MHz, DMSO) δ: 2.57 (s, 3H), 7.33-7.45 (m, 2H), 7.50 (d, J=8.5, 1H), 7.69-7.84 (m, 2H), 7.94 (d, J=7.3, 1H), 8.45 (d, J=2.4, 1H), 11.73 (s, 1H)

2-(3,5-Dimethoxyphenyl)-2H-1,2,4-benzothiadiazin-3(4H)-one 1,1-dioxide (IntA11)

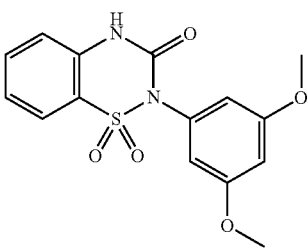 [SMILES: COc1cc(OC)cc(N2C(=O)Nc3ccccc3S2(=O)=O)c1]

The title compound (0.2 g, 0.60 mmol) was prepared in three steps from 2-nitrobenzenesulfonyl chloride (1.0 g, 4.51 mmol) and 3,5-dimethoxyaniline (0.7 g, 4.96 mmol) using the methods of (IntA1).
Mass spectroscopy: (ESI+ve) 335.1 [M+H]$^+$.
$^1$H NMR: (400 MHz, DMSO) δ: 3.77 (s, 6H), 6.56 (d, J=2.3, 2H), 6.68 (t, J=2.3, 1H), 7.29-7.42 (m, 2H), 7.70-7.82 (m, 1H), 7.89 (d, J=7.5, 1H), 11.57 (br s, 1H)

2-[3-(Methylsulfanyl)phenyl]-2H-1,2,4-benzothiadiazin-3(4H)-one 1,1-dioxide (IntA12)

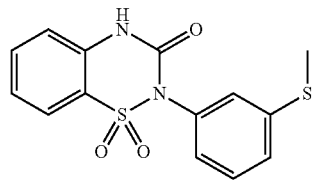 [SMILES: CSc1cccc(N2C(=O)Nc3ccccc3S2(=O)=O)c1]

The title compound (2.0 g, 6.24 mmol) was prepared in three steps from 2-nitrobenzenesulfonyl chloride 5.0 g, 22.6 mmol) and 3-(methylthio)aniline (3.45 g, 24.8 mmol) using the methods of (IntA1).
LCMS (Method B): m/z 321.2 (M+H)+ (ES+), 319.3 (M−H)− (ES−), at 2.65 min, 100%
$^1$H NMR: (400 MHz, DMSO) δ: 2.51 (s, 3H), 7.21 (d, J=7.6, 1H), 7.27 (s, 1H), 7.32-7.52 (m, 4H), 7.72-7.82 (m, 1H), 7.88-7.95 (m, 1H), 11.63 (s, 1H)

2-[(1,3-Dimethyl-1H-pyrazol-5-yl)methyl]-2H-1,2,4-benzothiadiazin-3(4H)-one 1,1-dioxide (IntA13)

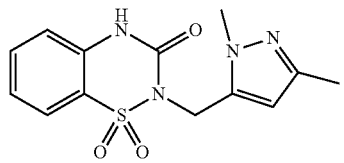 [SMILES: Cc1cc(CN2C(=O)Nc3ccccc3S2(=O)=O)n(C)n1]

The title compound (0.30 g, 0.98 mmol) was prepared in three steps from 2-nitrobenzenesulfonyl chloride (0.5 g, 2.25 mmol) and 1-(3-methyl-1H-pyrazol-5-yl)methanamine (0.32 g, 2.48 mmol) using the methods of (IntA1).
Mass spectroscopy: (ESI+ve) 307 [M+H]$^+$.

2-{3-[(Trifluoromethyl)sulfanyl]phenyl}-2H-1,2,4-benzothiadiazin-3(4H)-one 1,1-dioxide (IntA14)

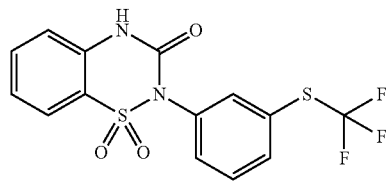 [SMILES: O=C1Nc2ccccc2S(=O)(=O)N1c1cccc(SC(F)(F)F)c1]

Step 1: Preparation of 2-nitro-N-{3-[(trifluoromethyl)sulfanyl]phenyl}benzenesulfonamide The title compound (1.26 g, 3.3 mmol) was prepared from 2-nitrobenzenesulfonyl chloride (1.1 g, 5.0 mmol) and 3-[(trifluoromethyl)sulfanyl]aniline (1.06 g, 5.5 mmol) using the methods of (IntA1), step 1.

LCMS (Method A): m/z 377 (M–H)– (ES–), at 1.21 min, 100%

Step 2: Preparation of 2-amino-N-{3-[(trifluoromethyl)sulfanyl]phenyl}benzenesulfonamide A solution of 2-nitro-N-{3-[(trifluoromethyl)sulfanyl]phenyl}benzenesulfonamide (605 mg, 1.6 mmol) in ethanol/H$_2$O (4:1, 50 mL total reaction volume) was added to a suspension of 10% palladium on charcoal (50 mg) in ethanol/H$_2$O (4:1) and the mixture stirred at rt under an atmosphere of H$_2$ for approximately 2 d. After this time further 10% palladium on charcoal (75 mg) was added and the reaction mixture stirred under an atmosphere of H$_2$ at rt for 3 h. Filtration and concentration in vacuo yielded the title compound (455 mg, 1.31 mmol).

LCMS (Method A): m/z 347 (M–H)– (ES–), at 1.37 min, >95%

$^1$H NMR: (400 MHz, DMSO) δ: 6.02 (br s, 2H), 6.47-6.62 (m, 1H), 6.76 (d, J=7.5, 1H), 7.16-7.27 (m, 2H), 7.28-7.34 (m, 1H), 7.34-7.44 (m, 2H), 7.51 (dd, J=8.0, 1.3, 1H)

Step 3: Preparation of 2-{3-[(trifluoromethyl)sulfanyl]phenyl}-2H-1,2,4-benzothiadiazin-3(4H)-one 1,1-dioxide A mixture of 2-amino-N-{3-[(trifluoromethyl)sulfanyl]phenyl}benzenesulfonamide (52 mg, 0.15 mmol), 1,1'-carbonyldiimidazole (97 mg, 0.60 mmol) and triethylamine (41 μL, 0.30 mmol) in DMF (0.75 mL) was heated in a sealed tube for 5 h at 100° C. After concentration in vacuo, DCM and 1M aqueous HCl were added, the phases were separated, the organic layer was washed with brine, dried over MgSO$_4$, filtered and concentrated in vacuo. Purification by flash chromatography, eluting with 3% MeOH in DCM yielded the title compound (45 mg, 0.21 mmol).

LCMS (Method A): m/z 373 (M–H)– (ES–), at 1.50 min, 100%

$^1$H NMR: (400 MHz, DMSO) δ 7.33-7.43 (m, 2H), 7.69-7.84 (m, 4H), 7.88-7.97 (m, 2H), 11.70 (s, 1H)

2-(6-Methoxypyridin-3-yl)-2H-1,2,4-benzothiadiazin-3(4H)-one 1,1-dioxide (IntA15)

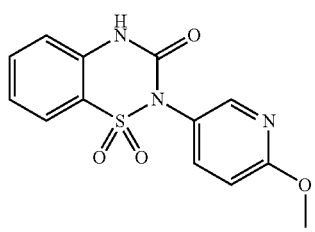 [SMILES: COc1ccc(N2C(=O)Nc3ccccc3S2(=O)=O)cn1]

Step 1: Preparation of N-(6-Methoxypyridin-3-yl)-2-nitrobenzenesulfonamide

The title compound (1.05 g, 3.4 mmol) was prepared from 2-nitrobenzenesulfonyl chloride (1.1 g, 5.0 mmol) and 5-amino-2-methoxypyridine (683 mg, 5.5 mmol) using the methods of (IntA1), step 1.

LCMS (Method A): m/z 310 (M+H)+ (ES+), at 0.41 min, 95%

Step 2: Preparation of 2-amino-N-(6-methoxypyridin-3-yl)benzenesulfonamide

The title compound (419 mg 1.50 mmol) was prepared from N-(6-Methoxypyridin-3-yl)-2-nitrobenzenesulfonamide (500 mg, 1.62 mmol) and 10% palladium on charcoal (50 mg) using the methods of (IntA14), step 2.

LCMS (Method A): m/z 280 (M+H)+ (ES+), at 0.88 min, 90%

Step 3: Preparation of 2-(6-Methoxypyridin-3-yl)-2H-1,2,4-benzothiadiazin-3(4H)-one 1,1-dioxide The title compound (143 mg, 0.47 mmol) was prepared from 2-amino-N-(6-methoxypyridin-3-yl)benzenesulfonamide (209 mg, 0.75 mmol), 1,1'-carbonyldiimidazole (486 mg, 3.0 mmol) and triethylamine (0.28 mL, 1.5 mmol) in DMF (3.75 mL) using the methods of (IntA14), step 3.

LCMS (Method A): m/z 306 (M+H)+ (ES+), at 1.05 min, 100%

$^1$H NMR: (400 MHz, DMSO) δ 3.93 (s, 3H), 7.00 (d, J=8.8, 1H), 7.30-7.44 (m, 2H), 7.73-7.84 (m, 2H), 7.93 (d, J=7.8, 1H), 8.21 (d, J=2.5, 1H), 11.66 (s, 1H)

2-Amino-4-fluoro-N-[3-(methylsulfanyl)phenyl]benzenesulfonamide (IntA16)

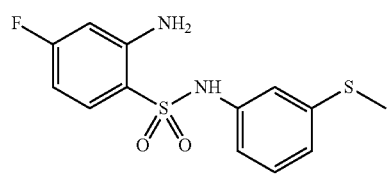 [SMILES: CSc1cccc(NS(=O)(=O)c2ccc(F)cc2N)c1]

Step 1: Preparation of 4-fluoro-N-[3-(methylsulfanyl)phenyl]-2-nitrobenzenesulfonamide A solution of 3-(methylsulfanyl)aniline (658 mg, 4.73 mmol) and pyridine (995 uL, 18.9 mmol) was cooled to 0° C. under N$_2$ before the dropwise addition of bis(trimethylsilyl)trifluorocetamide (1.76 mL, 9.45 mmol) over 5 min. After stirring for 5 min at 0° C., a solution of 4-fluoro-2-nitrobenzenesulfonyl chloride (1.19 g, 4.97 mmol) in 1,4-dioxane (7 mL) was added dropwise over 15 min. The mixture was stirred at rt for 1 h, then at 100° C. for 30 min. After cooling to rt, the mixture was concentrated in vacuo and partitioned between DCM and 1M aqueous HCl (25 mL each). The phases were separated and the aqueous layer extracted with DCM (2×25 mL). The combined organic layers were concentrated in vacuo and purified by gradient flash chromatography, eluting with 5-50% EtOAc in heptane to yield the title compound (865 mg, 2.53 mmol).

LCMS (Method B): m/z 341.2 (M−H)− (ES−), at 1.90 min, 90%

¹H NMR: (400 MHz, DMSO) δ 2.39 (s, 3H), 6.79-6.92 (m, 1H), 6.93-7.04 (m, 2H), 7.15-7.29 (m, 1H), 7.74 (td, J=8.4, 2.8, 1H), 8.04 (dd, J=8.8, 5.3, 1H), 8.13 (dd, J=8.2, 2.6, 1H), 10.84 (s, 1H)

Step 2: Preparation of 2-amino-4-fluoro-N-[3-(methylsulfanyl)phenyl]benzenesulfonamide The title compound (780 mg, 2.50 mmol) was prepared from 4-fluoro-N-[3-(methylsulfanyl)phenyl]-2-nitrobenzenesulfonamide (865 mg, 2.53 mmol) and SnCl₂ (1.44 g, 7.59 mmol) using the methods of (IntA1), Step 2.

LCMS (Method B): m/z 311.1 (M−H)− (ES−), at 2.17 min, 100%

¹H NMR: (400 MHz, DMSO) δ 2.39 (s, 3H), 6.27 (s, 2H), 6.41 (td, J=8.5, 2.5, 1H), 6.52 (dd, J=11.5, 2.5, 1H), 6.81 (dd, J=8.0, 1.0, 1H), 6.89 (dd, J=3.6, 1.6, 2H), 7.10-7.22 (m, 1H), 7.56 (dd, J=9.0, 6.5, 1H), 10.31 (s, 1H)

2-[6-(Dimethylamino)pyridin-2-yl]-2H-1,2,4-benzothiadiazin-3(4H)-one 1,1-dioxide (IntA17)

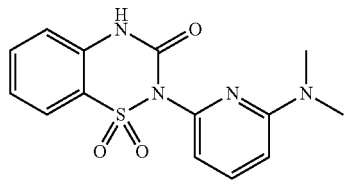 [SMILES: CN(C)c1cccc(N2C(=O)Nc3ccccc3S2(=O)=O)n1]

Step 1: Preparation of N-[6-(dimethylamino)pyridin-2-yl]-2-nitrobenzenesulfonamide A solution of N,N-dimethylpyridine-2,6-diamine (1.0 g, 7.2 mmol), 2-nitrobenzenesulfonyl chloride (1.45 g, 6.4 mmol) and pyridine (2.27 g, 28.8 mmol) in diethyl ether (25 mL) was heated at 30° C. for approximately 12 h with TLC monitoring (hexane:EtOAc, 1:1). After concentration in vacuo purification by gradient flash chromatography, eluting with 0-25% EtOAc in hexane yielded the target compound (1.0 g, 3.10 mmol).

TLC: Rf=0.70 (hexane:EtOAc, 1:1)
Mass spectroscopy: (ESI+ve) 322.9 [M+H]⁺

Step 2: Preparation of 2-amino-N-[6-(dimethylamino)pyridin-2-yl]benzenesulfonamide In a sealed tube, a mixture of N-[6-(dimethylamino)pyridin-2-yl]-2-nitrobenzenesulfonamide (1.0 g, 3.10 mmol) and Fe powder (0.85 g, 11.5 mmol) in acetic acid (10 mL) was heated at 60° C. for approximately 15 min with TLC monitoring (hexane:EtOAc, 1:1). The reaction mixture was poured into saturated aqueous NaHCO₃ solution (100 mL) and extracted with EtOAc (3×50 mL), the combined organic layers were dried over Na₂SO₄ and concentrated in vacuo. Purification by gradient flash chromatography, eluting with 0-45% EtOAc in hexane yielded the title compound (0.7 g, 2.39 mmol).

TLC: Rf=0.65 (hexane: EtOAc, 1:1)
Mass spectroscopy: (ESI+ve) 293.2 [M+H]⁺

Step 3: Synthesis of 2-[6-(dimethylamino)pyridin-2-yl]-2H-1,2,4-benzothiadiazin-3(4H)-one 1,1-dioxide The title compound (0.20 g, 0.63 mmol) was prepared from 2-amino-N-[6-(dimethylamino)pyridin-2-yl]benzenesulfonamide (0.7 g, 2.39 mmol) and triphosgene (2.5 g, 8.3 mmol) in 1,4-dioxane (25 mL) using the methods of (IntA1).

TLC: Rf=0.70 (hexane:EtOAc, 1:1)
Mass spectroscopy: (ESI+ve) 318.9 [M+H]⁺

2-[2-(Dimethylamino)pyridin-4-yl]-2H-1,2,4-benzothiadiazin-3(4H)-one 1,1-dioxide (IntA18)

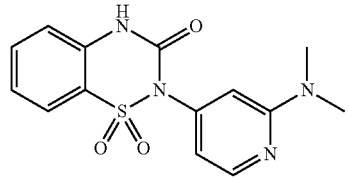 [SMILES: CN(C)c1cc(N2C(=O)Nc3ccccc3S2(=O)=O)ccn1]

The title compound (0.12 g, 0.38 mmol) was prepared in three steps from N²,N²-dimethylpyridine-2,4-diamine (2.29 g, 16.6 mmol), 2-nitrobenzenesulfonyl chloride (3.3 g, 15 mmol) and pyridine (13.1 g, 16.6 mmol) using the methods of (IntA17).

TLC: Rf=0.70 (hexane:EtOAc, 1:1)
Mass spectroscopy: (ESI+ve) 318.9 [M+H]⁺.

2-(5,6-Dimethoxypyridin-3-yl)-2H-1,2,4-benzothiadiazin-3(4H)-one 1,1-dioxide (IntA19)

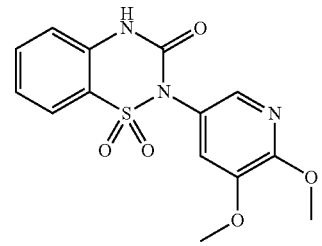 [SMILES: COc1cc(N2C(=O)Nc3ccccc3S2(=O)=O)cnc1OC]

Step 1: Preparation of N-(5,6-Dimethoxypyridin-3-yl)-2-nitrobenzenesulfonamide

The title compound (1.56 g, 4.60 mmol) was prepared from 2-nitrobenzenesulfonyl chloride (2.66 g, 12.0 mmol), 5,6-dimethoxy-3-pyridinamine (2.04 g, 13.2 mmol) and pyridine (2.9 mL, 36.0 mmol) using the methods of (IntA1), step 1.

LCMS (Method A): m/z 340 (M+H)+ (ES+), at 0.12 and 0.72 min, 90%

¹H NMR: (400 MHz, DMSO) δ: 3.72 (s, 3H), 3.79 (s, 3H), 7.03 (d, J=2.3, 1H), 7.39 (d, J=2.0, 1H), 7.81-7.89 (m, 2H), 7.97 (ddd, J=7.3, 5.4, 1.9, 2H), 10.52 (s, 1H)

Step 2: Preparation of 2-amino-N-(5,6-dimethoxypyridin-3-yl)benzenesulfonamide

The title compound (486 mg) was prepared from N-(5,6-dimethoxypyridin-3-yl)-2-nitrobenzenesulfonamide (509 mg, 1.5 mmol), Fe powder (559 mg, 15.0 mmol) and acetic acid (10 mL) using the methods of (IntA17), Step 2.

LCMS (Method B): m/z 310 (M+H)+ (ES+), at 0.11 and 1.02 min, 100%

¹H NMR: (400 MHz, DMSO) δ: 3.66 (s, 3H), 3.76 (s, 3H), 6.00 (br. s, 2H), 6.54 (t, J=7.2, 1H), 6.77 (d, J=8.3, 1H), 6.91 (d, J=2.3, 1H), 7.17-7.28 (m, 1H), 7.33 (d, J=2.3, 1H), 7.40 (dd, J=8.0, 1.3, 1H), 10.00 (br. s, 1H)

Step 3: 2-(5,6-Dimethoxypyridin-3-yl)-2H-1,2,4-benzothiadiazin-3(4H)-one 1,1-dioxide The title compound (257 mg, 0.77 mmol) was prepared from 2-amino-N-(5,6-dimethoxypyridin-3-yl)benzenesulfonamide (486 mg, 1.57 mmol), 1,1'-carbonyldiimidazole (1.02 g, 6.29 mmol) and triethylamine (0.44 mL, 3.14 mmol) in DMF (3 mL) using the methods of (IntA14), step 3.

LCMS (Method B): m/z 336 (M+H)+ (ES+), at 2.65 min, 100%

¹H NMR: (400 MHz, DMSO) δ: 3.79 (s, 3H), 3.94 (s, 3H), 7.18-7.52 (m, 3H), 7.63-7.85 (m, 2H), 7.93 (dd, J=8.2, 1.1, 1H), 11.65 (br. s, 1H)

2-(5,6-Dimethoxypyridin-2-yl)-2H-1,2,4-benzothiadiazin-3(4H)-one 1,1-dioxide (IntA20)

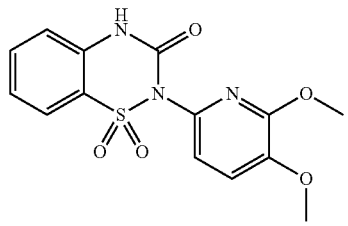 [SMILES: COc1ccc(N2C(=O)Nc3ccccc3S2(=O)=O)nc1OC]

The title compound (0.30 g, 0.89 mmol) was prepared in three steps from 2-nitrobenzenesulfonyl chloride (1.05 g, 4.72 mmol), 5,6-dimethoxypyridin-2-amine (0.80 g, 5.19 mmol) and pyridine (1.15 mL, 14.2 mmol) in 1,4-dioxane (19 mL) using the methods of (IntA19).

LCMS (Method A): m/z 334 (M−H)− (ES−), 336 (M+H)+ (ES+), at 0.17 and 1.11 min, 100%

¹H NMR: (400 MHz, DMSO) δ: 3.82 (s, 3H), 3.86 (s, 3H), 7.10 (d, J=8.0, 1H), 7.32-7.41 (m, 2H), 7.46 (d, J=8.0, 1H), 7.72-7.82 (m, 1H), 7.89 (dd, J=8.0, 1.3, 1H), 11.59 (s, 1H)

2-(2,6-Dimethoxypyridin-4-yl)-2H-1,2,4-benzothiadiazin-3(4H)-one 1,1-dioxide (IntA21)

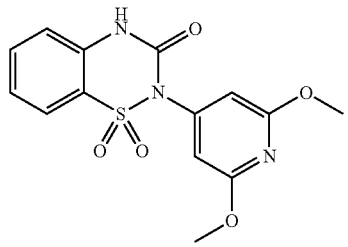 [SMILES: COc1cc(N2C(=O)Nc3ccccc3S2(=O)=O)cc(OC)n1]

The title compound (0.40 g, 1.19 mmol) was prepared in three steps from 2-nitrobenzenesulfonyl chloride (2.66 g, 12.0 mmol), 2,6-dimethoxypyridin-4-amine (2.04 g, 13.2 mmol) and pyridine (2.9 mL, 36.0 mmol) in 1,4-dioxane (48 mL) using the methods of (IntA19).

LCMS (Method B): m/z 336 (M+H)+ (ES+), at 2.12 min, 100%

¹H NMR: (400 MHz, DMSO) δ: 3.91 (s, 6H), 6.47 (s, 2H), 7.36 (t, J=8.2, 2H), 7.78 (dt, J=8.2, 0.9, 1H), 7.92 (d, J=7.8, 1H), 11.66 (br. s, 1H)

(2-Chloro-4,6-difluorophenyl)methanol (IntA22)

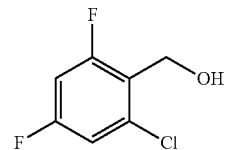

Step 1: Preparation of (4-chloro-2,6-difluorophenyl)trimethylsilane

A solution of 2.5M n-BuLi in hexanes (60 ml, 0.15 mol) was added dropwise to a solution of 1-chloro-3,5-difluorobenzene (19.2 g, 0.13 mol) in THF (200 mL) cooled to −70° C. under Ar. After the addition was complete, the mixture was stirred for 1 h before a solution of chlorotrimethylsilane (21.7 g, 0.2 mol) in THF (25 mL) was added dropwise. The reaction was allowed to warm to rt with stirring overnight before cooling and quenching with H₂O. The phases were separated and pentane (200 mL) was added; after washing with H₂O the solution was dried over MgSO₄ and carefully concentrated in vacuo to yield the title compound as a solution in THF (46 g) which was in the next step without further purification.

Step 2: Preparation of 6-chloro-2,4-difluoro-3-(trimethylsilyl)benzaldehyde

A solution of 2.5M n-BuLi in hexanes (60 ml, 0.15 mol) was added drop-wise to a solution of (4-chloro-2,6-difluorophenyl)trimethylsilane (assumed 0.13 mol) in THF (180 mL) cooled to −70° C. under Ar. After the addition was complete, the mixture was stirred for 1 h before a solution of N-formylmorpholine (20 mL, 0.2 mol) in THF (25 mL) was added dropwise. The reaction was allowed to warm to rt with stirring and then cooled to 0° C. and quenched with H₂O. Ether was added, the phases were separated, the aqueous phase was re-extracted with ether and the combined organics washed with brine, dried over MgSO₄ and concentrated in vacuo to give the title compound (35 g) as an orange oil which was used without further purification.

Step 3: Preparation of 2-chloro-4,6-difluorobenzaldehyde

CsF (approximately 0.2 g) was added to a mixture of crude 6-chloro-2,4-difluoro-3-(trimethylsilyl)benzaldehyde (10.5 g, approximately 42 mmol) in dimethylformamide (15 mL)/H₂O (2 mL). After stirring for 10 min the reaction was diluted with heptane and H₂O. The phases were separated and the aqueous extracted with further heptane. The combined organic layers were washed with H₂O, dried over MgSO₄ and concentrated in vacuo to a yellow oil. Purification by column chromatography (1:4 EtOAc:heptane) followed by trituration with pentane gave the title compound as a white solid (3.0 g, 17.0 mmol).

TLC: Rf=0.54 (8:7 heptane:EtOAc)

Step 4: Preparation of (2-chloro-4,6-difluorophenyl)methanol

Sodium borohydride (1.42 g, 37.5 mmol) was added in portions to an ice-cooled solution of 2-chloro-4,6-difluorobenzaldehyde (6.70 g, 38.0 mmol) in methanol (56 ml); once addition was complete the reaction was warmed to rt over 1 h and then concentrated in vacuo. The residue was partitioned between ether and saturated sodium bicarbonate solution, the phases were separated and the aqueous phase extracted with more ether. The combined organic phases were washed with $H_2O$, dried with $MgSO_4$ and concentrated in vacuo to yield the crude product as an oil which was diluted with pentane (20 mL) and allowed to stand in a freezer overnight. The liquors were decanted from the resultant white crystals which were then dried in vacuo to yield the title compound (5.60 g, 31.4 mmol).

TLC: Rf=0.43 (8:7 heptane:EtOAc)

$^1$H NMR: (400 MHz, DMSO) δ: 4.54 (dd, J=5.5, 2.3, 2H), 5.26 (t, J=5.5, 1H), 7.17-7.46 (m, 2H)

(2,4-Difluoro-6-methoxyphenyl)methanol (IntA23)

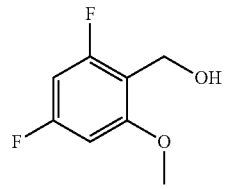

Step 1: Preparation of methyl 2,4-difluoro-6-methoxybenzoate

Methyl iodide (1.97 mL, 31.6 mmol) was added to a suspension of 2,4-difluoro-6-hydroxybenzoic acid (2.50 g, 14.4 mmol) and $K_2CO_3$ (5.96 g, 43.1 mmol) in acetone (50 mL) and the mixture heated at reflux for 12 h. After concentration in vacuo the material was suspended in DCM (50 mL) and filtered, rinsing the residue with DCM (2×50 mL). The combined filtrates were concentrated in vacuo and purified by gradient flash chromatography eluting with 5-40% EtOAc in iso-hexane to yield the title compound (1.15 g, 5.71 mmol).

$^1$H NMR: (400 MHz, DMSO) δ: 3.83 (s, 3H), 3.84 (s, 3H), 6.92-7.03 (m, 2H)

Step 2: Preparation of (2,4-difluoro-6-methoxyphenyl)methanol

A solution of $LiBH_4$ (2M in THF, 6.28 mL, 12.6 mmol) was added to a solution of methyl 2,4-difluoro-6-methoxybenzoate (1.15 g, 5.71 mmol) in THF (30 mL). The solution was stirred at rt for 23 h, then at 60° C. for 4.5 h, and reflux for 18.5 h. After cooling to rt, $H_2O$ (20 mL) was added dropwise and the mixture stirred for 5 min before being partially concentrated in vacuo. DCM (20 mL) was added, the phases were separated, and the aqueous phase was extracted with DCM (2×10 mL). The organic layers were concentrated in vacuo to yield the title compound (978 mg, 5.62 mmol).

LCMS (Method B): Molecular ions not observed, at 1.78 min, 85%

$^1$H NMR: (400 MHz, DMSO) δ: 3.83 (s, 3H), 4.41 (dd, J=5.4, 1.9, 2H), 4.85 (t, J=5.5, 1H), 6.69-6.86 (m, 2H)

(2-Chloro-6-fluoro-4-methylphenyl)methanol (IntA24)

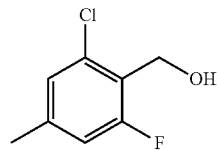

Step 1: Preparation of 2-chloro-6-fluoro-4-methylbenzaldehyde

Under Ar, a 2.5M solution of n-BuLi (6.0 mL, 15.0 mmol) was added slowly to a solution of 3-chloro-5-fluorotoluene (2.0, 13.8 mmol) in THF (20 mL) cooled in a dry ice/acetone bath at approximately −70° C. After the addition was complete, the reaction was stirred for 1 h at approximately −70° C. and a solution of N-formylmorpholine (2.3 g, 2.0 mmol) in THF (10 mL) was added dropwise. After stirring for 10 min, the reaction was allowed to warm to rt with stirring over 1 h, then cooled to −30° C. and quenched by the addition of $H_2O$ then 1M citric acid. The mixture was allowed to warm to rt with stirring and the phases were separated. The aqueous phase was extracted with EtOAc and the combined organic phases were washed with $H_2O$, dried with $MgSO_4$ and concentrated to yield the title compound as an oil which solidified on standing (2.2 g, 12.8 mmol).

TLC: Rf=0.22 (4:1 heptane:EtOAc)

Step 2: Preparation of (2-chloro-6-fluoro-4-methylphenyl)methanol

Sodium borohydride (1.42 g, 37.5 mmol) was added in portions to an ice-cooled solution of 2-chloro-6-fluoro-4-methylbenzaldehyde (6.25 g, 38.2 mmol) in methanol (56 mL); once addition was complete the reaction was allowed to warm rt with stirring over 1 h and then concentrated in vacuo. The residue was partitioned between ether and saturated aqueous sodium bicarbonate solution. The layers were separated and the aqueous re-extracted with ether. The organic layers were combined, washed with $H_2O$, dried with $MgSO_4$ and concentrated in vacuo to yield the crude product as an oil. This oil was diluted with pentane, cooled and stirred which resulted in a white solid. Filtration and drying in vacuo yielded the title compound (5.10 g, 29.2 mmol).

TLC: Rf=0.45 (8:7 heptane:EtOAc)

$^1$H NMR: (400 MHz, DMSO) δ: 2.36 (s, 3H), 4.58 (d, J=3.3, 2H), 5.20 (t, J=5.1, 1H), 7.10 (d, J=10.5, 1H), 7.21 (s, 1H)

2-Chloro-6-fluoro-4-methoxybenzyl alcohol (IntA25)

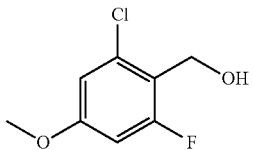

Step 1: Preparation of 3-chloro-5-fluoro-4-(hydroxymethyl)phenol

3-Chloro-5-fluorophenol (703 mg, 4.8 mmol) was added to a solution of potassium hydroxide (297 mg, 5.3 mmol) in H$_2$O (1.45 mL) and heated at 60° C. Formaldehyde (37 wt % in H$_2$O, 0.74 mL, 9.12 mmol) in H$_2$O (1.45 mL) was added dropwise and the reaction mixture left to stir at 40° C. overnight. The reaction mixture was cooled to rt and conc. HCl (approximately 6 mL) was added. The resultant precipitate was filtered, washed with H$_2$O and dried to yield the title compound as a cream solid (334 mg, 1.89 mmol).

LCMS (Method A): m/z 175, 177 (M−H)− (ES−), at 0.12 min, 95%

Step 2: Preparation of 2-chloro-6-fluoro-4-methoxybenzyl alcohol

Methyl iodide (0.13 mL, 2.08 mmol) was added dropwise to a solution of 3-chloro-5-fluoro-4-(hydroxymethyl)phenol (334 mg, 1.89 mmol) and potassium carbonate (287 mg, 2.08 mmol) in DMF (5 mL) and the reaction mixture stirred for 4 h at rt. The reaction mixture was partitioned between DCM and H$_2$O, the organic layer separated and the aqueous further extracted with DCM. The combined organic phases were concentrated in vacuo to yield the title compound as a yellow oil (360 mg, 1.89 mmol).

LCMS (Method A): No ionisation seen, at 1.24 min, 95%
$^1$H NMR: (400 MHz, DMSO) δ 3.79 (s, 3H), 4.50 (dd, J=5.3, 2.0, 2H), 5.07 (t, J=5.5, 1H), 6.86 (dd, J=11.5, 2.5, 1H), 6.90-6.95 (m, 1H)

(5-Fluoro-3-methylpyridin-2-yl)methanol (IntA26)

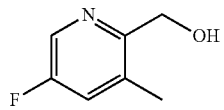

Sodium borohydride (125 mg, 3.3 mmol) was added to a solution of 5-fluoro-3-methylpyridine-2-carbaldehyde (417 mg, 3.0 mmol) in EtOH (10 mL) and stirred at rt for 3 h. The reaction was quenched by dropwise addition of saturated aqueous NH$_4$Cl solution (10 mL) and stirred for 15 h. The reaction mixture was extracted twice with DCM and the combined organic phases were concentrated in vacuo. Purification by gradient column chromatography, eluting with 10-60% EtOAc in iso-hexane to yield the title compound (218 mg, 51%).

LCMS (Method A): m/z 141.8 (M+H)+ (ES+), at 0.85 min, 95%

$^1$H NMR: (400 MHz, DMSO) δ: 2.36 (s, 3H), 4.55 (d, J=5.5, 2H), 5.07 (t, J=5.5, 1H), 7.57 (dd, J=9.8, 2.5, 1H), 8.31 (d, J=2.5, 1H)

4-(2,6-Difluoro-4-(tert-butyldimethylsilyloxy)benzyl)-2-(3,4-dimethoxyphenyl)-2H-1,2,4-benzothiadiazin-3(4H)-one 1,1-dioxide (IntA27)

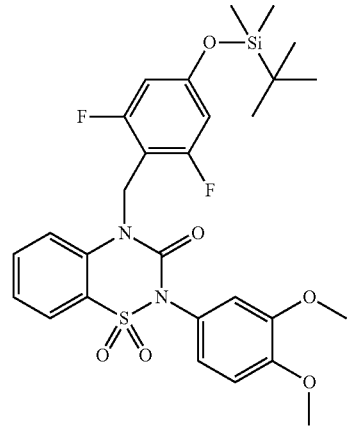 [SMILES: COc1ccc(N2C(=O)N(Cc3c(F)cc(O[Si](C)(C)C(C)(C)C)cc3F)c3ccccc3S2(=O)=O)cc1OC]

tert-Butyl(chloro)dimethylsilane (6.42 g, 42.6 mmol) was added to a solution of 2,6-difluoro-4-hydroxybenzoic acid (3.09 g, 17.8 mmol) in THF (50 mL), followed by the addition of N,N-diisopropylethylamine (9.19 mL, 51.5 mmol) over 5 min. After stirring at rt for 10 min the solution was concentrated in vacuo. Purification by gradient column chromatography, eluting with 10-50% solvent A in solvent B (A=DCM, B=DCM:MeOH:AcOH 95:5:1) yielded 2,6-difluoro-4-(tert-butyldimethylsilyloxy)benzoic acid (615 mg). This material was dissolved in THF (20 mL), borane-THF complex (1.0M in THF, 6.4 mL, 6.4 mmol) was added and the solution stirred at rt for 4 h. Further borane-THF complex (1.0M in THF, 6.4 mL, 6.4 mmol) was added and the solution stirred at rt for 18.5 h before concentration in vacuo. Purification by gradient column chromatography, eluting with 0-10% EtOAc in iso-hexane yielded 2,6-difluoro-4-(tert-butyldimethylsilyloxy)benzyl alcohol (470 mg). The title compound (533 mg, 0.90 mmol) was subsequently prepared from 2,6-difluoro-4-(tert-butyldimethylsilyloxy)benzyl alcohol (356 mg, 1.30 mmol) and (IntA1) (289 mg) using the methods of (77).

LCMS (Method B): m/z 591.2 (M+H)+ (ES+), at 6.35 min, 90%

TLC: Rf=0.86 (9:1 iso-hexane:EtOAc)

2-(6-Methoxy-5-methylpyridin-3-yl)-2H-1,2,4-benzothiadiazin-3(4H)-one 1,1-dioxide (IntA28)

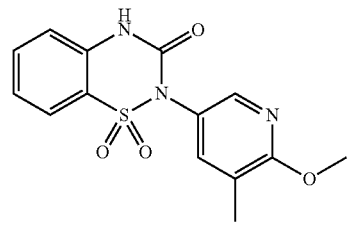 [SMILES: COc1ncc(N2C(=O)Nc3ccccc3S2(=O)=O)cc1C]

Step 1: Preparation of N-(6-methoxy-5-methylpyridin-3-yl)-2-nitrobenzenesulfonamide The title compound (2.69 g, 8.32 mmol) was prepared from 2-nitrobenzenesulfonyl chloride (2.41 g, 10.9 mmol), 6-methoxy-5-methylpyridin-3-amine (1.66 g, 12.0 mmol) and pyridine (2.64 mL, 32.7 mmol) in 1,4-dioxane (25 mL) at rt using the methods of (IntA1), step 1.

LCMS (Method B): m/z 324.2 (M+H)$^+$ (ES+), at 1.37 min, >95%

Step 2: Preparation of 2-amino-N-(6-methoxy-5-methylpyridin-3-yl)benzenesulfonamide A mixture of N-(6-methoxy-5-methylpyridin-3-yl)-2-nitrobenzenesulfonamide (2.69 g, 8.32 mmol) and 10% palladium on charcoal (1.35 g) in ethanol/EtOAc (1:1, 100 mL total reaction volume) was stirred at rt under an atmosphere of $H_2$ for approximately 2.5 h. Filtration and concentration in vacuo yielded the crude title compound (2.60 g).

Mass spectroscopy: (ESI+ve) 294.2 [M+H]$^+$

Step 3: Preparation of 2-(6-methoxy-5-methylpyridin-3-yl)-2H-1,2,4-benzothiadiazin-3(4H)-one 1,1-dioxide The title compound was prepared from 2-amino-N-(6-methoxy-5-methylpyridin-3-yl)benzenesulfonamide (2.60 g) and triphosgene (815 mg, 2.75 mmol) in anhydrous 1,4-dioxane (160 mL) using the methods of (IntA1) step 3. Concentration in vacuo after completion of the reaction yielded the title compound (3.38 g, 10.6 mmol, approximately 80% purity by LCMS) which was used without further purification.

LCMS (Method B): m/z 320.1 (M+H)+ (ES+), at 2.55 min, 80%

2-(5,6-Dimethylpyridin-3-yl)-2H-1,2,4-benzothiadiazin-3(4H)-one 1,1-dioxide (IntA29)

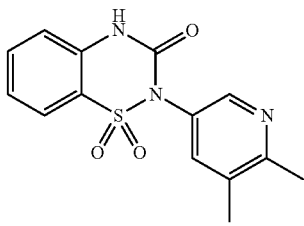 [SMILES: Cc1cc(N2C(=O)Nc3ccccc3S2(=O)=O)cnc1C]

Steps 1 and 2: Preparation of 2-amino-N-(5,6-dimethylpyridin-3-yl)benzenesulfonamide The title compound (2.7 g, 13.0 mmol) was prepared in two steps from 2-nitrobenzenesulfonyl chloride (3.20 g, 14.4 mmol) and 5,6-dimethylpyridin-3-amine (1.5 g, 12.3 mmol) in pyridine (20 mL) at rt; followed by $SnCl_2$ (8.88 g, 46.8 mmol) in ethanol at reflux for 2 h using the methods of (IntA1), steps 1 and 2. Mass spectroscopy: (ESI+ve) 277.7 [M+H]$^+$

Step 3: Preparation of 2-(5,6-dimethylpyridin-3-yl)-2H-1,2,4-benzothiadiazin-3(4H)-one 1,1-dioxide The title compound (2.17 g, 7.15 mmol) was prepared from 2-amino-N-(5,6-dimethylpyridin-3-yl)benzenesulfonamide (2.7 g, 13.0 mmol) and 1,1'-carbonyldiimidazole (4.74 g, 29.2 mmol) in 1,2-dichloroethane (25 mL) at 110° C. for 3 h using the methods of (IntA14), step 3.

LCMS (Method B): m/z 304.1 (M+H)+ (ES+), at 1.90 min, 95%

$^1$H NMR: (400 MHz, CDCl$_3$) δ: 2.38 (s, 3H), 2.61 (s, 3H), 7.19 (d, J=8.0, 1H), 7.35-7.39 (m, 1H), 7.62 (d, J=2.3, 1H), 7.66-7.71 (m, 1H), 7.94 (dd, J=7.9, 1.4, 1H), 8.42 (d, J=2.3, 1H), 8.72 (br. s, 1H)

tert-Butyl (6-amino-3-methoxypyridin-2-yl)methylcarbamate (IntA30)

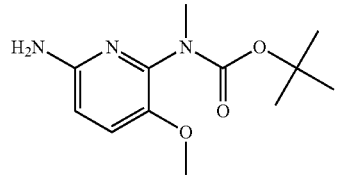 [SMILES: COc1ccc(N)nc1N(C)C(=O)OC(C)(C)C]

Step 1: Preparation of 6-bromo-3-methoxy-2-nitropyridine

To a stirred solution of 3-hydroxy-2-nitropyridine (50.0 g, 0.34 mol) in MeOH (1 L) was added 30% NaOMe in MeOH (83 mL). The solution was stirred at rt for 30 min then cooled to 0° C. and Br$_2$ (18 mL, 0.35 mol) was added dropwise maintaining this temperature. The reaction was then stirred at 0° C. for 2 h before the addition of glacial acetic acid (10 mL). Concentration in vacuo gave crude material (119 g), to which was added acetone (2 L) and K$_2$CO$_3$ (153 g, 0.8 mol) followed by iodomethane (85.5 mL, 1.4 mol). After stirring at 40° C. for 4 h the reaction was cooled to rt and filtered. After concentration of the filtrate in vacuo purification by flash chromatography eluting with 3:1 heptane-EtOAc yielded the title compound (14.4 g, 61.8 mmol).

$^1$H NMR: (400 MHz, CDCl$_3$) δ: 3.96 (s, 3H), 7.42 (d, J=8.7, 1H), 7.68 (d, J=8.7, 1H)

Step 2: Preparation of 6-bromo-3-methoxypyridin-2-amine

A mixture of 6-bromo-3-methoxy-2-nitropyridine (14.4 g, 61.8 mmol), AcOH (200 mL) and Fe powder (14.0 g, 0.25 mol) was stirred at 90° C. for 1.5 h. After cooling to rt and dilution with EtOAc the mixture was filtered through celite and the filtrate concentrated in vacuo. Purification by flash chromatography eluting with DCM yielded the title compound (10.2 g, 50.2 mmol) as a white solid.

$^1$H NMR (400 MHz, DMSO) δ: 3.81 (s, 3H), 4.78 (br. s, 2H), 6.73 (d, J=7.8, 2H)

Step 3: Preparation of tert-butyl (6-bromo-3-methoxypyridin-2-yl)carbamate

A mixture of 6-bromo-3-methoxypyridin-2-amine (10.2 g, 50.2 mmol), Boc$_2$O (38.2 g, 0.18 mol) and 4-(dimethylamino)pyridine (1.2 g, 9.82 mmol) in MeCN (550 mL) was refluxed for 2 h. After cooling to rt and concentration in vacuo EtOAc (500 mL) was added and the organic phase washed with water (100 mL) and brine (50 mL). The organic phase was dried (MgSO₄), filtered and the filtrate concentrated in vacuo. Purification by chromatography eluting with 4:1 DCM-heptane yielded a mixture of the title compound and di-tert-butyl (6-bromo-3-methoxypyridin-2-yl)imidodicarbonate (10.6 g) in an approximate ratio of 55:45.

To a solution of the title compound and di-tert-butyl (6-bromo-3-methoxypyridin-2-yl)imidodicarbonate (7.19 g, approximate ratio of 43:57) in MeOH (55 mL) at rt was added K₂CO₃ (7.39 g, 53.5 mmol). After stirring at 55° C. for 1.5 h the mixture was cooled to rt and combined with a previous reaction mixture derived from title compound and di-tert-butyl (6-bromo-3-methoxypyridin-2-yl)imidodicarbonate (8.83 g, approximate ratio of 43:57) and filtered. The residue was washed with EtOAc and the filtrate was concentrated in vacuo. Purification by gradient flash chromatography, eluting with 10-25% EtOAc in heptane yielded the title compound (8.38 g, 27.6 mmol) as a pale yellow solid.

¹H NMR (400 MHz, CDCl₃) δ: 1.52 (s, 9H), 3.85 (s, 3H), 6.94 (d, J=8.2, 1H), 7.07 (d, J=8.2, 1H), 7.23 (br. s, 1H)

Step 4: tert-butyl (6-amino-3-methoxypyridin-2-yl)methylcarbamate

NaH (60% in oil, 1.90 g, 47.5 mmol) was added to cooled (5° C.) anhydrous 2-MeTHF (120 mL) under argon, followed by a solution of tert-butyl (6-bromo-3-methoxypyridin-2-yl)carbamate (4.80 g, 15.8 mmol) in anhydrous 2-MeTHF (40 mL) slowly, maintaining the reaction temperature below 15° C. Once the addition was complete the reaction was stirred for 15 min prior to addition of iodomethane (2.76 mL, 44.3 mmol). After stirring at rt for 21 h, further iodomethane (2.76 mL, 44.3 mmol) was added and the reaction mixture stirred at rt for 1 d. After cooling to 5° C. saturated aqueous NH₄Cl and H₂O (1:1, 160 mL) was added with caution. The mixture was stirred at rt for 15 min, the phases were separated and the aqueous phase extracted with EtOAc (2×200 mL). The combined organic phases were washed with brine, dried (Na₂SO₄) and concentrated in vacuo before purification by gradient flash chromatography, eluting with 5-25% EtOAc in heptane yielded tert-butyl (6-bromo-3-methoxypyridin-2-yl)(methyl)carbamate (4.52 g, 14.3 mmol) as a colourless oil. Sodium tert-butoxide (2.74 g, 28.5 mmol), BINAP (355 mg, 0.57 mmol) and benzophenone imine (2.63 mL, 15.7 mmol) were added to a solution of tert-butyl (6-bromo-3-methoxypyridin-2-yl)(methyl)carbamate (4.52 g, 14.3 mmol) in degassed toluene (75 mL) under argon. Pd₂(dba)₃ (261 mg, 0.29 mmol) was added and the reaction heated at 80° C. for 2 h before cooling to rt and concentration in vacuo. THF (200 mL) and 0.5 M aqueous HCl (200 mL) were added and the mixture was stirred at rt for 1 h then quenched by addition of saturated aqueous NaHCO₃ (200 mL). After partial concentration in vacuo to remove the THF, EtOAc (500 mL) was added and the resulting emulsion was filtered through celite, rinsing with EtOAc. The filtrate layers were separated and the aqueous phase extracted with EtOAc (2×500 mL). The combined organic layers were washed with brine, dried (Na₂SO₄) and concentrated in vacuo before purification by flash chromatography eluting with 1:3 EtOAc in heptane followed by gradient elution with 50-60% EtOAc in heptane with 1% Et₃N yielded impure title compound containing BINAP-oxide. 0.5 M aqueous HCl (300 mL) and EtOAc (300 mL) were added, the phases were separated, and the aqueous phase washed with EtOAc (300 mL). The aqueous phase was then basified with solid Na₂CO₃ and extracted with EtOAc (3×300 mL). The combined organic phases were washed with brine, dried (Na₂SO₄) and concentrated in vacuo to yield the title compound (2.84 g, 11.21 mmol) as a brown solid.

LCMS (Method B): m/z 254.2 (M+H)+ (ES+), at 2.33 min, 95%

¹H NMR (400 MHz, CDCl₃) δ: 1.39 (s, 9H), 3.16 (s, 3H), 3.74 (s, 3H), 4.13 (br. s, 2H), 6.40 (d, J=8.5, 1H), 7.11 (d, 1H)

tert-Butyl [6-(1,1-dioxido-3-oxo-3,4-dihydro-2H-1,2,4-benzothiadiazin-2-yl)-3-methoxypyridin-2-yl]methylcarbamate (IntA31)

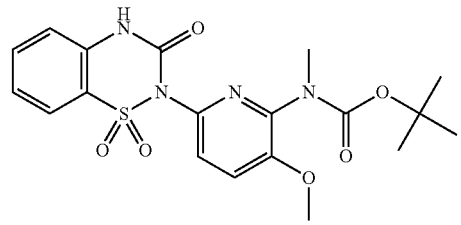 [SMILES: COc1ccc(N2C(=O)Nc3ccccc3S2(=O)=O)nc1N(C)C(=O)OC(C)(C)C]

The title compound (1.03 g, 2.37 mmol) was prepared in three steps from 2-nitrobenzenesulfonyl chloride (1.12 g, 5.05 mmol), tert-butyl (6-amino-3-methoxypyridin-2-yl)methylcarbamate (1.41 g, 5.56 mmol) and pyridine (1.23 mL, 15.2 mmol) in DCM (25 mL) at 0° C. to rt; followed by 10% Pd/C (895 mg) in EtOAc (40 mL); followed by 1,1'-carbonyldiimidazole (2.65 g, 16.4 mmol) and triethylamine (1.14 mL, 8.18 mmol) in DMF (80 mL) using the methods of (IntA17), step 1 and (IntA14), steps 2 and 3.

LCMS (Method B): m/z 435.2 (M+H)+ (ES+), at 2.72 min, 100%

¹H NMR: (400 MHz, DMSO) δ: 1.30 (s, 9H), 3.03 (s, 3H), 3.87 (s, 3H), 7.25-7.47 (m, 3H), 7.64 (d, J=8.7, 1H), 7.68-7.79 (m, 1H), 7.84 (dd, J=8.0, 1.1, 1H), 11.57 (s, 1H)

2-(4,5-Dimethoxypyrimidin-2-yl)-2H-1,2,4-benzothiadiazin-3(4H)-one 1,1-dioxide (IntA32)

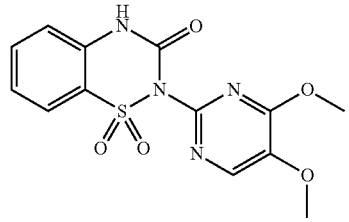 [SMILES: COc1cnc(N2C(=O)Nc3ccccc3S2(=O)=O)nc1OC]

Step 1: Preparation of N-(4,5-dimethoxypyrimidin-2-yl)-2-nitrobenzenesulfonamide 2-Nitrobenznesulfonyl chloride (649 mg, 2.93 mmol) and 4,5-dimethoxypyrimidin-2-amine (500 mg, 3.22 mmol) were dissolved in pyridine (12 mL) and heated at 50° C. overnight. After concentration in vacuo purification by gradient flash chromatography, eluting with 12-100% EtOAc in iso-hexane yielded the title compound (231 mg, 0.68 mmol).

TLC: R_f=0.09 (50% EtOAc in iso-hexane)

LCMS (Method A): m/z 339 (M−H)− (ES−), 341 (M+H)+ (ES+), at 0.10 and 0.73 min

Steps 2 and 3: Preparation of 2-(4,5-dimethoxypyrimidin-2-yl)-2H-1,2,4-benzothiadiazin-3(4H)-one 1,1-dioxide The title compound was prepared in two steps from N-(4,5-dimethoxypyrimidin-2-yl)-2-nitrobenzenesulfonamide (231 mg, 0.68 mmol), Fe powder (380 mg, 6.8 mmol) and acetic acid (5 mL); followed by 1,1'-carbonyldiimidazole (396 mg, 2.44 mmol) and triethylamine (0.17 mL, 1.22 mmol) in DMF (4.0 mL) using the methods of (IntA17), step 2 and (IntA14), step 3. The residue from step 3 was triturated with Et$_2$O to yield the title compound (104 mg, 0.31 mmol).

LCMS (Method A): m/z 335 (M−H)− (ES−), 337 (M+H)+ (ES+), at 0.11 and 1.01 min

2-(4,6-Dimethoxypyridin-2-yl)-2H-1,2,4-benzothiadiazin-3(4H)-one 1,1-dioxide (IntA33)

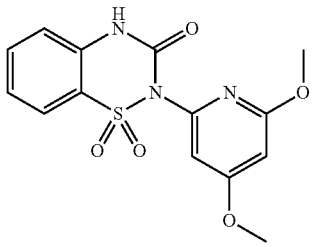 [SMILES: COc1cc(OC)nc(N2C(=O)Nc3ccccc3S2(=O)=O)c1]

The title compound (316 mg, 0.94 mmol) was prepared in three steps from 2-nitrobenzenesulfonyl chloride (2.15 g, 9.7 mmol), 4,6-dimethoxypyridin-2-amine hydrochloride (2.04 g, 10.7 mmol) and pyridine (2.35 mL, 29.1 mmol) in DCM (35 mL) at rt; followed by Fe powder (1.38 g, 24.7 mmol) and acetic acid (15 mL); followed by 1,1'-carbonyldiimidazole (1.62 g, 10.0 mmol) and triethylamine (0.70 mL, 5.0 mmol) in DMF (10.0 mL) using the methods of (IntA1), step 1, (IntA17), step 2 and (IntA14), step 3.

LCMS (Method B): m/z 334 (M−H)− (ES−), 336 (M+H)+ (ES+), at 1.91 min, 100%.

$^1$H NMR: (400 MHz, DMSO) δ: 3.77 (s, 3H), 3.81 (s, 3H), 6.50 (d, J=1.8, 1H), 6.71 (d, J=1.8, 1H), 7.26-7.39 (m, 2H), 7.68-7.78 (m, 1H), 7.80-7.88 (m, 1H), 11.60 (br. s, 1H)

tert-Butyl (5-amino-2-methoxypyridin-3-yl)methylcarbamate (IntA34)

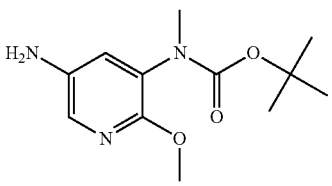 [SMILES: COc1ncc(N)cc1N(C)C(=O)OC(C)(C)C]

Steps 1 to 3: Preparation of N-(2-methoxy-5-nitropyridin-3-yl)acetamide

A solution of 2-methoxy-3-nitropyridine (50 g, 324.4 mmol) and 10% Pd/C (5 g) in MeOH (500 mL) was stirred under an atmosphere of H$_2$ for 3 h. The mixture was filtered through celite and the filter was washed with MeOH. The filtrate was concentrated in vacuo to yield 2-methoxypyridin-3-amine as a brown solid (38.9 g, 313.4 mmol).

$^1$H NMR: (300 MHz, CDCl$_3$) δ: 3.74 (br. s, 2H), 3.96 (s, 3H), 6.72 (m, 1H), 6.86 (m, 1H), 7.56 (d, J=1.8, 1H)

To a stirred solution of 2-methoxypyridin-3-amine (20 g, 161.1 mmol) and DIPEA (29.5 mL, 169.2 mmol) in DCM (120 mL) was added acetic anhydride (16 mL, 169.2 mmol) slowly. The reaction was then stirred at rt for 2 h before water (50 mL) was added and the phases were separated. The DCM layer was then washed with brine (20 mL), dried (MgSO$_4$) and concentrated in vacuo to yield a brown solid (26 g), which upon trituration with heptane gave N-(2-methoxypyridin-3-yl)acetamide as a beige solid (24 g, 144.4 mmol).

$^1$H NMR: (400 MHz, CDCl$_3$) δ: 2.15 (s, 3H), 4.04 (s, 3H), 6.88 (m, 1H), 7.65 (br. s, 1H), 7.82 (m, 1H), 8.55 (d, J=1.8, 1H)

To a stirred solution of N-(2-methoxypyridin-3-yl)acetamide (23 g, 139 mmol) in trifluoroacetic anhydride (TFAA) (90 mL) was added a solution of HNO$_3$ (5.84 mL, 139 mmol) in TFAA (140 mL) dropwise at rt. The reaction was stirred for 1.5 h at rt before being poured into an ice bath with stirring. The precipitated solid was filtered and washed with Et$_2$O (50 mL), then dissolved in EtOAc (1 L) and washed with saturated aqueous NaHCO$_3$ (100 mL) and brine (100 mL). The phases were separated and the organic phase dried (MgSO$_4$), and concentrated in vacuo to yield the title compound as a light yellow solid (21.2 g, 100.4 mmol).

$^1$H NMR: (400 MHz, CDCl$_3$) δ: 2.25 (s, 3H), 4.11 (s, 3H), 7.67 (br. s, 1H), 8.76 (d, J 2.8, 1H), 9.37 (d, J=2.8, 1H)

Steps 4 to 7: Preparation of tert-butyl (5-amino-2-methoxypyridin-3-yl)methylcarbamate To a stirred solution of N-(2-methoxy-5-nitropyridin-3-yl)acetamide (14 g, 66.7 mmol) in MeCN (600 mL) was added Boc-anhydride (36.4 mL, 166.7 mmol) followed by 4-(dimethylamino)pyridine (1.6 g, 13.4 mmol). After stirring at reflux for 5 h the mixture was concentrated in vacuo and the residue redissolved in EtOAc (300 mL) and washed with water (50 mL) and brine (50 mL), dried (MgSO$_4$) and concentrated in vacuo. Purification by flash column chromatography eluting with 4:1 DCM-heptane yielded tert-butyl acetyl(2-methoxy-5-nitropyridin-3-yl)carbamate as a light yellow solid (18.3 g, 58.8 mmol.

$^1$H NMR: (400 MHz, CDCl$_3$) δ: 1.38 (s, 9H), 2.64 (s, 3H), 4.09 (s, 3H), 8.17 (s, 1H), 9.05 (s, 1H)

To a stirred solution of tert-butyl acetyl(2-methoxy-5-nitropyridin-3-yl)carbamate (18.3 g, 58.9 mmol) in MeCN (450 mL) was added N,N-diethylethylenediamine (13.7 g, 117.8 mmol). After stirring at rt for 16 h the precipitated solids were isolated by filtration and washed with heptanes to yield a light yellow solid (4.1 g). The filtrate was concentrated in vacuo, cooled in an ice-bath and further solid precipitated from the solution. The solids were isolated by filtration and washed with heptanes to give another batch of light yellow solid. The two batches were combined to afford tert-butyl (2-methoxy-5-nitropyridin-3-yl)carbamate (12.2 g, 45.3 mmol).

$^1$H NMR: (400 MHz, CDCl$_3$) δ: 1.54 (s, 9H), 4.16 (s, 3H), 7.03 (br. s, 1H), 8.17 (s, 1H), 9.08 (s, 1H)

To a stirred solution of tert-butyl (2-methoxy-5-nitropyridin-3-yl)carbamate (12.2 g, 45.3 mmol) in anhydrous THF (400 mL) was added NaH (60% in mineral oil, 3.6 g, 90.8 mmol) at 0° C. and the mixture was stirred at 0° C. for 15 min. A solution of iodomethane (5.7 mL, 90.8 mmol) in THF (50 mL) was added dropwise to the mixture which was then warmed to rt and stirred for 16 h. After careful quenching with saturated aqueous NH$_4$Cl solids were removed by filtration and the filtrate was diluted with EtOAc (400 mL). The organic phase was washed with water and brine, dried (MgSO$_4$) and concentrated in vacuo. Purification by flash column chromatography eluting with 4:1 DCM-heptane yielded tert-butyl (2-methoxy-5-nitropyridin-3-yl)methylcarbamate (9.8 g, 34.6 mmol) as a yellow solid.

$^1$H NMR: (400 MHz, CDCl$_3$) δ: 1.39 (s, 9H), 3.15 (s, 3H), 4.08 (s, 3H), 8.23 (s, 1H), 8.96 (s, 1H)

10% Pd/C (1 g) was added to a solution of tert-butyl (2-methoxy-5-nitropyridin-3-yl)methylcarbamate (9.8 g, 34.6 mmol) in MeOH (150 mL) and DCM (75 mL) and the mixture stirred at rt for 7 h under an atmosphere of H$_2$. The reaction mixture was then filtered through celite and washed with MeOH and the filtrate concentrated in vacuo. Purification by flash column chromatography eluting with 2:1 to 1:1 heptane-EtOAc yielded the title compound (7.4 g, 29.2 mmol) as a tan solid.

$^1$H NMR: (400 MHz, CDCl$_3$) δ: 1.38 (s, 9H), 3.08 (s, 3H), 3.35 (br. s, 2H), 3.87 (s, 3H), 6.91 (s, 1H), 7.55 (s, 1H)

tert-Butyl [5-(1,1-dioxido-3-oxo-3,4-dihydro-2H-1,2,4-benzothiadiazin-2-yl)-2-methoxypyridin-3-yl]methylcarbamate (IntA35)

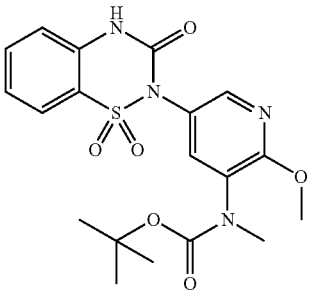 [SMILES: COc1ncc(N2C(=O)Nc3ccccc3S2(=O)=O)cc1N(C)C(=O)OC(C)(C)C]

The title compound (2.12 g, 4.84 mmol) was prepared in three steps from 2-nitrobenzenesulfonyl chloride (1.11 g, 5.0 mmol), tert-butyl (5-amino-2-methoxypyridin-3-yl)methylcarbamate (IntA34) (1.39 g, 5.5 mmol) and pyridine (1.21 mL, 15.0 mmol) in 1,4-dioxane (20 mL); followed by followed by 10% Pd/C (212 mg) in water/EtOH (1:1, 100 mL); followed by 1,1'-carbonyldiimidazole (1.14 g, 7.02 mmol) and triethylamine (0.49 mL, 3.51 mmol) in DMF (8 mL) using the methods of (IntA1), step 1 and (IntA14), steps 2 and 3.

LCMS (Method B): m/z 433 (M−H)− (ES−), 435 (M+H)+ (ES+), at 3.03 min, 100%

$^1$H NMR: (400 MHz, DMSO) δ: 1.30 (s, 9H), 3.02 (s, 3H), 3.93 (s, 3H), 7.24-7.38 (m, 2H), 7.66-7.77 (m, 2H), 7.83-7.94 (m, 1H), 8.09 (s, 1H), 11.66 (br. s, 1H)

Route 2

2-[(2-Chloro-6-fluorobenzyl)amino]-N-(1-methyl-6-oxo-1,6-dihydropyridin-3-yl)benzenesulfonamide (IntB1)

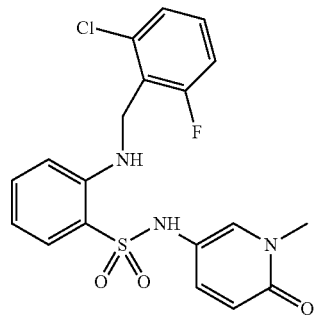 [SMILES: Cn1cc(NS(=O)(=O)c2ccccc2NCc2c(F)cccc2Cl)ccc1=O]

Step 1: Preparation of 2-Fluoro-N-(1-methyl-6-oxo-1,6-dihydropyridin-3-yl)benzenesulfonamide 2-Fluorobenzenesulfonyl chloride (0.46 mL, 3.5 mmol) was added to a solution of 5-amino-1-methyl-1,2-dihydropyridin-2-one (478 mg, 3.85 mmol) in 1,4-dioxane (10 mL) and stirred for 28 h at rt. After concentration in vacuo purification by column chromatography eluting with DCM:MeOH:7M NH$_3$ in MeOH (90:5:5) yielded the title compound (448 mg, 1.59 mmol).

LCMS (Method A): m/z 283 (M+H)+ (ES+), at 0.13 min, 100%

$^1$H NMR: (400 MHz, DMSO) δ: 3.35 (s, 3H), 6.26 (d, J=9.5, 1H), 7.03 (dd, J=9.7, 2.9, 1H), 7.30-7.40 (m, 1H), 7.47 (dd, J=10.0, 8.5, 1H), 7.52 (d, J=3.0, 1H), 7.65-7.79 (m, 2H), 9.96 (s, 1H)

Step 2: Preparation of 2-[(2-chloro-6-fluorobenzyl) amino]-N-(1-methyl-6-oxo-1,6-dihydropyridin-3-yl) benzenesulfonamide (IntB1)

A mixture of 2-fluoro-N-(1-methyl-6-oxo-1,6-dihydropyridin-3-yl)benzenesulfonamide (72 mg, 0.26 mmol) and 2-chloro-6-fluorobenzyl amine (0.33 mL, 2.6 mmol) in MeCN (1.5 mL) was heated at 180° C. for 6 h in a Biotage Initiator microwave reactor. After concentration in vacuo purification by gradient column chromatography eluting with 0-10% MeOH in DCM yielded impure title compound (151 mg) which was used without further purification.

LCMS (Method A): m/z 422.0, 423.9 (M+H)+ (ES+), at 0.13 and 1.11 min, 60%.

TLC: Rf=0.91 (DCM:MeOH, 9:1)

2-[(2-Chloro-6-fluorobenzyl)amino]-N-(2-methoxy-pyrimidin-5-yl)benzenesulfonamide (IntB2)

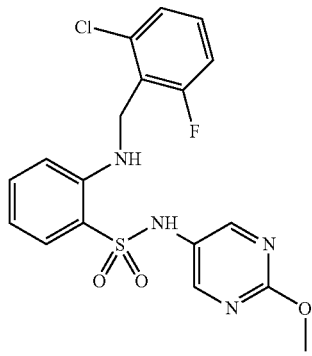 [SMILES: COc1ncc(NS(=O)(=O)c2ccccc2NCc2c(F)cccc2Cl)cn1]

The title compound (106 mg, impure, used without further purification) was prepared in two steps from 2-fluorobenzenesulfonyl chloride (0.46 mL, 3.5 mmol) and 5-amino-2-methoxypyrimidine (482 mg, 3.85 mmol) in 1,4-dioxane at 100° C.; followed by 2-chloro-6-fluorobenzyl amine (0.36 mL, 2.8 mmol) in MeCN (1.5 mL) at 180° C. in a Biotage Initiator microwave reactor using the methods of (IntB1).

LCMS (Method A): m/z 421.2, 423.2 (M−H)− (ES−), at 0.13 and 1.13 min, 95%

TLC: Rf=0.64 (iso-hexane:EtOAc)

5-Fluoro-2-{[1-(2-fluorophenyl)ethyl]amino}-N-[3-(methylsulfanyl)phenyl]benzenesulfonamide (IntB3)

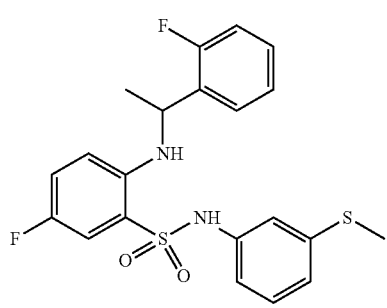 [SMILES: CSc1cccc(NS(=O)(=O)c2cc(F)ccc2NC(C)c2ccccc2F)c1]

The title compound (139 mg, 0.32 mmol) was prepared in two steps from 2,5-difluorobenzenesulfonyl chloride (1.07 g, 5.0 mmol) and 3-(methylsulfanyl)aniline (769 mg, 5.5 mmol) in 1,4-dioxane at 70° C.; followed by 1-(2-fluorophenyl)ethanamine (500 mg, 3.6 mmol) in MeCN (0.5 mL) at 200° C. in a Biotage Initiator microwave reactor using the methods of (IntB1).

LCMS (Method B): m/z 435 (M+H)+ (ES+), at 3.50 min, 95%

$^1$H NMR: (400 MHz, DMSO) δ: 1.52 (d, J=6.5, 3H), 2.39 (s, 3H), 4.86 (quin, J=6.5, 1H), 6.09 (d, J=5.8, 1H), 6.41 (dd, J=9.3, 4.3, 1H), 6.85-7.08 (m, 4H), 7.13-7.31 (m, 5H), 7.43 (dd, J=8.7, 3.1, 1H), 10.84 (s, 1H)

2-[(2-Chloro-6-fluorobenzyl)amino]-5-fluoro-N-[3-(methylsulfanyl)phenyl]benzenesulfonamide (IntB4)

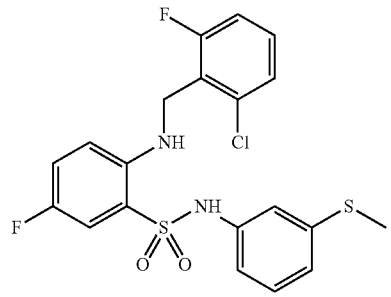 [SMILES: CSc1cccc(NS(=O)(=O)c2cc(F)ccc2NCc2c(F)cccc2Cl)c1]

The title compound (119 mg, 0.26 mmol) was prepared in two steps from 2,5-difluorobenzenesulfonyl chloride (1.07 g, 5.0 mmol) and 3-(methylsulfanyl)aniline (769 mg, 5.5 mmol) in 1,4-dioxane at 70° C.; followed by 2-chloro-6-fluorobenzyl amine (762 uL, 5.9 mmol) in MeCN (1.5 mL) at 180° C. in a Biotage Initiator microwave reactor using the methods of (IntB1).

LCMS (Method B): m/z 455, 457 (M+H)+ (ES+), at 3.45 min, >95%

TLC: Rf=0.52 (1:4 EtOAc:iso-hexane)

2-[(2-Chloro-6-fluorobenzyl)amino]-3-fluoro-N-(6-methoxypyridin-3-yl)benzenesulfonamide (IntB5)

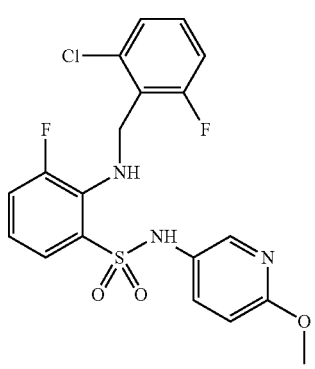 [SMILES: COc1ccc(NS(=O)(=O)c2cccc(F)c2NCc2c(F)cccc2Cl)cn1]

The title compound (139 mg, 0.32 mmol) was prepared in two steps from 2,3-difluorobenzenesulfonyl chloride (1.0 g, 4.7 mmol) and 6-methoxypyridin-3-amine (642 mg, 5.2 mmol) in 1,4-dioxane at 100° C.; followed by 2-chloro-6-fluorobenzyl amine (547 mg, 3.4 mmol) in MeCN (3 mL) at 180° C. in a Biotage Initiator microwave reactor using the methods of (IntB1).

LCMS (Method B): m/z 439.9, 441.9 (M+H)+ (ES+), at 2.35 min, 95%

3-Fluoro-N-(6-methoxypyridin-3-yl)-2-[(2-methyl-benzyl)amino]benzenesulfonamide (IntB6)

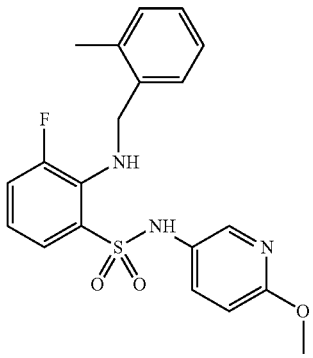 [SMILES: COc1ccc(NS(=O)(=O)c2cccc(F)c2NCc2ccccc2C)cn1]

The title compound (139 mg, 0.35 mmol) was prepared in two steps from 2,3-difluorobenzenesulfonyl chloride (1.0 g, 4.7 mmol) and 6-methoxypyridin-3-amine (642 mg, 5.2 mmol) in 1,4-dioxane at 100° C.; followed by 2-methylbenzyl amine (425 uL, 3.4 mmol) in MeCN (3 mL) at 180° C. in a Biotage Initiator microwave reactor using the methods of (IMB1).

LCMS (Method B): m/z 402.0 (M+H)+ (ES+), at 2.38 min, 95%

Route 4

2-Chloro-N-(3,4-dimethoxyphenyl)pyridine-3-sulfonamide (IntC1)

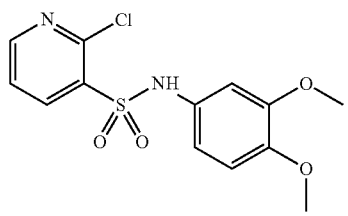 [SMILES: COc1ccc(NS(=O)(=O)c2cccnc2Cl)cc1OC]

A solution of 2-chloropyridine-3-sulfonyl chloride (500 mg, 2.36 mmol) and 3,4-dimethoxyaniline (397 mg, 2.59 mmol) in 1,4-dioxane (10 mL) was stirred for 1 h at 0° C. The reaction mixture was filtered, the residue washed with ether and the filtrate concentrated in vacuo. Purification by gradient column chromatography eluting with 10-60% EtOAc in iso-hexane yielded the title compound (352 mg, 1.07 mmol).

LCMS (Method A): m/z 327.2, 329.1 (M–H)– (ES–), at 0.12 min, 95%

$^1$H NMR: (400 MHz, DMSO) δ 3.64 (s, 3H), 3.65 (s, 3H), 6.59 (dd, J=8.7, 2.4, 1H), 6.72 (d, J=2.5, 1H), 6.80 (d, J=8.5, 1H), 7.59 (dd, J=7.8, 4.8, 1H), 8.36 (dd, J=7.8, 1.8, 1H), 8.61 (dd, J=4.8, 1.8, 1H), 10.53 (s, 1H)

2-Chloro-N-(2,6-dimethoxypyridin-4-yl)pyridine-3-sulfonamide (IntC2)

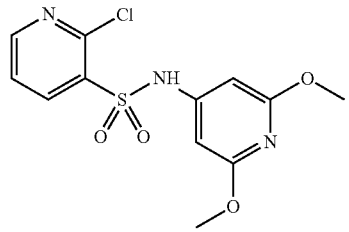 [SMILES: COc1cc(NS(=O)(=O)c2cccnc2Cl)cc(OC)n1]

The title compound (623 mg, 1.89 mmol) was prepared from 2-chloropyridine-3-sulfonyl chloride (530 mg, 2.5 mmol), 2,6-dimethoxy-4-pyridinamine (424 mg, 2.8 mmol) and pyridine (0.6 mL, 7.5 mmol) in DCM (10 mL) using the methods of (IntC1).

LCMS (Method A): m/z 328, 330 (M–H)– (ES–), 330, 332 (M+H)+ (ES+), at 0.13 and 0.73 min, 60%

$^1$H NMR: (400 MHz, DMSO) δ: 3.75 (s, 6H), 6.03 (s, 2H), 7.71 (dd, J=7.8, 4.8, 1H), 8.58 (dd, J=7.8, 1.8, 1H), 8.68 (dd, J=4.8, 1.8, 1H), 11.54 (br s, 1H)

2-Chloro-N-(5,6-dimethoxypyridin-2-yl)pyridine-3-sulfonamide (IntC3)

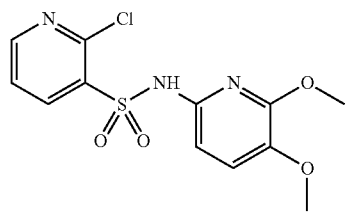 [SMILES: COc1ccc(NS(=O)(=O)c2cccnc2Cl)nc1OC]

The title compound (549 mg, 1.66 mmol) was prepared from 2-chloropyridine-3-sulfonyl chloride (530 mg, 2.5 mmol), 5,6-dimethoxypyridin-2-amine (424 mg, 2.8 mmol) and pyridine (0.6 mL, 7.5 mmol) in DCM (10 mL) using the methods of (IntC1).

LCMS (Method A): m/z 328, 330 (M–H)– (ES–), 330, 332 (M+H)+ (ES+), at 0.12 min, 100%

$^1$H NMR: (400 MHz, DMSO) δ: 3.42 (s, 3H), 3.68 (s, 3H), 6.52 (d, J=8.3, 1H), 7.26 (d, J=8.3, 1H), 7.67 (dd, J=7.8, 4.8, 1H), 8.58 (dd, J=7.9, 1.9, 1H), 8.64 (dd, J=4.8, 1.8, 1H), 11.22 (s, 1H)

2-Chloro-N-(5,6-dimethoxypyridin-3-yl)pyridine-3-sulfonamide (IntC4)

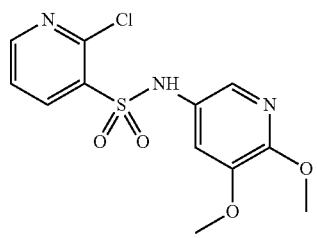 [SMILES: COc1cc(NS(=O)(=O)c2cccnc2Cl)cnc1OC]

The title compound (542 mg, 1.64 mmol) was prepared from 2-chloropyridine-3-sulfonyl chloride (530 mg, 2.5 mmol), 5,6-dimethoxypyridin-3-amine (424 mg, 2.8 mmol) and pyridine (0.6 mL, 7.5 mmol) in DCM (10 mL) using the methods of (IntC1).

LCMS (Method A): m/z 328, 330 (M−H)− (ES−), 330, 332 (M+H)+ (ES+), at 0.12 min, 95%

$^1$H NMR: (400 MHz, DMSO) δ: 3.70 (s, 3H), 3.77 (s, 3H), 7.02 (d, J=2.3, 1H), 7.39 (d, J=2.3, 1H), 7.61 (dd, J=8.0, 4.8, 1H), 8.38 (dd, J=7.8, 1.8, 1H), 8.64 (dd, J=4.8, 1.8, 1H), 10.71 (s, 1H)

2-Chloro-N-(3,4-dimethylphenyl)pyridine-3-sulfonamide (IntC5)

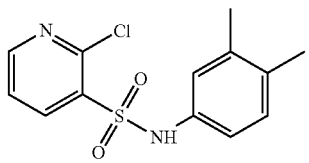 [SMILES: Cc1ccc(NS(=O)(=O)c2cccnc2Cl)cc1C]

The title compound (966 mg, 3.26 mmol) was prepared from 2-chloropyridine-3-sulfonyl chloride (1.11 g, 5.21 mmol) and 3,4-dimethylaniline (698 mg, 5.73 mmol) in 1,4-dioxane (30 mL) using the methods of (IntC1).

LCMS (Method B): m/z 295.3, 297.2 (M−H)− (ES−), at 1.38 min, 80%.

$^1$H NMR: (400 MHz, DMSO) δ 2.09 (s, 3H), 2.10 (s, 3H), 6.83 (dd, J=8.0, 2.0, 1H), 6.89 (d, J=1.8, 1H), 6.98 (d, J=8.0, 1H), 7.60 (dd, J=7.9, 4.9, 1H), 8.39 (dd, J=7.8, 1.8, 1H), 8.60 (dd, J=4.8, 2.0, 1H), 10.61 (s, 1H)

2-Chloro-N-(3,5-dimethylphenyl)pyridine-3-sulfonamide (IntC6)

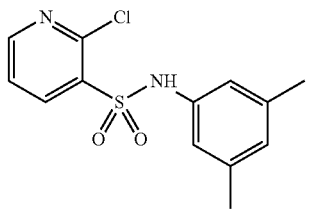 [SMILES: Cc1cc(C)cc(NS(=O)(=O)c2cccnc2Cl)c1]

The title compound (791 mg, 2.67 mmol) was prepared from 2-chloropyridine-3-sulfonyl chloride (1.09 g, 5.12 mmol) and 3,5-dimethylaniline (709 uL, 5.65 mmol) in 1,4-dioxane (30 mL) using the methods of (IntC1).

LCMS (Method B): m/z 295.3, 297.2 (M−H)− (ES−), at 1.38 min, 80%.

$^1$H NMR: (400 MHz, DMSO) δ 2.09 (s, 3H), 2.10 (s, 3H), 6.83 (dd, J=8.0, 2.0, 1H), 6.89 (d, J=1.8, 1H), 6.98 (d, J=8.0, 1H), 7.60 (dd, J=7.9, 4.9, 1H), 8.39 (dd, J=7.8, 1.8, 1H), 8.60 (dd, J=4.8, 2.0, 1H), 10.61 (s, 1H)

tert-Butyl (6-amino-2-methoxypyridin-3-yl)methylcarbamate (IntC7)

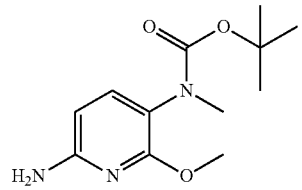 [SMILES: COc1nc(N)ccc1N(C)C(=O)OC(C)(C)C]

Step 1: Preparation of tert-butyl (6-bromo-2-methoxypyridin-3-yl)carbamate

To a stirred solution of 6-bromo-2-methoxypyridin-3-amine (6.27 g, 30.9 mmol) in MeCN (70 mL) at rt was added Boc$_2$O (14.8 g, 67.9 mmol). The resulting solution was stirred at 70° C. for 20 h before cooling to rt and the addition of further Boc$_2$O (14.8 g, 67.9 mmol). After stirring at 70° C. for 21 h the mixture was cooled to rt, further Boc$_2$O (14.8 g, 67.9 mmol) was added and the reaction was stirred at 70° C. for 23 h. After cooling to rt excess Boc$_2$O was destroyed by portion-wise addition of imidazole (23.5 g, 346 mmol) and the mixture stirred vigorously for 15 min. Silica gel (210 mL) was added and the mixture concentrated in vacuo. Purification by gradient column chromatography eluting with 2-5% EtOAc in heptane yielded the title compound (7.07 g, 23.3 mmol) as a red oil.

$^1$H NMR: (400 MHz, CDCl$_3$) δ: 1.51 (s, 9H), 3.99 (s, 3H), 6.86 (br. s, 1H), 7.01 (d, J=8.0, 1H), 8.17 (br. d, J=8.0, 1H)

Step 2: Preparation of tert-butyl (6-amino-2-methoxypyridin-3-yl)methylcarbamate The title compound was prepared from tert-butyl (6-bromo-2-methoxypyridin-3-yl)carbamate (7.07 g, 23.3 mmol) and iodomethane (6.17 mL, 98.0 mmol); followed by sodium tert-butoxide (2.17 g, 22.6 mmol), BINAP (1.41 g, 2.26 mmol), benzophenone imine (2.08 mL, 12.4 mmol), tert-butyl (6-bromo-2-methoxypyridin-3-yl)(methyl)carbamate (3.58 g, 11.3 mmol) and Pd$_2$(dba)$_3$ (1.03 g, 1.13 mmol) in toluene (60 mL) at 80° C. using the methods of (IntA30), step 4. Combination with batches of material derived from tert-butyl (6-bromo-2-methoxypyridin-3-yl)(methyl)carbamate (3.24 g and 576 mg) before purification using the methods of (IntA30), step 4 yielded the title compound (5.83 g, 23.0 mmol).

LCMS (Method B): m/z 254.2 (M+H)+ (ES+), at 2.92 min, 95%

$^1$H NMR: (400 MHz, CDCl$_3$) δ: 1.49, 1.33 (br. s, 9H, rotamers), 3.05 (s, 3H), 3.85 (s, 3H), 4.25 (br. s, 2H), 6.00 (J=8.0, 1H), 7.13 (d, J=8.0, 1H)

tert-Butyl (6-{[(2-chloropyridin-3-yl)sulfonyl]amino}-2-methoxypyridin-3-yl)methylcarbamate (IntC8)

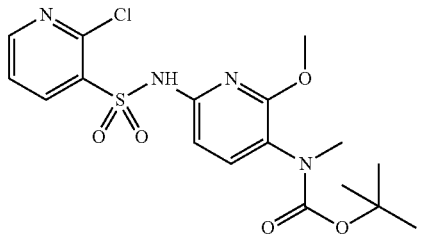 [SMILES: COc1nc(NS(=O)(=O)c2cccnc2Cl)ccc1N(C)C(=O)OC(C)(C)C]

The title compound (1.51 g, 3.53 mmol) was prepared from 2-chloropyridine-3-sulfonyl chloride (1.16 g, 5.48 mmol), tert-butyl (6-amino-2-methoxypyridin-3-yl)methylcarbamate (IntC7) (1.53 g, 6.03 mmol) and pyridine (1.33 mL, 16.4 mmol) in DCM (20 mL) at rt using the methods of (IntC1).

LCMS (Method B): m/z 429.2, 431.2 (M+H)+ (ES+), at 1.67 min, 100%

$^1$H NMR: (400 MHz, DMSO) δ: 1.16 (s, 6H), 1.35 (s, 3H), 2.87 (s, 3H), 3.40 (s, 3H), 6.46 (d, J=8.2, 1H), 7.46 (d, J=7.8, 1H), 7.65 (dd, J=7.3, 5.0, 1H), 8.57-8.64 (m, 2H), 11.64 (br. s, 1H)

N-(1,3-Benzothiazol-6-yl)-2-chloropyridine-3-sulfonamide (IntC9)

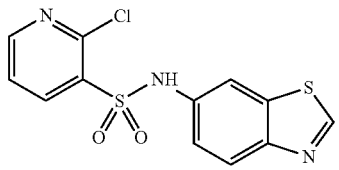 [SMILES: O=S(=O)(Nc1ccc2ncsc2c1)c1cccnc1Cl]

The title compound (1.1 g, 3.38 mmol) was prepared from 2-chloropyridine-3-sulfonyl chloride (1.56 g, 7.36 mmol), 1,3-benzothiazol-6-amine (1.0 g, 6.66 mmol) and pyridine (10 mL) at rt using the methods of (IntC1).

Mass spectroscopy: (ESI+ve) 326.0 [M+H]$^+$ $^1$H NMR: (400 MHz, DMSO) δ: 7.30 (d, J=8.9, 1H), 7.61 (dd, J=7.6, 4.9, 1H), 7.89 (s, 1H), 7.97 (d, J=8.6, 1H), 8.48 (d, J=7.9, 1H), 8.60 (d, J=4.9, 1H), 9.28 (s, 1H), 11.17 (s, 1H)

6-Methoxy-5-methylpyridin-2-amine (IntC10)

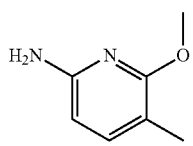

Step 1: Preparation of 2-acetamido-5-methylpyridine N-oxide m-CPBA (75% in H$_2$O, 89.6 g, 390 mmol) was added portion wise to a stirred solution of N-(5-methylpyridin-2-yl)acetamide (45.0 g, 300 mmol) in DCM (2.7 L) at rt, and the mixture stirred at rt for 4 h. 5% aqueous Na$_2$SO$_3$ (200 mL) was added slowly, the phases were separated and the organic layer washed with saturated NaHCO$_3$, brine (100 mL), dried (MgSO$_4$) and filtered. After concentration in vacuo purification by gradient column chromatography eluting with 2-5% MeOH in DCM yielded the title compound (37.5 g, 243 mmol) as a pale yellow solid.

$^1$H NMR: (400 MHz, CDCl$_3$) δ: 2.26 (s, 6H), 7.14 (J=8.7, 1H), 8.06 (s, 1H), 8.30 (d, J=8.7, 1H), 9.87 (br. s, 1H)

Step 2: Preparation of N-(6-methoxy-5-methylpyridin-2-yl)acetamide

A solution of 2-acetamido-5-methylpyridine N-oxide (28.2 g, 170 mmol) in acetic anhydride (840 mL) was stirred at 70° C. for 4 h. After cooling to rt and concentration in vacuo Et$_2$O (180 mL) was added and the resulting solids isolated by filtration and washed with MeOH to give 6-acetamido-3-methylpyridin-2-yl acetate (6.87 g, 33.0 mmol) as a pale brown solid.

$^1$H NMR: (400 MHz, CDCl$_3$) δ: 2.14 (s, 3H), 2.15 (s, 3H), 2.32 (s, 3H), 7.59 (d, J=8.0, 1H), 7.80 (br. s, 1H), 8.02 (d, J=8.0, 1H)

To a stirred solution of 6-acetamido-3-methylpyridin-2-yl acetate (3.44 g, 16.5 mmol) in 2:1 MeOH/DCM (105 mL) at rt was added Ag$_2$CO$_3$ (9.11 g, 33.0 mmol) followed by iodomethane (3.09 mL, 49.6 mmol). The resulting mixture was stirred at 35° C. for 18 h then stood at rt for 2 d. The reaction mixture was combined with 2 previous batches derived from 6-acetamido-3-methylpyridin-2-yl acetate (590 mg, 2.83 mmol and 3.44 g, 16.5 mmol) and the combined batches were filtered through celite, rinsing with DCM. After concentration of the filtrate in vacuo purification by gradient column chromatography eluting with 20-50% EtOAc in heptane yielded the title compound (4.27 g, 23.7 mmol) as a white solid.

$^1$H NMR: (400 MHz, CDCl$_3$) δ: 2.12 (s, 3H), 2.18 (s, 3H), 3.85 (s, 3H), 7.36 (d, J=7.8, 1H), 7.59 (br. s, 1H), 7.60 (d, J=7.8, 1H)

Step 3: Preparation of 6-methoxy-5-methylpyridin-2-amine

A 10% solution of aqueous NaOH (40 mL) was added to a solution of N-(6-methoxy-5-methylpyridin-2-yl)acetamide (2.21 g, 12.3 mmol) in MeOH (160 mL) and the reaction mixture was heated at 90° C. for 3 d. After cooling to rt and concentration in vacuo to remove the MeOH the aqueous residue was combined with that from a previous batch derived from N-(6-methoxy-5-methylpyridin-2-yl)acetamide (2.21 g, 12.3 mmol). The aqueous phase was diluted with H$_2$O (40 mL) and extracted with DCM (3×150 mL). The combined organic phases were washed with brine, dried (Na$_2$SO$_4$) and combined with a previous batch of crude 6-methoxy-5-methylpyridin-2-amine (266 mg). Concentration in vacuo yielded the title compound (3.30 g, 23.9 mmol).

LCMS (Method B): m/z 139.1 (M+H)+ (ES+), at 1.81 min, 95%

$^1$H NMR: (400 MHz, CDCl$_3$) δ: 2.04 (s, 3H), 3.86 (s, 3H), 4.11 (br. s, 2H), 5.98 (d, J=7.8, 1H), 7.14 (d, J=7.8, 1H)

2-Chloro-N-(6-methoxy-5-methylpyridin-2-yl)pyridine-3-sulfonamide (IntC11)

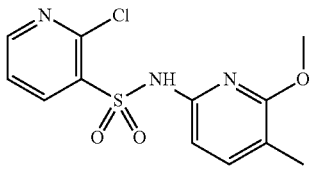 [SMILES: COc1nc(NS(=O)(=O)c2cccnc2Cl)ccc1C]

The title compound (1.60 g, 5.10 mmol) was prepared from 2-chloropyridine-3-sulfonyl chloride (1.35 g, 6.39 mmol), 6-methoxy-5-methylpyridin-2-amine (IntC10) (970 mg, 7.02 mmol) and pyridine (1.55 mL, 19.2 mmol) in 1,4-dioxane (25 mL) at rt using the methods of (IntC1).

LCMS (Method B): m/z 314.1, 316.1 (M+H)+ (ES+), at 0.11, 0.89 min, 95%

$^1$H NMR: (400 MHz, DMSO) δ: 1.93 (s, 3H), 3.38 (s, 3H), 6.40 (d, J=7.8, 1H), 7.38 (d, J=7.8, 1H), 7.64 (dd, J=7.8, 5.0, 1H), 8.49-8.69 (m, 2H), 11.40 (br. s, 1H)

tert-Butyl (5-amino-3-methylpyridin-2-yl)methylcarbamate (IntC12)

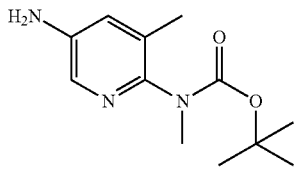 [SMILES: Cc1cc(N)cnc1N(C)C(=O)OC(C)(C)C]

Step 1: Preparation of tert-butyl methyl(3-methyl-5-nitropyridin-2-yl)carbamate 2-Chloro-3-methyl-5-nitropyridine (5.00 g, 29.0 mmol) was added portion wise to a cooled (0° C.) 35% solution of methylamine in EtOH (20 mL) and the reaction was allowed to warm to rt. After approximately 5 min an exotherm and gas evolution was observed and the reaction mixture solidified. EtOH (10 mL) was added and the reaction mixture was stirred at rt for 20 min, then diluted with ice/water (30 mL) and cooled to 0° C. The mixture was stirred vigorously for 15 min and then allowed to stand for 17 h. A solid was isolated by filtration, washed with H$_2$O and dried in vacuo to yield N,3-dimethyl-5-nitropyridin-2-amine (4.44 g) which was used without further purification. A mixture of N,3-dimethyl-5-nitropyridin-2-amine (4.44 g, 26.6 mmol), Boc$_2$O (11.6 g, 53.1 mmol) and 4-(dimethylamino)pyridine (649 mg, 5.31 mmol) in MeCN (230 mL) was stirred at 75° C. for 21 h. Further Boc$_2$O (2.32 g, 10.6 mmol) was added and heating at 75° C. was continued for 24 h, before cooling to rt. Imidazole (5.06 g, 74.4 mmol) was added and the mixture concentrated in vacuo. Purification by gradient flash chromatography eluting with 5-20% EtOAc in heptane yielded the title compound (6.20 g, 23.2 mmol) as a yellow oil which solidified upon standing.

$^1$H NMR: (400 MHz, CDCl$_3$) δ: 1.45 (s, 9H), 2.35 (s, 3H), 3.30 (s, 3H), 8.31 (d, J=2.3, 1H), 9.11 (d, J=2.3, 1H)

Step 2: Preparation of tert-butyl (5-amino-3-methylpyridin-2-yl)methylcarbamate 10% Pd/C (320 mg) was added to a solution of tert-butyl methyl(3-methyl-5-nitropyridin-2-yl)carbamate (3.20 g, 12.0 mmol) in 4:1 MeOH/DCM (100 mL) and the mixture stirred at rt under an atmosphere of H$_2$ for 3 h. The reaction mixture was filtered through celite, washing with 15:85 MeOH/DCM (100 mL) and the filtrate was combined with 2.88 g of a previously prepared batch of crude product. After concentration in vacuo purification by flash chromatography eluting with 100% EtOAc yielded the title compound (5.27 g, 22.2 mmol) as a brown solid.

LCMS (Method B): m/z 238.2 (M+H)+ (ES+), at 2.33 min, 95%

$^1$H NMR: (400 MHz, CDCl$_3$) δ: 1.34, 1.49 (br. s, 9H), 2.13 (s, 3H), 3.15 (s, 3H), 3.62 (br. s, 2H), 6.85 (d, J=2.9, 1H), 7.76 (d, J=2.9, 1H)

tert-Butyl (5-{[(2-chloropyridin-3-yl)sulfonyl]amino}-3-methylpyridin-2-yl)methylcarbamate (IntC13)

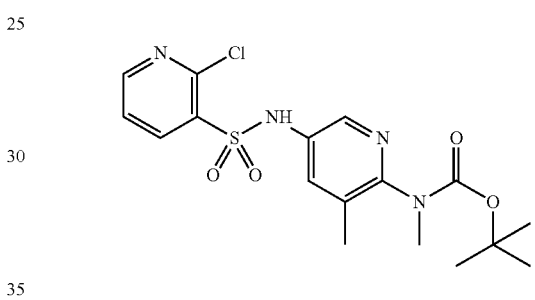

The title compound (1.98 g) was prepared from 2-chloropyridine-3-sulfonyl chloride (910 mg, 4.29 mmol), tert-butyl (5-amino-3-methylpyridin-2-yl)methylcarbamate (IntC12) (1.12 g, 4.72 mmol) and pyridine (1.04 mL, 12.9 mmol) in DCM (25 mL) at rt using the methods of (IntC1).

LCMS (Method B): m/z 413.0 (M+H)+ (ES+), at 1.66 min, 100%

$^1$H NMR: (400 MHz, DMSO) δ: 1.26 (br. s, 9H), 2.04-2.14 (m, 3H), 3.02 (s, 3H), 7.42 (d, J=2.3, 1H), 7.64 (dd, J=7.8, 4.8, 1H), 8.03 (d, J=2.8, 1H), 8.49 (dd, J=7.8, 1.8, 1H), 8.64 (dd, J=4.8, 1.8, 1H), 11.14 (s, 1H)

2-Chloro-N-(5-methoxy-6-methylpyridin-3-yl)pyridine-3-sulfonamide (IntC14)

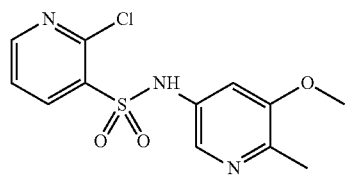 [SMILES: COc1cc(NS(=O)(=O)c2cccnc2Cl)cnc1C]

The title compound (117 mg, 0.372 mmol) was prepared from 2-chloropyridine-3-sulfonyl chloride (469 mg, 2.2 mmol), 5-methoxy-6-methylpyridin-3-amine (336 mg, 2.4 mmol) and pyridine (0.54 mL, 7.5 mmol) in DCM (9 mL) at 0° C. to rt using the methods of (IntC1).

LCMS (Method B): m/z 312, 314 (M−H)− (ES−), 314, 316 (M+H)+ (ES+), at 0.10 min, 80%

¹H NMR: (400 MHz, DMSO) δ: 2.24 (s, 3H), 3.74 (s, 3H), 7.05 (d, J=1.8, 1H), 7.64 (dd, J=7.8, 4.6, 1H), 7.77 (d, J=1.8, 1H), 8.48 (dd, J=8.2, 1.8, 1H), 8.65 (dd, J=4.6, 1.8, 1H), 11.03 (br. s, 1H)

tert-Butyl (5-{[(2-chloropyridin-3-yl)sulfonyl]amino}-2-methoxypyridin-3-yl)methylcarbamate (IntC15)

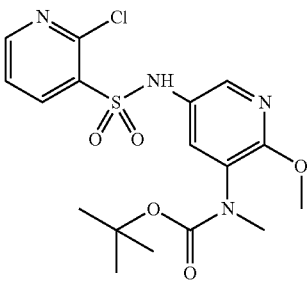 [SMILES: COc1ncc(NS(=O)(=O)c2cccnc2Cl)cc1N(C)C(=O)OC(C)(C)C]

The title compound (2.12 g, 4.94 mmol) was prepared from 2-chloropyridine-3-sulfonyl chloride (1.10 g, 5.20 mmol), tert-butyl (5-amino-2-methoxypyridin-3-yl)methylcarbamate (IntA34) (1.45 g, 5.72 mmol) and pyridine (1.26 mL, 15.6 mmol) in DCM (20 mL) at rt using the methods of (IntC1).

LCMS (Method B): m/z 427, 429 (M−H)− (ES−), 429, 431 (M+H)+ (ES+), at 0.10 and 1.44 min, 100%

¹H NMR: (400 MHz, DMSO) δ: 1.20 (s, 9H), 2.89 (s, 3H), 3.77 (s, 3H), 7.29 (s, 1H), 7.57 (dd, J=6.9, 5.0, 1H), 7.76 (s, 1H), 8.33 (d, J=7.8, 1H), 8.59 (d, J=2.7, 1H), 10.76 (br. s, 1H)

tert-Butyl (5-amino-3-methoxypyridin-2-yl)methylcarbamate (IntC16)

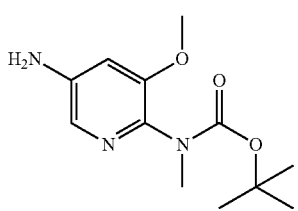 [SMILES: COc1cc(N)cnc1N(C)C(=O)OC(C)(C)C]

Step 1: Preparation of tert-butyl (3-methoxy-5-nitropyridin-2-yl)methylcarbamate 2-Chloro-3-methoxy-5-nitropyridine (8.00 g, 43.4 mmol) was added portion-wise to a 35% solution of methylamine in EtOH (14 mL). After standing for 10 min the mixture was cooled to 0° C. and further 35% methylamine in EtOH (14 mL) was added. After stirring at rt for 20 min ice/water (~28 mL) was added. The mixture was cooled to 0° C., stirred vigorously and then allowed to stand for 15 min. The resulting solids were isolation by filtration, washed with H₂O and dried to yield crude 3-methoxy-N-methyl-5-nitropyridin-2-amine (7.81 g) which was used without further purification.

¹H NMR: (400 MHz, CDCl₃) δ: 3.13 (d, J=5.0, 3H), 3.92 (s, 3H), 5.71 (br. s, 1H), 7.52 (d, J=2.3, 1H), 8.76 (d, J=2.3, 1H)

3-Methoxy-N-methyl-5-nitropyridin-2-amine (7.81 g, 42.6 mmol) was suspended in DCM (400 mL) at rt and Boc₂O (10.2 g, 46.9 mmol) followed by 4-(dimethylamino)pyridine (365 mg, 2.98 mmol) were added. After stirring at rt for 19 h, then 40° C. for 2 h, the mixture was cooled and concentrated in vacuo. MeCN (370 mL), Boc₂O (10.2 g, 46.9 mmol) followed by 4-(dimethylamino)pyridine (780 mg, 6.38 mmol) were added and the solution stirred at 75° C. for 3 d. After concentration in vacuo purification by gradient flash chromatography eluting with 5-35% EtOAc in heptane yielded the title compound (10.3 g, 36.4 mmol) as a yellow solid.

¹H NMR: (400 MHz, CDCl₃) δ: 1.41 (s, 9H), 3.30 (s, 3H), 3.93 (s, 3H), 7.91 (d, J=2.3, 1H), 8.88 (d, J=2.3, 1H)

Step 2: Preparation of tert-butyl (5-amino-3-methoxypyridin-2-yl)methylcarbamate A mixture of 10% Pd/C (530 mg) and tert-butyl 3-methoxy-5-nitropyridin-2-yl(methyl)carbamate (5.30 g, 18.7 mmol) in 4:1 MeOH/DCM (175 mL) was stirred at rt under and atmosphere of hydrogen 2.5 h. After filtration through celite and washing with 15:85 MeOH/DCM (200 mL) the filtrate was combined with 4.55 g of a previously prepared batch of crude product. The mixture was concentrated in vacuo and purified by column chromatography eluting with 100% EtOAc to yield the title compound (9.13 g, 36.0 mmol) as a pale brown solid.

¹H NMR: (400 MHz, CDCl₃) δ: 1.37 (br. s, 9H), 3.14 (s, 3H), 3.70 (br. s, 2H), 3.78 (s, 3H), 6.54 (d, J=2.3, 1H), 7.50 (d, J=2.3, 1H)

tert-Butyl (5-{[(2-chloropyridin-3-yl)sulfonyl]amino}-3-methoxypyridin-2-yl)methylcarbamate (IntC17)

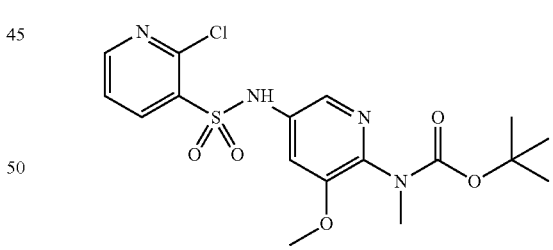

The title compound (2.21 g, 5.15 mmol) was prepared from 2-chloropyridine-3-sulfonyl chloride (1.10 g, 5.20 mmol), tert-butyl (5-amino-3-methoxypyridin-2-yl)methylcarbamate (IntC16) (1.45 g, 5.72 mmol) and pyridine (1.26 mL, 15.6 mmol) in DCM (20 mL) at rt using the methods of (IntC1).

LCMS (Method B): m/z 427, 429 (M−H)− (ES−), 429, 431 (M+H)+ (ES+), at 0.10 and 1.43 min, 100%

¹H NMR: (400 MHz, DMSO) δ: 1.25 (m, 9H), 2.93 (s, 3H), 3.72 (s, 3H), 7.12 (d, J=1.8, 1H), 7.59 (dd, J=7.8, 4.6, 1H), 7.66 (d, J=2.3, 1H), 8.48 (dd, J=7.8, 1.8, 1H), 8.59 (dd, J=5.0, 1.8, 1H), 11.16 (br. s, 1H)

Route 5

4-Chloro-N-(3,4-dimethoxyphenyl)pyridine-3-sulfonamide (IntD1)

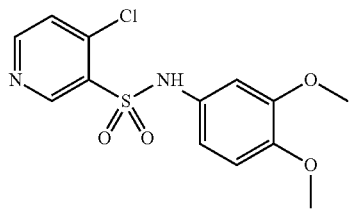 [SMILES: COc1ccc(NS(=O)(=O)c2cnccc2Cl)cc1OC]

A solution of 4-hydroxypyridine-3-sulfonic acid (5.0 g, 28.5 mmol), N,N-diisopropylethylamine (9.2 g, 71.3 mmol), phosphorus(V) oxychloride (10.9 g, 71.3 mmol) in 1,2-dichloroethane (50 mL) was heated at 90° C. for 45 min with TLC monitoring (hexane:EtOAc, 1:1). After cooling, the solution was added to 3,4-dimethoxyaniline (4.8 g, 31.0 mmol), N,N-diisopropylethylamine (7.35 g, 57.0 mmol) in 1,2-dichloroethane (50 mL) at −10° C. and the resulting mixture stirred for approximately 2 h at rt with TLC monitoring (hexane:EtOAc, 1:1). The mixture was then added to saturated aqueous NaHCO$_3$ (200 mL), extracted with DCM (3×50 mL) and the combined organic layers dried over Na$_2$SO$_4$ and concentrated in vacuo. Purification by gradient column chromatography eluting with 0-20% EtOAc in hexane yielded the title compound (2.2 g, 6.69 mmol).

Mass spectroscopy: (ESI+ve) 329.2, 331.2 [M+H]$^+$ $^1$H NMR: (400 MHz, DMSO) δ 3.65 (s, 3H), 3.65 (s, 3H), 6.60 (dd, J=8.5, 2.4, 1H), 6.72 (d, J=2.4, 1H), 6.81 (d, J=8.9, 1H), 7.78 (d, J=5.2, 1H), 8.72 (d, J=5.2, 1H), 8.96 (s, 1H), 10.52 (br s, 1H)

Route 6

4-(2-Chloro-6-fluorobenzyl)-2H-1,2,4-benzothiadiazin-3(4H)-one 1,1-dioxide (IntE1)

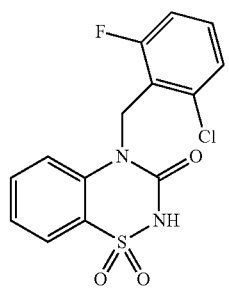 [SMILES: O=C1NS(=O)(=O)c2ccccc2N1Cc1c(F)cccc1Cl]

Step 1: Preparation of N-(2-chloro-6-fluorobenzyl)aniline

A mixture of aniline (3.95 mL, 43.3 mmol), 2-fluoro-6-chlorobenzaldehyde (7.46 g, 47.7 mmol) and glacial acetic acid (6.2 mL, 105.2 mmol) in dichloroethane (100 mL) was heated at 70° C. for 2 h. After cooling to rt, sodium triacetoxyborohydride (13.8 g, 65.1 mmol) was added and the mixture stirred at rt for 2.5 h, before further sodium triacetoxyborohydride (4.6 g, 21.7 mmol) was added and the mixture stirred at rt for 1 h. H$_2$O (100 mL) was added cautiously and the mixture was stirred for 5 min; 10M aqueous NaOH (20 mL) and DCM (50 mL) were added, the phases were separated, and the aqueous phase was extracted with DCM (2×50 mL). The combined organic phases were washed with brine (50 mL) and concentrated in vacuo. Purification by gradient column chromatography eluting with 0-10% EtOAc in iso-hexane yielded the title compound (10.5 g, 44.6 mmol).

LCMS (Method B): m/z 235.0, 237.0 (M+H)+ (ES+), 85%

$^1$H NMR: (400 MHz, DMSO) δ 4.33 (d, J=5.5, 2H), 5.77 (br s, 1H), 6.56 (t, J=7.3, 1H), 6.69 (d, J=8.0, 2H), 7.09 (t, J=7.9, 2H), 7.20-7.30 (m, 1H), 7.32-7.45 (m, 2H)

Step 2: Preparation of 4-(2-chloro-6-fluorobenzyl)-2H-1,2,4-benzothiadiazin-3(4H)-one 1,1-dioxide (IntE1)

A solution of chlorosulfonylisocyanate (5.04 mL, 57.9 mmol) in nitroethane (100 mL) was cooled to approximately −40° C. and a solution of N-(2-chloro-6-fluorobenzyl)aniline (10.5 g, 44.6 mmol) in nitroethane (80 mL) added dropwise over approximately 10 min. The mixture was stirred at −40° C. for 10 min, then rt for 1 h, before the addition of further chlorosulfonylisocyanate (1.94 mL, 22.3 mmol) and stirring for 30 min at rt. Aluminium chloride (8.32 g, 62.4 mmol) was added and the mixture heated at reflux for 30 min, before cooling to rt and cautious addition to stirred ice-H$_2$O (approximately 300 mL). After stirring for 15 min, the title compound (11.8 g, 34.6 mmol) was isolated by filtration.

LCMS (Method B): m/z 339.3, 341.3 (M−H)− (ES−), 100%

$^1$H NMR: (400 MHz, DMSO) δ 5.42 (s, 2H), 7.12-7.24 (m, 1H), 7.28-7.42 (m, 3H), 7.47 (d, J=8.5, 1H), 7.66-7.74 (m, 1H), 7.83 (d, J=7.8, 1H)

4-(4-Chloro-2-fluorobenzyl)-2H-1,2,4-benzothiadiazin-3(4H)-one 1,1-dioxide (IntE2)

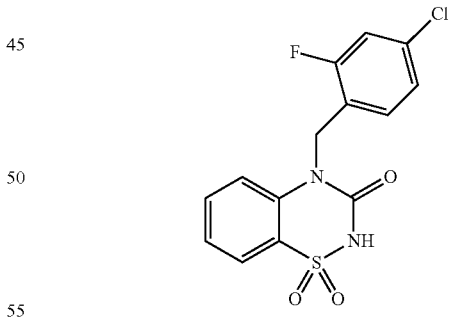

The title compound (4.2 g, 12.3 mmol) was prepared in two steps from aniline (8.8 g, 94.7 mmol), 2-fluoro-4-chlorobenzaldehyde (9.0 g, 63.0 mmol), glacial acetic acid (11.36 g, 183 mmol) and sodium triacetoxyborohydride (20.0 g, 94.5 mmol); followed by chlorosulfonylisocyanate (4.3 g, 30.0 mmol) and aluminium chloride (4.78 g, 35.7 mmol) using the methods of (IntE1).

Mass spectroscopy: m/z 341.3, 343.3 (M+H)+ (ES+)

$^1$H NMR: (400 MHz, DMSO) δ 5.31 (s, 2H), 6.98-7.14 (m, 1H), 7.23 (dd, J=8.2, 1.5, 1H), 7.31-7.40 (m, 2H), 7.50 (dd, J=10.2, 2.0, 1H), 7.61-7.71 (m, 1H), 7.83-7.92 (m, 1H)

4-(2,6-Difluorobenzyl)-2H-1,2,4-benzothiadiazin-3(4H)-one 1,1-dioxide (IntE3)

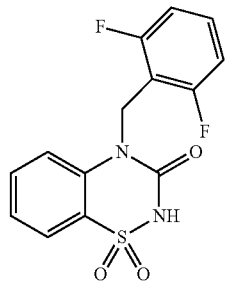 [SMILES: O=C1NS(=O)(=O)c2ccccc2N1Cc1c(F)cccc1F]

Step 1: Preparation of N-(2,6-difluorobenzyl)aniline

A mixture of aniline (2.26 g, 24.3 mmol), 2,6-difluorobenzaldehyde (3.79 g, 26.7 mmol) and glacial acetic acid (3.5 mL, 60.8 mmol) in dichloroethane (50 mL) was heated at 70° C. for 2 h. After cooling to rt, sodium triacetoxyborohydride (5.67 g, 26.8 mmol) was added and the mixture heated at 70° C. for 1.5 h, before cooling to rt, further sodium triacetoxyborohydride (5.67 g, 26.8 mmol) was added and the mixture was heated at 70° C. for a further 75 min before cooling to rt. $H_2O$ (50 mL), DCM (25 mL) and 1M aqueous NaOH (100 mL) were added and the phases were separated.

The aqueous phase was extracted with DCM (2×50 mL) and the combined organic phases were extracted with DCM (2×50 mL), washed with brine (50 mL) and concentrated in vacuo. Purification by gradient column chromatography eluting with 0-20% EtOAc in heptane yielded the title compound (2.88 g, 13.1 mmol).

LCMS (Method B): m/z 220 $(M+H)^+$ (ES+), at 4.38 min, 95%.

$^1$H NMR: (400 MHz, DMSO) δ 4.26 (d, J=5.8, 2H), 5.96 (t, J=5.8, 1H), 6.54 (t, J=7.3, 1H), 6.66 (d, J=7.8, 2H), 7.02-7.16 (m, 4H), 7.34-7.45 (m, 1H)

Step 2: 4-(2,6-difluorobenzyl)-2H-1,2,4-benzothiadiazin-3(4H)-one 1,1-dioxide (IntE3)

A solution of chlorosulfonylisocyanate (0.29 mL, 3.33 mmol) in nitroethane (5 mL) was cooled to approximately −40° C. and a solution of N-(2,6-difluorobenzyl)aniline (562 mg, 2.56 mmol) in nitroethane (3 mL) was added dropwise over approximately 10 min. The mixture was stirred at −40° C. for approximately 10 min, then at 0° for 15 min. Aluminium chloride (479 mg, 3.59 mmol) was then added and the mixture heated at reflux for 30 min before cooling to rt. Separately, the process was repeated using chlorosulfonylisocyanate (1.20 mL, 13.8 mmol) in nitroethane (20 mL), N-(2,6-difluorobenzyl)aniline (2.32 g, 10.6 mmol) in nitroethane (15 mL), followed by aluminium chloride (1.97 g, 14.8 mmol). The two reaction mixtures were combined and cautiously added to stirred ice-$H_2O$ (approximately 100 mL) and the title compound (3.04 g, 9.37 mmol) was isolated by filtration.

LCMS (Method B): m/z 323 $(M-H)^-$ (ES−), at 1.35 min, >95%

$^1$H NMR: (400 MHz, DMSO) δ 5.41 (s, 2H), 7.02-7.13 (m, 2H), 7.30-7.43 (m, 2H), 7.52 (d, J=8.3, 1H), 7.68-7.76 (m, 1H), 7.83 (dd, J=7.8, 1.5, 1H)

4-(2,4,6-Trifluorobenzyl)-2H-1,2,4-benzothiadiazin-3(4H)-one 1,1-dioxide (IntE4)

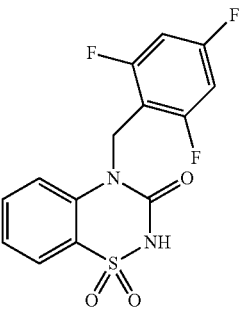 [SMILES: O=C1NS(=O)(=O)c2ccccc2N1Cc1c(F)cc(F)cc1F]

Step 1: Preparation of N-(2,4,6-trifluorobenzyl)aniline

A mixture of aniline (3.80 mL, 41.7 mmol), 2,4,6-trifluorobenzaldehyde (7.35 g, 45.9 mmol) and glacial acetic acid (6.0 mL, 104.4 mmol) in dichloroethane (100 mL) was heated at 70° C. for 2.5 h. After cooling to rt, sodium triacetoxyborohydride (17.7 g, 83.5 mmol) was added and the mixture stirred at rt for 1.5 h, before the cautious addition of $H_2O$ (100 mL), followed by 10M aqueous NaOH (30 mL) and DCM (50 mL). The phases were separated, and the aqueous phase was extracted with DCM (2×100 mL), the combined organic phases were washed with brine (50 mL) and concentrated in vacuo. Purification by gradient column chromatography eluting with 0-6% EtOAc in iso-hexane yielded the title compound (9.90 g, 41.7 mmol).

LCMS (Method B): m/z 238 (M+H)+ (ES+), at 4.33 min, 90%

$^1$H NMR: (400 MHz, DMSO) δ 4.21 (d, J=5.8, 2H), 5.96 (t, J=5.8, 1H), 6.55 (t, J=7.3, 1H), 6.64 (d, J=7.8, 2H), 7.04-7.12 (m, 2H), 7.17-7.27 (m, 2H)

Step 2: Preparation of 4-(2,4,6-trifluorobenzyl)-2H-1,2,4-benzothiadiazin-3(4H)-one 1,1-dioxide (IntE4)

A solution of chlorosulfonylisocyanate (4.72 mL, 54.2 mmol) in nitroethane (75 mL) was cooled to approximately −40° C. and a solution of N-(2,4,6-trifluorobenzyl)aniline (9.90 g, 41.7 mmol) in nitroethane (75 mL) added dropwise over approximately 10 min. The mixture was stirred at −40° C. for 10 min, then at 0° C. for 30 min. Aluminium chloride (5.56 g, 41.7 mmol) was added and the mixture heated at reflux for 30 min, before cooling to rt and cautious addition to stirred ice-$H_2O$ (approximately 250 mL). The title compound (6.12 g, 17.9 mmol) was isolated by filtration.

LCMS (Method B): m/z 341.1 (M−H)− (ES−), at 1.17 min, 95%

$^1$H NMR: (400 MHz, DMSO) δ 5.37 (s, 2H), 7.14-7.24 (m, 2H), 7.36 (t, J=7.7, 1H), 7.53 (d, J=8.5, 1H), 7.71-7.78 (m, 1H), 7.84 (dd, J=7.8, 1.3, 1H)

5-(Bromomethyl)-1,3-dimethyl-1H-pyrazole (IntE5)

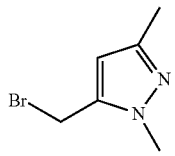

CBr$_4$ (4.7 g, 14.2 mmol) was added to a solution of (1,3-dimethyl-1H-pyrazol-5-yl)methanol (1.2 g, 9.5 mmol) and triphenylphosphine (3.7 g, 14.2 mmol) in THF (20 mL) at 0° C. and the resulting mixture was stirred for approximately 2 h at rt. After concentration in vacuo purification by column chromatography eluting with 2% EtOAc in hexane yielded the title compound (1.31 g, 6.93 mmol).
TLC: Rf=0.85 (EtOAc:hexane, 3:8)
Mass spectroscopy: (ESI+ve) 189.9 [M+H]$^+$ Route 7

2-(5,6-Dimethylpyridin-2-yl)-2H-pyrido[2,3-e][1,2,4]thiadiazin-3(4H)-one 1,1-dioxide (IntF1)

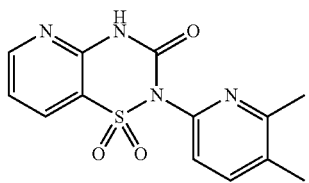 [SMILES: Cc1ccc(N2C(=O)Nc3ncccc3S2(=O)=O)nc1C]

Step 1: Preparation of 2-chloro-N-(5,6-dimethylpyridin-2-yl)pyridine-3-sulfonamide The title compound (5.0 g, 16.8 mmol) was prepared from 2-chloropyridine-3-sulfonyl chloride (5.0 g, 23.7 mmol) and 5,6-dimethylpyridin-2-amine (2.4 g, 19.6 mmol) in pyridine (25 mL) at rt using the methods of (IntC1), step 1.
Mass spectroscopy: (ESI+ve) 298.0 [M+H]+

Step 2: Preparation of 2-amino-N-(5,6-dimethylpyridin-2-yl)pyridine-3-sulfonamide A solution of 2-chloro-N-(5,6-dimethylpyridin-2-yl)pyridine-3-sulfonamide (2.0 g, 6.7 mmol) in THF (30 mL) was cooled to −50° C. NH$_3$(g) was purged into an autoclave and the mixture heated at 140° C. for 16 h. After filtration and concentration in vacuo purification by gradient flash chromatography eluting with 80-90% EtOAc in hexane yielded the title compound (0.6 g, 2.16 mmol).
Mass spectroscopy: (ESI+ve) 279.1 [M+H]+

Step 3: Preparation of 2-(5,6-dimethylpyridin-2-yl)-2H-pyrido[2,3-e][1,2,4]thiadiazin-3(4H)-one 1,1-dioxide The title compound (0.4 g, 1.31 mmol) was prepared from 2-amino-N-(5,6-dimethylpyridin-2-yl)pyridine-3-sulfonamide (0.6 g, 2.16 mmol) and triphosgene (0.7 g, 2.36 mmol) in 1,4-dioxane (15 mL) at 80° C. using the methods of (IntA1), step 3.

LCMS (Method B): m/z 305.0 (M+H)+ (ES+), at 0.10 and 0.98 min, 100%
$^1$H NMR: (400 MHz, DMSO) δ: 2.32 (s, 3H), 2.45 (s, 3H), 7.29 (d, J=7.9, 1H), 7.40-7.45 (m, 1H), 7.74 (d, J=7.9, 1H), 8.37-8.41 (m, 1H), 8.74 (dd, J=4.9, 1.5, 1H), 12.24 (s, 1H)

2-(4,6-Dimethylpyridin-2-yl)-2H-pyrido[2,3-e][1,2,4]thiadiazin-3(4H)-one 1,1-dioxide (IntF2)

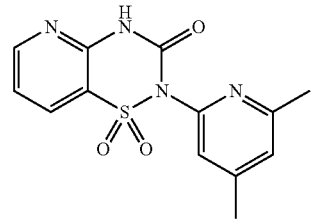 [SMILES: Cc1cc(C)nc(N2C(=O)Nc3ncccc3S2(=O)=O)c1]

The title compound (0.6 g, 1.97 mmol) was prepared in three steps from 2-chloropyridine-3-sulfonyl chloride (6.5 g, 30.0 mmol) and 4,6-dimethylpyridin-2-amine (2.5 g, 20.4 mmol) in pyridine (6 mL) at rt; followed by ammonia in an autoclave at 140° C. for 16 h; followed by triphosgene (930 mg, 3.14 mmol) in 1,4-dioxane (20 mL) at approximately 90° C. for 6 h using the methods of (IntF1).

LCMS (Method B): m/z 305.0 (M+H)+ (ES+), at 0.11 and 0.85 min, 95%
$^1$H NMR: (400 MHz, DMSO) δ: 2.35 (s, 3H), 2.45 (s, 3H), 7.18-7.25 (m, 1H), 7.27 (s, 1H), 7.43 (dd, J=7.9, 4.9, 1H), 8.39 (dd, J=7.8, 1.7, 1H), 8.74 (dd, J=4.9, 1.8, 1H), 12.26 (s, 1H)

2-(2,6-Dimethoxypyridin-4-yl)-2H-pyrido[2,3-e][1,2,4]thiadiazin-3(4H)-one 1,1-dioxide (IntF3)

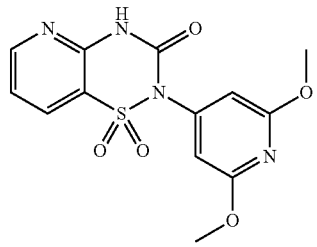 [SMILES: COc1cc(N2C(=O)Nc3ncccc3S2(=O)=O)cc(OC)n1]

The title compound (2.6 g, 7.73 mmol) was prepared in three steps from 2-chloropyridine-3-sulfonyl chloride (8.24 g, 38.9 mmol) and 2,6-dimethoxypyridin-4-amine (6.0 g, 38.9 mmol) in pyridine (25 mL) at rt; followed by ammonia in an autoclave at 100° C. for 16 h; followed by 1,1'-carbonyldiimidazole (6.2 g, 38.2 mmol) in 1,2-dichloroethane (100 mL) at 90° C. for 16 h using the methods of (IntF1), steps 1 and 2, and (IntA14), step 3.

LCMS (Method B): m/z 337.1 (M+H)+ (ES+), at 0.10 and 1.33 min, 100%
$^1$H NMR: (400 MHz, DMSO) δ: 3.91 (s, 6H), 6.51 (s, 2H), 7.42-7.45 (m, 1H), 8.44 (dd, J=7.8, 1.8, 1H), 8.75 (dd, J=4.8, 1.8, 1H), 12.33 (br. s, 1H)

2-(5,6-dimethoxypyridin-3-yl)-2H-pyrido[2,3-e][1,2,4]thiadiazin-3(4H)-one 1,1-dioxide (IntF4)

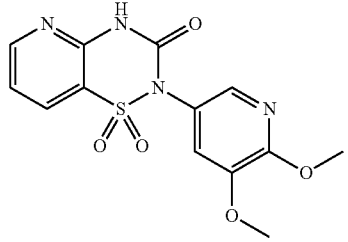 [SMILES: COc1cc(N2C(=O)Nc3ncccc3S2(=O)=O)cnc1OC]

Steps 1 and 2: Preparation of 2-amino-N-(5,6-dimethoxypyridin-3-yl)pyridine-3-sulfonamide 2-chloro-N-(5,6-dimethoxypyridin-3-yl)pyridine-3-sulfonamide (20.0 g, 60.7 mmol) was prepared from 2-chloropyridine-3-sulfonyl chloride (13.7 g, 64.9 mmol) and 5,6-dimethoxypyridin-3-amine (10 g, 64.9 mmol) in pyridine (50 mL) at rt using the methods of (IntC1), step 1. 2-Chloro-N-(5,6-dimethoxypyridin-2-yl) pyridine-3-sulfonamide (3.0 g, 9.09 mmol) was dissolved in THF (20 mL) and NH$_3$(g) bubbled through the reaction mixture at −40° C. for 15 min. The reaction mixture was stirred for 1 d at rt before concentration in vacuo. Purification by column chromatography eluting with 50-60% EtOAc in hexane yielded the title compound (2.0 g, 6.44 mmol) as a white solid.

Mass spectroscopy: (ESI+ve) 311.2 [M+H]+

Step 3: Preparation of 2-(5,6-dimethoxypyridin-3-yl)-2H-pyrido[2,3-e][1,2,4]thiadiazin-3(4H)-one 1,1-dioxide The title compound (1.4 g, 4.16 mmol) was prepared from 2-amino-N-(5,6-dimethoxypyridin-3-yl)pyridine-3-sulfonamide (2.0 g, 6.44 mmol) and 1,1'-carbonyldiimidazole (3.13 g, 19.3 mmol) in 1,2-dichloroethane (15 mL) at 90° C. for 16 h using the methods of (IntA14) step 3.

LCMS (Method B): m/z 337.0 (M+H)+ (ES+), at 0.10 and 1.02 min, 100%

$^1$H NMR: (400 MHz, DMSO) δ: 3.78 (s, 3H), 3.94 (s, 3H), 7.41-7.46 (m, 2H), 7.80 (d, J=2.0, 1H), 8.46 (dd, J=7.9, 1.6, 1H), 8.75 (dd, J=4.8, 1.8, 1H), 12.28 (s, 1H)

SYNTHESIS OF EXAMPLES

Route 1

Typical Mitsonobu coupling procedure for the preparation of examples from route 1, as exemplified by the preparation of 4-(2,6-Dimethylbenzyl)-2-(3,4-methoxyphenyl)-2H-1,2,4-benzothiadiazin-3(4H)-one 1,1-dioxide (77)

A mixture of (IntA1) (0.2 g, 0.59 mmol), triphenylphosphine (0.17 g, 0.65 mmol) and 2,6-dimethylbenzyl alcohol (0.08 g, 0.59 mmol) was dissolved in THF (3.0 mL) in a sealed tube and sonicated for 5 min. Diisopropyl azodicarboxylate (0.13 g, 0.65 mmol) was added and reaction was sonicated for another 2 h. H$_2$O (10 mL) was added and the mixture was extracted with EtOAc (3×25 mL). The combined organic layers were washed with H$_2$O (2×10 mL) and brine and dried over Na$_2$SO$_4$ followed by concentration in vacuo. Purification by gradient flash chromatography, eluting with 10-15% EtOAc yielded the title compound (0.05 g, 0.11 mmol).

LCMS (Method B): m/z 453.2 (M+H)+ (ES+), at 4.80 min, 100%

$^1$H NMR: (400 MHz, DMSO) δ: 2.32 (s, 6H), 3.70 (s, 3H), 3.80 (s, 3H), 5.29 (s, 2H), 6.79-6.88 (m, 2H), 6.94-7.11 (m, 4H), 7.44 (t, J=7.6, 1H), 7.69 (d, J=8.5, 1H), 7.78-7.88 (m, 1H), 7.95 (d, J=7.6, 1H)

4-(2-Fluoro-6-methylbenzyl)-2-(3,4-methoxyphenyl)-2H-1,2,4-benzothiadiazin-3(4H)-one 1,1-dioxide (79)

The title compound (0.05 g, 0.11 mmol) was prepared from (IntA1) (0.2 g, 0.59 mmol) and 2-fluoro-6-methylbenzylalcohol (0.08 g, 0.59 mmol) using the methods of (77).

LCMS (Method B): m/z 457.2 (M+H)+ (ES+), at 4.60 min, 100%

$^1$H NMR: (400 MHz, DMSO) δ: 2.33 (s, 3H), 3.70 (s, 3H), 3.79 (s, 3H), 5.39 (br s, 2H), 6.83 (br s, 1H), 6.90 (d, J=7.6, 1H), 6.94-7.14 (m, 3H), 7.21 (d, J=6.1, 1H), 7.42 (t, J=7.3, 1H), 7.66 (d, J=8.2, 1H), 7.81 (br s, 1H), 7.91 (d, J=7.0, 1H)

2-(3,4-Dimethoxyphenyl)-4-[(2,4-dimethylpyridin-3-yl)methyl]-2H-1,2,4-benzothiadiazin-3(4H)-one 1,1-dioxide (84)

The title compound (0.03 g, 0.07 mmol) was prepared from (IntA1) (0.15 g, 0.44 mmol) and 2,4-dimethyl-3-pyridinemethanol (0.07 g, 0.49 mmol) using the methods of (77).

LCMS (Method B): m/z 454.2 (M+H)+ (ES+), at 3.50 min, 100%

$^1$H NMR: (400 MHz, CDCl$_3$) δ: 2.62 (s, 3H), 2.92 (s, 3H), 3.86 (s, 3H), 3.91 (s, 3H), 5.25 (s, 2H), 6.72 (d, J=2.1, 1H), 6.80-6.87 (m, 1H), 6.88-6.95 (m, 1H), 7.44-7.61 (m, 3H), 7.87 (t, J=7.3, 1H), 8.04 (dd, J=7.8, 1.1, 1H), 8.67 (d, J=5.5, 1H)

4-[(5-Bromo-3-fluoropyridin-2-yl)methyl]-2-(3,4-dimethoxyphenyl)-2H-1,2,4-benzothiadiazin-3(4H)-one 1,1-dioxide (89)

The title compound (0.08 g, 0.15 mmol) was prepared from (IntA1) (0.2 g, 0.59 mmol) and 5-bromo-3-fluoro-2-pyridinemethanol (0.13 g, 0.65 mmol) using the methods of (77).

LCMS (Method B): m/z 522.1, 524.0 (M+H)+ (ES+), at 4.36 min, 100%

$^1$H NMR: (400 MHz, DMSO) δ: 3.73 (s, 3H), 3.81 (s, 3H), 5.46 (br s, 2H), 6.86 (br s, 1H), 6.94 (d, J=8.2, 1H), 7.08 (d, J=8.5, 1H), 7.39-7.50 (m, 1H), 7.54 (d, J=8.2, 1H), 7.78 (t, J=7.5, 1H), 7.99 (d, J=7.6, 1H), 8.26 (d, J=9.5, 1H), 8.48 (s, 1H)

4-(2-Chloro-6-fluorobenzyl)-2-(3,4,5-trimethoxyphenyl)-2H-1,2,4-benzothiadiazin-3(4H)-one 1,1-dioxide (78)

The title compound (0.05 g, 0.10 mmol) was prepared from (IntA2) (0.2 g, 0.54 mmol) and 2-chloro-6-fluorobenzyl alcohol (0.09 g, 0.60 mmol) using the methods of (77).

LCMS (Method B): m/z 507.2, 509.2 (M+H)+ (ES+), at 4.92 min, 100%

¹H NMR: (400 MHz, DMSO) δ: 3.72 (s, 3H), 3.77 (s, 6H), 5.36 (s, 2H), 6.80 (s, 2H), 7.19 (td, J=8.5, 2.1, 1H), 7.24-7.33 (m, 1H), 7.38 (d, J=8.5, 1H), 7.47 (t, J=7.6, 1H), 7.57 (dd, J=8.5, 2.1, 1H), 7.79 (t, J=7.9, 1H), 8.02 (d, J=7.6, 1H)

4-(2-Chloro-6-fluorobenzyl)-2-(6-methylpyridin-3-yl)-2H-1,2,4-benzothiadiazin-3(4H)-one 1,1-dioxide (142)

The title compound (0.03 g, 0.07 mmol) was prepared from (IntA3) (0.2 g, 0.69 mmol) and 2-chloro-6-fluorobenzyl alcohol (0.12 g, 0.76 mmol) using the methods of (77).
LCMS (Method B): m/z 432.1, 434.1 (M+H)+ (ES+), at 4.16 min, 100%
¹H NMR: (400 MHz, DMSO) δ: 2.55 (s, 3H), 5.52 (s, 2H), 7.17-7.30 (m, 1H), 7.31-7.53 (m, 4H), 7.67-7.79 (m, 2H), 7.87 (t, J=7.6, 1H), 7.98 (d, J=7.3, 1H), 8.39 (d, J=2.1, 1H)

4-(2-Chloro-6-fluorobenzyl)-2-(2-methoxypyridin-4-yl)-2H-1,2,4-benzothiadiazin-3(4H)-one 1,1-dioxide (143)

The title compound (0.11 g, 0.25 mmol) was prepared from (IntA4) (0.18 g, 0.59 mmol) and 2-chloro-6-fluorobenzyl alcohol (0.14 g, 0.88 mmol) using the methods of (77).
LCMS (Method B): m/z 448.1, 450.2 (M+H)+ (ES+), at 4.59 min, >95%
¹H NMR: (400 MHz, DMSO) δ: 3.91 (s, 3H), 5.50 (s, 2H), 6.85 (d, J=1.2, 1H), 7.03 (dd, J=5.5, 1.5, 1H), 7.17-7.29 (m, 1H), 7.30-7.52 (m, 3H), 7.74 (d, J=8.2, 1H), 7.82-7.93 (m, 1H), 7.93-8.02 (m, 1H), 8.33 (d, J=5.5, 1H)

2-(6-Methoxypyridin-2-yl)-4-(2,4,6-trifluorobenzyl)-2H-1,2,4-benzothiadiazin-3(4H)-one 1,1-dioxide (144)

The title compound (0.05 g, 0.11 mmol) was prepared from (IntA5) (0.2 g, 0.65 mmol) and 2,4,6-trifluorobenzyl alcohol (0.11 g, 0.72 mmol) using the methods of (77).
LCMS (Method B): m/z 450.2 (M+H)+ (ES+), at 4.54 min, >95%
¹H NMR: (400 MHz, DMSO) δ: 3.81 (s, 3H), 5.46 (s, 2H), 7.00 (d, J=8.2, 1H), 7.06 (d, J=7.3, 1H), 7.22 (t, J=8.7, 2H), 7.47 (t, J=7.6, 1H), 7.78 (d, J=8.5, 1H), 7.83-7.97 (m, 3H)

4-(2-Chloro-4-fluorobenzyl)-2-(4-methoxy-3,5-dimethylphenyl)-2H-1,2,4-benzothiadiazin-3(4H)-one 1,1-dioxide (80)

The title compound (0.16 g, 0.34 mmol) was prepared from (IntA6) (0.30 g, 0.90 mmol) and 2-chloro-4-fluorobenzyl alcohol (0.21 g, 1.35 mmol) using the methods of (77).
LCMS (Method B): m/z 475.2, 477.0 (M+H)+ (ES+), at 5.53 min, >95%
¹H NMR: (400 MHz, DMSO) δ: 2.26 (s, 6H), 3.71 (s, 3H), 5.35 (s, 2H), 7.09-7.29 (m, 4H), 7.34-7.51 (m, 2H), 7.56 (dd, J=8.7, 2.0, 1H), 7.79 (t, J=7.8, 1H), 8.00 (d, J=7.6, 1H)

2-(1,3-Benzothiazol-6-yl)-4-(2,4,6-trifluorobenzyl)-2H-1,2,4-benzothiadiazin-3(4H)-one 1,1-dioxide (124)

The title compound (0.05 g, 0.11 mmol) was prepared from (IntA7) (0.2 g, 0.60 mmol) and 2,4,6-trifluorobenzyl alcohol (0.1 g, 0.60 mmol)) using the methods of (77).
LCMS (Method B): m/z 476.1 (M+H)+ (ES+), at 4.36 min, 95%
¹H NMR: (400 MHz, DMSO) δ: 5.48 (br s, 2H), 7.23 (t, J=8.7, 2H), 7.43-7.54 (m, 2H), 7.78 (d, J=8.5, 1H), 7.90 (t, J=7.6, 1H), 7.98 (d, J=7.6, 1H), 8.22 (d, J=8.5, 1H), 8.30 (s, 1H), 9.55 (s, 1H)

2-[6-(Dimethylamino)pyridin-2-yl]-4-(2,4,6-trifluorobenzyl)-2H-1,2,4-benzothiadiazin-3(4H)-one 1,1-dioxide (158)

The title compound (0.08 g, 0.17 mmol) was prepared from (IntA17) (0.18 g, 0.58 mmol) and 2,4,6-trifluorobenzyl alcohol (0.10 g, 0.63 mmol) using the methods of (77).
LCMS (Method B): m/z 463.2 (M+H)+ (ES+), at 4.74 min, 100%
¹H NMR: (400 MHz, DMSO) δ: 2.99 (s, 6H), 5.44 (s, 2H), 6.54 (d, J=7.3, 1H), 6.72 (d, J=8.5, 1H), 7.21 (t, J=8.9, 2H), 7.44 (t, J=7.6, 1H), 7.64 (t, J=7.9, 1H), 7.74 (d, J=8.5, 1H), 7.81-7.96 (m, 2H)

2-[2-(Dimethylamino)pyridin-4-yl]-4-(2,4,6-trifluorobenzyl)-2H-1,2,4-benzothiadiazin-3(4H)-one 1,1-dioxide (159)

The title compound (0.07 g, 0.15 mmol) was prepared from (IntA18) (0.07 g, 0.22 mmol) and 2,4,6-trifluorobenzyl alcohol (0.04 g, 0.24 mmol) using the methods of (77).
LCMS (Method B): m/z 463.2 (M+H)+ (ES+), at 4.43 min, 100%
¹H NMR: (400 MHz, DMSO) δ: 3.02 (s, 6H), 5.45 (s, 2H), 6.55 (d, J=1.8, 2H), 7.22 (t, J=8.7, 2H), 7.46 (t, J=7.6, 1H), 7.75 (d, J=8.5, 1H), 7.83-7.91 (m, 1H), 7.95 (d, J=7.6, 1H), 8.16-8.24 (m, 1H)

4-(2-Chloro-6-fluorobenzyl)-2-[(1,3-dimethyl-1H-pyrazol-5-yl)methyl]-2H-1,2,4-benzothiadiazin-3(4H)-one 1,1-dioxide (127)

The title compound (90 mg, 0.20 mmol) was prepared from (IntA13) (0.3 g, 0.98 mmol) and 2-chloro-6-fluorobenzyl alcohol (45 mg, 0.28 mmol) using the methods of (77).
LCMS (Method B): m/z 449.2, 451.2 (M+H)+ (ES+), at 4.20 min, >95%
¹H NMR: (400 MHz, CDCl₃) δ: 2.21 (s, 3H), 3.88 (s, 3H), 5.09 (s, 2H), 5.51 (s, 2H), 6.15 (s, 1H), 6.93-7.04 (m, 1H), 7.15-7.34 (m, 3H), 7.39 (d, J=8.5, 1H), 7.55-7.68 (m, 1H), 7.88 (dd, J=7.8, 1.1, 1H)

4-(2-Chloro-6-fluoro-4-methoxybenzyl)-2-(3,4-dimethoxyphenyl)-2H-1,2,4-benzothiadiazin-3(4H)-one 1,1-dioxide (113)

A solution of diisopropyl azodicarboxylate (56 mg, 0.28 mmol) in THF (1 mL) was added to a solution of (IntA1) (84 mg, 0.25 mmol), (IntA25) (52 mg, 0.28 mmol) and triphenylphosphine (72 mg, 0.28 mmol) in THF (0.5 mL) and the mixture was stirred at rt for 2 d. After concentration in vacuo, purification by gradient flash chromatography, eluting with 12-100% EtOAc in iso-hexane yielded the title compound (63 mg, 0.12 mmol).
LCMS (Method B): m/z 507 (M+H)⁺ (ES⁺), at 4.59 min, 100%
¹H NMR: (400 MHz, DMSO) δ: 3.72 (s, 3H), 3.77 (s, 3H), 3.82 (s, 3H), 5.43 (s, 2H), 6.86-6.96 (m, 4H), 7.08 (d, J=8.8, 1H), 7.43 (t, J=7.7, 1H), 7.68 (d, J=8.3, 1H), 7.78-7.88 (m, 1H), 7.93 (dd, J=7.8, 1.3, 1H)

4-[(3,5-Difluoropyridin-4-yl)methyl]-2-(3,4-dimethoxyphenyl)-2H-1,2,4-benzothiadiazin-3(4H)-one 1,1-dioxide (85)

The title compound (47 mg, 0.10 mmol) was prepared from (IntA1) (167 mg, 0.50 mmol) and 3,5-difluoropyridine-4-methanol (109 mg, 0.75 mmol) using the methods of (113).

LCMS (Method B): m/z 462 (M+H)+ (ES+), at 3.62 min, 100%

$^1$H NMR: (400 MHz, DMSO) δ: 3.72 (s, 3H), 3.82 (s, 3H), 5.56 (s, 2H), 6.87 (d, J=2.3, 1H), 6.92 (dd, J=8.5, 2.3, 1H), 7.08 (d, J=8.5, 1H), 7.48 (t, J=7.5, 1H), 7.72 (d, J=8.5, 1H), 7.87 (t, J=7.3, 1H), 7.98 (d, J=8.0, 1H), 8.53 (s, 2H)

2-(3,4-Dimethoxyphenyl)-4-[(3-fluoropyridin-2-yl)methyl]-2H-1,2,4-benzothiadiazin-3(4H)-one 1,1-dioxide (88)

The title compound (152 mg, 0.34 mmol) was prepared from (IntA1) (167 mg, 0.50 mmol), and (3-fluoropyridin-2-yl)methanol (95 mg, 0.75 mmol) using the methods of (113).

LCMS (Method B): m/z 444 (M+H)+ (ES+), at 3.72 min, 100%

$^1$H NMR: (400 MHz, DMSO) δ: 3.73 (s, 3H), 3.81 (s, 3H), 5.51 (s, 2H), 6.87 (d, J=2.3, 1H), 6.95 (dd, J=8.5, 2.3, 1H), 7.08 (d, J=8.8, 1H), 7.40-7.46 (m, 2H), 7.53 (d, J=8.5, 1H), 7.75-7.80 (m, 2H), 7.99 (d, J=8.0, 1H), 8.31 (d, J=4.8, 1H)

4-[(3,5-Dichloropyridin-4-yl)methyl]-2-(3,4-dimethoxyphenyl)-2H-1,2,4-benzothiadiazin-3(4H)-one 1,1-dioxide (90)

The title compound (217 mg, 0.44 mmol) was prepared from (IntA1) (167 mg, 0.50 mmol), and 3,5-dichloro-4-hydroxymethylpyridine (133 mg, 0.75 mmol) using the methods of (113).

LCMS (Method B): m/z 494/496 (M+H)+ (ES+), at 3.80 min, 100%

$^1$H NMR: (400 MHz, DMSO) δ: 3.71 (s, 3H), 3.80 (s, 3H), 5.53 (s, 2H), 6.85-6.90 (m, 2H), 7.05 (d, J=8.8, 1H), 7.48 (t, J=7.5, 1H), 7.72 (d, J=8.5, 1H), 7.87 (t, J=7.3, 1H), 7.99 (d, J=7.8, 1H), 8.63 (s, 2H)

4-(2-Chloro-4,6-difluorobenzyl)-2-[3-(methylsulfanyl)phenyl]-2H-1,2,4-benzothiadiazin-3(4H)-one 1,1-dioxide (110)

The title compound (163 mg, 0.34 mmol) was prepared from (IntA12) (160 mg, 0.5 mmol) and (IntA22) (134 mg, 0.75 mmol) using the methods of (113).

LCMS (Method B): m/z 481 (M+H)+ (ES+), at 5.00 min, 100%

$^1$H NMR: (400 MHz, DMSO) δ: 2.49 (s, 3H), 5.46 (s, 2H), 7.13 (d, J=7.5, 1H), 7.18 (s, 1H), 7.31-7.39 (m, 1H), 7.40-7.50 (m, 4H), 7.73 (d, J=8.3, 1H), 7.87 (t, J=7.3, 1H), 7.96 (d, J=7.8, 1H)

4-(2-Chloro-4,6-difluorobenzyl)-2-(6-methoxypyridin-2-yl)-2H-1,2,4-benzothiadiazin-3(4H)-one 1,1-dioxide (139)

The title compound (162 mg, 0.35 mmol) was prepared from (IntA5) (152 mg, 0.5 mmol), and (2-chloro-4,6-difluorophenyl)methanol ((IntA22), 134 mg, 0.75 mmol) using the methods of (113).

LCMS (Method B): m/z 466 (M+H)+ (ES+), at 4.72 min, 100%

$^1$H NMR: (400 MHz, DMSO) δ: 3.81 (s, 3H), 5.46 (s, 2H), 6.99 (d, J=8.3, 1H), 7.05 (d, J=7.3, 1H), 7.35 (t, J=9.0, 1H), 7.41 (d, J=8.3, 1H), 7.47 (t, J=7.5, 1H), 7.77 (d, J=8.5, 1H), 7.85-7.95 (m, 3H)

4-(2-Chloro-4,6-difluorobenzyl)-2-(2-methoxypyridin-4-yl)-2H-1,2,4-benzothiadiazin-3(4H)-one 1,1-dioxide (141)

The title compound (130 mg, 0.28 mmol) was prepared from (IntA4) (152 mg, 0.5 mmol), and (2-chloro-4,6-difluorophenyl)methanol ((IntA22), 134 mg, 0.75 mmol) using the methods of (113).

LCMS (Method B): m/z 466/468 (M+H)+ (ES+), at 4.68 min, 100%

$^1$H NMR: (400 MHz, DMSO) δ: 3.91 (s, 3H), 5.45 (s, 2H), 6.84 (d, J=1.5, 1H), 7.02 (dd, J=5.5, 1.7, 1H), 7.36 (t, J=9.0, 1H), 7.42 (d, J=8.5, 1H), 7.47 (t, J=7.5, 1H), 7.76 (d, J=8.5, 1H), 7.89 (t, J=7.3, 1H), 7.79 (d, J=7.8, 1H), 8.32 (d, J=5.5, 1H)

4-[(3-Methylpyridin-2-yl)methyl]-2-[3-(methylsulfanyl)phenyl]-2H-1,2,4-benzothiadiazin-3(4H)-one 1,1-dioxide (87)

The title compound (11 mg, 0.03 mmol) was prepared from (IntA12) (48 mg, 0.15 mmol), and (3-methylpyridin-2-yl)methanol (28 mg, 0.23 mmol) using the methods of (113).

LCMS (Method B): m/z 426 (M+H)+ (ES+), at 4.46 min, 98%

$^1$H NMR: (400 MHz, DMSO) δ: 2.40 (s, 3H), 2.50 (s, 3H), 5.40 (s, 2H), 7.12-7.25 (m, 3H), 7.32 (d, J=8.5, 1H), 7.39-7.53 (m, 3H), 7.64 (d, J=7.0, 1H), 7.70-7.78 (m, 1H), 7.99 (dd, J=7.9, 1.4, 1H), 8.25 (d, J=3.8, 1H)

4-(Cyclohexylmethyl)-2-[3-(methylsulfanyl)phenyl]-2H-1,2,4-benzothiadiazin-3(4H)-one 1,1-dioxide (62)

The title compound (38 mg, 0.09 mmol) was prepared from (IntA12) (48 mg, 0.15 mmol), and cyclohexylmethanol (19 mg, 0.17 mmol) using the methods of (113).

LCMS (Method B): m/z 417 (M+H)+ (ES+), at 5.22 min, 100%

$^1$H NMR: (400 MHz, DMSO) δ: 0.90-1.05 (m, 2H), 1.06-1.18 (m, 3H), 1.54-1.75 (m, 6H), 2.49 (s, 3H), 4.11 (d, J=7.0, 2H), 7.18 (d, J=7.8, 1H), 7.21 (s, 1H), 7.39-7.50 (m, 3H), 7.80-7.90 (m, 2H), 7.96 (d, J=7.8, 1H)

4-(2,4-Difluoro-6-methoxybenzyl)-2-(3,4-dimethoxyphenyl)-2H-1,2,4-benzothiadiazin-3(4H)-one 1,1-dioxide (104)

The title compound (212 mg, 0.43 mmol) was prepared from (IntA1) (179 mg, 0.54 mmol), and (IntA23) (140 mg, 0.80 mmol) using the methods of (113).

LCMS (Method B): m/z 491 (M+H)+ (ES+), at 4.46 min, 95%

$^1$H NMR: (400 MHz, DMSO) δ: 3.73 (s, 3H), 3.79 (s, 3H), 3.83 (s, 3H), 5.37 (s, 2H), 6.76-6.92 (m, 3H), 6.96 (dd, J=8.5, 2.5, 1H), 7.10 (d, J=8.5, 1H), 7.39 (t, J=7.7, 1H), 7.65 (d, J=8.5, 1H), 7.75-7.85 (m, 1H), 7.89 (dd, J=7.9, 1.1, 1H)

4-(2-Chloro-6-fluoro-4-methylbenzyl)-2-(3,4-dimethoxyphenyl)-2H-1,2,4-benzothiadiazin-3(4H)-one 1,1-dioxide (106)

The title compound (199 mg, 0.41 mmol) was prepared from (IntA1) (149 mg, 0.44 mmol), and (IntA24) (116 mg, 0.66 mmol) using the methods of (113).

LCMS (Method B): m/z 491, 493 (M+H)+ (ES+), at 4.79 min, 100%

$^1$H NMR: (400 MHz, DMSO) δ: 2.28 (s, 3H), 3.72 (s, 3H), 3.82 (s, 3H), 5.46 (s, 2H), 6.87 (d, J=2.3, 1H), 6.93 (dd, J=8.5, 2.5, 1H), 7.06-7.09 (m, 2H), 7.19 (br. s, 1H), 7.42 (t, J=7.7, 1H), 7.67 (d, J=8.5, 1H), 7.83 (td, J=7.9, 1.3, 1H), 7.94 (dd, J=7.8, 1.3, 1H)

4-(2-Chloro-4,6-difluorobenzyl)-2-(3,4-dimethoxyphenyl)-2H-1,2,4-benzothiadiazin-3(4H)-one 1,1-dioxide (107)

The title compound (176 mg, 0.36 mmol) was prepared from (IntA1) (148 mg, 0.44 mmol), and (IntA22) (118 mg, 0.66 mmol) using the methods of (113).

LCMS (Method B): m/z 495, 497 (M+H)+ (ES+), at 4.59 min, 100%

$^1$H NMR: (400 MHz, DMSO) δ: 3.72 (s, 3H), 3.82 (s, 3H), 5.46 (s, 2H), 6.86 (d, J=2.3, 1H), 6.91 (dd, J=8.5, 2.3, 1H), 7.70 (d, J=8.5, 1H), 7.33-7.47 (m, 3H), 7.71 (d, 8.5, 1H), 7.85 (td, J=8.7, 1.4, 1H), 7.95 (dd, J=7.9, 1.4, 1H)

4-(2-Chloro-4,6-difluorobenzyl)-2-(2,6-dimethoxypyridin-4-yl)-2H-1,2,4-benzothiadiazin-3(4H)-one 1,1-dioxide (157)

The title compound (11 mg, 0.02 mmol) was prepared from (IntA21) (84 mg, 0.25 mmol) and (IntA22) (49 mg, 0.28 mmol) using the methods of (113).

LCMS (Method B): m/z 496/498 (M+H)+ (ES+), at 5.20 min, 100%

$^1$H NMR: (400 MHz, DMSO) δ: (400 MHz, DMSO) δ 3.90 (s, 6H), 5.44 (s, 2H), 6.38 (s, 2H), 7.32-7.40 (m, 1H), 7.41-7.50 (m, 2H), 7.74 (d, J=8.5, 1H), 7.83-7.92 (m, 1H), 7.96 (dd, J=8.0, 1.3, 1H)

4-(2-Chloro-6-fluoro-4-methylbenzyl)-2-(6-methoxypyridin-3-yl)-2H-1,2,4-benzothiadiazin-3(4H)-one 1,1-dioxide (135)

The title compound (44 mg, 0.10 mmol) was prepared from (IntA15) (76 mg, 0.25 mmol) and (IntA24) (48 mg, 0.28 mmol) using the methods of (113).

LCMS (Method B): m/z 462 (M+H)+ (ES+), at 4.99 min, 100%

$^1$H NMR: (400 MHz, DMSO) δ: 2.28 (s, 3H), 3.92 (s, 3H), 5.47 (s, 2H), 7.00 (d, J=8.8, 1H), 7.07 (d, J=11.0, 1H), 7.20 (s, 1H), 7.45 (t, J=7.7, 1H), 7.66-7.76 (m, 2H), 7.81-7.90 (m, 1H), 7.97 (dd, J=7.8, 1.3, 1H), 8.14 (d, J=2.5, 1H)

4-(2-Chloro-6-fluoro-4-methoxybenzyl)-2-(6-methoxypyridin-3-yl)-2H-1,2,4-benzothiadiazin-3(4H)-one 1,1-dioxide (154)

The title compound (35 mg, 0.07 mmol) was prepared from (IntA15) (76 mg, 0.25 mmol) and (IntA25) (52 mg, 0.28 mmol) using the methods of (113).

LCMS (Method B): m/z 478/480 (M+H)+ (ES+), at 4.70 min, 100%

$^1$H NMR: (400 MHz, DMSO) δ: 3.77 (s, 3H), 3.92 (s, 3H), 5.44 (s, 2H), 6.89 (dd, J=12.4, 2.4, 1H), 6.96 (s, 1H), 7.00 (d, J=8.8, 1H), 7.45 (t, J=7.7, 1H), 7.64-7.76 (m, 2H), 7.80-7.91 (m, 1H), 7.97 (dd, J=7.8, 1.3, 1H), 8.14 (d, J=2.5, 1H)

4-(2-Chloro-4,6-difluorobenzyl)-2-(5,6-dimethoxypyridin-3-yl)-2H-1,2,4-benzothiadiazin-3(4H)-one 1,1-dioxide (155

The title compound (28 mg, 0.06 mmol) was prepared from (IntA19) (84 mg, 0.25 mmol) and (IntA22) (49 mg, 0.28 mmol) using the methods of (113).

LCMS (Method B): m/z 496/498 (M+H)+ (ES+), at 4.58 min, 100%

$^1$H NMR: (400 MHz, DMSO) δ: 3.77 (s, 3H), 3.93 (s, 3H), 5.47 (s, 2H), 7.26 (d, J=2.0, 1H), 7.37 (ddd, J=11.5, 9.3, 2.5, 1H), 7.41-7.52 (m, 2H), 7.71 (d, J=2.3, 1H), 7.74 (d, J=8.3, 1H), 7.83-7.92 (m, 1H), 7.98 (dd, J=7.9, 1.4, 1H)

4-(2-Chloro-4,6-difluorobenzyl)-2-(5,6-dimethoxypyridin-2-yl)-2H-1,2,4-benzothiadiazin-3(4H)-one 1,1-dioxide (161)

The title compound (29 mg, 0.06 mmol) was prepared from (IntA20) (84 mg, 0.25 mmol) and (IntA22) (49 mg, 0.28 mmol) using the methods of (113).

LCMS (Method B): m/z 496/498 (M+H)+ (ES+), at 4.55 min, 100%

$^1$H NMR: (400 MHz, DMSO) δ: 3.79 (s, 3H), 3.85 (s, 3H), 5.45 (s, 2H), 7.01 (d, J=8.0, 1H), 7.30-7.39 (m, 1H), 7.40-7.50 (m, 3H), 7.74 (d, J=8.5, 1H), 7.81-7.90 (m, 1H), 7.93 (dd, J=7.8, 1.3, 1H)

2-(2,6-Dimethoxypyridin-4-yl)-4-[(5-fluoro-3-methylpyridin-2-yl)methyl]-2H-1,2,4-benzothiadiazin-3(4H)-one 1,1-dioxide (162)

A solution of TMAD (1,1'-azobis(N,N-dimethylformamide)) (47 mg, 0.28 mmol) in THF (0.5 mL) was added dropwise to a solution of (IntA21) (84 mg, 0.25 mmol), triphenyl phosphine (72 mg, 0.28 mmol) and (IntA26) (39 mg, 0.28 mmol) in THF (1 mL) and the reaction mixture stirred at rt for 5 h. Further (IntA26) (10 mg, 0.07 mmol) was added and the reaction stirred for 50 h at rt before the addition of further TMAD (47 mg, 0.28 mmol) and triphenyl phosphine (72 mg, 0.28 mmol) and stirring for 3 h at rt. The reaction mixture was partitioned between DCM and aqueous 1M HCl and the phases separated. The aqueous phase was extracted twice with DCM and the combined organic phases concentrated in vacuo. Purification by gradient column chromatography, eluting with 10-60% EtOAc in iso-hexane yielded the title compound (73 mg, 0.16 mmol).

LCMS (Method B): m/z 459 (M+H)+ (ES+), at 4.70 min, 100%

$^1$H NMR: (400 MHz, DMSO) δ: 2.43 (s, 3H), 3.91 (s, 6H), 5.39 (s, 2H), 6.38 (s, 2H), 7.34 (d, J=8.5, 1H), 7.44 (t, J=7.5, 1H), 7.66 (dd, J=9.5, 2.3, 1H), 7.71-7.79 (m, 1H), 7.99 (dd, J=7.8, 1.3, 1H), 8.25 (d, J=2.5, 1H)

Typical alkylation procedure for the preparation of examples by N-alkylation of cyclised intermediates from route 1, as exemplified by the preparation of 2-(4-methoxy-3,5-dimethylphenyl)-4-(2,4,6-trifluorobenzyl)-2H-1,2,4-benzothiadiazin-3(4H)-one 1,1-dioxide (115)

A solution of (IntA6) (0.40 g, 1.20 mmol), K$_2$CO$_3$ (0.33 g, 2.40 mmol) and 2,4,6-trifluorobenzyl bromide (0.27 g, 1.20 mmol) in DMF (10 mL) was heated at 80° C. for 5 h with TLC monitoring (hexane:EtOAc 1:1). After concentration in vacuo purification by column chromatography (10% EtOAc in hexane) yielded the title compound (0.50 g, 1.05 mmol).

LCMS (Method B): m/z 477.2 (M+H)+ (ES+), at 5.13 min, 100%

$^1$H NMR: (400 MHz, DMSO) δ: 2.25 (s, 6H), 3.71 (s, 3H), 5.44 (s, 2H), 7.01 (s, 2H), 7.21 (t, J=8.7, 2H), 7.45 (t, J=7.5, 1H), 7.73 (d, J=8.5, 1H), 7.82-7.90 (m, 1H), 7.90-7.96 (m, 1H)

4-(2-Chloro-6-fluorobenzyl)-2-(4-methoxy-3,5-dimethylphenyl)-2H-1,2,4-benzothiadiazin-3(4H)-one 1,1-dioxide (81)

The title compound (0.20 g, 0.42 mmol) was prepared from (IntA6) (0.35 g, 1.00 mmol), 2-chloro-6-fluorobenzyl bromide (0.34 g, 1.5 mmol) and K$_2$CO$_3$ (0.20 g, 1.5 mmol) in 1,4-Dioxane (10 mL) using the methods of (115).

LCMS (Method B): m/z 475.1, 477.2 (M+H)+ (ES+), at 5.21 min, >95%

$^1$H NMR: (400 MHz, DMSO) δ: 2.25 (s, 6H), 3.71 (s, 3H), 5.48 (s, 2H), 7.01 (s, 2H), 7.17-7.27 (m, 1H), 7.31-7.48 (m, 3H), 7.70 (d, J=8.2, 1H), 7.80-7.88 (m, 1H), 7.93 (d, J=7.6, 1H)

4-(2-Chloro-6-fluorobenzyl)-2-(1-ethyl-1H-pyrazol-4-yl)-2H-1,2,4-benzothiadiazin-3(4H)-one 1,1-dioxide (150)

The title compound (0.1 g, 0.23 mmol) was prepared from (IntA8) (0.14 g, 0.47 mmol), 2-chloro-6-fluorobenzyl bromide (0.10 g, 0.47 mmol) and K$_2$CO$_3$ (0.08 g, 0.62 mmol) in DMF (3 mL) using the methods of (115).

LCMS (Method B): m/z 435.1, 437.2 (M+H)+ (ES+), at 4.07 min, 95%

$^1$H NMR: (400 MHz, DMSO) δ: 1.39 (t, J=7.3, 3H), 4.17 (q, J=7.3, 2H), 5.49 (s, 2H), 7.15-7.27 (m, 1H), 7.30-7.56 (m, 4H), 7.69 (d, J=8.5, 1H), 7.80-7.91 (m, 1H), 7.95 (d, J=7.9, 1H), 8.08 (s, 1H)

4-(2-Chloro-6-fluorobenzyl)-2-[5-(methylsulfanyl)pyridin-3-yl]-2H-1,2,4-benzothiadiazin-3(4H)-one 1,1-dioxide (151)

The title compound (0.06 g, 0.13 mmol) was prepared from (IntA9) (0.1 g, 0.31 mmol), 2-chloro-6-fluorobenzyl bromide (0.07 g, 0.34 mmol) and K$_2$CO$_3$ (0.06 g, 0.46 mmol) in DMF (10 mL) using the methods of (115).

LCMS (Method B): m/z 464.1, 466.1 (M+H)+ (ES+), at 4.51 min, >95%

$^1$H NMR: (400 MHz, DMSO) δ: 2.56 (s, 3H), 5.52 (br s, 2H), 7.15-7.53 (m, 4H), 7.66-7.79 (m, 2H), 7.84-7.93 (m, 1H), 7.98 (d, J=7.6, 1H), 8.32 (s, 1H), 8.61 (s, 1H)

2-[5-(Methylsulfanyl)pyridin-3-yl]-4-(2,4,6-trifluorobenzyl)-2H-1,2,4-benzothiadiazin-3(4H)-one 1,1-dioxide (152)

The title compound (0.05 g, 0.11 mmol) was prepared from (IntA9) (0.1 g, 0.31 mmol), 2,4,6-trifluorobenzyl bromide (0.07 g, 0.34 mmol) and K$_2$CO$_3$ (0.06 g, 0.46 mmol) in DMF (10 mL) using the methods of (115).

LCMS (Method B): m/z 466.1 (M+H)+ (ES+), at 4.45 min, >95%

$^1$H NMR: (400 MHz, DMSO) δ: 2.56 (s, 3H), 5.47 (s, 2H), 7.23 (t, J=8.9, 2H), 7.48 (t, J=7.6, 1H), 7.70-7.84 (m, 2H), 7.90 (t, J=7.6, 1H), 7.98 (d, J=7.6, 1H), 8.32 (d, J=1.5, 1H), 8.62 (d, J=1.5, 1H)

2-[6-(Methylsulfanyl)pyridin-3-yl]-4-(2,4,6-trifluorobenzyl)-2H-1,2,4-benzothiadiazin-3(4H)-one 1,1-dioxide (160)

The title compound (0.1 g, 0.21 mmol) was prepared from (IntA10) (0.2 g, 0.21 mmol), K$_2$CO$_3$ (0.26 g, 1.86 mmol) and 2,4,6-trifluorobenzyl bromide (0.16 g, 0.68 mmol) in DMF (10 mL) using the methods of (115).

LCMS (Method B): m/z 466.1 (M+H)+ (ES+), at 4.80 min, >95%

$^1$H NMR: (400 MHz, DMSO) δ: 2.56 (s, 3H), 5.47 (s, 2H), 7.22 (t, J=8.7, 2H), 7.43-7.55 (m, 2H), 7.68 (dd, J=8.5, 2.4, 1H), 7.76 (d, J=8.5, 1H), 7.85-7.93 (m, 1H), 7.95-8.03 (m, 1H), 8.38 (d, J=2.1, 1H)

2-(3,4-Dimethoxyphenyl)-4-(2-fluorobenzyl)-2H-1,2,4-benzothiadiazin-3(4H)-one 1,1-dioxide (67)

The title compound (64 mg, 0.14 mmol) was prepared from (IntA1) (67 mg, 0.20 mmol), K$_2$CO$_3$ (83 mg, 0.60 mmol) and 2-fluorobenzyl bromide (45 mg, 0.24 mmol) in DMF (2 mL) using the methods of (115).

LCMS (Method B): m/z 443 (M+H)+ (ES+), at 3.98 min, 100%

$^1$H NMR: (400 MHz, CDCl$_3$) δ: 3.91 (s, 3H), 3.93 (s, 3H), 5.44 (s, 2H), 6.96-6.98 (m, 2H), 7.05-7.13 (m, 3H), 7.19-7.29 (m, 3H), 7.33 (t, J=7.5, 1H), 7.60 (t, J=7.3, 1H), 7.96 (d, J=7.8, 1H)

4-(2,6-Dichlorobenzyl)-2-(3,4-dimethoxyphenyl)-2H-1,2,4-benzothiadiazin-3(4H)-one 1,1-dioxide (68)

The title compound (52 mg, 0.11 mmol) was prepared from (IntA1) (67 mg, 0.20 mmol), K$_2$CO$_3$ (83 mg, 0.60 mmol) and 2,6-dichlorobenzyl chloride (47 mg, 0.24 mmol) in DMF (2 mL) using the methods of (115).

LCMS (Method B): m/z 493/495 (M+H)+ (ES+), at 4.26 min, 100%

$^1$H NMR: (400 MHz, CDCl$_3$) δ: 3.88 (s, 3H), 3.92 (s, 3H), 5.64 (s, 2H), 6.87 (d, J=2.5, 1H), 6.94 (d, J=8.5, 1H), 7.02 (dd, J=8.5, 2.3, 1H), 7.15-7.19 (m, 1H), 7.28-7.33 (m, 3H), 7.50 (d, J=8.3, 1H), 7.60-7.64 (t, J=7.3, 1H), 7.92 (d, J=7.8, 1H)

4-(2-Chloro-6-fluorobenzyl)-2-(3,5-dimethoxyphenyl)-2H-1,2,4-benzothiadiazin-3(4H)-one 1,1-dioxide (69)

The title compound (61 mg, 0.13 mmol) was prepared from (IntA11) (67 mg, 0.20 mmol), K$_2$CO$_3$ (83 mg, 0.60 mmol) and 2-chloro-6-fluorobenzyl bromide (54 mg, 0.24 mmol) in DMF (2 mL) using the methods of (115).

LCMS (Method B): m/z 477/479 (M+H)+ (ES+), at 4.42 min, 100%

$^1$H NMR: (400 MHz, CDCl$_3$) δ: 3.80 (s, 6H), 5.55 (s, 2H), 6.58 (s, 3H), 6.95-7.01 (m, 1H), 7.19-7.23 (m, 2H), 7.30 (t, J=7.3, 1H), 7.44 (d, J=8.3, 1H), 7.63 (t, J=7.3, 1H), 7.92 (d, J=7.8, 1H)

4-(2,6-Dichlorobenzyl)-2-(3,5-dimethoxyphenyl)-2H-1,2,4-benzothiadiazin-3(4H)-one 1,1-dioxide (70)

The title compound (38 mg, 0.08 mmol) was prepared from (IntA11) (67 mg, 0.20 mmol), $K_2CO_3$ (83 mg, 0.60 mmol) and 2,6-dichlorobenzyl chloride (47 mg, 0.24 mmol) in DMF (2 mL) using the methods of (115).

LCMS (Method B): m/z 493/495 (M+H)+ (ES+), at 4.63 min, 100%

$^1$H NMR: (400 MHz, CDCl$_3$) δ: 3.79 (s, 6H), 5.63 (s, 2H), 6.55-6.56 (m, 3H), 7.17 (t, J=8.3, 1H), 7.27-7.38 (m, 3H), 7.50 (d, J=8.3, 1H), 7.62 (dt, J=7.3, 1.2, 1H), 7.91 (dd, J=7.8, 1.2, 1H)

4-(3-Chloro-2-fluorobenzyl)-2-(3,4-dimethoxyphenyl)-2H-1,2,4-benzothiadiazin-3(4H)-one 1,1-dioxide (71)

The title compound (35 mg, 0.07 mmol) was prepared from (IntA1) (50 mg, 0.15 mmol), $K_2CO_3$ (62 mg, 0.45 mmol) and 3-chloro-2-fluorobenzyl bromide (40 mg, 0.18 mmol) in DMF (2 mL) using the methods of (115).

LCMS (Method B): m/z 477 (M+H)+ (ES+), at 4.43 min, 100%

$^1$H NMR: (400 MHz, CDCl$_3$) δ: 3.90 (s, 3H), 3.93 (s, 3H), 5.45 (s, 2H), 6.94-6.97 (m, 2H), 7.01-7.07 (m, 2H), 7.11 (t, J=6.3, 1H), 7.19 (d, J=8.3, 1H), 7.31-7.37 (m, 2H), 7.63 (t, J=7.3, 1H), 7.97 (d, J=7.8, 1H)

4-(4-Chloro-2-fluorobenzyl)-2-(3,4-dimethoxyphenyl)-2H-1,2,4-benzothiadiazin-3(4H)-one 1,1-dioxide (72)

The title compound (43 mg, 0.09 mmol) was prepared from (IntA1) (50 mg, 0.15 mmol), $K_2CO_3$ (62 mg, 0.45 mmol) and 4-chloro-2-fluorobenzyl bromide (40 mg, 0.18 mmol) in DMF (2 mL) using the methods of (115).

LCMS (Method B): m/z 477 (M+H)+ (ES+), at 4.50 min, 100%

$^1$H NMR: (400 MHz, CDCl$_3$) δ: 3.90 (s, 3H), 3.93 (s, 3H), 5.39 (s, 2H), 6.94-6.97 (m, 2H), 7.04-7.10 (m, 2H), 7.14-7.20 (m, 3H), 7.35 (t, J=7.8, 1H), 7.62 (t, J=8.5, 1H), 7.96 (t, J=7.8, 1H)

4-[(3,5-Dimethylpyridin-2-yl)methyl]-2-(3,4-dimethoxyphenyl)-2H-1,2,4-benzothiadiazin-3(4H)-one 1,1-dioxide (86)

The title compound (89 mg, 0.20 mmol) was prepared from (IntA1) (167 mg, 0.50 mmol), $K_2CO_3$ (207 mg, 1.5 mmol) and 2-(chloromethyl)-3,5-dimethylpyridine (93 mg, 0.6 mmol) in DMF (5 mL) using the methods of (115).

LCMS (Method B): m/z 454 (M+H)+ (ES+), at 3.97 min, 95%

$^1$H NMR: (400 MHz, DMSO) δ: 2.22 (s, 3H), 2.36 (s, 3H), 3.74 (s, 3H), 3.82 (s, 3H), 5.36 (s, 2H), 6.88 (s, 1H), 6.96 (d, J=8.3, 1H), 7.09 (d, J=8.5, 1H), 7.30-7.47 (m, 3H), 7.72 (t, J=7.5, 1H), 7.96 (d, J=7.8, 1H), 8.08 (s, 1H)

4-(2,6-Difluoro-4-methoxybenzyl)-2-[3-(methylsulfanyl)phenyl]-2H-1,2,4-benzothiadiazin-3(4H)-one 1,1-dioxide (109)

The title compound (186 mg, 0.39 mmol) was prepared from (IntA12) (160 mg, 0.50 mmol), $K_2CO_3$ (207 mg, 1.5 mmol) and 2,6-difluoro-4-methoxybenzyl bromide (142 mg, 0.6 mmol) in DMF (5 mL) using the methods of (115).

LCMS (Method B): m/z 477 (M+H)+ (ES+), at 4.86 min, 100%

$^1$H NMR: (400 MHz, DMSO) δ: 2.51 (s, 3H), 3.75 (s, 3H), 5.42 (s, 2H), 6.72-6.77 (m, 2H), 7.15 (d, J=7.5, 1H), 7.20 (s, 1H), 7.40-7.51 (m, 3H), 7.72 (d, J=8.5, 1H), 7.86 (t, J=7.3, 1H), 7.93 (d, J=7.8, 1H)

4-(2,6-Difluoro-4-methoxybenzyl)-2-(6-methoxypyridin-2-yl)-2H-1,2,4-benzothiadiazin-3(4H)-one 1,1-dioxide (138)

The title compound (99 mg, 0.21 mmol) was prepared from (IntA5) (92 mg, 0.30 mmol), $K_2CO_3$ (124 mg, 0.9 mmol) and 2,6-difluoro-4-methoxybenzyl bromide (85 mg, 0.36 mmol) in DMF (3 mL) using the methods of (115).

LCMS (Method B): m/z 462 (M+H)+ (ES+), at 4.38 min, 100%

$^1$H NMR: (400 MHz, DMSO) δ: 3.75 (s, 3H), 3.82 (s, 3H), 5.42 (s, 2H), 6.70-6.77 (m, 2H), 7.00 (d, J=8.3, 1H), 7.06 (d, J=7.5, 1H), 7.45 (t, J=7.5, 1H), 7.76 (d, J=8.3, 1H), 7.84-7.93 (m, 3H)

4-(2,6-Difluoro-4-methoxybenzyl)-2-(2-methoxypyridin-4-yl)-2H-1,2,4-benzothiadiazin-3(4H)-one 1,1-dioxide (140)

The title compound (179 mg, 0.39 mmol) was prepared from (IntA4) (152 mg, 0.50 mmol), $K_2CO_3$ (207 mg, 1.5 mmol) and 2,6-difluoro-4-methoxybenzyl bromide (142 mg, 0.6 mmol) in DMF (5 mL) using the methods of (115).

LCMS (Method B): m/z 462 (M+H)+ (ES+), at 4.49 min, 100%

$^1$H NMR: (400 MHz, DMSO) δ: 3.75 (s, 3H), 3.92 (s, 3H), 5.42 (s, 2H), 6.70-6.77 (m, 2H), 6.85 (dd, J=1.5, 1H), 7.03 (dd, J=5.5, 1.7, 1H), 7.46 (t, J=7.5, 1H), 7.75 (d, J=8.5, 1H), 7.88 (t, J=7.3, 1H), 7.95 (d, J=7.8, 1H), 8.34 (d, J=5.5, 1H)

4-[(1,3-Dimethyl-1H-pyrazol-5-yl)methyl]-2-[3-(methylsulfanyl)phenyl]-2H-1,2,4-benzothiadiazin-3(4H)-one 1,1-dioxide (83)

The title compound (41 mg, 0.10 mmol) was prepared from (IntA12) (48 mg, 0.15 mmol), $K_2CO_3$ (62 mg, 0.45 mmol) and 5-(chloromethyl)-1,3-dimethyl-1H-pyrazole (26 mg, 0.18 mmol) in DMF (2 mL) using the methods of (115).

LCMS (Method B): m/z 429 (M+H)+ (ES+), at 3.72 min, 100%

$^1$H NMR: (400 MHz, DMSO) δ: 2.03 (s, 3H), 2.05 (s, 3H), 3.76 (s, 3H), 5.42 (s, 2H), 5.92 (s, 1H), 7.22 (d, J=8.3, 1H), 7.29 (s, 1H), 7.42-7.51 (m, 3H), 7.68 (d, J=8.5, 1H), 7.84 (m, 1H), 7.98 (d, J=7.8, 1H)

4-(Cyclobutylmethyl)-2-[3-(methylsulfanyl)phenyl]-2H-1,2,4-benzothiadiazin-3(4H)-one 1,1-dioxide (61)

The title compound (37 mg, 0.10 mmol) was prepared from (IntA12) (64 mg, 0.2 mmol), $K_2CO_3$ (83 mg, 0.6 mmol) and (bromomethyl)cyclobutane (36 mg, 0.24 mmol) in DMF (2 mL) using the methods of (115).

LCMS (Method B): m/z 389 (M+H)+ (ES+), at 4.67 min, 93%

$^1$H NMR: (400 MHz, DMSO) δ: 1.69-1.86 (m, 4H), 1.89-2.00 (m, 2H), 2.49 (s, 3H), 2.67 (quin, J=7.5, 1H), 4.27

(d, J=7.0, 2H), 7.18 (d, J=7.8, 1H), 7.21-7.24 (m, 1H), 7.38-7.51 (m, 3H), 7.77 (d, J=8.5, 1H), 7.82-7.89 (m, 1H), 7.95 (dd, J=8.0, 1.3, 1H)

4-(2-Chloro-6-fluorobenzyl)-2-{3-[(trifluoromethyl)sulfanyl]phenyl}-2H-1,2,4-benzothiadiazin-3(4H)-one 1,1-dioxide (73)

The title compound (33 mg, 0.06 mmol) was prepared from (IntA14) (45 mg, 0.12 mmol), K$_2$CO$_3$ (50 mg, 0.36 mmol) and 2-chloro-6-fluorobenzyl bromide (31 mg, 0.14 mmol) in DMF (1.5 mL) using the methods of (115).

LCMS (Method B): m/z 517/519 (M+H)+ (ES+), at 5.29 min, 100%

$^1$H NMR: (400 MHz, DMSO) δ: 5.51 (s, 2H), 7.20-7.28 (m, 1H), 7.33-7.43 (m, 2H), 7.46 (t, J=7.5, 1H), 7.62-7.68 (m, 1H), 7.69-7.78 (m, 3H), 7.84-7.93 (m, 2H), 7.97 (dd, J=7.8, 1.3, 1H)

4-(2,6-Difluorobenzyl)-2-{3-[(trifluoromethyl)sulfanyl]phenyl}-2H-1,2,4-benzothiadiazin-3(4H)-one 1,1-dioxide (75)

The title compound (32 mg, 0.06 mmol) was prepared from (IntA14) (50 mg, 0.13 mmol), K$_2$CO$_3$ (55 mg, 0.40 mmol) and 2,6-difluorobenzyl bromide (33 mg, 0.16 mmol) in DMF (2 mL) using the methods of (115).

LCMS (Method B): m/z No ionisation observed, at 5.57 min, 100%

$^1$H NMR: (400 MHz, DMSO) δ: 5.52 (s, 2H), 7.11 (t, J=8.2, 2H), 7.36-7.44 (m, 1H), 7.46 (t, J=7.7, 1H), 7.63-7.68 (m, 1H), 7.70-7.79 (m, 3H), 7.85-7.94 (m, 2H), 7.97 (dd, J=7.8, 1.3, 1H)

2-(3,4-Dimethoxyphenyl)-4-(2,4,6-trifluorobenzyl)-2H-1,2,4-benzothiadiazin-3(4H)-one 1,1-dioxide (105)

The title compound (29 mg, 0.06 mmol) was prepared from (IntA1) (84 mg, 0.25 mmol), K$_2$CO$_3$ (104 mg, 0.75 mmol) and 2,4,6-trifluorobenzyl bromide (68 uL, 0.30 mmol) in DMF (2 mL) using the methods of (115).

LCMS (Method B): m/z 478 (M+H)+ (ES+), at 4.43 min, 100%

$^1$H NMR: (400 MHz, DMSO) δ: 3.72 (s, 3H), 3.82 (s, 3H), 5.46 (s, 2H), 6.87 (d, J=2.3, 1H), 6.92 (dd, J=8.5, 2.3, 1H), 7.08 (d, J=8.8, 1H), 7.22 (t, J=8.8, 2H), 7.45 (t, J=7.5, 1H), 7.73 (d, J=8.5, 1H), 7.82-7.90 (m, 1H), 7.94 (dd, J=8.0, 1.3, 1H)

2-(3,4-Dimethoxyphenyl)-4-(2,6-difluoro-4-methoxybenzyl)-2H-1,2,4-benzothiadiazin-3(4H)-one 1,1-dioxide (108)

The title compound (59 mg, 0.12 mmol) was prepared from (IntA1) (84 mg, 0.25 mmol), K$_2$CO$_3$ (104 mg, 0.75 mmol) and 2,6-difluoro-4-methoxybenzyl bromide (71 mg, 0.30 mmol) in DMF (2 mL) using the methods of (115).

LCMS (Method B): m/z 491 (M+H)+ (ES+), at 4.47 min, 100%

$^1$H NMR: (400 MHz, DMSO) δ: 3.73 (s, 3H), 3.75 (s, 3H), 3.82 (s, 3H), 5.42 (s, 2H), 6.74 (d, J=10.3, 2H), 6.87 (d, J=2.3, 1H), 6.93 (dd, J=8.5, 2.3, 1H), 7.09 (d, J=8.5, 1H), 7.43 (t, J=7.7, 1H), 7.70 (d, J=8.3, 1H), 7.81-7.88 (m, 1H), 7.93 (dd, J=7.8, 1.3, 1H)

4-(2-Chloro-6-fluorobenzyl)-2-(6-methoxypyridin-3-yl)-2H-1,2,4-benzothiadiazin-3(4H)-one 1,1-dioxide (122)

The title compound (79 mg, 0.18 mmol) was prepared from (IntA15) (75 mg, 0.25 mmol), K$_2$CO$_3$ (104 mg, 0.75 mmol) and 2-chloro-6-fluorobenzyl bromide (67 mg, 0.30 mmol) in DMF (2 mL) using the methods of (115).

LCMS (Method B): m/z 448, 450 (M+H)+ (ES+), at 4.24 min, 100%

$^1$H NMR: (400 MHz, DMSO) δ: 3.92 (s, 3H), 5.52 (s, 2H), 7.00 (d, J=8.8, 1H), 7.23 (ddd, J=9.8, 7.8, 1.8, 1H), 7.33-7.43 (m, 2H), 7.46 (t, J=7.7, 1H), 7.68-7.76 (m, 2H), 7.83-7.90 (m, 1H), 7.98 (dd, J=7.8, 1.3, 1H), 8.15 (d, J=2.5, 1H)

4-(2-Chloro-6-fluorobenzyl)-6-fluoro-2-[3-(methylsulfanyl)phenyl]-2H-1,2,4-benzothiadiazin-3(4H)-one 1,1-dioxide (76)

A solution of (IntA16) (780 mg, 2.50 mmol) and triphosgene (245 mg, 0.82 mmol) in 1,4-dioxane (40 mL) was divided equally into two sealed tubes and both heated at 100° C. for 8.5 h before combination and concentration in vacuo. Purification by gradient flash chromatography, eluting with eluting with 5-40% EtOAc in heptane yielded 6-fluoro-2-[3-(methylsulfanyl)phenyl]-2H-1,2,4-benzothiadiazin-3(4H)-one 1,1-dioxide (220 mg, approximately 60% purity by LCMS analysis) which was used without further purification.

LCMS (Method B): m/z 337.1 (M–H)– (ES–), at 2.21 min, 60%

The title compound (74 mg, 0.15 mmol) was subsequently prepared from 6-fluoro-2-[3-(methylsulfanyl)phenyl]-2H-1,2,4-benzothiadiazin-3(4H)-one 1,1-dioxide (110 mg), K$_2$CO$_3$ (180 mg, 1.30 mmol) and 2-chloro-6-fluorobenzyl bromide (89 uL, 0.65 mmol) in DMF (5 mL) using the methods of (115).

LCMS (Method B): m/z 481 (M+H)+ (ES+), at 5.33 min, 95%

$^1$H NMR: (400 MHz, DMSO) δ: 2.49 (s, 3H), 5.47 (s, 2H), 7.13 (d, J=7.8, 1H), 7.18 (br s, 1H), 7.23-7.49 (m, 6H), 7.70 (dd, J=11.0, 2.0, 1H), 8.06 (dd, J=8.8, 5.8, 1H)

4-(2,6-Difluoro-4-methoxybenzyl)-2-(6-methoxypyridin-3-yl)-2H-1,2,4-benzothiadiazin-3(4H)-one 1,1-dioxide (136)

The title compound (58 mg, 0.13 mmol) was prepared from (IntA15) (76 mg, 0.25 mmol), K$_2$CO$_3$ (104 mg, 0.75 mmol) and 2,6-difluoro-4-methoxybenzyl bromide (71 mg, 0.30 mmol) in DMF (2 mL) using the methods of (115).

LCMS (Method B): m/z 462 (M+H)$^+$ (ES$^+$), at 4.62 min, 100%

$^1$H NMR: (400 MHz, DMSO) δ: 3.75 (s, 3H), 3.92 (s, 3H), 5.43 (s, 2H), 6.75 (d, J=10.3, 2H), 7.01 (d, J=8.8, 1H), 7.46 (t, J=7.7, 1H), 7.67-7.77 (m, 2H), 7.83-7.92 (m, 1H), 7.96 (dd, J=7.8, 1.3, 1H), 8.15 (d, J=2.5, 1H)

2-(5,6-Dimethoxypyridin-3-yl)-4-(2,4,6-trifluorobenzyl)-2H-1,2,4-benzothiadiazin-3(4H)-one 1,1-dioxide (145)

The title compound (103 mg, 0.21 mmol) was prepared from (IntA19) (84 mg, 0.25 mmol), K$_2$CO$_3$ (104 mg, 0.75 mmol) and 2,4,6-trifluorobenzyl bromide (68 mg, 0.30 mmol) in DMF (2 mL) using the methods of (115).

LCMS (Method B): m/z 480 (M+H)+ (ES+), at 4.25 min, 100%

¹H NMR: (400 MHz, DMSO) δ: 3.78 (s, 3H), 3.94 (s, 3H), 5.47 (s, 2H), 7.22 (t, J=8.8, 2H), 7.27 (d, J=2.3, 1H), 7.47 (t, J=7.5, 1H), 7.72 (d, J=2.0, 1H), 7.76 (d, J=8.5, 1H), 7.85-7.93 (m, 1H), 7.97 (dd, J=7.8, 1.3, 1H)

4-(2,6-difluoro-4-methoxybenzyl)-2-(5,6-dimethoxy-pyridin-3-yl)-2H-1,2,4-benzothiadiazin-3(4H)-one 1,1-dioxide (146)

The title compound (97 mg, 0.20 mmol) was prepared from (IntA19) (84 mg, 0.25 mmol), $K_2CO_3$ (104 mg, 0.75 mmol) and 2,6-difluoro-4-methoxybenzyl bromide (71 mg, 0.30 mmol) in DMF (2 mL) using the methods of (115).

LCMS (Method B): m/z 492 (M+H)+ (ES+), at 4.39 min, 99%

¹H NMR: (400 MHz, DMSO) δ: 3.75 (s, 3H), 3.78 (s, 3H), 3.94 (s, 3H), 5.43 (s, 2H), 6.74 (d, J=10.0, 2H), 7.27 (d, J=2.0, 1H), 7.45 (t, J=7.7, 1H), 7.70-7.77 (m, 2H), 7.82-7.91 (m, 1H), 7.95 (dd, J=7.8, 1.3, 1H)

4-(2,6-Difluoro-4-methoxybenzyl)-2-(5,6-dimethoxypyridin-2-yl)-2H-1,2,4-benzothiadiazin-3(4H)-one 1,1-dioxide (153)

The title compound (38 mg, 0.08 mmol) was prepared from (IntA20) (84 mg, 0.25 mmol), 2,6-difluoro-4-methoxybenzyl bromide (71 mg, 0.30 mmol) and $K_2CO_3$ (104 mg, 0.75 mmol) using the methods of (115).

LCMS (Method B): m/z 492 (M+H)⁺ (ES⁺), at 4.26 min, 100%

¹H NMR: (400 MHz, DMSO) δ: 3.75 (s, 3H), 3.80 (s, 3H), 3.86 (s, 3H), 5.41 (s, 2H), 6.73 (d, J=10.3, 2H), 7.03 (d, J=8.0, 1H), 7.40-7.50 (m, 2H), 7.73 (d, J=8.5, 1H), 7.82-7.88 (m, 1H), 7.91 (d, J=7.8, 1H)

2-(5,6-Dimethoxypyridin-2-yl)-4-(2,4,6-trifluorobenzyl)-2H-1,2,4-benzothiadiazin-3(4H)-one 1,1-dioxide (147)

The title compound (62 mg, 0.13 mmol) was prepared from (IntA20) (84 mg, 0.25 mmol), 2,4,6-trifluorobenzyl bromide (68 mg, 0.30 mmol) and $K_2CO_3$ (104 mg, 0.75 mmol) using the methods of (115).

LCMS (Method B): m/z 480 (M+H)+ (ES+), at 4.32 min, 100%

¹H NMR: (400 MHz, DMSO) δ: 3.75 (s, 3H), 3.80 (s, 3H), 3.86 (s, 3H), 5.41 (s, 2H), 6.73 (d, J=10.3, 2H), 7.03 (d, J=8.0, 1H), 7.39-7.50 (m, 2H), 7.71-7.77 (m, 1H), 7.81-7.88 (m, 1H), 7.91 (d, J=7.8, 1H)

2-(2,6-Dimethoxypyridin-4-yl)-4-(2,4,6-trifluorobenzyl)-2H-1,2,4-benzothiadiazin-3(4H)-one 1,1-dioxide (148)

The title compound (103 mg, 0.21 mmol) was prepared from (IntA21,) (84 mg, 0.25 mmol), 2,4,6-trifluorobenzyl bromide (68 mg, 0.30 mmol) and $K_2CO_3$ (104 mg, 0.75 mmol) using the methods of (115).

LCMS (Method B): m/z 480 (M+H)+ (ES⁺), at 4.95 min, 99%

¹H NMR: (400 MHz, DMSO) δ: 3.91 (s, 6H), 5.45 (s, 2H), 6.38 (s, 2H), 7.21 (t, J=8.8, 2H), 7.47 (t, J=7.7, 1H), 7.76 (d, J=8.5, 1H), 7.84-7.92 (m, 1H), 7.95 (dd, J=7.9, 1.1, 1H)

4-(2,6-Difluoro-4-methoxybenzyl)-2-(2,6-dimethoxypyridin-4-yl)-2H-1,2,4-benzothiadiazin-3(4H)-one 1,1-dioxide (149)

The title compound (92 mg, 0.19 mmol) was prepared from (IntA21) (84 mg, 0.25 mmol), 2,6-difluoro-4-methoxybenzyl bromide (71 mg, 0.30 mmol) and $K_2CO_3$ (104 mg, 0.75 mmol) using the methods of (115).

LCMS (Method B): m/z 492 (M+H)+ (ES+), at 4.98 min, 99%

¹H NMR: (400 MHz, DMSO) δ: 3.75 (s, 3H), 3.91 (s, 6H), 5.41 (s, 2H), 6.39 (s, 2H), 6.74 (d, J=10.3, 2H), 7.45 (t, J=7.7, 1H), 7.73 (d, J=8.5, 1H), 7.83-7.90 (m, 1H), 7.94 (dd, J=7.8, 1.3, 1H)

4-(2-Chloro-6-fluorobenzyl)-2-(2,6-dimethoxypyridin-4-yl)-2H-1,2,4-benzothiadiazin-3(4H)-one 1,1-dioxide (166)

The title compound (48 mg, 0.10 mmol) was prepared from (IntA21) (101 mg, 0.34 mmol), 2-chloro-6-fluorobenzyl bromide (80 mg, 0.36 mmol) and $K_2CO_3$ (124 mg, 0.9 mmol) in DMF (1.5 mL) using the methods of (115).

LCMS (Method B): m/z 480, 478 (M+H)+ (ES+), at 5.16 min, 100%

¹H NMR: (400 MHz, DMSO) δ: 3.90 (s, 6H), 5.49 (s, 2H), 6.38 (s, 2H), 7.19-7.27 (m, 1H), 7.31-7.42 (m, 2H), 7.45 (t, J=7.7, 1H), 7.73 (d, J=8.5, 1H), 7.82-7.91 (m, 1H), 7.96 (dd, J=7.8, 1.3, 1H)

4-(2,6-Difluorobenzyl)-2-(2,6-dimethoxypyridin-4-yl)-2H-1,2,4-benzothiadiazin-3(4H)-one 1,1-dioxide (167)

The title compound (45 mg, 0.10 mmol) was prepared from (IntA21) (101 mg, 0.34 mmol), 2,6-difluorobenzyl bromide (75 mg, 0.36 mmol) and $K_2CO_3$ (124 mg, 0.9 mmol) in DMF (1.5 mL) using the methods of (115).

LCMS (Method B): m/z 462 (M+H)+ (ES+), at 4.95 min, 100%

¹H NMR: (400 MHz, DMSO) δ: 3.91 (s, 6H), 5.49 (s, 2H), 6.39 (s, 2H), 7.10 (t, J=8.2, 2H), 7.35-7.50 (m, 2H), 7.75 (d, J=8.5, 1H), 7.83-7.91 (m, 1H), 7.95 (dd, J=7.8, 1.3, 1H)

4-(2,6-Difluoro-4-hydroxybenzyl)-2-(3,4-dimethoxyphenyl)-2H-1,2,4-benzothiadiazin-3(4H)-one 1,1-dioxide (116)

A solution of (IntA27) (533 mg, 0.90 mmol) in glacial acetic acid/THF/H₂O (3:1:1, 20 mL) was stirred at rt for 22 h before further glacial acetic acid (6 mL) was added. After stirring for 4 d, further glacial acetic acid (6 mL) was added and the mixture stirred at rt for 15.5 h then at 50° C. for 1 d. After concentration in vacuo, purification by gradient column chromatography, eluting with 10-70% EtOAc in iso-hexane yielded the title compound (75 mg, 0.16 mmol).

LCMS (Method B): m/z 477 (M+H)+ (ES⁺), at 2.15 min, 100%

¹H NMR: (400 MHz, DMSO) δ: 3.76 (s, 3H), 3.86 (s, 3H), 5.41 (s, 2H), 6.47 (d, J=10.0, 2H), 6.91 (d, J=2.5, 1H), 6.97 (dd, J=8.5, 2.3, 1H), 7.12 (d, J=8.5, 1H), 7.46 (t, J=7.7, 1H), 7.72 (d, J=8.3, 1H), 7.84-7.91 (m, 1H), 7.95 (dd, J=7.8, 1.3, 1H), 10.5 (br. s, 1H)

4-(2,6-Difluoro-4-methoxybenzyl)-2-[3-(methylsulfonyl)phenyl]-2H-1,2,4-benzothiadiazin-3(4H)-one 1,1-dioxide (111)

A mixture of 3-chloroperoxybenzoic acid (approximately 70% purity, 60 mg, approximately 0.22 mmol) and (109) (48 mg, 0.1 mmol) in DCM (1 mL) was stirred at rt for 3 h. DCM (10 mL) and saturated aqueous sodium carbonate (5 mL) were added, the phases were separated and the organic phase concentrated in vacuo to yield the title compound (46 mg, 0.09 mmol).

LCMS (Method B): m/z 509 (M+H)+/526 (M+18)+ (ES+), at 4.16 min, 100%

$^1$H NMR: (400 MHz, DMSO) δ: 3.32 (s, 3H), 3.33 (s, 3H), 5.43 (s, 2H), 6.68-6.81 (m, 2H), 7.47 (t, J=7.7, 1 H), 7.72-7.82 (m, 2H), 7.82-8.00 (m, 4H), 8.13 (d, J=7.8, 1H)

2-[3-(Methylsulfonyl)phenyl]-4-(2,4,6-trifluorobenzyl)-2H-1,2,4-benzothiadiazin-3(4H)-one 1,1-dioxide (112)

2-[3-(methylsulfanyl)phenyl]-4-(2,4,6-trifluorobenzyl)-2H-1,2,4-benzothiadiazin-3(4H)-one 1,1-dioxide (212 mg, 0.45 mmol) was prepared from (IntA12) (160 mg, 0.5 mmol), 2,4,6-trifluorobenzyl bromide (135 mg, 0.6 mmol) and K$_2$CO$_3$ (207 mg, 1.5 mmol) in DMF (5 mL) using the methods of (115).

The title compound (46 mg, 0.09 mmol) was then prepared from 2-[3-(methyl sulfanyl)phenyl]-4-(2,4,6-trifluorobenzyl)-2H-1,2,4-benzothiadiazin-3(4H)-one 1,1-dioxide (46 mg, 0.1 mmol), and 3-chloroperoxybenzoic acid (approximately 70% purity, 60 mg, approximately 0.22 mmol) using the methods of (111).

LCMS (Method B): m/z 497 (M+H)+/514 (M+18)+ (ES+), at 4.09 min, 100%

$^1$H NMR: (400 MHz, DMSO) δ: 3.31 (s, 3H), 5.47 (s, 2H), 7.19-7.26 (m, 2H), 7.48 (t, J=7.5, 1H), 7.75-7.80 (m, 2H), 7.83-7.94 (m, 3H), 7.98 (d, J=7.8, 1H), 8.13 (d, J=8.0, 1H)

2-(4-Hydroxy-3,5-dimethylphenyl)-4-(2,4,6-trifluorobenzyl)-2H-1,2,4-benzothiadiazin-3(4H)-one 1,1-dioxide (114)

To a solution of (115) (0.2 g, 0.42 mmol) in DCM (5 mL) was added boron tribromide (1.0M solution in DCM, 0.46 mL, 0.46 mmol) at −70° C. The resulting mixture was stirred for approximately two h at rt with TLC monitoring (hexane:EtOAc, 1:1). The reaction mixture was poured into saturated aqueous NaHCO$_3$ solution (50 mL), extracted with EtOAc (3×50 mL), and the combined organic layer was dried over Na$_2$SO$_4$ and concentrated in vacuo. Purification by trituration with DCM in pentane (1:9) yielded the title compound (0.11 g, 0.24 mmol).

LCMS (Method B): m/z 463.2 (M+H)+ (ES+), at 4.12 min, 100%

$^1$H NMR: (400 MHz, DMSO) δ: 2.18 (s, 6H), 5.43 (s, 2H), 6.88 (s, 2H), 7.21 (t, J=8.7, 2H), 7.43 (t, J=7.6, 1H), 7.70 (d, J=8.5, 1H), 7.79-7.88 (m, 1H), 7.92 (dd, J=7.9, 1.2, 1H), 8.76 (s, 1H)

4-(2-Chloro-6-fluorobenzyl)-2-(4-hydroxy-3,5-dimethylphenyl)-2H-1,2,4-benzothiadiazin-3(4H)-one 1,1-dioxide (82)

The title compound (0.12 g, 0.26 mmol) was prepared from (81) (0.23 g, 0.48 mmol) and boron tribromide (1.0M solution in DCM, 0.60 mL, 0.60 mmol) using the methods of (114).

LCMS (Method B): m/z 461.1, 463.2 (M+H)+ (ES+), at 4.22 min, 100%

$^1$H NMR: (400 MHz, DMSO) δ: 2.18 (s, 6H), 5.48 (s, 2H), 6.88 (s, 2H), 7.14-7.28 (m, 1H), 7.31-7.49 (m, 3H), 7.67 (d, J=8.2, 1H), 7.83 (t, J=7.3, 1H), 7.92 (d, J=7.6, 1H), 8.74 (s, 1H)

4-(2,6-Difluoro-4-methoxybenzyl)-2-(6-methoxy-5-methylpyridin-3-yl)-2H-1,2,4-benzothiadiazin-3 (4H)-one 1,1-dioxide (171)

The title compound (60 mg, 0.13 mmol) was prepared from 2-(6-methoxy-5-methylpyridin-3-yl)-2H-1,2,4-benzothiadiazin-3(4H)-one 1,1-dioxide (IntA28) (161 mg, 0.50 mmol), 2,6-difluoro-4-methoxybenzyl bromide (179 mg, 0.76 mmol) and K$_2$CO$_3$ (104 mg, 0.75 mmol) in DMF (3 mL) using the methods of (115).

LCMS (Method B): m/z 476.1 (M+H)+ (ES+), at 4.90 min, 95%

$^1$H NMR: (400 MHz, DMSO) δ: 2.15 (s, 3H), 3.71 (s, 3H), 3.90 (s, 3H), 5.38 (s, 2H), 6.60-6.81 (m, 2H), 7.41 (t, J=7.6, 1H), 7.54 (dd, J=2.3, 0.9, 1H), 7.68 (d, J=8.2, 1H), 7.83 (td, J=7.9, 1.6, 1H), 7.87-8.00 (m, 2H)

4-(2,6-Difluoro-4-methoxybenzyl)-2-(5,6-dimethylpyridin-3-yl)-2H-1,2,4-benzothiadiazin-3(4H)-one 1,1-dioxide (178)

The title compound (58 mg, 0.13 mmol) was prepared from 2-(5,6-dimethylpyridin-3-yl)-2H-1,2,4-benzothiadiazin-3(4H)-one 1,1-dioxide (IntA29) (150 mg, 0.49 mmol), 2,6-difluoro-4-methoxybenzyl bromide (129 mg, 0.54 mmol) and K$_2$CO$_3$ (102 mg, 0.74 mmol) in DMF (3 mL) at 50° C. using the methods of (115).

LCMS (Method B): m/z 460.0 (M+H)+ (ES+), at 4.32 min, 95%

$^1$H NMR: (400 MHz, CDCl$_3$) δ: 2.38 (s, 3H), 2.60 (s, 3H), 3.77 (s, 3H), 5.45 (s, 2H), 6.43-6.51 (m, 2H), 7.35 (t, J=7.5, 1H), 7.49-7.51 (m, 1H), 7.62-7.73 (m, 2H), 7.93 (dd, J=7.8, 1.5, 1H), 8.37 (d, J=2.3, 1H)

4-(2,6-Difluoro-4-methoxybenzyl)-2-[5-methoxy-6-(methylamino)pyridin-2-yl]-2H-1,2,4-benzothiadiazin-3(4H)-one 1,1-dioxide (179)

Step 1: Preparation of tert-butyl {6-[4-(2,6-difluoro-4-methoxybenzyl)-1,1-dioxido-3-oxo-3,4-dihydro-2H-1,2,4-benzothiadiazin-2-yl]-3-methoxypyridin-2-yl}methylcarbamate The title compound (301 mg, 0.51 mmol) was prepared from tert-butyl [6-(1,1-dioxido-3-oxo-3,4-dihydro-2H-1,2,4-benzothiadiazin-2-yl)-3-methoxypyridin-2-yl]methylcarbamate (IntA31) (343 mg, 0.79 mmol), 2,6-difluoro-4-methoxybenzyl bromide (225 mg, 0.95 mmol) and K$_2$CO$_3$ (164 mg, 1.19 mmol) in DMF (4 mL) at 11 using the methods of (115).

LCMS (Method B): m/z 591.2 (M+H)+ (ES+), at 5.04 min, 100%

Step 2: Preparation of 4-(2,6-difluoro-4-methoxybenzyl)-2-[5-methoxy-6-(methylamino)pyridin-2-yl]-2H-1,2,4-benzothiadiazin-3(4H)-one 1,1-dioxide A solution of tert-butyl {6-[4-(2,6-difluoro-4-methoxybenzyl)-1,1-dioxido-3-oxo-3,4-dihydro-2H-1,2,4-benzothiadiazin-2-yl]-3-methoxypyridin-2-yl}methylcarbamate (295 mg, 0.50 mmol) and TFA (2 mL) in DCM (3 mL) was stirred at rt for 2 h before concentration in vacuo. DCM and saturated aqueous NaHCO$_3$ solution (5 mL each) were added and the phases were separated. The organic phase was extracted with DCM (2×5 mL) and the combined organic phases were concentrated in vacuo. Purification by gradient column chromatography, eluting with 15-80% EtOAc in iso-hexane yielded the title compound (132 mg, 0.27 mmol) as a white solid.

LCMS (Method B): m/z 491.1 (M+H)+ (ES+), at 4.37 min, 100%

$^1$H NMR: (400 MHz, DMSO) δ: 2.67 (d, J=4.6, 3H), 3.71 (s, 3H), 3.80 (s, 3H), 5.36 (s, 2H), 6.38 (q, J=4.6, 1H), 6.47 (d, J=7.8, 1H), 6.58-6.80 (m, 2H), 7.04 (d, J=7.8, 1H), 7.38 (t, J=7.6, 1H), 7.67 (d, J=8.2, 1H), 7.73-7.90 (m, 2H)

2-(4,5-Dimethoxypyrimidin-2-yl)-4-(2,4,6-trifluorobenzyl)-2H-1,2,4-benzothiadiazin-3(4H)-one 1,1-dioxide (170)

The title compound was prepared from 2-(4,5-dimethoxypyrimidin-2-yl)-2H-1,2,4-benzothiadiazin-3(4H)-one 1,1-dioxide (IntA32) (50 mg, 0.15 mmol), 2,4,6-trifluorobenzyl bromide (41 mg, 0.18 mmol) and K$_2$CO$_3$ (62 mg, 0.45 mmol) in DMF (1.5 mL) using the methods of (115). After purification by gradient column chromatography further purification by preparative HPLC (method C) yielded the title compound (8 mg, 0.02 mmol).

LCMS (Method B): m/z 481.0 (M+H)+ (ES+), at 4.12 min, 95%

$^1$H NMR: (400 MHz, DMSO) δ: 3.91 (s, 3H), 3.95 (s, 3H), 5.46 (s, 2H), 7.21 (t, J=8.7, 2H), 7.47 (t, J=7.5, 1H), 7.79 (d, J=8.5, 1H), 7.88 (dt, J=8.7, 1.5, 1H), 7.93 (dd, J=7.9, 1.1, 1H), 8.34 (s, 1H)

4-(2,6-Difluoro-4-methoxybenzyl)-2-(4,6-dimethoxypyridin-2-yl)-2H-1,2,4-benzothiadiazin-3(4H)-one 1,1-dioxide (183)

The title compound was prepared from 2-(4,6-dimethoxypyridin-2-yl)-2H-1,2,4-benzothiadiazin-3(4H)-one 1,1-dioxide (IntA33) (101 mg, 0.3 mmol), 2,6-difluoro-4-methoxybenzyl bromide (85 mg, 0.36 mmol) and K$_2$CO$_3$ (124 mg, 0.9 mmol) in DMF (1.5 mL) using the methods of (115). After trituration with Et$_2$O further purification by preparative HPLC (method C) yielded the title compound (7 mg, 0.01 mmol).

LCMS (Method B): m/z 492.1 (M+H)+ (ES+), at 4.66 min, 100%

$^1$H NMR: (400 MHz, DMSO) δ: 3.75 (s, 3H), 3.80 (s, 3H), 3.85 (s, 3H), 5.41 (s, 2H), 6.52 (d, J=1.8, 1H), 6.65 (d, J=1.8, 1H), 6.73 (d, J=10.3, 2H), 7.44 (t, J=7.5, 1H), 7.75 (d, J=8.3, 1H), 7.83-7.88 (m, 1H), 7.91 (dd, J=7.8, 1.3, 1H)

4-(2,6-Difluoro-4-methoxybenzyl)-2-[6-methoxy-5-(methylamino)pyridin-3-yl]-2H-1,2,4-benzothiadiazin-3(4H)-one 1,1-dioxide (181) The title compound (120 mg, 0.24 mmol) was prepared in two steps from tert-butyl [5-(1,1-dioxido-3-oxo-3,4-dihydro-2H-1,2,4-benzothiadiazin-2-yl)-2-methoxypyridin-3-yl]methylcarbamate (IntA35) (130 mg, 0.3 mmol), 2,6-difluoro-4-methoxybenzyl bromide (85 mg, 0.36 mmol) and K$_2$CO$_3$ (124 mg, 0.9 mmol) in DMF (1.5 mL); followed by TFA (2 mL) in DCM (3 mL) at rt using the methods of (179).

LCMS (Method B): m/z 491.1 (M+H)+ (ES+), at 4.46 min, 100%

$^1$H NMR: (400 MHz, DMSO) δ: 2.62 (d, J=4.6, 3H), 3.70 (s, 3H), 3.90 (s, 3H), 5.38 (s, 2H), 5.69 (d, J=4.6, 1H), 6.51 (s, 1H), 6.71 (d, J=10.1, 2H), 7.27 (s, 1H), 7.39 (t, J=7.6, 1H), 7.66 (d, J=8.7, 1H), 7.81 (t, J=7.8, 1H), 7.89 (d, J=7.8, 1H)

Route 2

4-(2-Chloro-6-fluorobenzyl)-2-(1-methyl-6-oxo-1,6-dihydropyridin-3-yl)-2H-1,2,4-benzothiadiazin-3 (4H)-one 1,1-dioxide (132)

A mixture of (IntB1) (151 mg), 1,1'-carbonyldiimidazole (232 mg, 1.4 mmol) and triethylamine (0.1 mL, 0.70 mmol) in DMF (1 mL) was heated at 100° C. in a sealed tube for 4 h. After concentration in vacuo, purification by gradient column chromatography eluting with 0-5% MeOH in DCM yielded the title compound (17 mg, 0.04 mmol).

LCMS (Method B): m/z 448 (M+H)+ (ES+), at 3.53 min, 100%

$^1$H NMR: (400 MHz, DMSO) δ: 3.46 (s, 3H), 5.50 (s, 2H), 6.48 (d, J=9.5, 1H), 7.23 (ddd, J=9.5, 7.8, 1.5, 1H), 7.31-7.41 (m, 3H), 7.45 (t, J=7.7, 1H), 7.71 (d, J=8.5, 1H), 7.82-7.89 (m, 1H), 7.97 (dd, J=7.8, 1.3, 1H), 8.02 (d, J=2.8, 1H)

4-(2-Chloro-6-fluorobenzyl)-2-(2-methoxypyrimidin-5-yl)-2H-1,2,4-benzothiadiazin-3(4H)-one 1,1-dioxide (137)

The title compound (40 mg, 0.09 mmol) was prepared from (IntB2) (106 mg), 1,1'-carbonyldiimidazole (162 mg, 1.0 mmol) and triethylamine (0.07 mL, 0.50 mmol) using the methods of (132).

LCMS (Method B): m/z 449 (M+H)+ (ES+), at 4.22 min, 99%

$^1$H NMR: (400 MHz, DMSO) δ: 4.00 (s, 3H), 5.53 (s, 2H), 7.19-7.28 (m, 1H), 7.31-7.44 (m, 2H), 7.48 (t, J=7.5, 1H), 7.75 (d, J=8.5, 1H), 7.84-7.93 (m, 1H), 8.01 (dd, J=7.8, 1.3, 1H), 8.67 (s, 2H)

4-(2-Chloro-6-fluorobenzyl)-7-fluoro-2-[3-(methylsulfanyl)phenyl]-2H-1,2,4-benzothiadiazin-3(4H)-one 1,1-dioxide (74)

The title compound (81 mg, 0.17 mmol) was prepared from (IntB4) (119 mg, 0.26 mmol), 1,1'-carbonyldiimidazole (169 mg, 1.0 mmol) and triethylamine (0.07 mL, 0.50 mmol) using the methods of (132).

LCMS (Method B): m/z 481, 483 (M+H)+ (ES+), at 4.89 min, 95%

$^1$H NMR: (400 MHz, DMSO) δ: 5.51 (s, 2H), 7.13-7.21 (m, 3H), 7.32-7.49 (m, 4H), 7.67-7.79 (m, 3H)

4-(2-Chloro-6-fluorobenzyl)-5-fluoro-2-(6-methoxypyridin-3-yl)-2H-1,2,4-benzothiadiazin-3(4H)-one 1,1-dioxide (123)

The title compound (130 mg, 0.28 mmol) was prepared from (IntB5) (139 mg, 0.32 mmol), 1,1'-carbonyldiimidazole (205 mg, 1.3 mmol) and triethylamine (88 uL, 0.64 mmol) using the methods of (132).

LCMS (Method B): m/z 466, 468 (M+H)+ (ES+), at 4.72 min, 95%

$^1$H NMR: (400 MHz, DMSO) δ: 3.89 (s, 3H), 5.42 (s, 2H), 6.96 (d, J=8.8, 1H), 7.19 (t, J=8.8, 1H), 7.32-7.42 (m, 2H), 7.55-7.60 (m, 1H), 7.65 (dd, J=8.8, 2.8, 1H), 7.82-7.88 (m, 2H), 8.08 (d, J=2.5, 1H)

5-Fluoro-2-(6-methoxypyridin-3-yl)-4-(2-methylbenzyl)-2H-1,2,4-benzothiadiazin-3(4H)-one 1,1-dioxide (130)

The title compound (127 mg, 0.30 mmol) was prepared from (IntB6) (139 mg, 0.35 mmol), 1,1'-carbonyldiimidazole (225 mg, 1.4 mmol) and triethylamine (97 uL, 0.70 mmol) using the methods of (132).

LCMS (Method B): m/z 428 (M+H)+ (ES+), at 4.81 min, 95%

$^1$H NMR: (400 MHz, DMSO) δ: 2.32 (s, 3H), 3.91 (s, 3H), 5.32 (s, 2H), 7.01 (d, J=8.8, 1H), 7.07-7.21 (m, 4H), 7.53 (td, J=8.0, 4.0, 1H), 7.73 (dd, J=13.3, 8.3, 1H), 7.80 (dd, J=8.9, 2.6, 1H), 7.86 (d, J=7.5, 1H), 8.23 (d, J=2.5, 1H)

7-Fluoro-4-[1-(2-fluorophenyl)ethyl]-2-[3-(methylsulfanyl)phenyl]-2H-1,2,4-benzothiadiazin-3(4H)-one 1,1-dioxide (63)

A solution of (IntB3) (139 mg, 0.32 mmol) and triphosgene (32 mg, 0.11 mmol) in 1,4-dioxane (6 mL) was heated in a sealed vial at 100° C. for approximately 3 d, with the addition of further triphosgene (32 mg, 0.11 mmol) after 1 d. After concentration in vacuo, purification by gradient column chromatography eluting with 5-40% EtOAc in iso-hexane yielded the title compound (18 mg, 0.04 mmol).

LCMS (Method B): m/z 461 (M+H)+ (ES+), at 5.24 min, 95%

$^1$H NMR: (400 MHz, DMSO) δ: (400 MHz, DMSO) δ: 1.95 (d, J=7.0, 3H), 2.48 (s, 3H), 5.93 (q, J=6.9, 1H), 7.09 (d, J=7.8, 1H), 7.15-7.23 (m, 3H), 7.34-7.46 (m, 3H), 7.61 (t, J=7.5, 1H), 7.67-7.76 (m, 2H), 7.91 (dd, J=7.0, 2.8, 1H)

Route 4

2-(3,4-Dimethoxyphenyl)-4-(2,4,6-trifluorobenzyl)-2H-pyrido[2,3-e][1,2,4]thiadiazin-3(4H)-one 1,1-dioxide (93)

Step 1: Preparation of N-(3,4-dimethoxyphenyl)-2-[(2,4,6-trifluorobenzyl)amino]pyridine-3-sulfonamide A solution of (IntC1) (82 mg, 0.25 mmol) and 2,4,6-trifluorobenzyl amine (120 mg, 0.75 mmol) in acetonitrile (1.5 mL) was heated at 100° C. in a Biotage Initiator microwave reactor for 1 h. Further 2,4,6-trifluorobenzyl amine (120 mg, 0.75 mmol) was added and the mixture heated at 180° C. in a Biotage Initiator microwave reactor for 2 h. After concentration in vacuo purification by gradient column chromatography eluting with 15-60% EtOAc in iso-hexane yielded the title compound (98 mg, 0.22 mmol).

LCMS (Method B): m/z 454 (M+H)+ (ES+), at 1.22 min.

Step 2: Preparation of 2-(3,4-dimethoxyphenyl)-4-(2,4,6-trifluorobenzyl)-2H-pyrido[2,3-e][1,2,4]thiadiazin-3(4H)-one 1,1-dioxide The title compound (63 mg, 0.13 mmol) was prepared from N-(3,4-dimethoxyphenyl)-2-[(2,4,6-trifluorobenzyl)amino]pyridine-3-sulfonamide (98 mg, 0.22 mmol), 1,1'-carbonyldiimidazole (143 mg, 0.88 mmol) and triethylamine (0.06 mL, 0.44 mmol) using the methods of (132).

LCMS (Method B): m/z 480 (M+H)+ (ES+), at 4.49 min, 100%

$^1$H NMR: (400 MHz, DMSO) δ: 3.72 (s, 3H), 3.82 (s, 3H), 5.58 (s, 2H), 6.92-7.00 (m, 2H), 7.04-7.11 (m, 1H), 7.18 (t, J=8.8, 2H), 7.51 (dd, J=7.8, 5.0, 1H), 8.47 (dd, J=7.8, 1.5, 1H), 8.82 (dd, J=5.0, 1.5, 1H)

4-(2-Chloro-6-fluorobenzyl)-2-(3,4-dimethoxyphenyl)-2H-pyrido[2,3-e][1,2,4]thiadiazin-3(4H)-one 1,1-dioxide (94)

The title compound (48 mg, 0.10 mmol) was prepared in two steps from (IntC1) (82 mg, 0.25 mmol) and 2-chloro-6-fluorobenzyl amine (0.1 mL, 0.75 mmol); followed by 1,1'-carbonyldiimidazole (191 mg, 1.18 mmol) and triethylamine (0.08 mL, 0.59 mmol) using the methods of (93).

LCMS (Method B): m/z 478 (M+H)+ (ES+), at 4.55 min, 100%

$^1$H NMR: (400 MHz, DMSO) δ: 3.72 (s, 3H), 3.82 (s, 3H), 5.63 (s, 2H), 6.92-6.98 (m, 2H), 7.04-7.10 (m, 1H), 7.15-7.23 (m, 1H), 7.29-7.41 (m, 2H), 7.49 (dd, J=7.8, 4.8, 1H), 8.47 (dd, J=7.8, 1.5, 1H), 8.81 (dd, J=4.9, 1.6, 1H)

4-(2,6-Difluoro-4-methoxybenzyl)-2-(3,4-dimethoxyphenyl)-2H-pyrido[2,3-e][1,2,4]thiadiazin-3(4H)-one 1,1-dioxide (95)

Step 1: Preparation of 2-[(2,6-difluoro-4-methoxybenzyl)amino]-N-(3,4-dimethoxyphenyl)pyridine-3-sulfonamide A solution of (IntC1) (128 mg, 0.39 mmol) and 2,4-difluoro-4-methoxybenzyl amine (404 mg, 2.34 mmol) in acetonitrile (1.5 mL) was heated at 180° C. in a Biotage Initiator microwave reactor for 2 h. After concentration in vacuo purification by gradient column chromatography eluting with 10-60% EtOAc in iso-hexane yielded the title compound (198 mg, 0.43 mmol).

LCMS (Method A): m/z 466 (M+H)+ (ES+), at 1.26 min, 95%

Step 2: Preparation of 4-(2,6-difluoro-4-methoxybenzyl)-2-(3,4-dimethoxyphenyl)-2H-pyrido[2,3-e][1,2,4]thiadiazin-3(4H)-one 1,1-dioxide The title compound (89 mg, 0.18 mmol) was prepared from 2-[(2,6-difluoro-4-methoxybenzyl)amino]-N-(3,4-dimethoxyphenyl)pyridine-3-sulfonamide (198 mg, 0.43 mmol), 1,1'-carbonyldiimidazole (279 mg, 1.72 mmol) and triethylamine (0.12 mL, 0.86 mmol) using the methods of (132).

LCMS (Method B): m/z 492 (M+H)+ (ES+), at 4.48 min, 100%

$^1$H NMR: (400 MHz, DMSO) δ: 3.72 (s, 3H), 3.75 (s, 3H), 3.82 (s, 3H), 5.54 (s, 2H), 6.71 (d, J=10.0, 2H), 6.91-7.00 (m, 2H), 7.04-7.12 (m, 1H), 7.49 (dd, J=7.8, 5.0, 1H), 8.46 (dd, J=7.8, 1.8, 1H), 8.82 (dd, J=4.9, 1.6, 1H)

4-[(3,5-Difluoropyridin-2-yl)methyl]-2-(3,4-dimethoxyphenyl)-2H-pyrido[2,3-e][1,2,4]thiadiazin-3(4H)-one 1,1-dioxide (96)

The title compound (16 mg, 0.03 mmol) was prepared in two steps from (IntC1) (82 mg, 0.25 mmol) and (3,5-difluoropyridin-2-yl)methanamine (108 mg, 0.75 mmol); followed by 1,1'-carbonyldiimidazole (65 mg, 0.4 mmol) and triethylamine (28 uL, 0.2 mmol) using the methods of (95).

LCMS (Method B): m/z 463 (M+H)+ (ES+), at 3.86 min, 100%

$^1$H NMR: (400 MHz, DMSO) δ: 3.74 (s, 3H), 3.83 (s, 3H), 5.63 (s, 2H), 6.94 (d, J=2.5, 1H), 6.99 (dd, J=8.5, 2.2, 1H), 7.10 (d, J=8.8, 1H), 7.49 (dd, J=8.0, 5.0, 1H), 7.99 (t, J=8.5, 1H), 8.37 (d, J=2.3, 1H), 8.52 (d, J=7.8, 1H), 8.72 (d, J=4.8, 1H)

4-(4-Chloro-2,6-difluorobenzyl)-2-(3,4-dimethoxyphenyl)-2H-pyrido[2,3-e][1,2,4]thiadiazin-3(4H)-one 1,1-dioxide (97)

The title compound (38 mg, 0.08 mmol) was prepared in two steps from (IntC1) (208 mg, 0.63 mmol), 2,6-difluoro- 4-chlorobenzylamine (135 mg, 0.76 mmol) and N,N-diisopropylethylamine (113 uL, 0.63 mmol); followed by 1,1'-carbonyldiimidazole (166 mg, 1.0 mmol) in DMF (8.5 mL) using the methods of (95).

LCMS (Method B): m/z 496, 498 (M+H)+ (ES+), at 4.82 min, 100%

¹H NMR: (400 MHz, DMSO) δ: 3.72 (s, 3H), 3.82 (s, 3H), 5.58 (s, 2H), 6.89-7.00 (m, 2H), 7.02-7.12 (m, 1H), 7.36 (d, J=7.8, 2H), 7.51 (dd, J=7.8, 4.8, 1H), 8.48 (dd, J=7.8, 1.5, 1H), 8.82 (dd, J=4.8, 1.5, 1H)

2-(2,6-Dimethoxypyridin-4-yl)-4-(2,4,6-trifluorobenzyl)-2H-pyrido[2,3-e][1,2,4]thiadiazin-3(4H)-one 1,1-dioxide (98)

The title compound (82 mg, 0.17 mmol) was prepared in two steps from (IntC2) (165 mg, 0.5 mmol), 2,4,6-trifluorobenzylamine (0.18 mL, 1.5 mmol); followed by 1,1'-carbonyldiimidazole (233 mg, 1.44 mmol), triethylamine (0.10 mL, 0.72 mmol) in DMF (1.5 mL) using the methods of (95).

LCMS (Method B): m/z 481 (M+H)+ (ES+), at 5.12 min, 100%

¹H NMR: (400 MHz, DMSO) S: 3.90 (s, 6H), 5.56 (s, 2H), 6.44 (s, 2H), 7.17 (t, J=8.8, 2H), 7.52 (dd, J=7.8, 5.0, 1H), 8.48 (dd, J=7.8, 1.5, 1H), 8.84 (dd, J=4.8, 1.5, 1H)

2-(5,6-Dimethoxypyridin-2-yl)-4-(2,4,6-trifluorobenzyl)-2H-pyrido[2,3-e][1,2,4]thiadiazin-3(4H)-one 1,1-dioxide (99)

The title compound (118 mg, 0.25 mmol) was prepared in two steps from (IntC3) (165 mg, 0.5 mmol), 2,4,6-trifluorobenzylamine (0.18 mL, 1.5 mmol); followed by 1,1'-carbonyldiimidazole (246 mg, 1.52 mmol), triethylamine (0.11 mL, 0.76 mmol) in DMF (1.5 mL) using the methods of (95).

LCMS (Method B): m/z 481 (M+H)+ (ES+), at 4.47 min, 100%

¹H NMR: (400 MHz, DMSO) δ: 3.82 (s, 3H), 3.85 (s, 3H), 5.58 (s, 2H), 7.08 (d, J=8.0, 1H), 7.19 (t, J=8.8, 2H), 7.46 (d, J=8.3, 1H), 7.52 (dd, J=7.9, 4.9, 1H), 8.47 (dd, J=7.9, 1.6, 1H), 8.83 (dd, J=4.9, 1.6, 1H)

2-(5,6-Dimethoxypyridin-3-yl)-4-(2,4,6-trifluorobenzyl)-2H-pyrido[2,3-e][1,2,4]thiadiazin-3(4H)-one 1,1-dioxide (100)

The title compound (159 mg, 0.33 mmol) was prepared in two steps from (IntC4) (165 mg, 0.5 mmol), 2,4,6-trifluorobenzylamine (0.18 mL, 1.5 mmol); followed by 1,1'-carbonyldiimidazole (311 mg, 1.92 mmol), triethylamine (0.13 mL, 0.96 mmol) in DMF (1.5 mL) using the methods of (95).

LCMS (Method B): m/z 481 (M+H)+ (ES+), at 4.49 min, 100%

¹H NMR: (400 MHz, DMSO) δ: 3.77 (s, 3H), 3.93 (s, 3H), 5.59 (s, 2H), 7.19 (t, J=8.8, 2H), 7.35 (d, J=2.0, 1H), 7.53 (dd, J=7.8, 4.8, 1H), 7.75 (d, J=2.0, 1H), 8.51 (dd, J=7.8, 1.8, 1H), 8.85 (dd, J=4.9, 1.6, 1H)

4-(2,6-Difluoro-4-methoxybenzyl)-2-(2,6-dimethoxypyridin-4-yl)-2H-pyrido[2,3-e][1,2,4]thiadiazin-3(4H)-one 1,1-dioxide (163)

The title compound (108 mg, 0.22 mmol) was prepared in two steps from (IntC2) (165 mg, 0.5 mmol), 2,6-difluoro-4-methoxybenzylamine (90 uL, 0.6 mmol) and N,N-diisopropylethylamine (180 uL, 1.0 mmol); followed by 1,1'-carbonyldiimidazole (246 mg, 1.52 mmol), triethylamine (0.10 mL, 0.72 mmol) in DMF (1.5 mL) using the methods of (95).

LCMS (Method B): m/z 493 (M+H)+ (ES+), at 5.05 min, 100%

¹H NMR: (400 MHz, DMSO) δ: 3.75 (s, 3H), 3.91 (s, 6H), 5.53 (s, 2H), 6.44 (s, 2H), 6.70 (d, J=10.3, 2H), 7.51 (dd, J=7.9, 4.9, 1H), 8.47 (dd, J=7.8, 1.5, 1H), 8.84 (dd, J=4.8, 1.8, 1H)

4-(2,6-Difluoro-4-methoxybenzyl)-2-(5,6-dimethoxypyridin-2-yl)-2H-pyrido[2,3-e][1,2,4]thiadiazin-3(4H)-one 1,1-dioxide (164)

The title compound (112 mg, 0.23 mmol) was prepared in two steps from (IntC3) (165 mg, 0.5 mmol), 2,6-difluoro-4-methoxybenzylamine (90 uL, 0.6 mmol) and N,N-diisopropylethylamine (180 uL, 1.0 mmol); followed by 1,1'-carbonyldiimidazole (253 mg, 1.56 mmol), triethylamine (0.11 mL, 0.79 mmol) in DMF (1.5 mL) using the methods of (95).

LCMS (Method B): m/z 493 (M+H)+ (ES+), at 4.43 min, 100%

¹H NMR: (400 MHz, DMSO) δ: 3.75 (s, 3H), 3.82 (s, 3H), 3.86 (s, 3H), 5.54 (s, 2H), 6.70 (d, J=10.3, 2H), 7.07 (d, J=8.0, 1H), 7.46 (d, J=8.0, 1H), 7.51 (dd, J=7.8, 5.0, 1H), 8.44 (dd, J=7.8, 1.8, 1H), 8.83 (dd, J=4.9, 1.6, 1H)

4-(2,6-Difluoro-4-methoxybenzyl)-2-(5,6-dimethoxypyridin-3-yl)-2H-pyrido[2,3-e][1,2,4]thiadiazin-3(4H)-one 1,1-dioxide (165)

The title compound (134 mg, 0.27 mmol) was prepared in two steps from (IntC4) (165 mg, 0.5 mmol), 2,6-difluoro-4-methoxybenzylamine (90 uL, 0.6 mmol) and N,N-diisopropylethylamine (180 uL, 1.0 mmol); followed by 1,1'-carbonyldiimidazole (331 mg, 2.04 mmol), triethylamine (0.14 mL, 1.00 mmol) in DMF (1.5 mL) using the methods of (95).

LCMS (Method B): m/z 493 (M+H)+ (ES+), at 4.45 min, 100%

¹H NMR: (400 MHz, DMSO) δ: 3.76 (s, 3H), 3.77 (s, 3H), 3.94 (s, 3H), 5.55 (s, 2H), 6.64-6.76 (m, 2H), 7.35 (d, J=2.0, 1H), 7.52 (dd, J=7.8, 5.0, 1H), 7.75 (d, J=2.3, 1H), 8.48 (dd, J=7.9, 1.6, 1H), 8.84 (dd, J=4.9, 1.6, 1H)

4-(2-Chloro-6-fluorobenzyl)-2-(5,6-dimethoxypyridin-2-yl)-2H-pyrido[2,3-e][1,2,4]thiadiazin-3(4H)-one 1,1-dioxide (168)

The title compound (157 mg, 0.33 mmol) was prepared in two steps from (IntC3) (165 mg, 0.5 mmol), 2-chloro-6-fluorobenzylamine (75 uL, 0.6 mmol) and N,N-diisopropylethylamine (180 uL, 1.0 mmol); followed by 1,1'-carbonyldiimidazole (298 mg, 1.84 mmol), triethylamine (0.13 mL, 0.93 mmol) in DMF (1.5 mL) using the methods of (95).

LCMS (Method B): m/z 481, 479 (M+H)+ (ES+), at 4.57 min, 100%

¹H NMR: (400 MHz, DMSO) δ: δ 3.81 (s, 3H), 3.85 (s, 3H), 5.63 (s, 2H), 7.07 (d, J=8.0, 1H), 7.14-7.23 (m, 1H), 7.28-7.42 (m, 2H), 7.45 (d, J=8.0, 1H), 7.51 (dd, J=7.8, 5.0, 1H), 8.46 (dd, J=7.8, 1.8, 1H), 8.82 (dd, J=4.9, 1.6, 1H)

4-(2,6-Difluorobenzyl)-2-(5,6-dimethoxypyridin-2-yl)-2H-pyrido[2,3-e][1,2,4]thiadiazin-3(4H)-one 1,1-dioxide (169)

The title compound (57 mg, 0.12 mmol) was prepared in two steps from (IntC3) (165 mg, 0.5 mmol), 2,6-difluorobenzylamine (70 uL, 0.6 mmol) and N,N-diisopropylethylamine (180 uL, 1.0 mmol); followed by 1,1'-carbonyldiimidazole (305 mg, 1.88 mmol), triethylamine (0.13 mL, 0.93 mmol) in DMF (1.5 mL) using the methods of (95).

LCMS (Method B): m/z 463 (M+H)+ (ES+), at 4.34 min, 100%

$^1$H NMR: (400 MHz, DMSO) δ: 3.82 (s, 3H), 3.85 (s, 3H), 5.62 (s, 2H), 6.98-7.13 (m, 3H), 7.32-7.43 (m, 1H), 7.46 (d, J=8.0, 1H), 7.52 (dd, J=7.8, 5.0, 1H), 8.46 (dd, J=7.9, 1.6, 1H), 8.83 (dd, J=4.8, 1.5, 1H)

2-(3,4-Dimethylphenyl)-4-(2,4,6-trifluorobenzyl)-2H-pyrido[2,3-e][1,2,4]thiadiazin-3(4H)-one 1,1-dioxide (101)

The title compound (64 mg, 0.14 mmol) was prepared in two steps from (IntC5) (217 mg, 0.73 mmol), 2,4,6-trifluorobenzylamine (0.11 mL, 0.88 mmol) and N,N-diisopropylethylamine (261 uL, 1.46 mmol); followed by 1,1'-carbonyldiimidazole (289 mg, 1.78 mmol) in DMF (7.1 mL) using the methods of (95).

LCMS (Method B): m/z 448 (M+H)+ (ES+), at 5.24 min, 98%

$^1$H NMR: (400 MHz, DMSO) δ: 2.26 (s, 3H), 2.29 (s, 3H), 5.57 (s, 2H), 7.03-7.23 (m, 4H), 7.29 (d, J=8.0, 1H), 7.51 (dd, J=7.8, 5.0, 1H), 8.46 (d, J=7.5, 1H), 8.82 (d, J=3.8, 1H)

4-(2,6-Difluoro-4-methoxybenzyl)-2-(3,4-dimethylphenyl)-2H-pyrido[2,3-e][1,2,4]thiadiazin-3(4H)-one 1,1-dioxide (102)

The title compound (45 mg, 0.10 mmol) was prepared in two steps from (IntC5) (217 mg, 0.73 mmol), 2,6-difluoro-4-methoxybenzylamine (125 uL, 0.88 mmol) and N,N-diisopropylethylamine (261 uL, 1.46 mmol); followed by 1,1'-carbonyldiimidazole (362 mg, 2.23 mmol) in DMF (8.9 mL) using the methods of (95).

LCMS (Method B): m/z 460 (M+H)+ (ES+), at 5.22 min, 95%

$^1$H NMR: (400 MHz, DMSO) δ: 2.26 (s, 3H), 2.28 (s, 3H), 3.71-3.80 (m, 3H), 5.53 (s, 2H), 6.65-6.75 (m, 2H), 7.06-7.18 (m, 2H), 7.29 (d, J=8.0, 1H), 7.49 (dd, J=7.9, 4.9, 1H), 8.45 (dd, J=7.8, 1.5, 1H), 8.82 (dd, J=4.8, 1.8, 1H)

2-(3,5-Dimethylphenyl)-4-(2,4,6-trifluorobenzyl)-2H-pyrido[2,3-e][1,2,4]thiadiazin-3(4H)-one 1,1-dioxide (103)

The title compound (89 mg, 0.20 mmol) was prepared in two steps from (IntC6) (209 mg, 0.71 mmol), 2,4,6-trifluorobenzylamine (107 uL, 0.88 mmol) and N,N-diisopropylethylamine (252 uL, 1.41 mmol); followed by 1,1'-carbonyldiimidazole (386 mg, 2.38 mmol) and triethylamine (114 uL, 0.82 mmol) in DMF (9.5 mL) using the methods of (95).

LCMS (Method B): m/z 448 (M+H)+ (ES+), at 5.26 min, 95%

$^1$H NMR: (400 MHz, DMSO) δ: 2.31 (s, 6H), 5.57 (s, 2H), 7.00 (s, 2H), 7.11-7.25 (m, 3H), 7.51 (dd, J=7.8, 5.0, 1H), 8.47 (dd, J=7.9, 1.6, 1H), 8.83 (dd, J=4.9, 1.6, 1H)

2-[6-Methoxy-5-(methylamino)pyridin-2-yl]-4-(2,4,6-trifluorobenzyl)-2H-pyrido[2,3-e][1,2,4]thiadiazin-3(4H)-one 1,1-dioxide (172)

The title compound (266 mg, 0.55 mmol) was prepared in three steps from tert-butyl (6-{[(2-chloropyridin-3-yl)sulfonyl]amino}-2-methoxypyridin-3-yl)methylcarbamate (IntC8) (755 mg, 1.76 mmol), 2,4,6-trifluorobenzylamine (1.13 g, 7.01 mmol) and N,N-diisopropylethylamine (0.46 mL, 2.64 mmol) in MeCN (10 mL) at 120° C. for 12 hours; followed by 1,1'-carbonyldiimidazole (832 mg, 5.13 mmol) and triethylamine (358 uL, 2.57 mmol) using the methods of (95); followed by TFA (2 mL) in DCM (3 mL) at rt using the method of (179), step 2.

LCMS (Method B): m/z 480.1 (M+H)+ (ES+), at 4.62 min, 100%

$^1$H NMR: (400 MHz, DMSO) δ: 2.70 (d, J=5.0, 3H), 3.78 (s, 3H), 5.53 (s, 2H), 5.77 (d, J=5.0, 1H), 6.73 (d, J=8.2, 1H), 6.87 (d, J=7.8, 1H), 7.14 (t, J=8.9, 2H), 7.46 (dd, J=7.8, 5.0, 1H), 8.17-8.42 (m, 1H), 8.60-8.79 (m, 1H)

4-(2,6-Difluoro-4-methoxybenzyl)-2-(6-methoxy-5-methylpyridin-2-yl)-2H-pyrido[2,3-e][1,2,4]thiadiazin-3(4H)-one 1,1-dioxide (175)

The title compound (110 mg, 0.23 mmol) was prepared in two steps from 2-chloro-N-(6-methoxy-5-methylpyridin-2-yl)pyridine-3-sulfonamide (IntC11) (320 mg, 1.02 mmol) and 2,6-difluoro-4-methoxybenzylamine (212 mg, 1.22 mmol); followed by 1,1'-carbonyldiimidazole (403 mg, 2.49 mmol) and triethylamine (173 uL, 1.24 mmol) using the methods of (95).

LCMS (Method B): m/z 477.1 (M+H)+ (ES+), at 4.96 min, 95%

$^1$H NMR: (400 MHz, DMSO) δ: 2.16 (s, 3H), 3.71 (s, 3H), 3.80 (s, 3H), 5.50 (s, 2H), 6.65 (s, 1H), 6.68 (s, 1H), 6.98 (d, J=7.3, 1H), 7.47 (dd, J=7.8, 5.0, 1H), 7.69 (dd, J=7.3, 0.9, 1H), 8.41 (dd, J=7.8, 1.4, 1H), 8.79 (dd, J=4.8, 1.6, 1H)

4-(2,6-Difluoro-4-methoxybenzyl)-2-[5-methyl-6-(methylamino)pyridin-3-yl]-2H-pyrido[2,3-e][1,2,4]thiadiazin-3(4H)-one 1,1-dioxide (184)

The title compound (150 mg, 0.32 mmol) was prepared in three steps from tert-butyl (5-{[(2-chloropyridin-3-yl)sulfonyl]amino}-3-methylpyridin-2-yl)methylcarbamate (IntC13) (660 mg, 1.60 mmol), 2,6-difluoro-4-methoxybenzylamine (1.11 g, 6.41 mmol) and N,N-diisopropylethylamine (0.57 mL, 3.20 mmol) in MeCN (10 mL) at 120° C. for 12 hours; followed by 1,1'-carbonyldiimidazole (688 mg, 1.20 mmol) and triethylamine (296 uL, 2.12 mmol) using the methods of (95); followed by TFA (2 mL) in DCM (3 mL) at rt using the method of (179), step 2.

LCMS (Method B): m/z 476.1 (M+H)+ (ES+), at 4.23 min, 100%

$^1$H NMR: (400 MHz, DMSO) δ: 1.84 (s, 3H), 2.65 (d, J=4.5, 3H), 3.52 (s, 3H), 5.30 (s, 2H), 6.23 (d, J=4.5, 1H), 6.46 (s, 1H), 6.49 (s, 1H), 6.97 (dd, J=2.5, 1.0, 1H), 7.26 (dd, J=7.9, 4.9, 1H), 7.60 (d, J=2.3, 1H), 8.24 (dd, J=7.9, 1.6, 1H), 8.59 (dd, J=4.9, 1.6, 1H)

2-(1,3-Benzothiazol-6-yl)-4-(2,6-difluoro-4-methoxybenzyl)-2H-pyrido[2,3-e][1,2,4]thiadiazin-3(4H)-one 1,1-dioxide (182)

The title compound (60 mg, 0.12 mmol) was prepared in two steps from N-(1,3-benzothiazol-6-yl)-2-chloropyridine-3-sulfonamide (IntC9) (300 mg, 0.92 mmol) and 2,6-difluoro-4-methoxybenzylamine (176 mg, 1.01 mmol) at 140° C. in a sealed tube; followed by triphosgene (288 mg, 0.97 mmol) in 1,4-dioxane (5 mL) at 110° C. for 16 h using the methods of (95) then (63).

LCMS (Method B): m/z 510.0 (M+H)+ (ES+), at 4.39 min, 100%

¹H NMR: (400 MHz, DMSO) δ: 3.76 (s, 3H), 5.56 (s, 2H), 6.72 (d, J=9.8, 2H), 7.51-7.58 (m, 2H), 8.23 (d, J=8.6, 1H), 8.34 (s, 1H), 8.51 (d, J=7.0, 1H), 8.86 (d, J=5.5, 1H), 9.56 (s, 1H)

2-(5-Methoxy-6-methylpyridin-3-yl)-4-(2,4,6-trifluorobenzyl)-2H-pyrido[2,3-e][1,2,4]thiadiazin-3(4H)-one 1,1-dioxide (176)

The title compound (52 mg, 0.11 mmol) was prepared in two steps from (IntC14) (88 mg, 0.28 mmol), 2,4,6-trifluorobenzyl amine (58 mg, 0.36 mmol) and N,N-diisopropylethylamine (100 uL, 0.57 mmol); followed by 1,1'-carbonyldiimidazole (110 mg, 0.68 mmol) and triethylamine (45 uL, 0.32 mmol) using the methods of (97).

LCMS (Method B): m/z 465.1 (M+H)+ (ES+), at 4.32 min, 100%

¹H NMR: (400 MHz, DMSO) δ: 2.44 (s, 3H), 3.82 (s, 3H), 5.60 (s, 2H), 7.19-7.23 (m, 2H), 7.45 (d, J=1.8, 1H), 7.55 (dd, J=8.0, 4.8, 1H), 8.06 (d, J=1.8, 1H), 8.53 (dd, J=7.8, 1.4, 1H), 8.87 (dd, J=5.0, 1.8, 1H)

4-(2,6-Difluoro-4-methoxybenzyl)-2-[6-methoxy-5-(methylamino)pyridin-3-yl]-2H-pyrido[2,3-e][1,2,4]thiadiazin-3(4H)-one 1,1-dioxide (186)

The title compound (155 mg, 0.32 mmol) was prepared in three steps from tert-butyl (5-{[(2-chloropyridin-3-yl)sulfonyl]amino}-2-methoxypyridin-3-yl)methylcarbamate (IntC15) (214 mg, 0.5 mmol), 2,6-difluoro-4-methoxybenzylamine (0.28 mL, 2.0 mmol) and N,N-diisopropylethylamine (0.18 mL, 1.0 mmol) in MeCN (3 mL) at 120° C. for 6 hours; followed by 1,1'-carbonyldiimidazole (350 mg, 2.16 mmol) and triethylamine (0.15 mL, 1.08 mmol) using the methods of (95); followed by TFA (2 mL) in DCM (3 mL) at rt using the method of (179), step 2.

LCMS (Method B): m/z 492.0 (M+H)+ (ES+), at 4.53 min, 100%

¹H NMR: (400 MHz, DMSO) δ: 2.61 (d, J=5.0, 3H), 3.71 (s, 3H), 3.89 (s, 3H), 5.50 (s, 2H), 5.70 (d, J=5.0, 1H), 6.57 (d, J=1.8, 1H), 6.67 (d, J=10.1, 2H), 7.29 (d, J=2.3, 1H), 7.45 (dd, J=7.8, 4.6, 1H), 8.42 (dd, J=8.0, 1.6, 1H), 8.78 (dd, J=4.8, 1.6, 1H)

2-[5-Methoxy-6-(methylamino)pyridin-3-yl]-4-(2,6-difluoro-4-methoxybenzyl)-2H-pyrido[2,3-e][1,2,4]thiadiazin-3(4H)-one 1,1-dioxide (177)

The title compound (133 mg, 0.27 mmol) was prepared in three steps from tert-butyl (5-{[(2-chloropyridin-3-yl)sulfonyl]amino}-3-methoxypyridin-2-yl)methyl carbamate (IntC17) (214 mg, 0.5 mmol), 2,6-difluoro-4-methoxybenzylamine (0.28 mL, 2.0 mmol) and N,N-diisopropylethylamine (0.18 mL, 1.0 mmol) in MeCN (3 mL) at 120° C. for 6 hours; followed by 1,1'-carbonyldiimidazole (259 mg, 1.6 mmol) and triethylamine (0.11 mL, 0.8 mmol) using the methods of (95); followed by TFA (2 mL) in DCM (3 mL) at rt using the method of (179), step 2.

LCMS (Method B): m/z 492.1 (M+H)+ (ES+), at 4.17 min, 95%

¹H NMR: (400 MHz, DMSO) δ: 2.81 (d, J=4.6, 3H), 3.71 (s, 3H), 3.72 (s, 3H), 5.50 (s, 2H), 6.58 (d, J=4.6, 1H), 6.67 (d, J=10.1, 2H), 6.88 (d, J=1.4, 1H), 7.45 (dd, J=7.6, 4.8, 1H), 7.54 (d, J=1.4, 1H), 8.43 (d, J=6.9, 1H), 8.78 (d, J=3.7, 1H)

Route 5

4-(2-Chloro-6-fluorobenzyl)-2-(3,4-dimethoxyphenyl)-2H-pyrido[4,3-e][1,2,4]thiadiazin-3(4H)-one 1,1-dioxide (91)

Step 1: Preparation of 4-[(2-chloro-6-fluorobenzyl)amino]-N-(3,4-dimethoxyphenyl)pyridine-3-sulfonamide A solution of 4-Chloro-N-(3,4-dimethoxyphenyl)pyridine-3-sulfonamide (IntD1) (0.5 g, 1.50 mmol), 2-chloro-6-fluoro-benzylamine (0.26 g, 1.67 mmol) and K₂CO₃ (0.41 g, 3.0 mmol) in DMF (10 mL) was heated at 130° C. for 4 h. The mixture was added to saturated aqueous NaHCO₃ (50 mL), extracted with EtOAc (3×25 mL) and the combined organic phases dried over Na₂SO₄ and concentrated in vacuo. Purification by gradient column chromatography eluting with 0-45% EtOAc in hexane yielded the title compound (40 mg, 0.09 mmol).

LCMS (Method B): (ESI+ve) 451.8. [M+H]⁺.

Step 2: Preparation of 4-(2-chloro-6-fluorobenzyl)-2-(3,4-dimethoxyphenyl)-2H-pyrido[4,3-e][1,2,4]thiadiazin-3(4H)-one 1,1-dioxide A solution of 4-[(2-chloro-6-fluorobenzyl)amino]-N-(3,4-dimethoxyphenyl)pyridine-3-sulfonamide (0.04 g, 0.09 mmol) and 1,1'-carbonyldiimidazole (56 mg, 0.34 mmol) in 1,2-dichloroethane (10 mL) was heated for 30 min at 100° C., then cooled and concentrated in vacuo. Purification by gradient column chromatography eluting with 0-30% EtOAc in hexane yielded the title compound (10 mg, 0.02 mmol).

LCMS (Method B): m/z 478.2, 480.1 (M+H)+ (ES+), at 3.93 min, 100%

¹H NMR: (400 MHz, DMSO) δ: 3.72 (s, 3H), 3.82 (s, 3H), 5.49 (s, 2H), 6.85-6.99 (m, 2H), 7.08 (d, J=8.5, 1H), 7.19-7.30 (m, 1H), 7.33-7.47 (m, 2H), 7.72 (d, J=5.8, 1H), 8.91 (d, J=6.1, 1H), 9.07 (s, 1H)

4-(4-Chloro-2-fluorobenzyl)-2-(3,4-dimethoxyphenyl)-2H-pyrido[4,3-e][1,2,4]thiadiazin-3(4H)-one 1,1-dioxide (92)

The title compound (110 mg, 0.23 mmol) was prepared in two steps from 4-Chloro-N-(3,4-dimethoxyphenyl)pyridine-3-sulfonamide (IntD1) (300 mg, 0.90 mmol), 2-fluoro-4-chlorobenzylamine (146 mg, 0.90 mmol) and K₂CO₃ (378 mg, 2.73 mmol); followed by 1,1'-carbonyldiimidazole (0.22 g, 1.32 mmol) using the methods of (91).

LCMS (Method B): m/z 478.2, 480.0 (M+H)+ (ES+), at 4.28 min, 100%

¹H NMR: (400 MHz, DMSO) δ: 3.73 (s, 3H), 3.82 (s, 3H), 5.40 (br s, 2H), 6.98-7.14 (m, 3H), 7.22-7.30 (m, 1H), 7.31-7.40 (m, 1H), 7.48-7.64 (m, 2H), 8.84 (d, J=6.1, 1H), 9.11 (s, 1H)

Route 6

4-(2-Chloro-6-fluorobenzyl)-2-(pyridin-2-ylmethyl)-2H-1,2,4-benzothiadiazin-3(4H)-one 1,1-dioxide (128)

A mixture of (IntE1) (0.3 g, 0.88 mmol), 2-(bromomethyl)pyridine (0.33 g, 1.32 mmol) and Cs₂CO₃ (0.86 g, 2.64 mmol) in 1,4-dioxane (15 mL) was heated at 75° C. for 8 h. After cooling to rt, H₂O was added and the mixture extracted with EtOAc, dried over Na₂SO and concentrated in vacuo. Purification by gradient column chromatography eluting with 0-30% EtOAc in hexane yielded the title compound (150 mg, 0.35 mmol).

LCMS (Method B): m/z 432.1, 434.1 (M+H)+ (ES+), at 4.20 min, >95%

¹H NMR: (400 MHz, DMSO) δ: 5.27 (s, 2H), 5.54 (s, 2H), 6.92-7.05 (m, 1H), 7.13-7.50 (m, 6H), 7.65 (dt, J=16.3, 8.0, 2H), 7.90 (d, J=7.6, 1H), 8.55 (d, J=4.3, 1H)

4-(2-Chloro-6-fluorobenzyl)-2-(cyclohexylmethyl)-2H-1,2,4-benzothiadiazin-3(4H)-one 1,1-dioxide (64)

The title compound (25 mg, 0.06 mmol) was prepared from (IntE1) (0.3 g, 0.88 mmol), 2-(bromomethyl)cyclohexane (0.18 g, 1.05 mmol) and K₂CO₃ (0.36 g, 2.60 mmol) using the methods of (128).

LCMS (Method B): m/z 437.2, 439.2 (M+H)+ (ES+), at 5.40 min, >95%

¹H NMR: (400 MHz, DMSO) δ: 0.79-0.99 (m, 2H), 1.01-1.31 (m, 3H), 1.48-1.73 (m, 6H), 4.14 (d, J=6.1, 2H), 5.53 (s, 2H), 7.18-7.30 (m, 1H), 7.35-7.51 (m, 3H), 7.58-7.68 (m, 1H), 7.68-7.79 (m, 1H), 7.86 (d, J=7.9, 1H)

4-(2-Chloro-6-fluorobenzyl)-2-(tetrahydro-2H-pyran-4-ylmethyl)-2H-1,2,4-benzothiadiazin-3(4H)-one 1,1-dioxide (117)

The title compound (150 mg, 0.34 mmol) was prepared from (IntE1) (0.3 g, 0.88 mmol), 4-(bromomethyl)tetrahydro-2H-pyran (0.20 g, 1.05 mmol) and K₂CO₃ (0.36 g, 2.60 mmol) using the methods of (128).

LCMS (Method B): m/z 439.2, 441.2 (M+H)+ (ES+), at 4.42 min, >95%

¹H NMR: (400 MHz, DMSO+D₂O) δ: 0.95-1.25 (m, 3H), 1.43 (d, J=12.2, 2H), 3.16 (t, J=10.8, 2H), 3.58-3.85 (m, 4H), 5.40 (br s, 2H), 7.14 (d, J=9.2, 1H), 7.22-7.47 (m, 3H), 7.59 (d, J=8.2, 1H), 7.74 (t, J=7.8, 1H), 7.85 (d, J=7.6, 1H)

4-(2-Chloro-6-fluorobenzyl)-2-[(3-methyloxetan-3-yl)methyl]-2H-1,2,4-benzothiadiazin-3(4H)-one 1,1-dioxide (118)

The title compound (123 mg, 0.29 mmol) was prepared from (IntE1) (0.3 g, 0.88 mmol), 3-(bromomethyl)-3-methyloxetane (0.21 g, 1.32 mmol) and Cs₂CO₃ (0.86 g, 2.64 mmol) using the methods of (128).

LCMS (Method B): m/z 425.2, 427.2 (M+H)+ (ES+), at 4.22 min, >95%

¹H NMR: (400 MHz, DMSO) δ: 1.21 (d, J=1.8, 3H), 3.92-4.15 (m, 4H), 4.48 (dd, J=5.6, 2.3, 2H), 5.47 (br s, 2H), 7.13-7.29 (m, 1H), 7.29-7.51 (m, 3H), 7.59-7.72 (m, 1H), 7.81 (t, J=7.5, 1H), 7.93 (d, J=7.6, 1H)

4-(2-Chloro-6-fluorobenzyl)-2-[(5-methyl-1,2-oxazol-3-yl)methyl]-2H-1,2,4-benzothiadiazin-3(4H)-one 1,1-dioxide (129)

The title compound (0.16 g, 0.37 mmol) was prepared from (IntE1) (0.3 g, 0.88 mmol), 3-(bromomethyl)-5-methyl-1,2-oxazole (0.11 g, 0.63 mmol) and Cs₂CO₃ (0.86 g, 2.64 mmol) using the methods of (128).

LCMS (Method B): m/z 436.2, 438.2 (M+H)+ (ES+), at 4.47 min, 95%

¹H NMR: (400 MHz, DMSO) δ: 2.36 (s, 3H), 5.00 (s, 2H), 5.48 (s, 2H), 6.09 (s, 1H), 7.15-7.47 (m, 4H), 7.67 (d, J=8.5, 1H), 7.76-7.87 (m, 1H), 7.93 (d, J=7.9, 1H)

4-(4-Chloro-2-fluorobenzyl)-2-[(1,3-dimethyl-1H-pyrazol-5-yl)methyl]-2H-1,2,4-benzothiadiazin-3(4H)-one 1,1-dioxide (134)

The title compound (0.17 g, 0.38 mmol) was prepared from (IntE2) (0.6 g, 1.76 mmol), 5-(Bromomethyl)-1,3-dimethyl-1H-pyrazole (IntE5) (0.40 g, 1.2 mmol) and K₂CO₃ (1.21 g, 8.8 mmol) using the methods of (128).

LCMS (Method B): m/z 449.1, 451.2 (M+H)+ (ES+), at 4.21 min, >95%

¹H NMR: (400 MHz, DMSO) δ: 2.03 (s, 3H), 3.73 (s, 3H), 4.99 (s, 2H), 5.47 (s, 2H), 5.87 (s, 1H), 7.16-7.26 (m, 1H), 7.30-7.47 (m, 3H), 7.64 (d, J=8.2, 1H), 7.75-7.85 (m, 1H), 7.93 (d, J=7.6, 1H)

4-{[4-(2,6-Difluorobenzyl)-1,1-dioxido-3-oxo-3,4-dihydro-2H-1,2,4-benzothiadiazin-2-yl]methyl}-2-fluorobenzonitrile (65)

A mixture of (IntE3) (100 mg, 0.31 mmol), 4-(bromomethyl)-2-fluorobenzonitrile (165 mg, 0.77 mmol) and K₂CO₃ (107 mg, 0.77 mmol) in DMF (5 mL) was heated in a CEM Discover microwave reactor at 100° C. for 3 h before EtOAc (40 mL) and H₂O (10 mL) were added and the phases were separated. The organic phase was washed with brine (5×10 mL), dried over MgSO₄ and concentrated in vacuo. Purification by preparative HPLC (method A) yielded the title compound (11 mg, 0.02 mmol).

LCMS (Method B): m/z 458.3 (M+H)+ (ES+), at 4.87 min, 100%

¹H NMR: (400 MHz, DMSO) δ: 5.13 (s, 2H), 5.48 (s, 2H), 7.06-7.12 (m, 2H), 7.33-7.46 (m, 4H), 7.63-7.70 (m, 1H), 7.85 (t, J=7.3, 1H), 7.94 (t, J=6.4, 2H)

4-(2,6-Difluorobenzyl)-2-[2-(3-methoxyphenyl)ethyl]-2H-1,2,4-benzothiadiazin-3(4H)-one 1,1-dioxide (66)

A mixture of (IntE3) (50 mg, 0.15 mmol), 1-(2-bromoethyl)-3-methoxybenzene (37 μl, 0.23 mmol) and K₂CO₃ (32.0 mg, 0.23 mmol) in DMF (3 mL) in a sealed tube was heated at 100° C. overnight. After cooling to rt, further 1-(2-bromoethyl)-3-methoxybenzene (25 μl, 0.15 mmol) and K₂CO₃ (21.3 mg, 0.15 mmol) were added and the mixture was heated in a CEM Discover microwave reactor at 100° C. for 1 h. EtOAc (40 mL) and H₂O (10 mL) were added and the phases were separated. The organic phase was washed with water (4×10 mL) and brine (10 mL), dried over MgSO₄ and concentrated in vacuo. Purification by preparative HPLC (method A) yielded the title compound (26.4 mg, 0.06 mmol).

LCMS (Method B): m/z 459.3 (M+H)+ (ES+), at 5.12 min, 100%

¹H NMR: (400 MHz, DMSO) δ: 2.88 (t, J=7.5, 2H), 3.66 (s, 3H), 4.02 (t, J=7.5, 2H), 5.45 (s, 2H), 6.67-6.76 (m, 3H), 7.04-7.15 (m, 3H), 7.34-7.44 (m, 2H), 7.63 (d, J=8.5, 1H), 7.76-7.84 (m, 2H)

4-(2,6-Difluorobenzyl)-2-[(2-oxo-1,2-dihydroquinolin-4-yl)methyl]-2H-1,2,4-benzothiadiazin-3(4H)-one 1,1-dioxide (126)

A mixture of (IntE3) (50 mg, 0.15 mmol), 4-(bromomethyl)quinolin-2(1H)-one (184 mg, 0.77 mmol) and K₂CO₃

(107 mg, 0.77 mmol) in DMF (5 mL) in a sealed tube was heated at 100° C. for approximately 4 h. 4-(Bromomethyl)quinolin-2(1H)-one (37 mg, 0.15 mmol) was added and the mixture heated at 100° C. overnight, before the addition of further 4-(bromomethyl)quinolin-2(1H)-one (37 mg, 0.15 mmol) and $K_2CO_3$ (21.3 mg, 0.15 mmol) and heating in a CEM Discover microwave reactor at 100° C. for 1 h. EtOAc (40 mL) and brine (10 mL) were added, the phases were separated and the organic phase was washed with brine (4×10 mL), dried over $MgSO_4$ and concentrated in vacuo. Purification by preparative HPLC (method A) yielded the title compound (5.8 mg, 0.01 mmol).

LCMS (Method B): m/z 482.2 (M+H)+ (ES+), at 3.88 min, 95%

$^1$H NMR: (400 MHz, DMSO) δ: 5.31 (s, 2H), 5.52 (s, 2H), 6.13 (s, 1H), 7.06-7.14 (m, 2H), 7.23 (t, J=8.0, 1H), 7.35 (d, J=8.0, 1H), 7.41 (t, J=8.3, 1H), 7.48 (t, J=7.5, 1H), 7.53 (t, J=7.3, 1H), 7.74 (d, J=8.5, 1H), 7.89 (t, J=8.5, 2H), 7.98 (d, J=7.8, 1H), 11.78 (s, 1H)

4-(2,6-Difluorobenzyl)-2-[(2-methyl-1,3-thiazol-4-yl)methyl]-2H-1,2,4-benzothiadiazin-3(4H)-one 1,1-dioxide (119)

A mixture of (IntE3) (50 mg, 0.15 mmol), 4-(chloromethyl)-2-methylthiazole hydrochloride (71.0 mg, 0.39 mmol), KI (5.1 mg, 0.03 mmol) and $K_2CO_3$ (74.6 mg, 0.54 mmol) in DMF (3 mL) was heated in a CEM Discover microwave reactor at 100° C. for 3 h. Further 4-(chloromethyl)-2-methylthiazole hydrochloride (28.4 mg, 0.15 mmol), KI (5.1 mg, 0.03 mmol) and $K_2CO_3$ (42.6 mg, 0.31 mmol) were added and the mixture heated in a CEM Discover microwave reactor at 100° C. for 3 h. EtOAc (40 mL) and brine (10 mL) were added, the phases were separated and the organic phase was washed with brine (3×10 mL), dried over $Na_2SO_4$ and concentrated in vacuo. Purification by preparative HPLC (method A) yielded the title compound (9.1 mg, 0.02 mmol).

LCMS (Method B): m/z 436.2 (M+H)+ (ES+), at 4.18 min, 95%

$^1$H NMR: (400 MHz, DMSO) δ: 2.58 (s, 3H), 5.04 (s, 2H), 5.47 (s, 2H), 7.01-7.08 (m, 2H), 7.14 (s, 1H), 7.35-7.43 (m, 2H), 7.65 (d, J=8.5, 1H), 7.80 (t, J=7.8, 1H), 7.88 (d, J=7.8, 1H)

4-(2,6-Difluorobenzyl)-2-[(3,4-dimethoxypyridin-2-yl)methyl]-2H-1,2,4-benzothiadiazin-3(4H)-one 1,1-dioxide (121)

A mixture of (IntE3) (100 mg, 0.31 mmol), 2-(chloromethyl)-3,4-dimethoxypyridine hydrochloride (173 mg, 0.77 mmol), KI (10.2 mg, 0.06 mmol) and $K_2CO_3$ (170 mg, 1.23 mmol) in DMF (6 mL) was heated at 100° C. for 1 d. After cooling to rt, EtOAc (40 mL) and $H_2O$ (10 mL) were added, the phases were separated and the organic phase was washed with $H_2O$ (4×10 mL), dried over $MgSO_4$ and concentrated in vacuo. Purification by preparative HPLC (method A) yielded the title compound (20 mg, 0.04 mmol).

LCMS (Method B): m/z 476.1 (M+H)+ (ES+), at 4.19 min, 95%

$^1$H NMR: (400 MHz, DMSO) δ: 3.79 (s, 3H), 3.87 (s, 3H), 5.12 (s, 2H), 5.45 (s, 2H), 6.95 (d, J=5.5, 1H), 7.04 (t, J=8.3, 2H), 7.34-7.41 (m, 2H), 7.69 (d, J=8.3, 1H), 7.79 (t, J=8.3, 2H), 7.88 (d, J=5.5, 1H)

4-(2,6-Difluorobenzyl)-2-[(1-methyl-1H-imidazol-2-yl)methyl]-2H-1,2,4-benzothiadiazin-3(4H)-one 1,1-dioxide (131)

Diisopropyl azodicarboxylate (0.16 ml, 0.77 mmol) was added dropwise to a solution of (IntE3) (100 mg, 0.31 mmol), (1-methyl-1H-imidazol-2-yl)methanol (86 mg, 0.77 mmol) and triphenylphosphine (202 mg, 0.77 mmol) in THF (2 mL) at 0° C. The reaction mixture was allowed to warm to rt with stirring overnight before concentration in vacuo. Purification by preparative HPLC (method A) yielded the title compound (28 mg, 0.07 mmol).

LCMS (Method B): m/z 419.2 (M+H)+ (ES+), at 3.38 min, 100%

$^1$H NMR: (400 MHz, DMSO) δ: 3.65 (s, 3H), 5.04 (s, 2H), 5.46 (s, 2H), 6.67 (s, 1H), 7.02 (s, 1H), 7.04-7.10 (m, 2H), 7.35-7.43 (m, 2H), 7.70 (d, J=8.5, 1H), 7.82 (t, J=7.5, 1H), 7.88 (d, J=7.8, 1H)

4-(2,4,6-Trifluorobenzyl)-2-[(2-oxo-1,2-dihydroquinolin-4-yl)methyl]-2H-1,2,4-benzothiadiazin-3(4H)-one 1,1-dioxide (156)

A mixture of (IntE4) (60 mg, 0.18 mmol), 4-(bromomethyl)quinolin-2(1H)-one (104 mg, 0.44 mmol) and $K_2CO_3$ (60.6 mg, 0.44 mmol) in DMF (5 mL) was heated in a sealed tube at 100° C. for 1 h. After concentration in vacuo, purification by gradient column chromatography, eluting with 0-100% EtOAc in iso-hexane, followed by preparative HPLC (method B) yielded the title compound (10 mg, 0.02 mmol).

LCMS (Method B): m/z 500.1 (M+H)+ (ES+), at 4.03 min, 100%

$^1$H NMR: (400 MHz, DMSO) δ: 5.30 (s, 2H), 5.47 (s, 2H), 6.11 (s, 1H), 7.12-7.27 (m, 3H), 7.35 (d, J=8.0, 1H), 7.44-7.60 (m, 2H), 7.75 (d, J=8.5, 1H), 7.85-7.94 (m, 2H), 7.96-8.04 (m, 1H), 11.78 (s, 1H)

4-(2,6-Difluorobenzyl)-2-[2-(3,5-dimethyl-1,2-oxazol-4-yl)ethyl]-2H-1,2,4-benzothiadiazin-3(4H)-one 1,1-dioxide (120)

A mixture of (IntE3) (100 mg, 0.31 mmol), 4-(2-chloroethyl)-3,5-dimethylisoxazole (123 mg, 0.77 mmol), KI (10.2 mg, 0.06 mmol) and $K_2CO_3$ (107 mg, 0.77 mmol) in DMF (5 mL) was heated in a CEM Discover microwave reactor for 3 h. EtOAc (40 mL) and $H_2O$ (10 mL) were added, the phases were separated and the organic phase was washed with $H_2O$ (4×10 mL) and brine (20 mL), dried over $MgSO_4$ and concentrated in vacuo. Purification by preparative HPLC (method A) yielded the title compound (24 mg, 0.05 mmol).

LCMS (Method B): m/z 448.2 (M+H)+ (ES+), at 4.33 min, 100%

$^1$H NMR: (400 MHz, DMSO) δ: 2.03 (s, 3H), 2.09 (s, 3H), 2.65 (t, J=6.8, 2H), 3.90 (t, J=6.8, 2H), 5.45 (s, 2H), 7.05 (m, 2H), 7.35-7.43 (m, 2H), 7.68 (d, J=8.5, 1H), 7.78-7.84 (m, 2H)

4-(2,6-Difluorobenzyl)-2-[(1-methyl-1H-indazol-3-yl)methyl]-2H-1,2,4-benzothiadiazin-3(4H)-one 1,1-dioxide (125)

The title compound (11 mg, 0.02 mmol) was prepared from (IntE3) (50 mg, 0.154 mmol), 3-(chloromethyl)-1-methyl-1H-indazole (69.6 mg, 0.39 mmol), KI (5.1 mg, 0.03 mmol) and K₂CO₃ (53.3 mg, 0.39 mmol) in DMF (3 mL) in a CEM Discover microwave reactor (100° C., 1 h) using the methods of (120).

LCMS (Method B): m/z 469.2 (M+H)+ (ES+), at 4.66 min, 100%

¹H NMR: (400 MHz, DMSO) δ: 3.95 (s, 3H), 5.32 (s, 2H), 5.47 (s, 2H), 7.03-7.10 (m, 3H), 7.34-7.43 (m, 3H), 7.57 (d, J=8.5, 1H), 7.66 (d, J=8.5, 1H), 7.71 (d, J=8.0, 1H), 7.80 (t, J=7.3, 1H), 7.92 (d, J=7.8, 1H)

4-(2,6-Difluorobenzyl)-2-(1-ethylpiperidin-3-yl)-2H-1,2,4-benzothiadiazin-3(4H)-one 1,1-dioxide (133)

The title compound (42 mg, 0.09 mmol) was prepared from (IntE3) (100 mg, 0.31 mmol), 3-chloro-1-ethylpiperidine hydrochloride (142 mg, 0.77 mmol), KI (10.2 mg, 0.06 mmol) and K₂CO₃ (107 mg, 0.77 mmol) in DMF (5 mL) in a CEM Discover microwave reactor (100° C., 1 h) using the methods of (120).

LCMS (Method B): m/z 436.2 (M+H)+ (ES+), at 4.46 and 4.63 min, >95%

¹H NMR: (400 MHz, DMSO) δ: 0.92-1.00 (m, 3H), 1.53-1.66 (m, 2H), 2.09-2.55 (m, 4H), 2.65-3.00 (m, 3H), 3.68-3.75 (m, 2H), 5.39-5.51 (m, 2H), 7.04-7.10 (m, 2H), 7.35-7.43 (m, 2H), 7.63-7.66 (m, 1H), 7.77-7.82 (m, 1H), 7.86-7.91 (m, 1H)

Route 7

4-(2,6-Difluoro-4-methoxybenzyl)-2-(5,6-dimethylpyridin-2-yl)-2H-pyrido[2,3-e][1,2,4]thiadiazin-3(4H)-one 1,1-dioxide (173)

The title compound (182 mg, 0.40 mmol) was prepared from 2-(5,6-dimethylpyridin-2-yl)-2H-pyrido[2,3-e][1,2,4]thiadiazin-3(4H)-one 1,1-dioxide (IntF1) (181 mg, 0.60 mmol), 2,6-difluoro-4-methoxybenzyl bromide (169 mg, 0.71 mmol) and K₂CO₃ (123 mg, 0.89 mmol) in DMF (3 mL) using the methods of (115).

LCMS (Method B): m/z 461.1 (M+H)+ (ES+), at 4.53 min, 95%

¹H NMR: (400 MHz, DMSO) δ: 2.27 (s, 3H), 2.39 (s, 3H), 3.71 (s, 3H), 5.49 (s, 2H), 6.65 (s, 1H) 6.67 (s, 1H), 7.20 (d, J=7.8, 1H), 7.46 (dd, J=8.0, 4.8, 1H), 7.69 (d, J=7.8, 1H), 8.39 (dd, J=8.0, 1.6, 1H), 8.79 (dd, J=5.0, 1.8, 1H)

4-(2,6-Difluoro-4-methoxybenzyl)-2-(4,6-dimethylpyridin-2-yl)-2H-pyrido[2,3-e][1,2,4]thiadiazin-3(4H)-one 1,1-dioxide (174)

The title compound (85 mg, 0.18 mmol) was prepared from 2-(4,6-dimethylpyridin-2-yl)-2H-pyrido[2,3-e][1,2,4]thiadiazin-3(4H)-one 1,1-dioxide (IntF2) (110 mg, 0.36 mmol), 2,6-difluoro-4-methoxybenzyl bromide (103 mg, 0.43 mmol) and K₂CO₃ (75 mg, 0.54 mmol) in DMF (3 mL) using the methods of (115).

LCMS (Method B): m/z 461.1 (M+H)+ (ES+), at 4.53 min, 95%

¹H NMR: (400 MHz, DMSO) δ: 2.29 (s, 3H), 2.40 (s, 3H), 3.71 (s, 3H), 5.49 (s, 2H), 6.65 (s, 1H) 6.67 (s, 1H), 7.13 (s, 1H), 7.22 (s, 1H), 7.47 (dd, J=7.8, 5.0, 1H), 8.39 (dd, J=8.0, 1.6, 1H), 8.80 (dd, J=4.81, 1.60, 1H)

4-(2-Chloro-4,6-difluorobenzyl)-2-(2,6-dimethoxypyridin-4-yl)-2H-pyrido[2,3-e][1,2,4]thiadiazin-3(4H)-one 1,1-dioxide (180)

The title compound (74 mg, 0.15 mmol) was prepared from 2-(2,6-dimethoxypyridin-4-yl)-2H-pyrido[2,3-e][1,2,4]thiadiazin-3(4H)-one 1,1-dioxide (IntF3) (101 mg, 0.30 mmol), 2-chloro-4,6-difluorobenzyl alcohol (IntA22) (59 mg, 0.33 mmol), TMAD (57 mg, 0.33 mmol) and triphenyl phosphine (86 mg, 0.33 mmol) in DCM (3 mL) using the methods of (162).

LCMS (Method B): m/z 497.0, 499.0 (M+H)+ (ES+), at 5.26 min, 100%

¹H NMR: (400 MHz, DMSO) δ: 3.86 (s, 6H), 5.53 (s, 2H), 6.40 (s, 2H), 7.24-7.31 (m, 1H), 7.34 (d, J=8.7, 1H), 7.47 (dd, J=7.8, 5.0, 1H), 8.44 (dd, J=7.8, 1.4, 1H), 8.79 (dd, J=4.8, 1.6, 1H)

4-(2-Chloro-4,6-difluorobenzyl)-2-(5,6-dimethoxypyridin-3-yl)-2H-pyrido[2,3-e][1,2,4]thiadiazin-3(4H)-one 1,1-dioxide (185)

The title compound (118 mg, 0.24 mmol) was prepared from 2-(5,6-dimethoxypyridin-3-yl)-2H-pyrido[2,3-e][1,2,4]thiadiazin-3(4H)-one 1,1-dioxide (IntF4) (101 mg, 0.30 mmol), 2-chloro-4,6-difluorobenzyl alcohol (IntA22) (59 mg, 0.33 mmol), TMAD (103 mg, 0.6 mmol) and triphenyl phosphine (157 mg, 0.6 mmol) in DCM (3 mL) using the methods of (162).

LCMS (Method B): m/z 497.0, 499.0 (M+H)+ (ES+), at 4.69 min, 100%

¹H NMR: (400 MHz, DMSO) δ: 3.72 (s, 3H), 3.88 (s, 3H), 5.55 (s, 2H), 7.25-7.38 (m, 3H), 7.48 (dd, J=7.8, 5.0, 1H), 7.70 (d, J=2.3, 1H), 8.46 (dd, J=7.8, 1.4, 1H), 8.79 (dd, J=5.0, 1.4, 1H).

Biological Testing

Membrane Preparation cDNA encoding the human Orexin-2 receptor was transfected into HEK293 cells using the transfection reagent Genejuice (Novagen). Fourty-eight hours after transfection, cells were harvested and washed twice with ice cold phosphate-buffered saline. The pellet was resuspended in ice-cold buffer containing 20 mM Tris-HCl, pH 7.4, 1 mM EDTA and homogenised with an Ultraturax for 30 s at maximum speed. After centrifugation at 48,000 g for 30 min at 4° C., the pellet was resuspended and spun again. The final pellet was resuspended and frozen at −80° C. before use. Protein concentration was determined using the BCA protein assay method.

³H-EMPA Radioligand Binding Assay

After thawing, membrane homogenates were re-suspended in the binding buffer (8.5 mM HEPES, pH 7.4, 1.3 mM CaCl₂, 1.2 mM MgSO₄, 118 mM NaCl, 4.7 mM KCl, 4 mM NaHCO₃, 1.2 mM KH₂PO₄, 11 mM Glucose) to a final assay concentration of 2.5 protein per well. Saturation isotherms were determined by the addition of various concentrations of ³H-EMPA (Malherbe et al, Br. J. Pharmacol. 2009, 156, 1326) in a total reaction volume of 250 µL for 60 min at room temperature. At the end of the incubation, membranes were filtered onto a unifilter, a 96-well white microplate with bonded GF/B filter pre-incubated with 0.5% polyethylenimine, with a Tomtec cell harvester and washed 4 times with distilled water. Non-specific binding (NSB) was measured in the presence of 10 µM (2S)-1-(3,4-Dihydro-6,7-dimethoxy-2(1H)-isoquinolinyl)-3,3-dimethyl-2-[(4-pyridinylmethyl)amino]-1-butanone hydrochloride (TCS OX2 29, Tocris bioscience, catalogue number 3371). Radioactivity on the filter was counted (1 min) on a micro-beta counter after addition of 50 µL of scintillation fluid. For inhibition experiments, membranes were incubated with ³H-EMPA at a concentration equal to the $K_D$ value of the radioligand and 10 concentrations of the inhibitory compound (0.001-10 µM). $IC_{50}$ values were derived from the inhibition curve and the equilibrium dissociation constant ($K_i$) values were calculated using the Cheng-Prussoff equation. Data is given in Table 1 for all examples.

Ex vivo orexin-2 receptor occupancy Male Sprague Dawley rats were dosed orally with either vehicle, example 145, (0.3-10 mg/kg po) or example 100, (1 mg/kg, po). Vehicle for example 145 was 90% PEG400/10% Tween-80; for example 100 10% DMAC+10% Solutol+80% (10% HPβCD in water). 1 h post-dose, animals were sacrificed and brains removed. A coronal block containing the cortex was rapidly frozen in isopentane for sectioning and autoradiography. 20 µm thick sections were mounted onto slides and incubated with [³H]EMPA (total binding) or [³H]EMPA and 1 µM TCS OX2 29 (non-specific binding) for 20 min at rt. Binding was terminated by aspiration and washing with ice-cold assay buffer and allowed to air dry. Levels of bound radioactivity in the sections were determined using a beta imager over a 16 h period. Occupancy was determined as mean specific binding with the vehicle treated control taken as 100%. Example 145 occupied cortical orexin-2 receptors in a dose dependent manner, with an estimated ED50 of 5.8 mg/kg (po). At a dose of 1 mg/kg, example 100 occupied 57% of orexin-2 receptors, suggesting that the ED50 value is <1 mg/kg (po).

Rat Telemetered Sleep Study

Example 100 was assessed for activity in a rat CT18 sleep model. Adult male CD rats (250-300 g) were implanted with telemetric probes fixed to the skull to record cortical electroencephalogram (EEG), and with telemetric probes fixed to the skeletal muscles of the neck to record electromyogram (neck EMG), and allowed to recover for 3 weeks to re-establish normal sleep patterns. Rats were administered with example 100 (3, 10 and 30 mg/kg, po) or vehicle (80% v/v PEG400, 20% v/v Cremophor EL, 2 ml/kg) at Circadian Time (CT) 18, six hours after lights off. EEG and neck EMG traces were recorded for 5 hours after treatment and analysed to determine time spent awake and in NREM sleep and REM sleep. ANOVA (analysis of variance) statistical analysis over 3 hours post-treatment indicated that at a dose of e.g. 3 mg/kg example 100 induced a statistically significant decrease in time spent awake, with statistically significant increases in REM and NREM sleep. The positive control zolpidem confirmed experiment validity, demonstrating a hypnotic effect which was characterized by a decrease in NREM latency, a decrease in time spent awake and an increase in NREM sleep.

The invention claimed is:

1. A method of treatment of a disorder, wherein the disorder is insomnia, a headache disorder, obesity, a movement disorder, an anxiety disorder, a panic disorder, a binge eating disorder, a compulsive disorder, an impulse control disorder and Alzheimer's disease, comprising administering an effective amount of the compound of formula (1) to a subject in need thereof, wherein the compound of formula (1) is

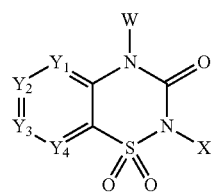

wherein $Y_2$, $Y_3$ are independently a carbon or a nitrogen atom; and
$Y_4$ is C-alkyl, C-halogen, C—H or N; and W is a methylene group substituted by substituted aryl, or optionally substituted heteroaryl or heterocycloalkyl moiety, wherein the substituents and optional substituents forming part of W are selected from the group consisting of halo, alkyl, hydroxyl and alkoxy; and X comprises an optionally substituted aryl, optionally substituted heteroaryl, optionally substituted cycloalkyl, or optionally substituted heterocycloalkyl moiety, wherein X is not cyclopropyl and wherein the optional substituents forming part of X are selected from the group consisting of fluoro, chloro, bromo, iodo, oxo, $C_{1-4}$ alkyl, $C_{1-4}$ alkylsulfanyl, $C_{1-4}$ alkylsulfinyl, $C_{1-4}$ alkylsulphonyl, $C_{3-6}$ cycloalkyl, hydroxy, $C_{1-4}$ alkoxy, cyano, nitro, amino, $C_{1-4}$ alkylamino, $C_{2-4}$ alkenylamino, di-$C_{1-4}$ alkylamino, $C_{1-4}$ acylamino, phenyl, phenylamino, benzoylamino, benzylamino, phenylamido, carboxy, $C_{1-4}$ alkoxycarbonyl, phenyl-$C_{1-10}$ alkoxycarbonyl, carbamoyl, mono-$C_{1-4}$ carbamoyl, di-$C_{1-4}$ carbamoyl and any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

2. The method of claim 1 wherein $Y_1$ is nitrogen.

3. The method of claim 1 wherein $Y_4$ is CH or N.

4. The method of claim 1, wherein X is an optionally substituted heteroaryl or heterocycloalkyl moiety.

5. The method of claim 4, wherein X is selected from

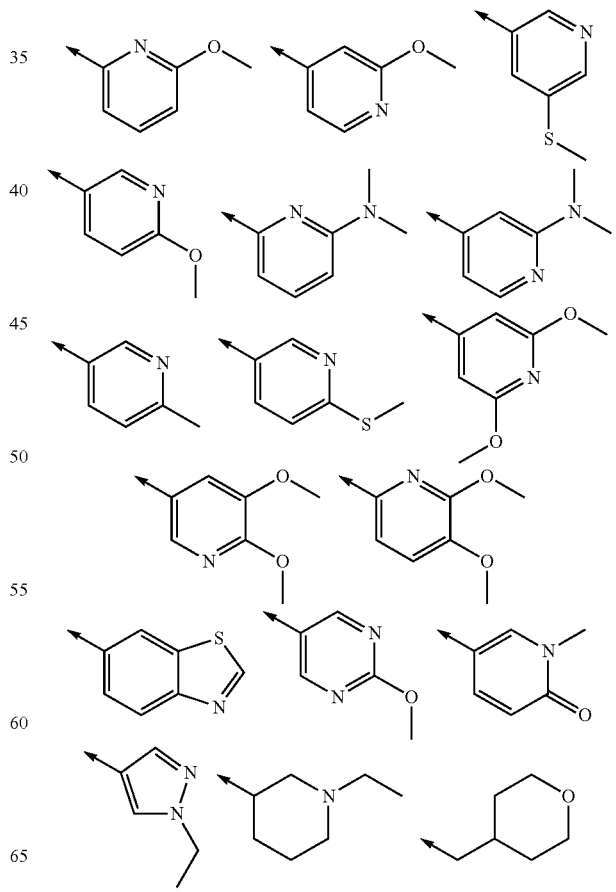

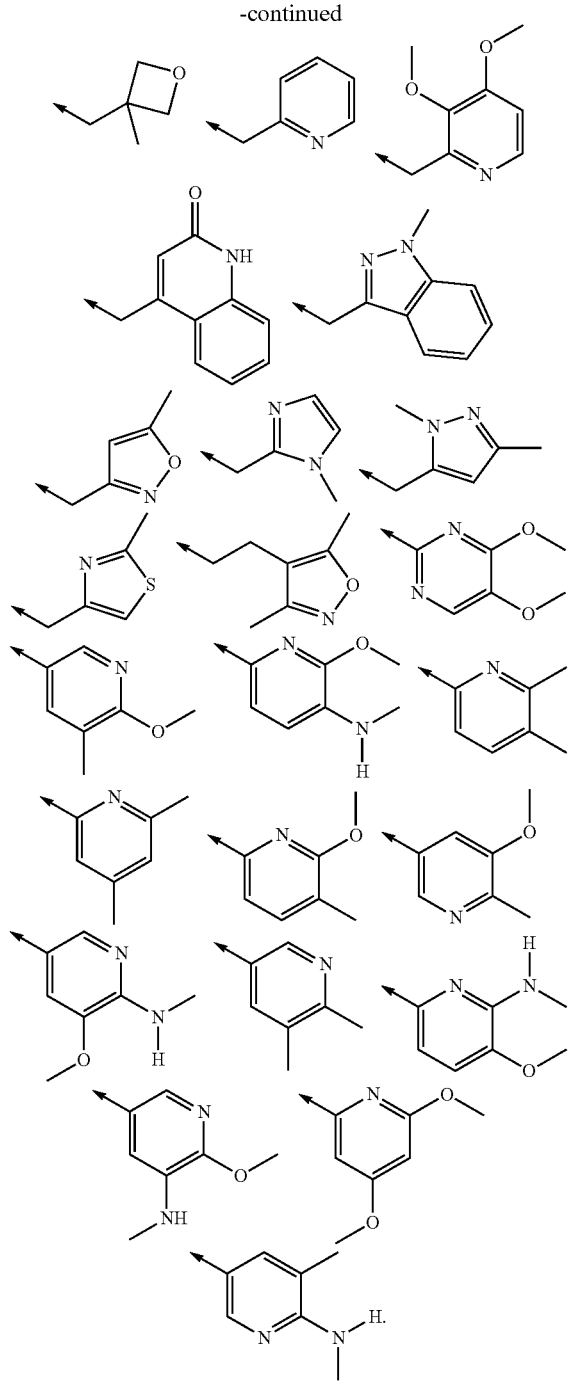

6. The method of claim 1, wherein the disorder is migraine, cluster headache or other headache disorders.

7. The method of claim 1, wherein the disorder is obesity.

8. The method of claim 1, wherein the disorder is movement disorders, anxiety disorders, panic disorders, binge eating disorder, compulsive disorders, impulse control disorders, or Alzheimer's disease.

9. The method of claim 6, wherein the headache disorder is migraine or cluster headache.

10. The method of claim 1 wherein the compound is selected from the group consisting of
4-(1,3-benzodioxol-5-ylmethyl)-2-(3,4-dimethoxyphenyl)-2H-1,2,4-benzothiadiazin-3(4H)-one 1,1-dioxide,
2-(3,4-dimethoxyphenyl)-4-(3-fluoro-4-methoxybenzyl)-2H-1,2,4-benzothiadiazin-3(4H)-one 1,1-dioxide,
2-(3,5-dimethoxyphenyl)-4-(3-methoxybenzyl)-2H-1,2,4-benzothiadiazin-3(4H)-one 1,1-dioxide,
3-{[2-(3,4-dimethoxyphenyl)-1,1-dioxido-3-oxo-2,3-dihydro-4H-1,2,4-benzothiadiazin-4-yl]methyl}benzonitrile,
4-benzyl-2-(3,4-dimethoxyphenyl)-2H-1,2,4-benzothiadiazin-3(4H)-one 1,1-dioxide,
2-(3,5-dimethoxyphenyl)-4-(3-methylbenzyl)-2H-1,2,4-benzothiadiazin-3(4H)-one 1,1-dioxide,
2-(3,4-dimethoxyphenyl)-4-(4-methylbenzyl)-2H-1,2,4-benzothiadiazin-3(4H)-one 1,1-dioxide,
2-(3,4-dimethoxyphenyl)-4-(4-fluorobenzyl)-2H-1,2,4-benzothiadiazin-3(4H)-one 1,1-dioxide,
4-(3-bromobenzyl)-2-[3-(methylsulfanyl)phenyl]-2H-1,2,4-benzothiadiazin-3 (4H)-one 1,1-dioxide,
4-(3-fluoro-4-methoxybenzyl)-2-(3-methoxyphenyl)-2H-1,2,4-benzothiadiazin-3(4H)-one 1,1-dioxide,
2-(3-ethylphenyl)-4-(3-fluoro-4-methoxybenzyl)-2H-1,2,4-benzothiadiazin-3(4H)-one 1,1-dioxide,
4-(3-fluorobenzyl)-2-(3-chloro-4-methylphenyl)-2H-1,2,4-benzothiadiazin-3(4H)-one 1,1-dioxide,
2-(3,5-dimethoxyphenyl)-4-(2-fluorobenzyl)-2H-1,2,4-benzothiadiazin-3(4H)-one 1,1-dioxide,
4-(2-fluorobenzyl)-2-(3-methoxyphenyl)-2H-1,2,4-benzothiadiazin-3(4H)-one 1,1-dioxide,
2-(3,5-dimethoxyphenyl)-4-(2-methylbenzyl)-2H-1,2,4-benzothiadiazin-3(4H)-one 1,1-dioxide,
4-(2-chlorobenzyl)-2-(3,5-dimethoxyphenyl)-2H-1,2,4-benzothiadiazin-3(4H)-one 1,1-dioxide,
methyl 3-{[2-(3,5-dimethoxyphenyl)-1,1-dioxido-3-oxo-2,3-dihydro-4H-1,2,4-benzothiadiazin-4-yl]methyl}-4-methoxybenzoate,
2-(3,4-dimethoxyphenyl)-4-(2-methylbenzyl)-2H-1,2,4-benzothiadiazin-3(4H)-one 1,1-dioxide,
4-(2-chlorobenzyl)-2-(3,4-dimethoxyphenyl)-2H-1,2,4-benzothiadiazin-3(4H)-one 1,1-dioxide,
4-(2-chloro-6-fluorobenzyl)-2-(3,4-dimethoxyphenyl)-2H-1,2,4-benzothiadiazin-3(4H)-one 1,1-dioxide,
4-(2-chloro-4-fluorobenzyl)-2-(3,4-dimethoxyphenyl)-2H-1,2,4-benzothiadiazin-3(4H)-one 1,1-dioxide,
4-(2-chlorobenzyl)-2-[3-(methylsulfanyl)phenyl]-2H-1,2,4-benzothiadiazin-3(4H)-one 1,1-dioxide,
4-(2-fluorobenzyl)-2-[3-(methylsulfanyl)phenyl]-2H-1,2,4-benzothiadiazin-3(4H)-one 1,1-dioxide,
4-(2-chloro-6-fluorobenzyl)-2-(4-chlorophenyl)-2H-1,2,4-benzothiadiazin-3(4H)-one 1,1-dioxide,
4-(2-chloro-6-fluorobenzyl)-2-(3-chloro-4-methylphenyl)-2H-1,2,4-benzothiadiazin-3(4H)-one 1,1-dioxide,
4-(2-chloro-6-fluorobenzyl)-2-phenyl-2H-1,2,4-benzothiadiazin-3(4H)-one 1,1-dioxide,
4-(2-chloro-6-fluorobenzyl)-2-(3,5-dimethylphenyl)-2H-1,2,4-benzothiadiazin-3(4H)-one 1,1-dioxide,
4-(2-chloro-6-fluorobenzyl)-2-(4-methylphenyl)-2H-1,2,4-benzothiadiazin-3(4H)-one 1,1-dioxide,
4-(2-chloro-6-fluorobenzyl)-2-(4-ethoxyphenyl)-2H-1,2,4-benzothiadiazin-3(4H)-one 1,1-dioxide,
2-(4-acetylphenyl)-4-(2-chloro-6-fluorobenzyl)-2H-1,2,4-benzothiadiazin-3(4H)-one 1,1-dioxide,
4-(2-chloro-6-fluorobenzyl)-2-(3-methylphenyl)-2H-1,2,4-benzothiadiazin-3(4H)-one 1,1-dioxide,
4-(2-chloro-6-fluorobenzyl)-2-(2,5-dimethylphenyl)-2H-1,2,4-benzothiadiazin-3(4H)-one 1,1-dioxide,
4-(2-chloro-6-fluorobenzyl)-2-(2-ethylphenyl)-2H-1,2,4-benzothiadiazin-3(4H)-one 1,1-dioxide, 4-(2-chloro-6-fluorobenzyl)-2-(3,4-dimethylphenyl)-2H-1,2,4-benzothiadiazin-3(4H)-one 1,1-dioxide,
4-(2-chloro-6-fluorobenzyl)-2-(2-methoxyphenyl)-2H-1,2,4-benzothiadiazin-3(4H)-one 1,1-dioxide,
4-(2-chloro-6-fluorobenzyl)-2-(3-methoxyphenyl)-2H-1,2,4-benzothiadiazin-3(4H)-one 1,1-dioxide,
4-(2-chloro-6-fluorobenzyl)-2-(4-ethylphenyl)-2H-1,2,4-benzothiadiazin-3(4H)-one 1,1-dioxide,
4-(2-chloro-6-fluorobenzyl)-2-(2,3-dimethylphenyl)-2H-1,2,4-benzothiadiazin-3(4H)-one 1,1-dioxide,
4-(2-chloro-6-fluorobenzyl)-2-(4-fluorobenzyl)-2H-1,2,4-benzothiadiazin-3(4H)-one 1,1-dioxide,
2-benzyl-4-(2-chloro-6-fluorobenzyl)-2H-1,2,4-benzothiadiazin-3(4H)-one 1,1-dioxide,
4-(2-chloro-6-fluorobenzyl)-2-(5-chloro-2-methylphenyl)-2H-1,2,4-benzothiadiazin-3(4H)-one 1,1-dioxide,
4-(2-chloro-6-fluorobenzyl)-2-(3-chlorophenyl)-2H-1,2,4-benzothiadiazin-3(4H)-one 1,1-dioxide,
4-(2-chloro-6-fluorobenzyl)-2-(3-fluoro-4-methylphenyl)-2H-1,2,4-benzothiadiazin-3(4H)-one 1,1-dioxide,
4-(2-chloro-6-fluorobenzyl)-2-(4-fluorophenyl)-2H-1,2,4-benzothiadiazin-3(4H)-one 1,1-dioxide,
4-(2-chloro-6-fluorobenzyl)-2-(2,4-dimethylphenyl)-2H-1,2,4-benzothiadiazin-3(4H)-one 1,1-dioxide,
4-(2-chloro-6-fluorobenzyl)-2-(2,5-difluorophenyl)-2H-1,2,4-benzothiadiazin-3(4H)-one 1,1-dioxide,
4-(2-chloro-6-fluorobenzyl)-2-(3-ethylphenyl)-2H-1,2,4-benzothiadiazin-3(4H)-one 1,1-dioxide,
4-(2-chloro-6-fluorobenzyl)-2-[4-(propan-2-yl)phenyl]-2H-1,2,4-benzothiadiazin-3(4H)-one 1,1-dioxide,
4-(2-chloro-6-fluorobenzyl)-2-[3-(methylsulfanyl)phenyl]-2H-1,2,4-benzothiadiazin-3(4H)-one 1,1-dioxide,
4-(2-chloro-4-fluorobenzyl)-2-[3-(methylsulfanyl)phenyl]-2H-1,2,4-benzothiadiazin-3(4H)-one 1,1-dioxide,
4-(2,5-dimethylbenzyl)-2-[3-(methylsulfanyl)phenyl]-2H-1,2,4-benzothiadiazin-3(4H)-one 1,1-dioxide,
methyl 3-({2-[3-(methylsulfanyl)phenyl]-1,1-dioxido-3-oxo-2,3-dihydro-4H-1,2,4-benzothiadiazin-4-yl}methyl)-4-methoxybenzoate,
4-(2-fluorobenzyl)-2-(3-chloro-4-methylphenyl)-2H-1,2,4-benzothiadiazin-3(4H)-one 1,1-dioxide,
4-(2-methylbenzyl)-2-(3-chloro-4-methylphenyl)-2H-1,2,4-benzothiadiazin-3(4H)-one 1,1-dioxide,
4-(2-chlorobenzyl)-2-(3,5-dimethylphenyl)-2H-1,2,4-benzothiadiazin-3(4H)-one 1,1-dioxide,
4-(2-fluorobenzyl)-2-(3,5-dimethylphenyl)-2H-1,2,4-benzothiadiazin-3(4H)-one 1,1-dioxide,
4-(2-fluorobenzyl)-2-(3,4-dimethylphenyl)-2H-1,2,4-benzothiadiazin-3(4H)-one 1,1-dioxide,
2-benzyl-4-(2-chlorobenzyl)-2H-1,2,4-benzothiadiazin-3(4H)-one 1,1-dioxide,
4-(2-chlorobenzyl)-2-(3,4-dimethylphenyl)-2H-1,2,4-benzothiadiazin-3(4H)-one 1,1-dioxide,
methyl 3-{[2-(3,4-dimethoxyphenyl)-1,1-dioxido-3-oxo-2,3-dihydro-4H-1,2,4-benzothiadiazin-4-yl]methyl}-4-methoxybenzoate,
4-(Cyclobutylmethyl)-2-[3-(methylsulfanyl)phenyl]-2H-1,2,4-benzothiadiazin-3(4H)-one 1,1-dioxide,
4-(Cyclohexylmethyl)-2-[3-(methylsulfanyl)phenyl]-2H-1,2,4-benzothiadiazin-3(4H)-one 1,1-dioxide,
7-Fluoro-4-[1-(2-fluorophenyl)ethyl]-2-[3-(methylsulfanyl)phenyl]-2H-1,2,4-benzothiadiazin-3(4H)-one 1,1-dioxide,
4-(2-Chloro-6-fluorobenzyl)-2-(cyclohexylmethyl)-2H-1,2,4-benzothiadiazin-3(4H)-one 1,1-dioxide,
4-{[4-(2,6-Difluorobenzyl)-1,1-dioxido-3-oxo-3,4-dihydro-2H-1,2,4-benzothiadiazin-2-yl]methyl}-2-fluorobenzonitrile,
4-(2,6-Difluorobenzyl)-2-[2-(3-methoxyphenyl)ethyl]-2H-1,2,4-benzothiadiazin-3(4H)-one 1,1-dioxide,
2-(3,4-Dimethoxyphenyl)-4-(2-fluorobenzyl)-2H-1,2,4-benzothiadiazin-3(4H)-one 1,1-dioxide,
4-(2,6-Dichlorobenzyl)-2-(3,4-dimethoxyphenyl)-2H-1,2,4-benzothiadiazin-3(4H)-one 1,1-dioxide,
4-(2-Chloro-6-fluorobenzyl)-2-(3,5-dimethoxyphenyl)-2H-1,2,4-benzothiadiazin-3(4H)-one 1,1-dioxide,
4-(2,6-Dichlorobenzyl)-2-(3,5-dimethoxyphenyl)-2H-1,2,4-benzothiadiazin-3(4H)-one 1,1-dioxide,
4-(3-Chloro-2-fluorobenzyl)-2-(3,4-dimethoxyphenyl)-2H-1,2,4-benzothiadiazin-3(4H)-one 1,1-dioxide,
4-(4-Chloro-2-fluorobenzyl)-2-(3,4-dimethoxyphenyl)-2H-1,2,4-benzothiadiazin-3(4H)-one 1,1-dioxide,
4-(2-Chloro-6-fluorobenzyl)-2-{3-[(trifluoromethyl) sulfanyl]phenyl}-2H-1,2,4-benzothiadiazin-3(4H)-one 1,1-dioxide,
4-(2-Chloro-6-fluorobenzyl)-7-fluoro-2-[3-(methylsulfanyl)phenyl]-2H-1,2,4-benzothiadiazin-3(4H)-one 1,1-dioxide,
4-(2,6-Difluorobenzyl)-2-{3-[(trifluoromethyl) sulfanyl]phenyl}-2H-1,2,4-benzothiadiazin-3 (4H)-one 1,1-dioxide,
4-(2-Chloro-6-fluorobenzyl)-6-fluoro-2-[3-(methylsulfanyl)phenyl]-2H-1,2,4-benzothiadiazin-3(4H)-one 1,1-dioxide,
4-(2,6-Dimethylbenzyl)-2-(3,4-methoxyphenyl)-2H-1,2,4-benzothiadiazin-3(4H)-one 1,1-dioxide,
4-(2-Chloro-6-fluorobenzyl)-2-(3,4,5-trimethoxyphenyl)-2H-1,2,4-benzothiadiazin-3(4H)-one 1,1-dioxide,
4-(2-Fluoro,6-methylbenzyl)-2-(3,4-methoxyphenyl)-2H-1,2,4-benzothiadiazin-3(4H)-one 1,1-dioxide,
4-(2-Chloro-4-fluorobenzyl)-2-(4-methoxy-3,5-dimethylphenyl)-2H-1,2,4-benzothiadiazin-3(4H)-one 1,1-dioxide,
4-(2-chloro-6-fluorobenzyl)-2-(4-methoxy-3,5-dimethylphenyl)-2H-1,2,4-benzothiadiazin-3(4H)-one 1,1-dioxide, and
4-(2-Chloro-6-fluorobenzyl)-2-(4-hydroxy-3,5-dimethylphenyl)-2H-1,2,4-benzothiadiazin-3(4H)-one 1,1-dioxide.

* * * * *